United States Patent
Saoud et al.

(10) Patent No.: US 11,464,744 B2
(45) Date of Patent: Oct. 11, 2022

(54) GASTRO-RESISTANT CONTROLLED RELEASE ORAL DOSAGE FORMS

(71) Applicant: Minerva Neurosciences, Inc., Burlington, MA (US)

(72) Inventors: Jay Saoud, Waltham, MA (US); Remy Luthringer, Geneva (CH); Sandra Werner, Ostwald (FR); Nadine Noel, Gildwiller (FR); Emmanuelle Georgi, Colmar (FR)

(73) Assignee: Minerva Neurosciences, Inc., Burlington, MA (US)

( * ) Notice: Subject to any disclaimer, the term of this patent is extended or adjusted under 35 U.S.C. 154(b) by 0 days.

(21) Appl. No.: 16/015,151

(22) Filed: Jun. 21, 2018

(65) Prior Publication Data

US 2019/0038561 A1 Feb. 7, 2019

Related U.S. Application Data

(60) Provisional application No. 62/523,204, filed on Jun. 21, 2017.

(51) Int. Cl.
| | |
|---|---|
| A61K 9/20 | (2006.01) |
| A61K 31/454 | (2006.01) |
| A61K 9/28 | (2006.01) |
| A61K 31/4439 | (2006.01) |

(52) U.S. Cl.
CPC ............ *A61K 9/205* (2013.01); *A61K 9/2009* (2013.01); *A61K 9/2018* (2013.01); *A61K 9/2054* (2013.01); *A61K 9/28* (2013.01); *A61K 9/2846* (2013.01); *A61K 31/4439* (2013.01); *A61K 31/454* (2013.01)

(58) Field of Classification Search
CPC .................................. A61K 9/28; A61K 9/2054
See application file for complete search history.

(56) References Cited

U.S. PATENT DOCUMENTS

| | | | |
|---|---|---|---|
| 4,908,369 A | 3/1990 | Schechter et al. | |
| 7,166,617 B2 | 1/2007 | Yamabe et al. | |
| 8,968,779 B2 | 3/2015 | Fujinaga et al. | |
| 9,458,130 B2 | 10/2016 | Luthringer et al. | |
| 9,730,920 B2 | 8/2017 | Luthringer et al. | |
| 9,732,059 B2 | 8/2017 | Luthringer et al. | |
| 10,258,614 B2 | 4/2019 | Luthringer et al. | |
| 10,799,493 B2 | 10/2020 | Luthringer et al. | |
| 11,083,723 B2 | 8/2021 | Luthringer | |
| 2008/0050429 A1 | 2/2008 | Rocca et al. | |
| 2010/0029726 A1 | 2/2010 | Blackaby et al. | |
| 2013/0273156 A1* | 10/2013 | Loeches Blas | A61K 9/2054 424/465 |
| 2013/0274290 A1 | 10/2013 | Luthringer et al. | |
| 2014/0018348 A1 | 1/2014 | Javitt | |
| 2016/0152597 A1 | 6/2016 | Luthringer et al. | |
| 2019/0216793 A1 | 7/2019 | Luthringer | |
| 2020/0061046 A1 | 2/2020 | Luthringer | |

FOREIGN PATENT DOCUMENTS

| | | |
|---|---|---|
| GB | 2462611 A | 2/2000 |
| JP | 2009527477 A | 7/2009 |
| WO | WO 91/06297 A1 | 5/1991 |
| WO | WO 2010/122134 A1 | 10/2010 |
| WO | WO 2012/012543 A1 | 1/2012 |
| WO | WO 2012/123922 A1 | 9/2012 |
| WO | WO 2014/011590 A2 | 1/2014 |
| WO | WO 2015/174534 A1 | 11/2015 |
| WO | WO 2015/191554 A1 | 12/2015 |
| WO | WO 2017/205393 A1 | 11/2017 |

OTHER PUBLICATIONS

"It's not Rocket Science to Reach Higher Coating Efficiency: PlasACRYL makes it possible", Evonik Industries AG, Oct. 2012.*
"Using Dow excipients for controlled release of drugs in hydrophilic matrix systems", 2006, Dow.*
Addington et al., "Assessing Depression in Schizophrenia: The Calgary Depression Scale," British Journal of Psychiatry (1993), 163 (suppl. 22), 39-44.
Ameen et al., "Negative Symptoms in the Remission Phase of Bipolar Disorder," German Journal of Psychiatry, 2007; 10: 1-7.
Barrantes-Vidal et al., "Psychopathology, social adjustment and personality correlates of schizotypy clusters in a large nonclinical sample," Schizophrenia Research 122 (2010) 219-225.
Bastiaansen et al., "Diagnosing Autism Spectrum Disorders in Adults: the Use of Autism Diagnostic Observation Schedule (ADOS) Module 4," J. Autism Dev. Disord. (2011), 41:1256-1266.

(Continued)

*Primary Examiner* — Gina C Justice
(74) *Attorney, Agent, or Firm* — Cooley LLP

(57) ABSTRACT

This disclosure relates to gastro-resistant, controlled release dosage forms comprising Compound (I):

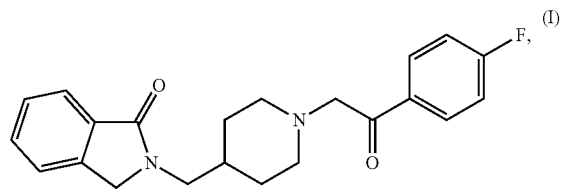

or a pharmaceutically acceptable salt and/or solvate thereof, the pharmacokinetic properties of these dosage forms, and the preparation of the same. The novel dosage forms disclosed herein are useful in reducing the risk of QT prolongation in a subject and in treating a disorder in a subject in need thereof, e.g., a subject diagnosed with schizophrenia, for example, in treating the negative symptoms in a subject diagnosed with schizophrenia having the CYP2D6 EM genotype.

12 Claims, 31 Drawing Sheets

(28 of 31 Drawing Sheet(s) Filed in Color)

(56) References Cited

OTHER PUBLICATIONS

Boone et al., "Relationship between positive and negative symptoms and neuropsychological scores in frontotemporal dementia and Alzheimer's disease," Journal of the International Neuropsychological Society (2003), 9, 698-709.
Chaudhury et al., "Neuropsychiatric Sequelae of Head Injury," Indian Journal of Neurotrauma (IJNT), 2005, vol. 2, No. 1, 13-21.
Galynker et al., "Negative Symptoms in Patients With Major Depressive Disorder: A Preliminary Report," Neuropsychiatry, Neuropsychology, and Behavioral Neurology, Jul. 2000, vol. 13, No. 3, 171-176.
Galynker et al., "Negative Symptoms in Stroke Patients and Length of Hospital Stay," The Journal of Nervous & Mental Disease, vol. 185(10), 1997, 616-621.
Getz et al., "Negative Symptoms in Temporal Lobe Epilepsy," Am. J. Psychiatry, 2002; 159:644-651.
Herbener et al., "Longitudinal Assessment of Negative Symptoms in Schizophrenia/Schizoaffective Patients, Other Psychotic Patients, and Depressed Patients," Schizophrenia Bulletin, 27(3):527-537, 2001.
Hussan et al., "A review on recent advances of enteric coating," IOSR Journal of Pharmacy, vol. 2, Issue 6, 2012, 5-11.
Kamel et al., "Pharmaceutical significance of cellulose: A review," eXPRESS Polymer Letters, vol. 2, No. 11 (2008) 758-778.
Werbeloff et al., "The Association between Negative Symptoms, Psychotic Experiences and Later Schizophrenia: A Population-Based Longitudinal Study," PLoS ONE 10(3): e0119852 (2015) 12 pages.
White et al., "Empirical Assessment of the Factorial Structure of Clinical Symptoms in Schizophrenia," Psychopathology 1997;30:263-274.
Winograd-Gurvich et al., "Negative symptoms: A review of schizophrenia, melancholic depression and Parkinson's disease," Brain Research Bulletin 70 (2006) 312-321.
Thase, M.E., "Depression, Sleep, and Antidepressants," J Clin Psychiatry 1998; 59(Suppl 4): 55-65.
Cole et al., "Enteric coated HPMC capsules designed to achieve intestinal targeting," International Journal of Pharmaceutics (2002) 231: 83-95.
Vilar et al., "Polymers and Drug Delivery Systems," Current Drug Delivery, 2012, 9(4), 367-394.
Li et al., "Lubricants in Pharmaceutical Solid Dosage Forms," Lubricants 2014, 2(1), 21-43.
Pertsev, I.M., Pharmaceutical and Medico-Biological Aspects of Drugs, vol. 1, 1999, pp. 253-254, Kharkiv, UkrFA Publishing House, 10 pages (English translation of Russian Office Action for Russian Application No. 2020102015 attached).
Williams, R. O., III et al., "Investigation of excipient type and level on drug release from controlled release tablets containing HPMC," Pharmaceutical Development and Technology, 7(2):181-193 (2002).
Alon, A. et al., "Identification of the gene that codes for the σ2 receptor," PNAS, Jul. 3, 2017;114(27):7160-7165.
An energy nerve magazine, 2009, 111 (3), p. 288-292 (English translation of Japanese Office Action for Japanese Application No. 2017-225061 attached).
Arnt, J. et al. "Do Novel Antipsychotics Have Similar Pharmacological Characteristics? A Review of the Evidence", Neuropsychopharmacology, 1998, vol. 18, No. 2, pp. 63-101.
Balbach, S. et al. "Pharmaceutical evaluation of early development candidates: 'The 100 mg-approach'," International Journal of Pharmaceutics, (2004), 275, pp. 1-12.
Bastin, R.J et al., "Salt Selection and Optimisation Procedures for Pharmaceutical New Chemical Entities," Organic Process & Development, 2000, 4(5), pp. 427-435.
Bi et al., "Childhood trauma interacted with BDNF Val66Met influence schizophrenic symptoms," Medicine, 2018, 97(13):e0160, 5 pages.

Bishara et al. "Upcoming Agents for the Treatment of Schizophrenia Mechanism of Action, Efficacy and Tolerability," Drugs, vol. 68, No. 16, pp. 2269-2292, 2008.
Bonhaus D. et al., "[3H]BIMU-1, a 5-Hydroxytryptamine3 Receptor Ligand in NG-108 Cells, Selectively Labels Sigma-2 Binding Sites in Guinea Pig Hippocampus", The Journal of Pharmacology and Experimental Therapeutics, vol. 267, No. 2, p. 961-970, 1993.
Buchanan et al. "Olanzapine Treatment of Residual Positive and Negative Symptoms", American Journal of Psychiatry, 2005, vol. 162, pp. 124-129.
Buchanan et al. "Positive and Negative Symptom Response to Clozapine in Schizophrenic Patients With and Without the Deficit Syndrome", American Journal of Psychiatry, 1998, vol. 155, pp. 751-760.
Buckley, P.F. et al. "Pharmacological treatment of negative symptoms of schizophrenia: therapeutic opportunity or Cul-de-sac?" Acta Psychiatrica Scandinavica, vol. 115, No. 2, 2007, pp. 93-100.
Caira, "Crystalline Polymorphism of Organic Compounds," Topics in Current Chemistry, Springer, Berlin, De, vol. 198, Jan. 1, 1998, pp. 163-208.
Cohrs, "Sleep Disturbances in Patients with Schizophrenia", CNS Drugs, (2008), vol. 22, No. 11, pp. 939-962.
Costa e Silva, "Sleep disorders in psychiatry," Metabolism Clinical and Experimental, 2006, 55, Supplement 2, S40-S44.
Davidson, M. et al., "MIN-101: A Drug in Development for the Treatment of Negative Symptoms in Schizophrenia", Poster presentation at the 55th Annual Meeting of the American College of Neuropsychopharmacology, held Dec. 4-8, 2016 in Hollywood, Florida, available on goo.gl/MIR7Tn.
Davidson, M. et al., "MIN-101: A sigma2 and 5HT2 antagonist drug in development for the treatment of symptomatically stable schizophrenia patients with negative symptoms", Oral Presentation at the 55th Annual Meeting of the American College of Neuropsychopharmacology, Dec. 4-8, 2016 in Hollywood, Florida, available on goo.Jl/xF5rdR.
Dumont M. et al. "Interaction of 1,3-di(2-[5-3H]tolyl) guanidine with σ2 binding sites in rat heart membrane preparations," European Journal of Pharmacology, 1991, vol. 209, pp. 245-248.
Dutheil et al. "Xenobiotic metabolozing enzymes in the central nervous system: Contribution of cytochrome P450 enzymes in normal and pathological human brain," Biochimie, vol. 90, Issue 3, Mar. 2008, pp. 426-436.
Foussias, G. et al. "Negative Symptoms in Schizophrenia: Avolition and Occam's Razor," Schizophrenia Bulletin, 2010, vol. 36, No. 2, pp. 359-369.
Garza H. et al., "Characterization of a (+)-Azidophenazocine-Sensitive Sigma Receptor on Splenic Lymphocytes," The Journal of Immunology, 1993, vol. 151, pp. 4672-4680.
Giacobbo et al., "Brain-Derived Neurotrophic Factor in Brain Disorders: Focus on Neuroinflammation," Molecular Neurobiology, 2019, vol. 56, Issue 5, pp. 3295-3312.
Gilmore, D. et al., "Review of the Pharmacological and Clinical Profile of Rimcazole", CNS Drug Reviews, 2004, vol. 10, No. 1, pp. 1-22.
Hashimoto et al., "Interactions of erythro-ifenprodil, threo-ifenprodil, erythro-iodoifenprodil, and eliprodil with subtypes of sigma- receptors" European Journal of Pharmacology, 273 (1995), pp. 307-310.
Hashimoto et al., "Sigma Receptor Ligands: Possible Application as Therapeutic Drugs and as Radiopharmaceuticals," Current Pharmaceutical Design, 2006, vol. 12, No. 30, pp. 3857-3876.
Ishihara et al., Japanese Journal of Neuropsychopharmacology, (2002), vol. 22, No. 1, pp. 23-30 with partial English translation.
Jaen J. et al., "Evaluation-of the Effects of the Enantiomers of Reduced Haloperidol, Azaperol, and Related 4-Amino-1-arylbutanols on Dopamine and σ Receptors," J. Med. Chem., 1993, vol. 36, pp. 3929-3936.
Jeste, "Schizoaffective Disorder," National Alliance on Mental Illness, http://www.nami.org/Template.cfm?Section=By_Illness&Template=/ContentManagement!ContentDisplay.cfm&ContentiD=23043 Wayback Internet Archive, (Nov. 7, 2008).
Jones C. et al., "Animal Models of Schizophrenia," British Journal of Pharmacology, 2011, vol. 164, pp. 1162-1194.

(56) References Cited

OTHER PUBLICATIONS

Kay, "The Positive and-Negative Syndrome Scale (PANSS) for Schizophrenia," Schizophrenia Bulletin, 1987, vol. 13, No. 2, pp. 261-276.

Keefe et al., "Cognitive Effects of MIN-101 in Patients With Schizophrenia and Negative Symptoms Results From a Randomized Controlled Trial," J Clin Psychiatry, May/Jun. 2018, 79:3, e1-e6.

Kropp et al., "Cytochrome P-450 2D6 and 2C19 polymorphisms and length of hospitalization in psychiatry", Clinical Laboratory, 2006, 52(5-6), pp. 237-240. Abstract.

Luthringer, R., "Comparison of Three Sigma2 Ligands on Negative and Positive Symptoms of Schizophrenia", Exhibit C to Supplemental Declaration or Remy Luthringer Under 37 C.F.R. 1.132, Submitted Jan. 17, 2017 in U.S. Appl. No. 13/810,772, 14 pages.

Marder et al., "Aripiprazole in the treatment of schizophrenia: safety and tolerability in short-term, placebo-controlled trials," Schizophrenia Research, 2003, vol. 61, pp. 123-136.

Mash et al., "Sigma Receptors Are Associated With Cortical Limbic Areas in the Primate Brain," Synapse, 1992, vol. 12, pp. 195-205.

Maurice et al., "The attenuation of learning impairments induced after exposure to CO or trimethyltin in mice by sigma($\sigma$) receptor ligands involves both $\sigma_1$ and $\sigma_2$ sites," British Journal of Pharmacology, May 1999, 127(2), pp. 335-342.

Meltzer et al., "Lack of Involvement if Haloperidol-Sensitive Sigma Binding Sites in Modulation of Dopamine Activity and Induction of Dystonias by Antipsychotic Drugs," Neuropharmacology, 1992, vol. 31, No. 9, pp. 961-967.

Modell S. et al., "Efficacy and Safety of an Opiate Sigma-Receptor Antagonist (SL 82.0715) in Schizophrenic Patients with Negative Symptoms: and Open Dose-Tange Study," Pharmacopsychiat., 1996, vol. 29, pp. 63-66.

Nieto et al., "BDNF and schizophrenia: from neurodevelopment to neuronal plasticity, learning and memory," Frontiers in Psychiatry, Jun. 2013, 4:45, 11 pages.

Nokhodchi, et al., "The Role of Oral Controlled Release matrix Tablets in Drug Delivery Systems", BioImpacts, 2012, 2(4), pp. 175-187.

Paykel, Eugene S., "Basic Concepts of Depression", Dialogues in Clinical Neuroscience, 2008, vol. 10, No. 3, pp. 279-289.

Quirion et al., "A proposal for the classification of sigma binding sites", TiPS, Mar. 1992, vol. 13, pp. 85-86.

Rusconi et al., "SSRI antidepressants and negative schizophrenic symptoms: differences between paroxetine and fluvoxamine in patients treated with olanzapine," Riv Psichiatr. Sep.-Oct. 2009;44(5):313-319 (English abstract only).

Sahlholm, K. et al., "The dopamine stabilizers ACR16 and (−)-OSU6162 display nanomolar affinities at the $\sigma$-1 receptor," Mol. Psychiatry. (2013);18(1):12-14.

Schwarcz G. et al., "Open Label Evaluation of the Novel Antipsychotic Compound BW234U in Chronic Schizophrenics," Drug Development Research, 1985, vol. 5, pp. 387-393.

SEC Form 8-K filed Jun. 6, 2016, Minerva Neurosciences. Inc., 57 pages.

Seo, M.K. et al., "Effects of Antipsychotic Drugs on the Epigenetic Modification of Brain-Derived Neurotrophic Factor Gene Expression in the Hippocampi of Chronic Restraint Stress Rats," Neural Plasticity, 2018, vol. 2018, Article ID 2682037, 10 pages.

Sie, M., "An Update on Sleep Disorders and Their Treatment," Progress in Neurology and Psychiatry, 2010, 14(3): pp. 9-20.

Singhal, D et al., "Drug Polymorphism and Dosage Form Design: A practical perspective," Advanced Drug Delivery Reviews, 2004, 56, pp. 335-347.

Siris, Samuel G., "Depression in Schizophrenia: Perspective in the Era of 'Atypical' Antipsychotic Agents?" Am. J. Psychiatry, Sep. 2000, vol. 157, No. 9, pp. 1379-1389.

Summary of 3rd Quarter Financial Results for year ended Mar. 31, 2010 (Unaudited); Mitsubishi Tanabe Pharma Corporation; Jan. 28, 2010, available on http://www.mt-pharma.co.jp/.

Takahashi et al. "Antipsychotic reverse abnormal EEG complexity in drug-naïve schizophrenia: A multiscale entropy analysis," NeuroImage, (2010), vol. 51, pp. 173-182.

Takasu et al., Today's Therapy 2002, vol. 44, pp. 609-612.

Tokuda, "Pharmacological action of antipsychotic drugs," Folia Pharmacologica Japonica, (2006), vol. 128, pp. 173-176. (with English abstract).

Utami et al., "BDNF (brain-derived neurotrophic factor) serum levels in schizophrenic patients with cognitive deficits," IOP Conference Series: Earth and Environmental Science, 2018, vol. 125, 012181, 6 pages.

"View of NCT00861796 on Mar. 12, 2009", ClinicalTrials.gov archive, Mar. 12, 2009 Retrieved from the Internet: URL:http://clinicaltrials.gov/archive/NCT00861796/2009_03_12.

Walker J. M. et al., "Sigma Receptors: Biology and Function," Pharmacological Reviews, 1990, vol. 42, No. 4, p. 355-402.

Whittemore E. et al. "Antagonism of N-Methyl-D-Aspartate Receptors by s Site Ligands: Potency, Subtype-Selectivity and Mechanisms of Inhibition," The Journal of Pharmacology and Experimental Therapeutics, 1997, vol. 282, No. 1, p. 326-338.

Yang et al. "Clinical significance of sleep EEG abnormalities in chronic schizophrenia", Schizophrenia Research, 2006, vol. 82, pp. 251-260.

Okuyama, S. Nippon Yakurigaku Zasshi, Folia Pharmacologica Japonica, 1999, vol. 114, pp. 12-23 (English abstract only).

Zhanpei, Zhen "Negative Symptoms of Schizophrenia", Foreign Medicine, Psychiatry Volume, Mar. 1988. (English translation of Chinese Office Action for Chinese Application No. 201180045067.1 attached).

Zhou et al., "A new form of rapid binocular plasticity in adult with amblyopia," Scientific Reports, Sep. 2013, 3:2638, 5 pages.

Evonik Industries AG, Technical Information and Technical Information—Quickstart, Eudragit® L 30 D-55, INFO 7.5/E, May 2014, 8 pages.

\* cited by examiner

GASTRO-RESISTANT CONTROLLED RELEASE ORAL DOSAGE FORMS

RELATED APPLICATIONS

This application claims priority to, and the benefit of, U.S. Provisional Application No. 62/523,204, filed Jun. 21, 2017. The contents of which are incorporated herein by reference in their entirety.

FIELD OF THE DISCLOSURE

The present disclosure relates generally to oral gastro-resistant (GR) controlled release (CR) dosage forms that reduce the risk of QT prolongation in patients treated with the compound identified as 1H-Isoindol-1-one, 2-[[1-[2-(4-Fluorophenyl)-2-oxoethyl]-4-piperidinyl]methyl]-2,3-dihydro-, hydrochloride, hydrate (1:1:2), and to the use of these dosage forms for treating schizophrenia and other diseases.

BACKGROUND

The QT interval is a measurement of the duration of ventricular de- and repolarization. Prolongation of the QT interval, referred to as QT prolongation, can result in increased risk for ventricular arrhythmias, including torsades de pointes (TdP). Since a number of drugs have been shown to induce QT prolongation, development of new drugs typically includes assessment of their QT prolongation potential.

An investigational medicine, roluperidone hydrochloride, with the code name MIN-101 is being developed by Minerva Neurosciences, Inc. (Waltham, Mass.) for treating negative symptoms in schizophrenia patients. The active ingredient in MIN-101 (previously known as CYR-101 and MT-210) has the chemical name 1H-Isoindol-1-one, 2-[[1-[2-(4-Fluorophenyl)-2-oxoethyl]-4-piperidinyl]methyl]-2,3-dihydro-, hydrochloride, hydrate (1:1:2). Formula I below shows the structure of the free base (Compound (I)):

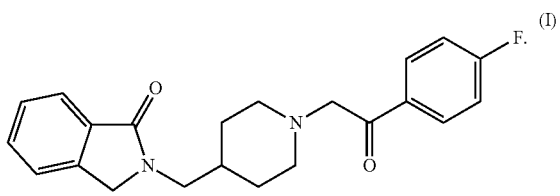 [SMILES: O=C(CN1CCC(CN2Cc3ccccc3C2=O)CC1)c1ccc(F)cc1]

As disclosed in U.S. Pat. No. 9,458,130, the contents of which are incorporated herein in their entirety, QT prolongation in patients treated with MIN-101 has been observed and appears to be related to plasma levels of Compound (I) and more specifically to a metabolite identified as BFB-520. The '130 patent discloses that QT prolongation induced by administration of MIN-101 can be reduced by administering this agent in a modified release (MR) formulation that provides a maximum plasma concentration ($C_{max}$) of Compound (I) and BFB-520 below 80 ng/mL and 12 ng/mL, respectively. However, a need exists for a formulation that further reduces the potential for QT prolongation after oral administration of MIN-101 in either a fasted state or a fed state, while maintaining a therapeutically effective level of Compound (I) throughout a dosing interval.

SUMMARY

The present disclosure is based, in part, on the finding that minimizing the release of Compound (I) during the first four hours after oral administration of a dosage form comprising Compound (I) is a key factor for maintaining low plasma levels of BFB-520.

In one aspect, the present disclosure provides a gastro-resistant, controlled release dosage form comprising:
  i. about 2 mg to about 200 mg of Compound (I), or an equivalent amount of a pharmaceutically acceptable salt and/or solvate thereof; and
  ii. at least one controlled release agent.

In one aspect, the present disclosure provides a gastro-resistant, controlled release dosage form comprising:
  i. about 2 mg to about 200 mg of Compound (I), or an equivalent amount of a pharmaceutically acceptable salt and/or solvate thereof; and
  ii. at least one controlled release agent;
wherein the dosage form produces, upon oral administration to the subject, a plasma pharmacokinetic profile for Compound (I) which comprises a $T_{max}$ between about 4 hours and about 22 hours.

In one aspect, the present disclosure provides a gastro-resistant, controlled release dosage form comprising:
  i. about 4 mg to about 100 mg of Compound (I), or an equivalent amount of a pharmaceutically acceptable salt and/or solvate thereof; and
  ii. at least one controlled release agent.

In one aspect, the present disclosure provides a gastro-resistant, controlled release dosage form comprising:
  i. about 4 mg to about 100 mg of Compound (I), or an equivalent amount of a pharmaceutically acceptable salt and/or solvate thereof; and
  ii. at least one controlled release agent;
wherein the dosage form produces, upon oral administration to the subject, a plasma pharmacokinetic profile for Compound (I) which comprises a $T_{max}$ between about 1 hours and about 22 hours.

In one aspect, the present disclosure provides a gastro-resistant, controlled release dosage form comprising:
  i. about 4 mg to about 100 mg of Compound (I), or an equivalent amount of a pharmaceutically acceptable salt and/or solvate thereof; and
  ii. at least one controlled release agent;
wherein the dosage form produces, upon oral administration to the subject, a plasma pharmacokinetic profile for Compound (I) which comprises a $T_{max}$ between about 1.5 hours and about 22 hours.

In one aspect, the present disclosure provides a gastro-resistant, controlled release dosage form comprising:
  i. about 4 mg to about 100 mg of Compound (I), or an equivalent amount of a pharmaceutically acceptable salt and/or solvate thereof; and
  ii. at least one controlled release agent;
wherein the dosage form produces, upon oral administration to the subject, a plasma pharmacokinetic profile for Compound (I) which comprises a $T_{max}$ between about 2 hours and about 22 hours.

In one aspect, the present disclosure provides a gastro-resistant, controlled release dosage form comprising:
  i. about 4 mg to about 100 mg of Compound (I), or an equivalent amount of a pharmaceutically acceptable salt and/or solvate thereof; and ii. at least one controlled release agent;
wherein the dosage form produces, upon oral administration to the subject, a plasma pharmacokinetic profile for Compound (I) which comprises a $T_{max}$ between about 2.5 hours and about 22 hours.

In one aspect, the present disclosure provides a gastro-resistant, controlled release dosage form comprising:
i. about 4 mg to about 100 mg of Compound (I), or an equivalent amount of a pharmaceutically acceptable salt and/or solvate thereof; and
ii. at least one controlled release agent;
wherein the dosage form produces, upon oral administration to the subject, a plasma pharmacokinetic profile for Compound (I) which comprises a $T_{max}$ between about 3 hours and about 22 hours.

In one aspect, the present disclosure provides a gastro-resistant, controlled release dosage form comprising:
i. about 4 mg to about 100 mg of Compound (I), or an equivalent amount of a pharmaceutically acceptable salt and/or solvate thereof; and
ii. at least one controlled release agent;
wherein the dosage form produces, upon oral administration to the subject, a plasma pharmacokinetic profile for Compound (I) which comprises a $T_{max}$ between about 3.5 hours and about 22 hours.

In one aspect, the present disclosure provides a gastro-resistant, controlled release dosage form comprising:
i. about 4 mg to about 100 mg of Compound (I), or an equivalent amount of a pharmaceutically acceptable salt and/or solvate thereof; and
ii. at least one controlled release agent;
wherein the dosage form produces, upon oral administration to the subject, a plasma pharmacokinetic profile for Compound (I) which comprises a $T_{max}$ between about 4 hours and about 22 hours.

In one aspect, the present disclosure provides a gastro-resistant, controlled release dosage form comprising Compound (I), wherein the amount of Compound (I) is 4 mg to 8 mg, 8 mg to 16 mg, 16 mg to 32 mg, 32 mg to 40 mg, 40 mg to 64 mg, 64 mg to 80 mg, or 80 mg to 100 mg.

In one aspect, the present disclosure provides a gastro-resistant, controlled release dosage form comprising Compound (I), wherein the amount of Compound (I) is 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, or 100 mg.

In one aspect, the present disclosure provides a gastro-resistant, controlled release dosage form comprising Compound (I), wherein the amount of Compound (I) is 4 mg, 8 mg, 16 mg, 24 mg, 32 mg, 40 mg, 64 mg, 80 mg, 96 mg, or 100 mg.

In one aspect, the present disclosure provides a gastro-resistant, controlled release dosage form comprising:
i. about 32 mg of Compound (I), or an equivalent amount of a pharmaceutically acceptable salt and/or solvate thereof; and
ii. at least one controlled release agent.

In one aspect, the present disclosure provides a gastro-resistant, controlled release dosage form comprising:
i. about 32 mg of Compound (I), or an equivalent amount of a pharmaceutically acceptable salt and/or solvate thereof; and
ii. at least one controlled release agent;
wherein the dosage form produces, upon oral administration to the subject, a plasma pharmacokinetic profile for Compound (I) which comprises a $T_{max}$ between about 4 hours and about 22 hours.

In one aspect, the present disclosure provides a gastro-resistant, controlled release dosage form comprising:
i. about 64 of Compound (I), or an equivalent amount of a pharmaceutically acceptable salt and/or solvate thereof; and
ii. at least one controlled release agent.

In one aspect, the present disclosure provides a gastro-resistant, controlled release dosage form comprising:
i. about 64 mg of Compound (I), or an equivalent amount of a pharmaceutically acceptable salt and/or solvate thereof; and
ii. at least one controlled release agent;
wherein the dosage form produces, upon oral administration to the subject, a plasma pharmacokinetic profile for Compound (I) which comprises a $T_{max}$ between about 4 hours and about 22 hours.

In one aspect, the present disclosure provides a gastro-resistant, controlled release dosage forms comprising Compound (I) disclosed herein, wherein the amount of Compound (I) is about 32 mg and the $AUC_{0-4\,H}$ of Compound (I) is less than about 68 h*ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 16 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 17 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 18 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 19 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 20 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 21 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 22 ng/mL.

In one aspect, the present disclosure provides a gastro-resistant, controlled release dosage forms comprising Compound (I) disclosed herein, wherein the amount of Compound (I) is about 32 mg and the $C_{max}$ of Compound (I) is less than about 23 ng/mL.

In one aspect, the present disclosure provides a gastro-resistant, controlled release dosage forms comprising Compound (I) disclosed herein, wherein the amount of Compound (I) is about 32 mg and the $AUC_{0\text{-}24\,hr}$ of Compound (I) is between about 50 h*ng/mL to about 400 h*ng/mL.

In one aspect, the present disclosure provides a gastro-resistant, controlled release dosage forms comprising Compound (I) disclosed herein, wherein the amount of Compound (I) is about 32 mg and the $AUC_{0\text{-}24\,hr}$ of Compound (I) is between about 75 h*ng/mL to about 350 h*ng/mL.

In one aspect, the present disclosure provides a gastro-resistant, controlled release dosage forms comprising Compound (I) disclosed herein, wherein the amount of Compound (I) is about 32 mg and the $AUC_{0\text{-}24\,hr}$ of Compound (I) is between about 75 h*ng/mL to about 300 h*ng/mL.

In one aspect, the present disclosure provides a gastro-resistant, controlled release dosage forms comprising Compound (I) disclosed herein, wherein the amount of Compound (I) is about 32 mg and the $AUC_{0\text{-}24\,hr}$ of Compound (I) is between about 100 h*ng/mL to about 300 h*ng/mL.

In one aspect, the present disclosure provides a gastro-resistant, controlled release dosage forms comprising Compound (I) disclosed herein, wherein the amount of Compound (I) is about 32 mg and the plasma pharmacokinetic profile for the BFB-520 metabolite of Compound (I) comprises a $C_{max}$ that is below 3.0 ng/mL, below 2.5 ng/mL, below 2.0 ng/mL, below 1.5 ng/mL or below 1.0 ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 50 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 60 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 70 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 80 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 90 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 100 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 110 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 120 h*ng/mL.

In one aspect, the present disclosure provides a gastro-resistant, controlled release dosage forms comprising Compound (I) disclosed herein, wherein the amount of Compound (I) is about 64 mg and the $AUC_{0\text{-}4\,H}$ of Compound (I) is less than about 130 h*ng/mL.

In one aspect, the present disclosure provides a gastro-resistant, controlled release dosage forms comprising Compound (I) disclosed herein, wherein the amount of Compound (I) is about 64 mg and the $C_{max}$ of Compound (I) is less than about 36 ng/mL or less than about 25 ng/mL.

In one aspect, the present disclosure provides a gastro-resistant, controlled release dosage forms comprising Compound (I) disclosed herein, wherein the amount of Compound (I) is about 64 mg and the $AUC_{0\text{-}24\,hr}$ of Compound (I) is between about 200 h*ng/mL to about 600 h*ng/mL.

In one aspect, the present disclosure provides a gastro-resistant, controlled release dosage forms comprising Compound (I) disclosed herein, wherein the amount of Compound (I) is about 64 mg and the plasma pharmacokinetic profile for the BFB-520 metabolite of Compound (I) comprises a $C_{max}$ that is below 4.0 ng/mL, below 3.5 ng/mL, below 3.0 ng/mL, or below 2.5 ng/mL.

In one embodiment, the gastro-resistant, controlled release dosage forms disclosed herein are in the form of a tablet which comprises a core tablet and an enteric coating.

In one embodiment, the core tablet of the gastro-resistant, controlled release dosage forms disclosed herein comprises Compound (I), or a pharmaceutically acceptable salt and/or solvate thereof, and a controlled release agent.

In one embodiment, the core tablet of the gastro-resistant, controlled release dosage forms disclosed herein comprises Compound (I), or a pharmaceutically acceptable salt and/or solvate thereof, a controlled release agent, a filler, a glidant, and a lubricant.

In one embodiment, the core tablet of the gastro-resistant, controlled release dosage forms disclosed herein comprises Compound (I), or a pharmaceutically acceptable salt and/or solvate thereof, a controlled release agent, a filler, a glidant, a lubricant and a coating.

In one embodiment, the controlled release agent in the core tablet of the gastro-resistant, controlled release dosage forms disclosed herein comprises one or more hypromelloses.

In one embodiment, the controlled release agent in the core tablet of the gastro-resistant, controlled release dosage forms disclosed herein comprises one or more hypromelloses selected from the group consisting of Metolose® 90SH K15M 100 SR, Metolose® 90SH 100 SR, Methocel™ K100M CR, Methocel™ K15M CR, Methocel™ K4M CR, and Methocel™ K100LV CR, or equivalent grade.

In one embodiment, the controlled release agent in the core tablet of the gastro-resistant, controlled release dosage forms disclosed herein comprises a mixture of (i) a low viscosity hypromellose with a viscosity of between about 15 millipascal-seconds (mPa·s) to about 100 mPa·s and (ii) a high viscosity hypromellose with a viscosity of about 100,000 mPa·s, wherein each of the low and high viscosity hypromelloses is a controlled release or sustained-release grade and is further characterized by a methoxy content of 19.0% to 24.0% and a hydroxypropoxy content of 4.0% to 12.0%.

In one embodiment, the glidant in the core tablet of the gastro-resistant, controlled release dosage forms disclosed herein is silica colloidal anhydrous.

In one embodiment, the lubricant in the core tablet of the gastro-resistant, controlled release dosage forms disclosed herein is magnesium stearate.

In one embodiment, the enteric coating of the gastro-resistant, controlled release dosage forms disclosed herein comprises at least one polymeric controlled release agent with a dissolution property of greater than pH 5.5, 6.0 or 6.5, and an anti-tacking agent.

In one embodiment, the enteric coating of the gastro-resistant, controlled release dosage forms disclosed herein further comprises a plasticizer.

In one embodiment, the polymeric controlled release agent of the enteric coating of the gastro-resistant, controlled release dosage forms disclosed herein comprises Eudragit L30D55.

In one embodiment, the anti-tacking agent of the enteric coating of the gastro-resistant, controlled release dosage forms disclosed herein is Plasacryl HTP20.

In one aspect, the present disclosure provides a gastro-resistant, controlled release dosage form comprising:
about 7 to about 17% w/w Compound (I), or a pharmaceutically acceptable salt and/or solvate thereof;
about 4 to about 14% w/w hypromellose (Metolose® 90SH K15M 100 SR);
about 17 to about 27% w/w hypromellose (Methocel™ K100M CR);
about 25 to about 35% w/w microcrystalline cellulose;
about 13 to about 23% w/w lactose monohydrate
about 0.1 to about 4% w/w silica colloidal anhydrous;
about 0.1 to about 4% magnesium stearate;
about 1 to about 10% w/w Eudragit L30D55; and
about 0.5 to about 5% w/w Plasacryl HTP20.

In one aspect, the present disclosure provides a gastro-resistant, controlled release dosage form comprising:
about 12% w/w Compound (I), or a pharmaceutically acceptable salt and/or solvate thereof;
about 9% w/w hypromellose (Metolose® 90SH K15M 100 SR);
about 23% w/w hypromellose (Methocel™ K100M CR);
about 30% w/w microcrystalline cellulose;
about 19% w/w lactose monohydrate
about 0.5% w/w silica colloidal anhydrous;
about 1% magnesium stearate;
about 5% w/w Eudragit L30D55; and
about 1% w/w Plasacryl HTP20.

In one aspect, the present disclosure provides a gastro-resistant, controlled release dosage form comprising:
about 7 to about 17% w/w compound (I), or a pharmaceutically acceptable salt and/or solvate thereof;
about 4 to about 14% w/w hypromellose (Methocel™ K15M CR);
about 17 to about 27% w/w hypromellose (Methocel™ K100M CR);
about 25 to about 35% w/w microcrystalline cellulose;
about 13 to about 23% w/w lactose monohydrate;
about 0.1 to about 4% w/w silica colloidal anhydrous;
about 0.1 to about 4% w/w magnesium stearate;
about 1 to about 10% Eudragit L30D55;
about 0.5 to about 5% w/w Plasacryl HTP20; and
about 0.5 to about 5% w/w Surelease E-7-19040.

In one aspect, the present disclosure provides a gastro-resistant, controlled release dosage form comprising:
about 12% w/w Compound (I), or a pharmaceutically acceptable salt and/or solvate thereof;
about 9% w/w hypromellose (Methocel™ K15M CR);
about 23% w/w hypromellose (Methocel™ K100M CR);
about 30% w/w microcrystalline cellulose;
about 19% w/w lactose monohydrate;
about 0.5% w/w silica colloidal anhydrous;
about 1% w/w magnesium stearate;
about 5% w/w Eudragit L30D55;
about 1% w/w Plasacryl HTP20; and
about 1% w/w Surelease E-7-19040.

In one aspect, the present disclosure provides a gastro-resistant, controlled release dosage form comprising:
about 7 to about 17% w/w Compound (I), or a pharmaceutically acceptable salt and/or solvate thereof;
about 4 to about 14% w/w hypromellose (Methocel™ K100LV CR);
about 17 to about 27% w/w hypromellose (Methocel™ K100M CR);
about 25 to about 35% w/w microcrystalline cellulose;
about 13 to about 23% w/w lactose monohydrate
about 0.1 to about 4% w/w silica colloidal anhydrous;
about 0.1 to about 4% magnesium stearate;
about 1 to about 10% w/w Eudragit L30D55; and
about 0.5 to about 5% w/w Plasacryl HTP20.

In one aspect, the present disclosure provides a gastro-resistant, controlled release dosage form comprising:
about 12% w/w Compound (I), or a pharmaceutically acceptable salt and/or solvate thereof;
about 9% w/w hypromellose (Methocel™ K100LV CR);
about 23% w/w hypromellose (Methocel™ K100M CR);
about 30% w/w microcrystalline cellulose;
about 19% w/w lactose monohydrate;
about 0.5% w/w silica colloidal anhydrous;
about 0.5% w/w magnesium stearate;
about 5% w/w Eudragit L30D55; and
about 1% w/w Plasacryl HTP20.

In one aspect, the present disclosure provides a gastro-resistant, controlled release dosage form comprising:
about 12% w/w Compound (I), or a pharmaceutically acceptable salt and/or solvate thereof;
about 9% w/w hypromellose (Methocel™ K100LV CR);
about 23% w/w hypromellose (Methocel™ K100M CR);
about 30% w/w microcrystalline cellulose;
about 19% w/w lactose monohydrate;
about 0.5% w/w silica colloidal anhydrous;
about 1% w/w magnesium stearate;
about 5% w/w Eudragit L30D55; and
about 1% w/w Plasacryl HTP20.

In one aspect, the present disclosure provides a gastro-resistant, controlled release dosage form comprising:
about 19 to about 29% w/w Compound (I), or a pharmaceutically acceptable salt and/or solvate thereof;
about 4 to about 14% w/w hypromellose (Methocel™ K100LV CR);
about 17 to about 27% w/w hypromellose (Methocel™ K100M CR);
about 19 to about 29% w/w microcrystalline cellulose;
about 8 to about 18% w/w lactose monohydrate
about 0.1 to about 4% w/w silica colloidal anhydrous;
about 0.1 to about 4% magnesium stearate;
about 1 to about 10% w/w Eudragit L30D55; and
about 0.5 to about 5% w/w Plasacryl HTP20.

In one aspect, the present disclosure provides a gastro-resistant, controlled release dosage form comprising:
about 24% w/w Compound (I), or a pharmaceutically acceptable salt and/or solvate thereof;
about 9% w/w hypromellose (Methocel™ K100LV CR);
about 23% w/w hypromellose (Methocel™ K100M CR);

about 24% w/w microcrystalline cellulose;
about 13% w/w lactose monohydrate;
about 0.5% w/w silica colloidal anhydrous;
about 0.5% w/w magnesium stearate;
about 5% w/w Eudragit L30D55; and
about 1% w/w Plasacryl HTP20.

In one aspect, the present disclosure provides a gastro-resistant, controlled release dosage form comprising:
about 24% w/w Compound (I), or a pharmaceutically acceptable salt and/or solvate thereof;
about 9% w/w hypromellose (Methocel™ K100LV CR);
about 23% w/w hypromellose (Methocel™ K100M CR);
about 24% w/w microcrystalline cellulose;
about 13% w/w lactose monohydrate;
about 0.5% w/w silica colloidal anhydrous;
about 1% w/w magnesium stearate;
about 5% w/w Eudragit L30D55; and
about 1% w/w Plasacryl HTP20.

In one aspect, the present disclosure provides a method of reducing a risk of QT prolongation when treating a subject with Compound (I), or a pharmaceutically acceptable salt and/or solvate thereof, the method comprising oral administration to the subject of a gastro-resistant, controlled release dosage form described herein.

In one aspect, the present disclosure provides a method of treating a disorder (e.g., negative symptoms of schizophrenia) in a subject in need thereof, the method comprising an oral administration to the subject of a gastro-resistant, controlled release dosage form described herein, wherein the subject has a diagnosis of the disorder, e.g., schizophrenia.

In one aspect, the present disclosure provides a method of treating a disorder (e.g., negative symptoms of schizophrenia) in a subject in need thereof, the method comprising a once daily oral administration to the subject of a gastro-resistant, controlled release dosage form described herein, wherein the subject has a diagnosis of the disorder, e.g., schizophrenia.

In one aspect, the present disclosure provides a method of treating a disorder (e.g., negative symptoms of schizophrenia) in a subject in need thereof, the method comprising an oral administration to the subject of a gastro-resistant, controlled release dosage form described herein, wherein the subject has a diagnosis of, e.g., schizophrenia, wherein the subject having a diagnosis of schizophrenia has a CYP2D6 EM genotype.

In one aspect, the present disclosure provides a method of treating a disorder (e.g., negative symptoms of schizophrenia) in a subject in need thereof, the method comprising a once daily oral administration to the subject of a gastro-resistant, controlled release dosage form described herein, wherein the subject has a diagnosis of, e.g., schizophrenia, wherein the subject having a diagnosis of schizophrenia has a CYP2D6 EM genotype.

In one aspect, the present disclosure provides a method of treating a disorder (e.g., negative symptoms of schizophrenia) in a subject in need thereof, the method comprising an oral administration to the subject of a gastro-resistant, controlled release dosage form described herein (e.g., including a low dose of Compound (I), such as about 4 mg, 5 mg, 6 mg, 7 mg, 8 mg, or about 16 mg), wherein the subject has a diagnosis of, e.g., schizophrenia, wherein the subject having a diagnosis of schizophrenia has a CYP2D6 IM or PM genotype.

In one aspect, the present disclosure provides a method of treating a disorder (e.g., negative symptoms of schizophrenia) in a subject in need thereof, the method comprising a once daily oral administration to the subject of a gastro-resistant, controlled release dosage form described herein (e.g., including a low dose of Compound (I), such as about 4 mg, 5 mg, 6 mg, 7 mg, 8 mg, or about 16 mg), wherein the subject has a diagnosis of, e.g., schizophrenia, wherein the subject having a diagnosis of schizophrenia has a CYP2D6 IM or PM genotype.

In one aspect, for any of the methods disclosed herein, the subject is in fed state prior to oral administration of the gastro-resistant, controlled release dosage form described herein.

In one aspect, for any of the methods disclosed herein, the subject is in fasted state prior to oral administration of the gastro-resistant, controlled release dosage form described herein.

In one aspect, the present disclosure provides a gastro-resistant, controlled release dosage form disclosed herein for use in reducing a risk of QT prolongation.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 EM genotype.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, 8 mg, or about 16 mg.

In one aspect, the present disclosure provides a gastro-resistant, controlled release dosage form disclosed herein for use in reducing a risk of QT prolongation, wherein the gastro-resistant, controlled release dosage form is administered once daily.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the gastro-resistant, controlled release dosage form is administered once daily.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the gastro-resistant, controlled release dosage form is administered once daily.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, 8 mg, or about 16 mg, wherein the gastro-resistant, controlled release dosage form is administered once daily In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject is in fed state prior to oral administration of the dosage form.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject is in fasted state prior to oral administration of the dosage form.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the subject is in fed state prior to oral administration of the dosage form.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the subject is in fasted state prior to oral administration of the dosage form In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, 8 mg, or about 16 mg, wherein the subject is in fed state prior to oral administration of the dosage form.

In one aspect, the present disclosure provides a gastro-resistant, controlled release dosage form disclosed herein for use in treating a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, 8 mg, or about 16 mg, wherein the subject is in fasted state prior to oral administration of the dosage form.

In one aspect, the present disclosure provides for a use of a gastro-resistant, controlled release dosage form disclosed herein in the manufacture of medicament for reducing a risk of QT prolongation.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 EM genotype.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, or about 8 mg.

In one aspect, the present disclosure provides for a use of a gastro-resistant, controlled release dosage form disclosed herein in the manufacture of medicament for reducing a risk of QT prolongation, wherein the gastro-resistant, controlled release dosage form is administered once daily.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the gastro-resistant, controlled release dosage form is administered once daily.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the gastro-resistant, controlled release dosage form is administered once daily.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, or about 8 mg, wherein the gastro-resistant, controlled release dosage form is administered once daily.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject is in fasted state prior to oral administration of the dosage form.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the subject is in fasted state prior to oral administration of the dosage form.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, or about 8 mg, wherein the subject is in fasted state prior to oral administration of the dosage form.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject is in fed state prior to oral administration of the dosage form.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 EM genotype, wherein the subject is in fed state prior to oral administration of the dosage form.

In one aspect, the present disclosure provides for a use of a gastro-resistant, controlled release dosage form disclosed herein in the manufacture of medicament for the treatment of a disorder (e.g., negative symptoms of schizophrenia) in a subject in need thereof, e.g., the subject has a diagnosis of schizophrenia, wherein the subject having a diagnosis of schizophrenia has a CYP2D6 IM or PM genotype and the dosage form has a low dose of Compound (I), e.g., about 4 mg, 5 mg, 6 mg, 7 mg, or about 8 mg, wherein the subject is in fed state prior to oral administration of the dosage form.

Thus, in one aspect, the present disclosure provides a gastro-resistant, controlled release oral dosage form, which comprises (i) about 4 mg to about 100 mg of Compound (I), or an equivalent amount of a pharmaceutically acceptable salt and/or solvate thereof, and (ii) at least one controlled release agent, wherein the dosage form produces, upon oral administration to a subject, a plasma pharmacokinetic (PK) profile for Compound (I) which comprises a $T_{max}$ of between about 4 and about 11 hours. In an embodiment, the $T_{max}$ of Compound (I) in the plasma PK profile is between about 5 and about 10 hours; between about 6 and about 9 hours, between about 7 and about 9 hours, or between about 6 and about 8 hours.

In some embodiments, the amount of Compound (I) in the oral dosage form is 4 mg to 8 mg, 8 to 16 mg, 16 mg to 32 mg, 32 mg to 40 mg, 40 mg to 64 mg, 64 mg to 80 mg, 80 mg to 100 mg or is about any of 4 mg, 8 mg, 16 mg, 24 mg, 32 mg, 40 mg, 64 mg, 80 mg, 96 mg, or 100 mg.

In an embodiment, the dosage form comprises about 32 mg of Compound (I), or an equivalent amount of a pharmaceutically acceptable salt and/or solvate thereof, and the plasma PK profile further comprises: (a) an $AUC_{0-4\,H}$ of less than about 68 h*ng/mL; (b) a $C_{max}$ of Compound (I) of less than about 16 ng/mL, 17 ng/mL, 18 ng/mL, 19 ng/mL, 20 ng/mL, 21 ng/mL, 22 ng/mL, or 23 ng/mL; and (c) an $AUC_{0-24\,hr}$ of between about 75 h*ng/mL to about 350 h*ng/mL or between about 100 h*ng/mL to 300 h*ng/mL. In an embodiment, the plasma PK profile for the BFB-520 metabolite of Compound (I) comprises a $C_{max}$ that is below 3.0 ng/mL, below 2.5 ng/mL, below 2.0 ng/mL, below 1.5 ng/mL or below 1.0 ng/mL.

In an embodiment, the dosage form comprises about 4 mg of Compound (I), or an equivalent amount of a pharmaceutically acceptable salt and/or solvate thereof, and the plasma PK profile further comprises: (a) an $AUC_{0-4\,H}$ of less than about 8 h*ng/mL; (b) a $C_{max}$ of Compound (I) of less than about 2.5 ng/mL; and (c) an $AUC_{0-24\,hr}$ of between about 12 h*ng/mL to 35 h*ng/mL. In an embodiment, the plasma PK profile for the BFB-520 metabolite of Compound (I) comprises a $C_{max}$ that is below 2.0 ng/mL, below 1.5 ng/mL, below 1.0 ng/mL, or below 0.5 ng/mL.

In an embodiment, the dosage form comprises about 8 mg of Compound (I), or an equivalent amount of a pharmaceutically acceptable salt and/or solvate thereof, and the plasma PK profile further comprises: (a) an $AUC_{0-4\,H}$ of less than about 16 h*ng/mL; (b) a $C_{max}$ of Compound (I) of less than about 5 ng/mL; and (c) an $AUC_{0-24\,hr}$ of between about 25 h*ng/mL to 75 h*ng/mL. In an embodiment, the plasma PK profile for the BFB-520 metabolite of Compound (I) comprises a $C_{max}$ that is below 2.5 ng/mL, below 2.0 ng/mL, below 1.5 ng/mL, or below 1.0 ng/mL.

In an embodiment, the dosage form comprises about 16 mg of Compound (I), or an equivalent amount of a pharmaceutically acceptable salt and/or solvate thereof, and the plasma PK profile further comprises: (a) an $AUC_{0-4\,H}$ of less than about 32 h*ng/mL; (b) a $C_{max}$ of Compound (I) of less than about 10 ng/mL or less than about 6 ng/mL; and (c) an $AUC_{0-24\,hr}$ of between about 50 h*ng/mL to 150 h*ng/mL. In an embodiment, the plasma PK profile for the BFB-520 metabolite of Compound (I) comprises a $C_{max}$ that is below 2.5 ng/mL, below 2.0 ng/mL, below 1.5 ng/mL, or below 1.0 ng/mL.

In an embodiment, the dosage form comprises about 40 mg of Compound (I), or an equivalent amount of a pharmaceutically acceptable salt and/or solvate thereof, and the plasma PK profile further comprises: (a) an $AUC_{0-4\,H}$ of less than about 80 h*ng/mL; (b) a $C_{max}$ of Compound (I) of less than about 24 ng/mL or less than about 20 ng/mL; and (c) an $AUC_{0-24\,hr}$ of between about 125 h*ng/mL to 375 h*ng/mL. In an embodiment, the plasma PK profile for the BFB-520 metabolite of Compound (I) comprises a $C_{max}$ that is below 3.5 ng/mL, below 3.0 ng/mL, below 2.5 ng/mL, or below 2.0 ng/mL.

In an embodiment, the dosage form comprises about 64 mg of Compound (I), or an equivalent amount of a pharmaceutically acceptable salt and/or solvate thereof, and the plasma PK profile further comprises: (a) an $AUC_{0-4\,H}$ of less than about 50, 60, 70, 80, 90, 100, 110, 120, or 130 h*ng/mL; (b) a $C_{max}$ of Compound (I) of less than about 36 ng/mL or less than about 25 ng/mL; and (c) an $AUC_{0-24\,hr}$ of between about 200 h*ng/mL to 600 h*ng/mL. In an embodiment, the plasma PK profile for the BFB-520 metabolite of Compound (I) comprises a $C_{max}$ that is below 4.0 ng/mL, below 3.5 ng/mL, below 3.0 ng/mL, or below 2.5 ng/mL.

In an embodiment, the dosage form comprises about 80 mg of Compound (I), or an equivalent amount of a pharmaceutically acceptable salt and/or solvate thereof, and the plasma PK profile further comprises: (a) an $AUC_{0-4\,H}$ of less than about 160 h*ng/mL; (b) a $C_{max}$ of Compound (I) of less than about 48 ng/mL or less than about 40 ng/mL; and (c) an $AUC_{0-24\,hr}$ of between about 250 h*ng/mL to 750 h*ng/mL. In an embodiment, the plasma PK profile for the BFB-520 metabolite of Compound (I) comprises a $C_{max}$ that is below 4.5 ng/mL, below 4.0 ng/mL, below 3.5 ng/mL, or below 3.0 ng/mL.

In an embodiment, the dosage form comprises about 100 mg of Compound (I), or an equivalent amount of a pharmaceutically acceptable salt and/or solvate thereof, and the plasma PK profile further comprises: (a) an $AUC_{0-4\,H}$ of less than about 220 h*ng/mL; (b) a $C_{max}$ of Compound (I) of less than about 72 ng/mL; and (c) an $AUC_{0-24\,hr}$ of between about 325 h*ng/mL to 975 h*ng/mL. In an embodiment, the plasma PK profile for the BFB-520 metabolite of Compound (I) comprises a $C_{max}$ that is below 5.0 ng/mL, below 4.5 ng/mL, below 4.0 ng/mL, or below 3.5 ng/mL.

In some embodiments of any of the above dosage forms, the plasma PK parameters are values determined after two once daily administrations of a single unit of the dosage form. In an embodiment, the PK parameter is determined after the 3$^{rd}$ or 4$^{th}$ administration.

In an embodiment, the dosage form comprises about 32 mg of Compound (I) and, when administered to a subject, produces a plasma pharmacokinetic (PK) profile for Compound (I) which is similar to the target profile shown in FIG. 1.

In some embodiments of any of the above dosage forms, the plasma PK profile for one or both of Compound (I) and the metabolite BFB-520 is produced after the 1$^{st}$, 2$^{nd}$, 3$^{rd}$, or 4$^{th}$ once daily administration of a single unit of the dosage form.

In some embodiments, the plasma PK profile for one or both of Compound (I) and the metabolite BFB-520 is produced when administered to a subject in the fasted state. In other embodiments, the plasma PK profile for one or both of Compound (I) and the metabolite BFB-520 is produced when administered to a subject in the fed state.

In an embodiment, a controlled release dosage form of the disclosure comprises about 4 to about 100 mg of Compound (I) and produces a target in vitro dissolution profile using a 24-hour, two-stage in vitro dissolution method which comprises a 2-hour acid stage and a 22-hour buffer stage. The target in vitro dissolution profile comprises (a) no detectable release of Compound (I) during the first 2.0 hours of the dissolution method and (b) release of at least 80% of the total amount of Compound (I) in the dosage form over a time period of 16-19 hours. In an embodiment, the target in vitro dissolution profile comprises release of at least 85%, 90% or 95% of the amount of Compound (I) in the dosage form by hour 24 of the dissolution method.

In an embodiment, the target in vitro dissolution profile further comprises release of Compound (I) at a release rate that produces each of the following cumulative percentages of the starting total amount:
  (i) less than 0.6% by 2.5 hours;
  (ii) from 0.2 to 7.9% by 3.0 hours;
  (iii) from 2.5 to 19.2% by 4 hours;
  (iv) from 12.7 to 34.0% by 6 hours;
  (v) from 22.8 to 44.3% by 8 hours;
  (vi) from 35.5 to 75.7% by 13 hours;
  (vii) from 43.3 to 89.0% by 16 hours; and
  (viii) from 59.3 to 96.9% by 19 hours.

In an embodiment, the target in vitro dissolution profile further comprises release of Compound (I) at a release rate that produces each of the following cumulative percentages of the starting total amount:
  (i) less than about 0.5% by 2.5 hours;
  (ii) from about 2.8 to about 3.1% by 3.0 hours;
  (iii) from about 9.0 to about 11.0% by 4 hours;
  (iv) from about 14.5 to about 18.0% by 5 hours;
  (v) from about 19.5 to about 24.5% by 6 hours;
  (vi) from about 30.5 to about 38.0% by 8 hours;
  (vii) from about 41.5 to about 51.0% by 10 hours;
  (viii) from about 54.5 to about 67.0% by 13 hours;
  (ix) from about 58.5 to about 71.5% by 14 hours;
  (x) from about 61.5 to about 75.5% by 15 hours;
  (xi) from about 70.0 to about 86.0% by 18 hours; and
  (xii) from about 77.5 to about 95.0% by 21 hours.

In an embodiment, the CR dosage form comprises 32 mg of Compound (I) and generates in vitro cumulative dissolution and dissolution rate profiles that are substantially similar to the target profile shown in FIG. 1 or to the target profile shown in Tables 6 and 7 in the Examples below.

In an embodiment, the target in vitro dissolution profile further comprises release of Compound (I) at a release rate that produces each of the following cumulative percentages of the starting total amount:
  (xiii) less than about 0.5% by 2 hours;
  (xiv) from about 19 to about 29% by 4 hours;
  (xv) from about 54 to about 64% by 8 hours; and
  (xvi) from about 83 to about 93% by 16 hours.

In an embodiment, the target in vitro dissolution profile further comprises release of Compound (I) at a release rate that produces each of the following cumulative percentages of the starting total amount:
  (xvii) less than about 0.5% by 2 hours;
  (xviii) about 24.1% by 4 hours;
  (xix) about 59.2% by 8 hours; and
  (xx) about 88.6% by 16 hours.

In each of the above embodiments, the dissolution method is preferably conducted according to the dissolution method described in the Examples below.

In an embodiment, the CR oral dosage form is a tablet which comprises a core tablet and an enteric coating. The core tablet comprises a desired amount of Compound (I), a controlled release agent, a filler, a glidant and a lubricant and the enteric coating comprises at least one polymeric controlled release agent with a dissolution property of greater than pH 5.5, and an anti-tacking agent. In an embodiment, the enteric coating dissolves at a pH greater than 6.0 or 6.5.

In an embodiment, the CR oral dosage form is a tablet which comprises a core tablet and an enteric coating. The core tablet comprises a desired amount of Compound (I) or a pharmaceutically acceptable salt and/or solvate thereof (e.g., MIN-101), a controlled release agent, a filler, a glidant and a lubricant and the enteric coating comprises at least one polymeric controlled release agent with a dissolution property of greater than pH 5.5, and an anti-tacking agent. In an embodiment, the enteric coating dissolves at a pH greater than 6.0 or 6.5.

In some embodiments, the controlled release agent in the core tablet comprises a mixture of (i) a low viscosity hypromellose with a viscosity of between about 15 millipascal-seconds (mPa·s) to about 100 mPa·s and (ii) a high viscosity hypromellose with a viscosity of about 100,000 mPa·s, wherein each of the low and high viscosity hypromelloses is a controlled release or sustained-release grade and is further characterized by a methoxy content of 19.0% to 24.0% and a hydroxypropoxy content of 4.0% to 12.0%. In an embodiment, the high viscosity hypromellose is characterized by a methoxy content of 22.0% to 24.0% and a hydroxypropoxy content of 9.5% to 11.5%. In an embodiment, the low viscosity hypromellose comprises about 10% of the weight of the core tablet and the high viscosity hypromellose comprises about 24% of the weight of the core tablet.

In an embodiment, the core tablet comprises 38.4 mg of 1H-Isoindol-1-one, 2-[[1-[2-(4-Fluorophenyl)-2-oxoethyl]-4-piperidinyl]methyl]-2,3-dihydro-, hydrochloride, hydrate (1:1:2) and the controlled release agent in the core table consists essentially of (i) 9.45% w/w of a hypromellose having the chemical and physical characteristics of the hypromellose product marketed as METOLOSE® 90 SH 100 SR by Shin-Etsu Chemical Co., Ltd., or METHOCEL™ K100LV CR; and (ii) 22.67% w/w of a hypromellose having the chemical and physical characteristics of the hypromellose product marketed as METHOCEL™ K100M CR by The Dow Chemical Company.

In an embodiment, the dosage form further comprises a controlled release coating located between the core tablet and the enteric coating. The controlled release coating comprises at least one controlled release reagent. In an embodiment, the controlled release coating comprises a semipermeable membrane which comprises ethylcellulose as the controlled release agent.

In an embodiment of the dosage form that comprises a controlled release coating, the core tablet comprises 38.4 mg of 1H-Isoindol-1-one, 2-[[1-[2-(4-Fluorophenyl)-2-oxoethyl]-4-piperidinyl]methyl]-2,3-dihydro-, hydrochloride, hydrate (1:1:2) and the controlled release agent in the core table consists essentially of 9.36% w/w of a hypromellose having the chemical and physical characteristics of the hypromellose product marketed as METHOCEL™ K15M CR by The Dow Chemical Company, or METHOCEL™ K100LV CR; and 22.46% of a hypromellose having the chemical and physical characteristics of the hypromellose product marketed as METHOCEL™ K100M CR by The Dow Chemical Company and the controlled release agent in the controlled release coating consists essentially of 0.94% w/w of an ethylcellulose having the chemical and physical characteristics of the ethylcellulose product marketed as Surelease® E-7-19040 by Colorcon.

In some embodiments of any of the above dosage forms, the enteric coating consists essentially of a mixture of (i) 4.68% w/w of a copolymer of methacrylic acid and ethyl acrylate having the same physical and chemical properties as the copolymer marketed as EUDRAGIT® L 30 D-55 by Evonik Industries AG and (ii) 0.80% w/w of an anti-tacking agent having the chemical and physical characteristics of the anti-tacking product marketed as PlasACRYL™ by Evonik Industries AG.

In an embodiment, the gastro-resistant CR tablet of the disclosure has a round shape, an oval shape, a capsule shape or an oblong shape. In an embodiment, the tablet is round, with a diameter of 10 mm and a curvature radius (R) of 10.

In other aspects, the present disclosure provides a batch composition and a process for manufacturing a gastro-resistant CR oral dosage form described herein.

In yet another aspect, the present disclosure provides a method of reducing a risk of QT prolongation when treating a subject with Compound (I), the method comprising administering to the subject a gastro-resistant CR oral dosage form described herein.

In a still further aspect, the present disclosure provides a method of treating a disorder (e.g., negative symptoms of schizophrenia) in a subject in need thereof, the method comprising a once daily administration to the patient of a gastro-resistant CR oral dosage form described herein. In one embodiment, the subject, e.g., a patient, has a diagnosis of schizophrenia. In an embodiment, the patient has a diagnosis of schizophrenia, a CYP2D6 extensive metabolizer (EM) genotype and the oral dosage form comprises 32 mg to 64 mg of Compound (I). In another embodiment, the patient has a diagnosis of schizophrenia, a CYP2D6 poor metabolizer (PM) genotype and the gastro-resistant CR oral dosage form comprises 4 mg to 16 mg of Compound (I). In another embodiment, the patient has a diagnosis of schizophrenia, a CYP2D6 intermediate metabolizer (IM) genotype and the gastro-resistant CR oral dosage form comprises 8 mg to 32 mg of Compound (I).

In another aspect, the present disclosure provides a gastro-resistant CR oral dosage form described herein for use in treating negative symptoms in a patient. In an embodiment, the patient has a diagnosis of schizophrenia. In an embodiment, the dosage form is intended for use in improving one or both of negative symptoms and cognitive impairment in patients with a diagnosis of schizophrenia.

In another aspect, the present disclosure provides the use of a gastro-resistant CR oral dosage form described herein for the preparation of a medicament for treating negative symptoms in a patient. In an embodiment, the patient has a diagnosis of schizophrenia.

In another aspect, the present disclosure provides a kit for use in treating negative symptoms in a patient, the kit comprising a gastro-resistant CR oral dosage form described herein and instructions for use of the dosage form. In an embodiment, the instructions include instructions for testing the patient to determine the patient's CYP2D6 genotype. In an embodiment, the instructions include instructions for administrating the dosage form to the patient in a fed state or in a fasted state.

In all of the above aspects and embodiments of the invention, Compound (I) may be provided in the gastro-resistant CR oral dosage form as 1H-Isoindol-1-one, 2-[[1-[2-(4-Fluorophenyl)-2-oxoethyl]-4-piperidinyl]methyl]-2,3-dihydro-, hydrochloride, hydrate (1:1:2).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the Drawings, various graphs are shown which include the plasma concentrations time profile of various compounds, including, for example, 1H-Isoindol-1-one, 2-[[1-[2-(4-Fluorophenyl)-2-oxoethyl]-4-piperidinyl]methyl]-2,3-dihydro-, i.e., Compound (I). In these Drawings, the use of the "MIN-101" or "MIN101" is intended to refer to the free base, i.e., Compound (I).

The foregoing summary, as well as the following detailed description of the disclosure, will be better understood when read in conjunction with the appended drawings.

Figure 1:
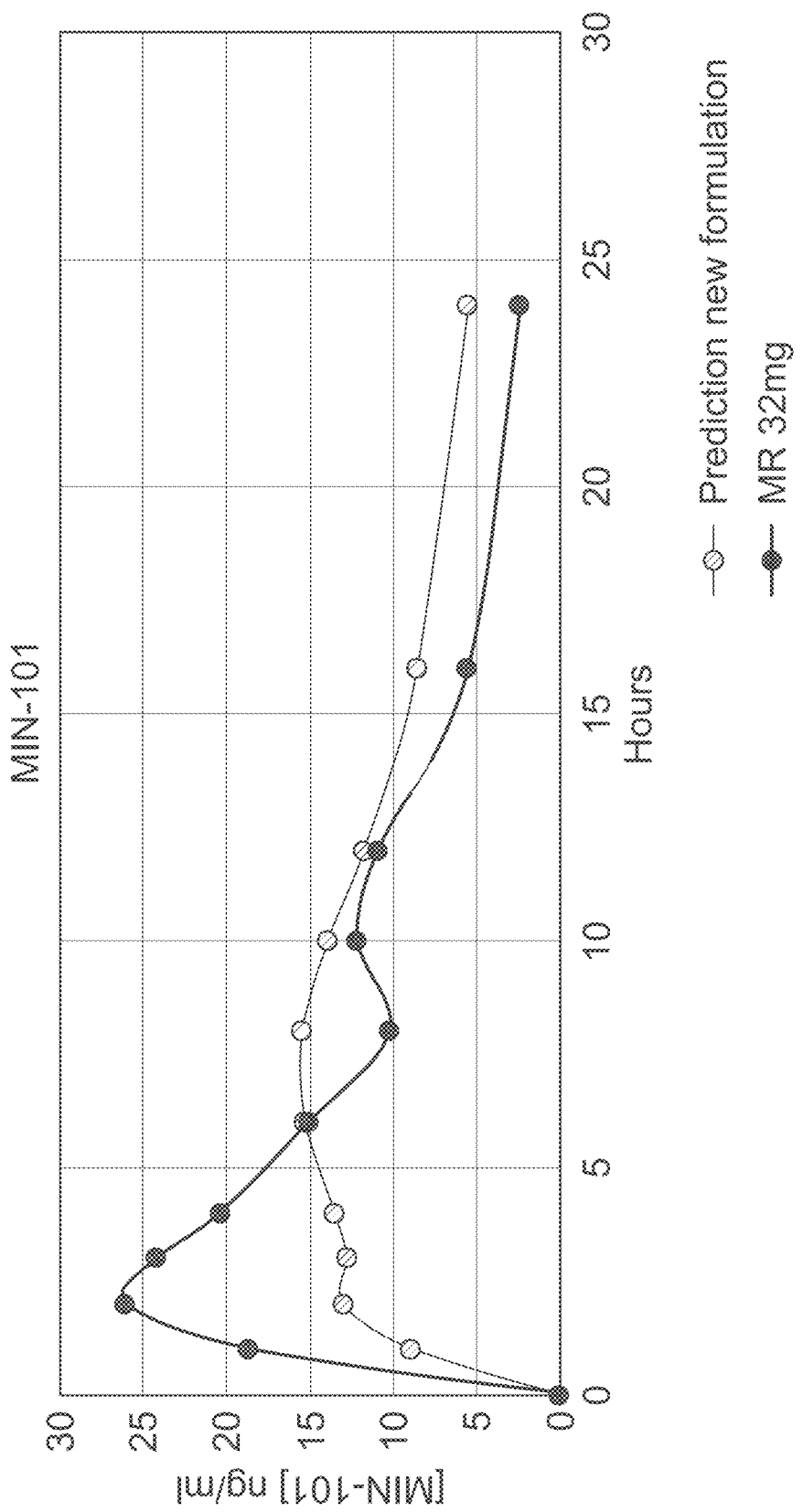

FIG. 1 shows an exemplary target plasma PK profile for Compound (I) produced by oral administration of a gastro-resistant, controlled release dosage form comprising 32 mg of Compound (I) ("Prediction new formulation") compared to the observed plasma PK profile for Compound (I) produced by a previous 32 mg modified release MIN-101 tablet (described in Example 1) ("MR 32 mg"). The time profile is through 24 hours.

Figure 2:
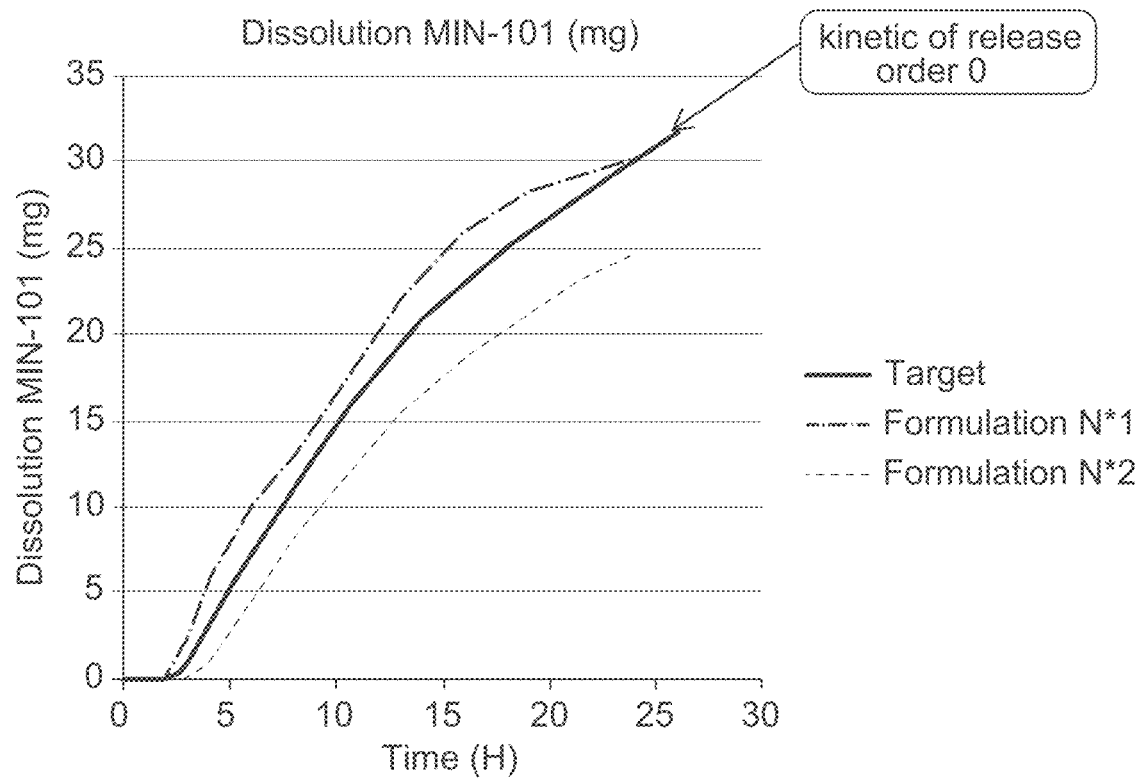
Figure 2:
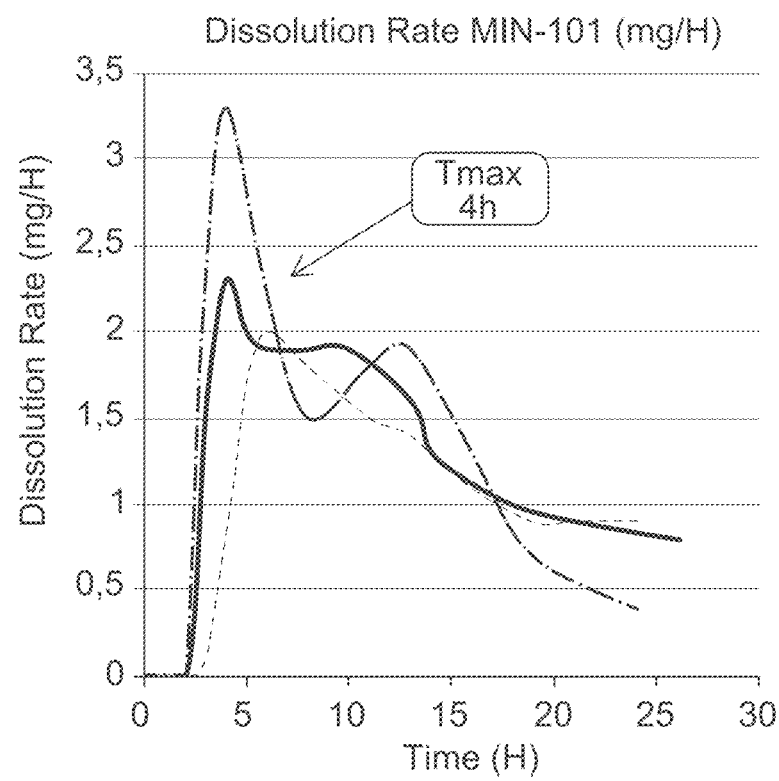

FIG. 2 compares target in vitro dissolution profiles for Compound (I) (Target, red curve) with observed dissolution profiles for two exemplary gastro-resistant CR 32 mg tablets of the present disclosure, with the upper graph showing cumulative dissolution profiles and the lower graph showing dissolution rate profiles. The time profile is through 24 hours.

Figure 3:
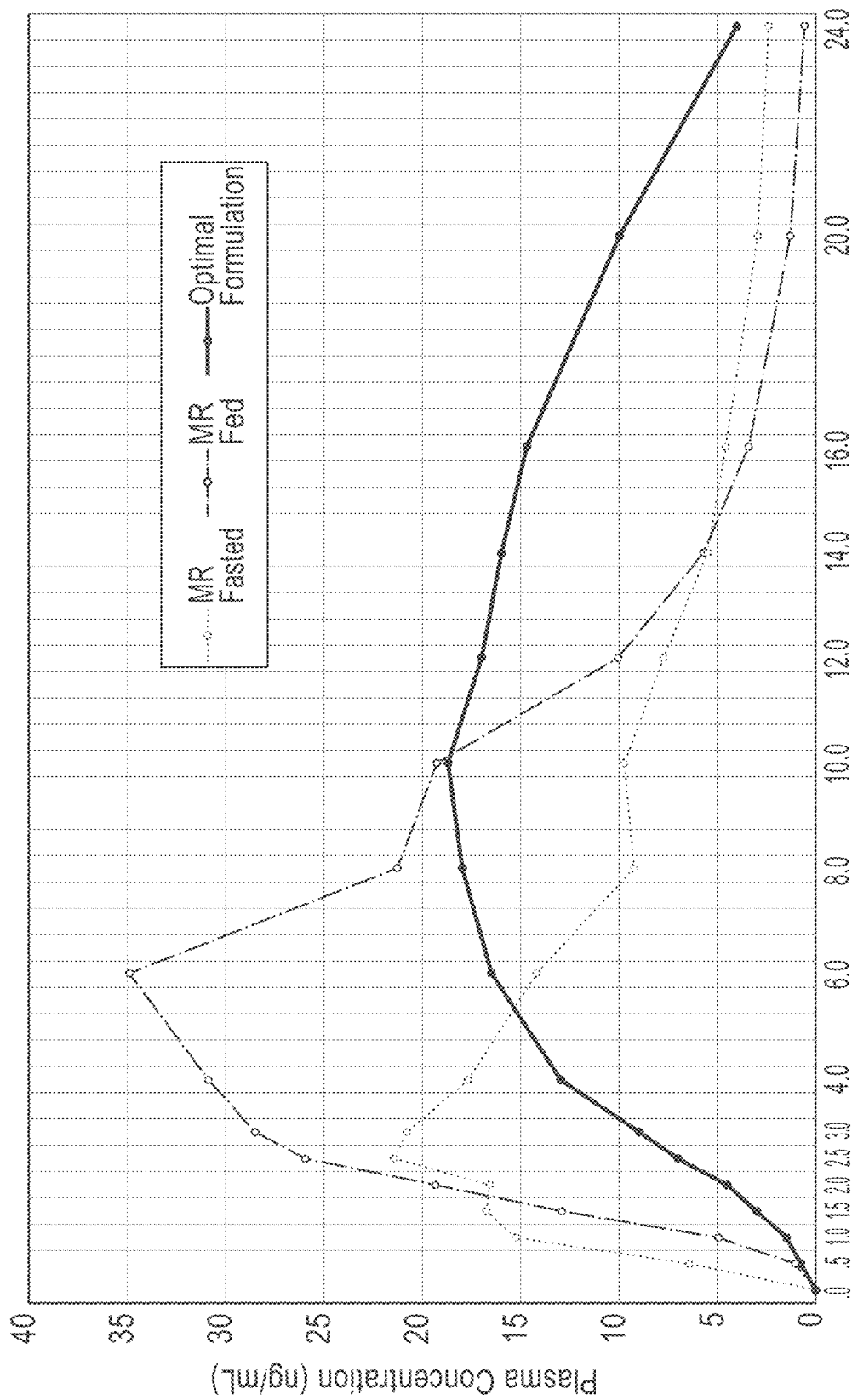

FIG. 3 shows another exemplary target plasma PK profile for Compound (I) produced by oral administration of a gastro-resistant, controlled release dosage form comprising 32 mg of Compound (I) to a subject in either the fed state or fasted state ("Optimal formulation") compared to the observed plasma PK profiles for Compound (I) produced by a previous 32 mg modified release MIN-101 tablet (described in Example 1) in patients in the fasted state or fed state. The time profile is through 24 hours.

Figure 4:
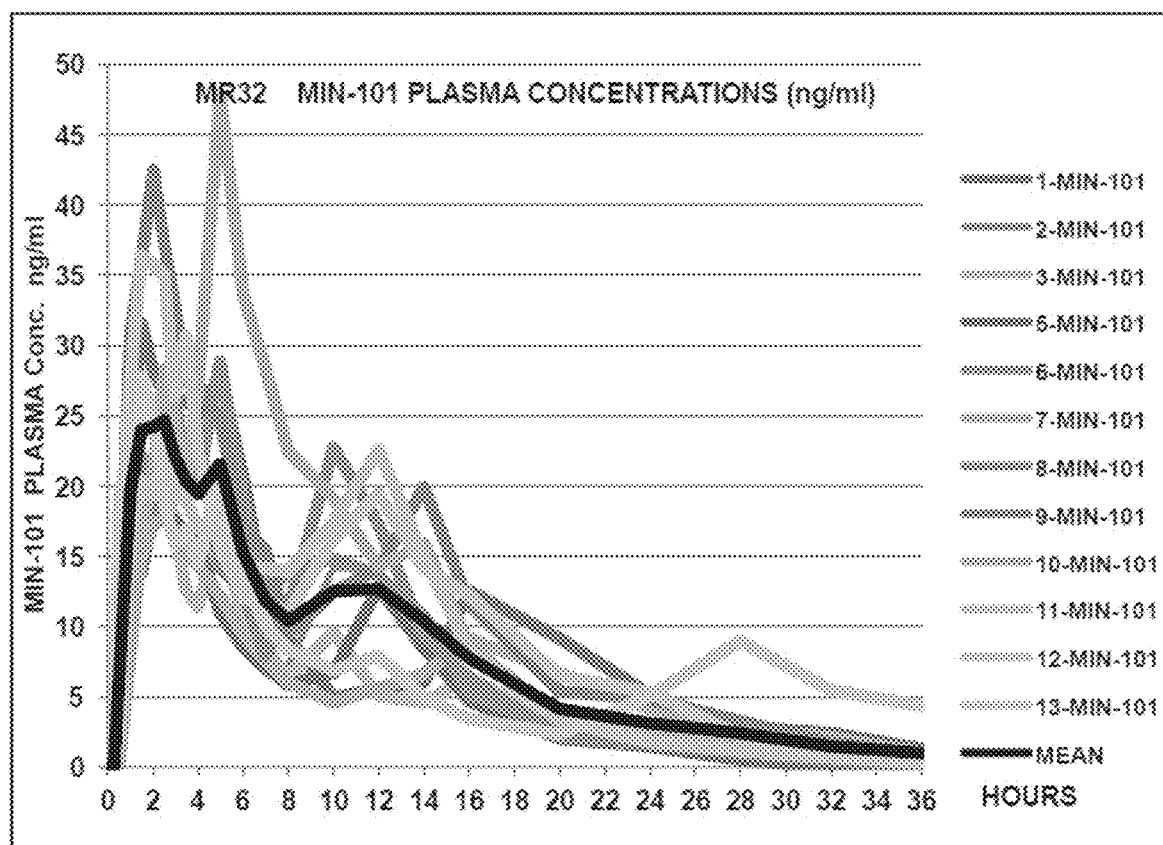

FIG. 4 is a graph of Compound (I) plasma concentrations time profile for subjects administered a MR 32 mg tablet. The time profile is through 36 hours.

Figure 5:
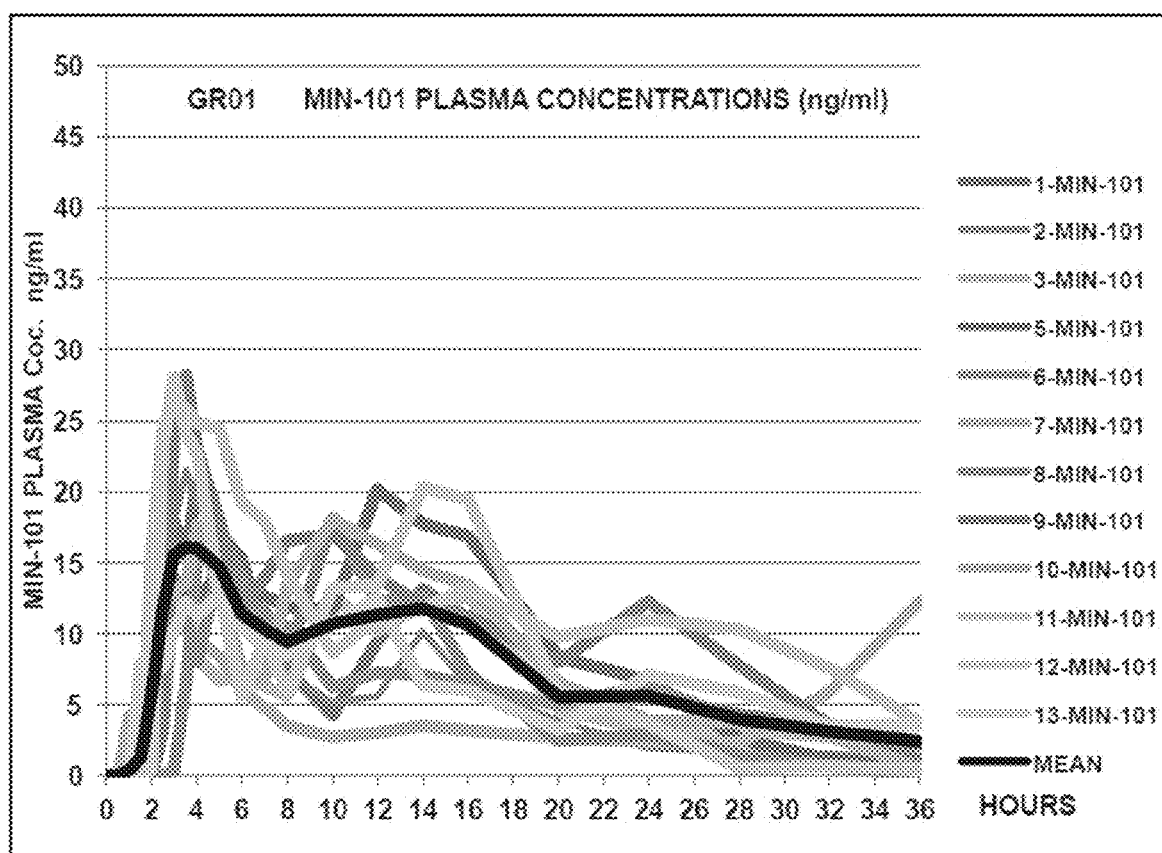

FIG. 5 is a graph of Compound (I) plasma concentrations time profile for subjects administered a GR-01 tablet. The time profile is through 36 hours.

Figure 6:
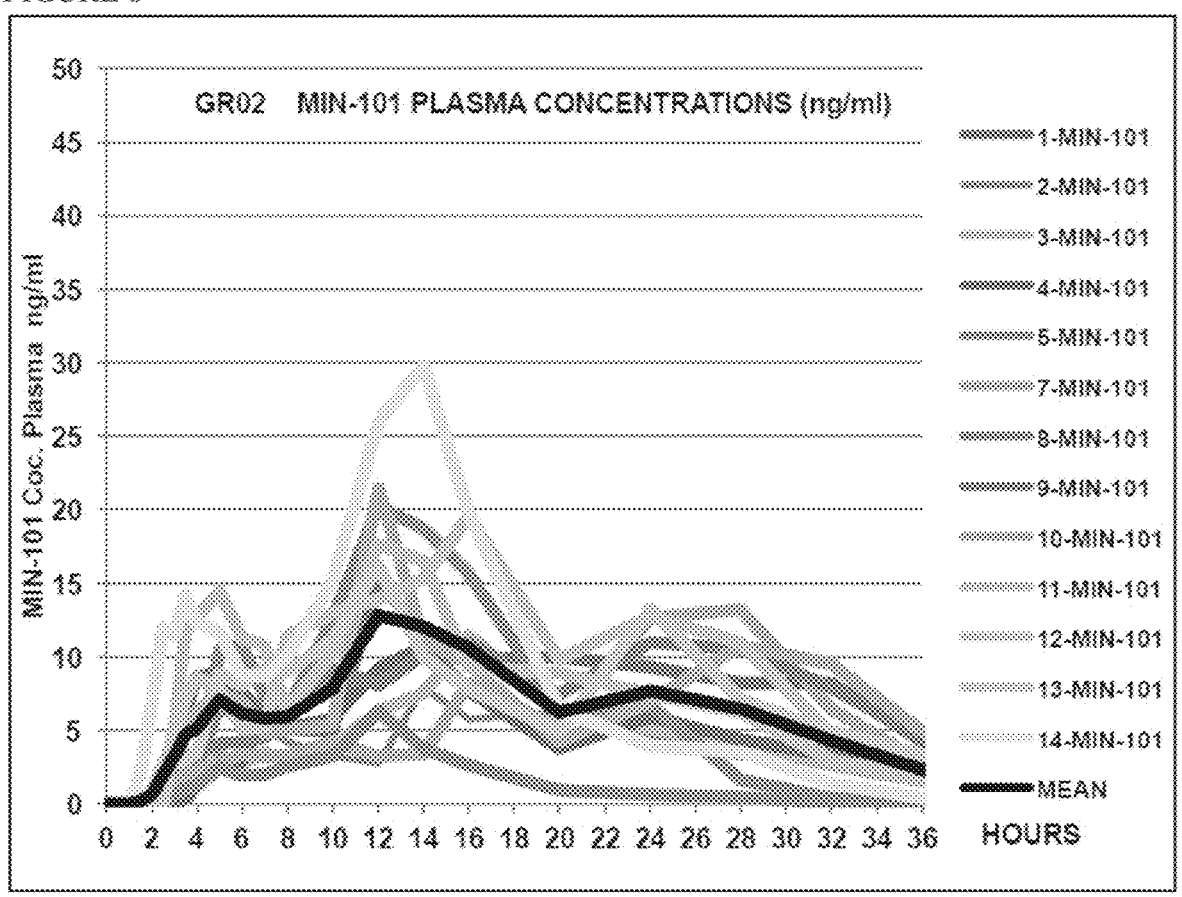

FIG. 6 is a graph of Compound (I) plasma concentrations time profile for subjects administered a GR-02 tablet. The time profile is through 36 hours.

Figure 7:
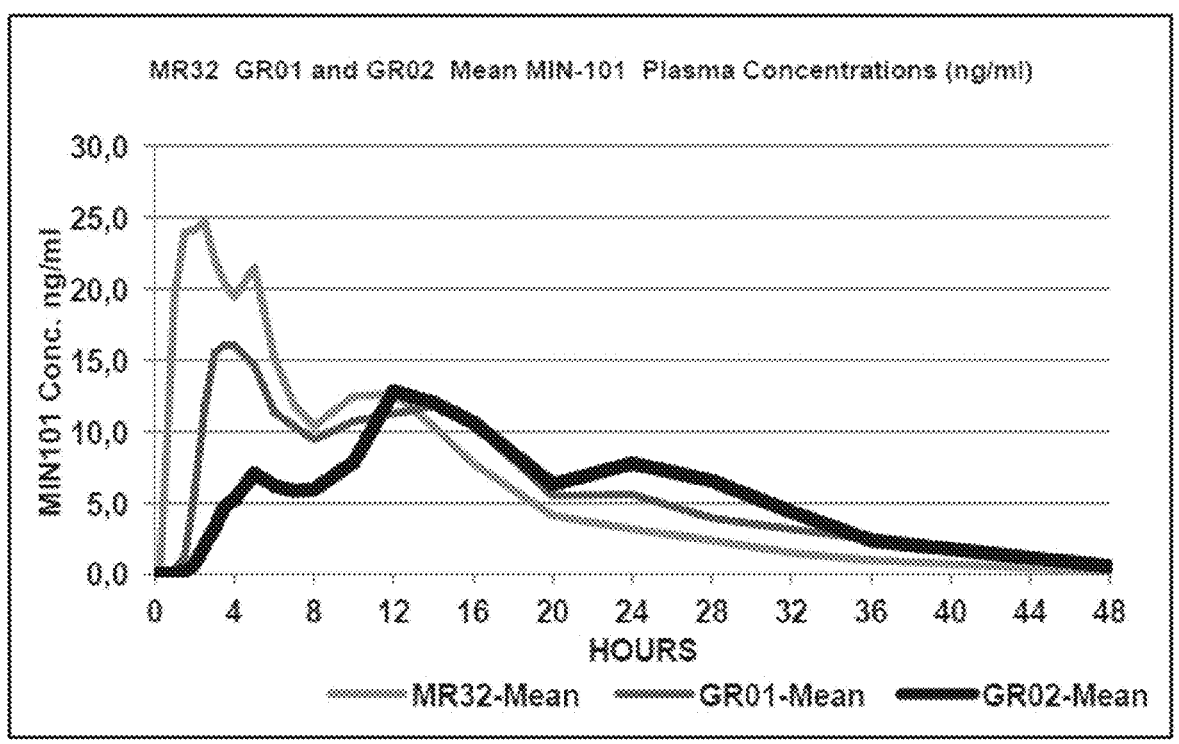

FIG. 7 is a graph of mean Compound (I) plasma concentrations time profile for subjects administered MR 32 mg tablets, GR-01 tablets, or GR-02 tablets. The time profile is through 48 hours.

Figure 8:
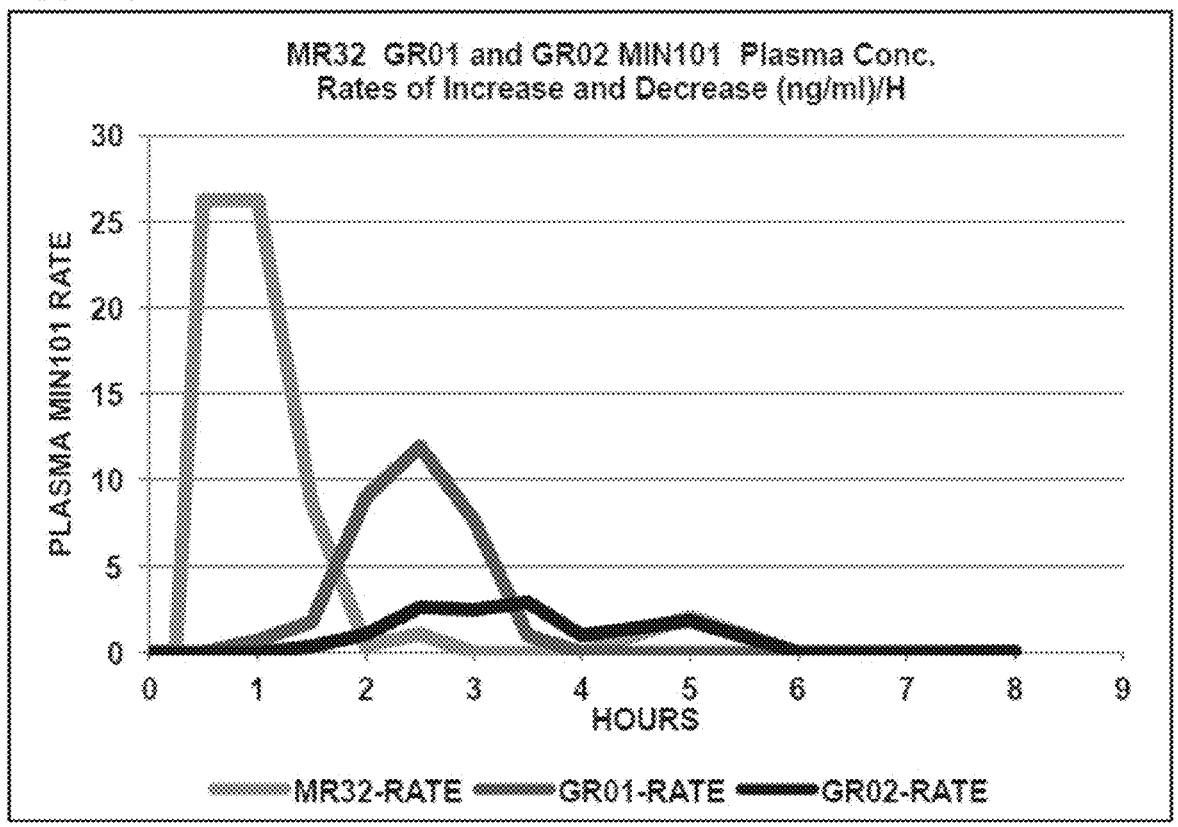

FIG. 8 is a graph of the rates of increase or decrease in Compound (I) plasma concentrations time profile for subjects administered MR 32 mg tablets, GR-01 tablets, or GR-02 tablets. The time profile is through 8 hours.

Figure 9:
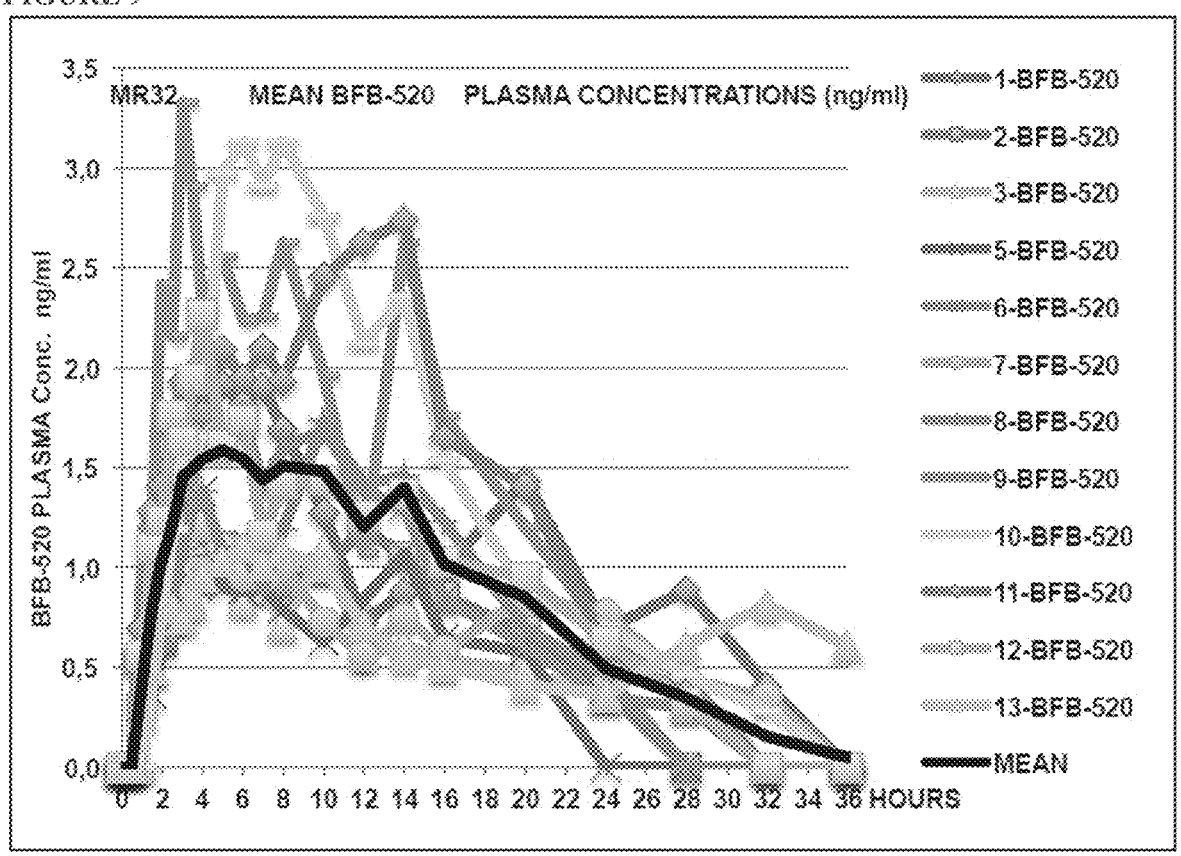

FIG. 9 is a graph of BFB-520 plasma concentrations time profile for subjects administered a MR 32 mg tablet. The time profile is through 36 hours.

Figure 10:
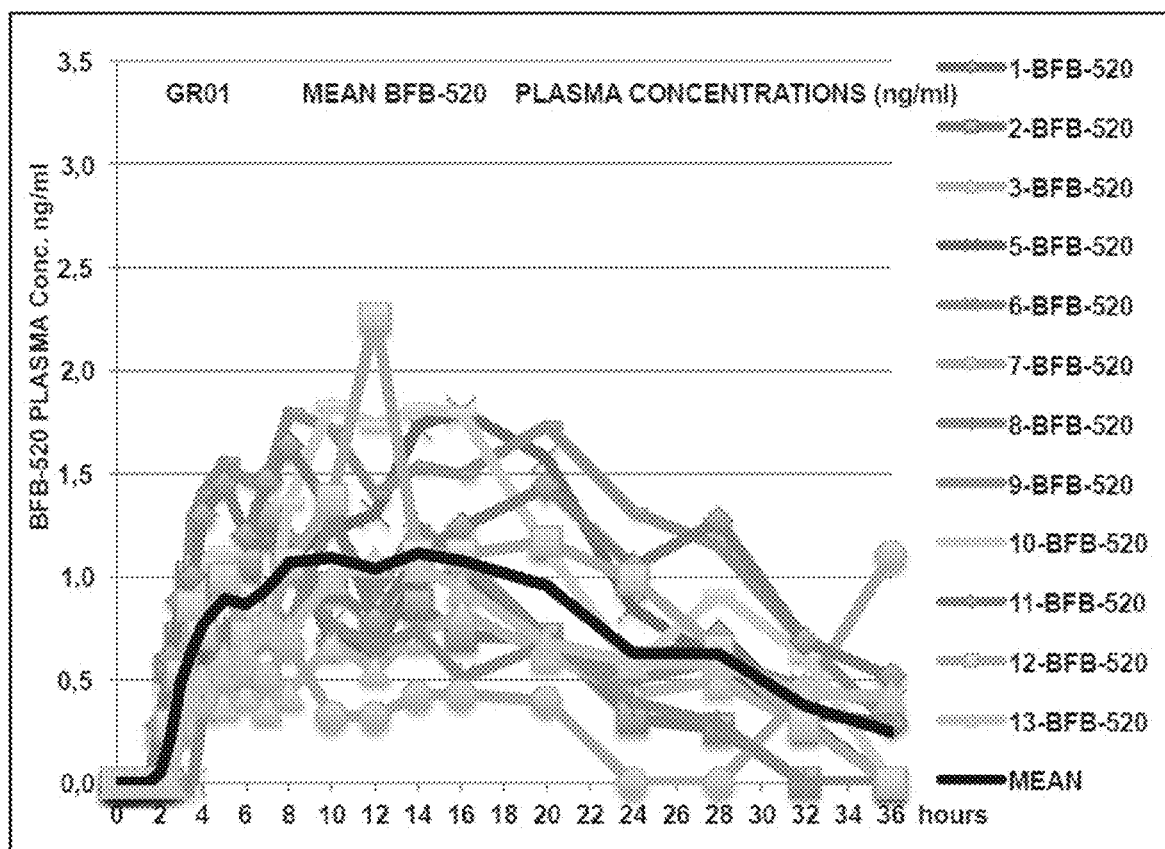

FIG. 10 is a graph of BFB-520 plasma concentrations time profile for subjects administered a GR-01 tablet. The time profile is through 36 hours.

Figure 11:
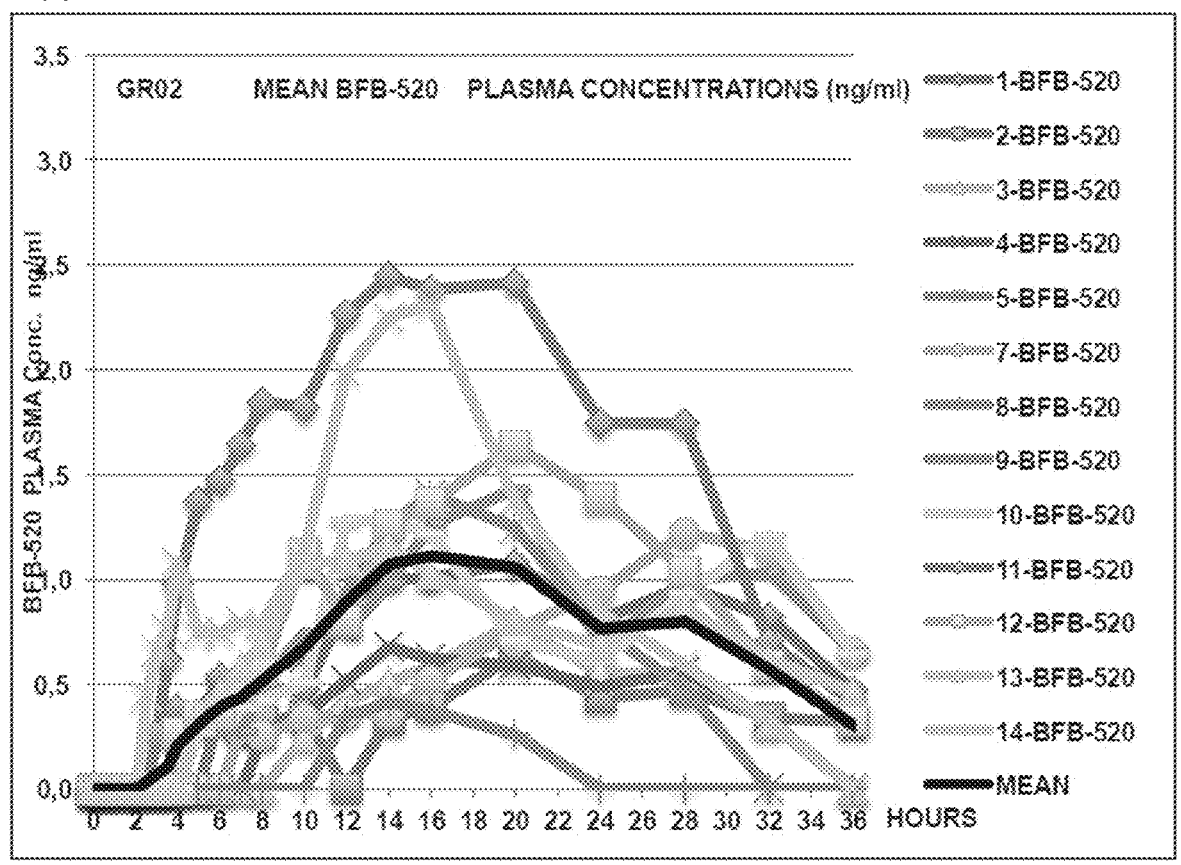

FIG. 11 is a graph of BFB-520 plasma concentrations time profile for subjects administered a GR-02 tablet. The time profile is through 36 hours.

Figure 12:
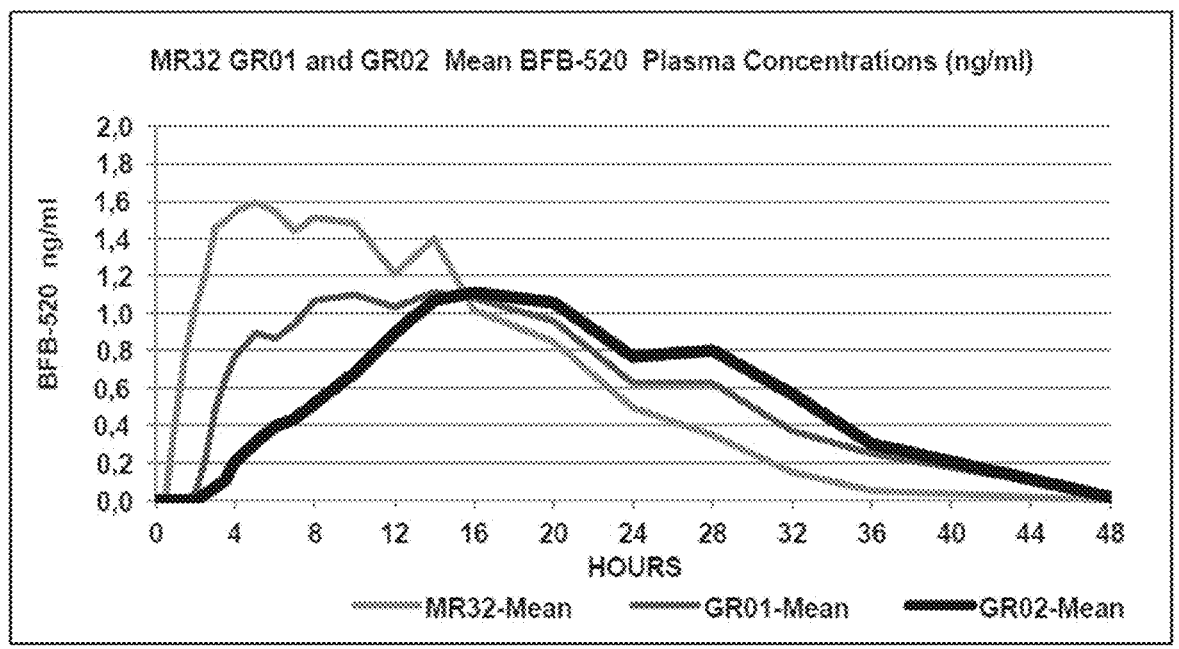

FIG. 12 is a graph of mean BFB-520 plasma concentrations time profile for subjects administered MR 32 mg tablets, GR-01 tablets, or GR-02 tablets. The time profile is through 48 hours.

Figure 13:
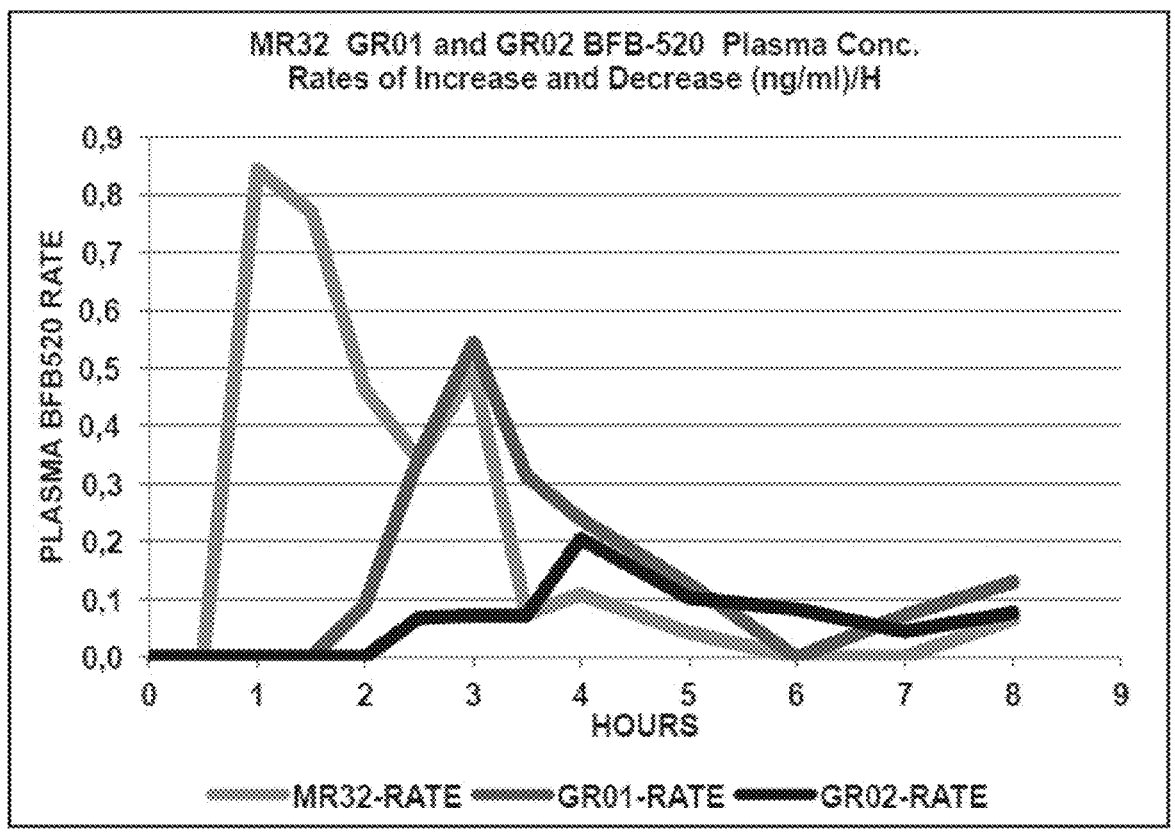

FIG. 13 is a graph of the rates of increase or decrease in BFB-520 plasma concentrations time profile for subjects administered MR 32 mg tablets, GR-01 tablets, or GR-02 tablets. The time profile is through 8 hours.

Figure 14:
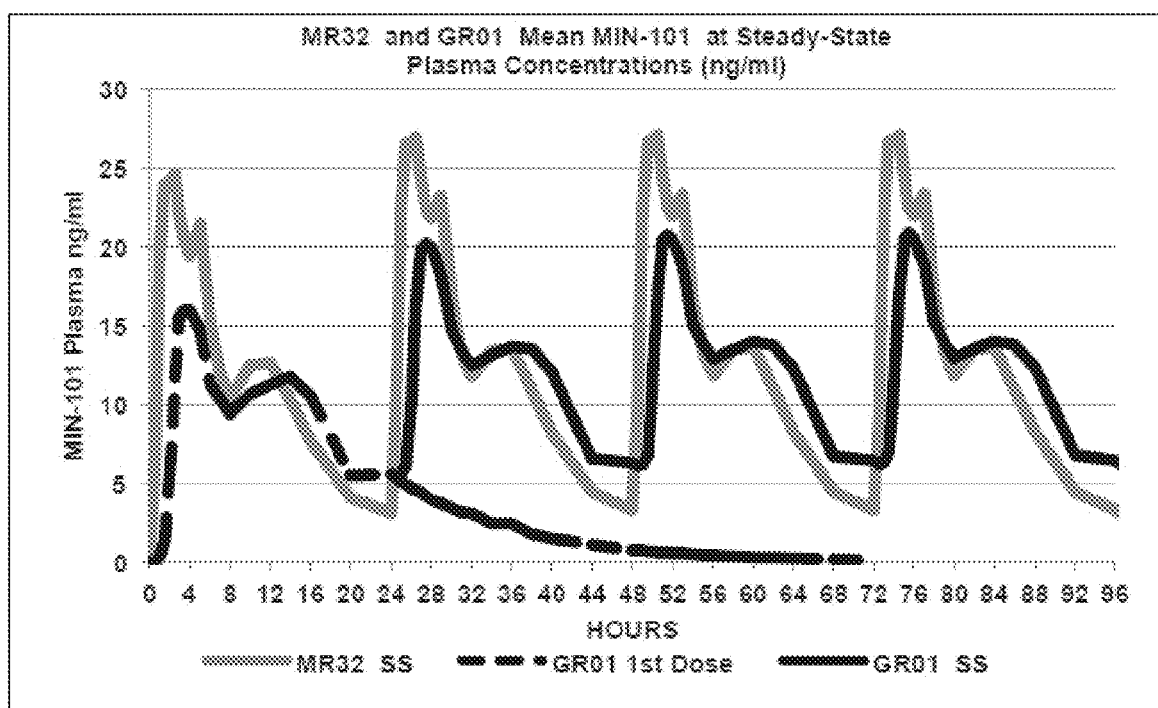
Figure 14:
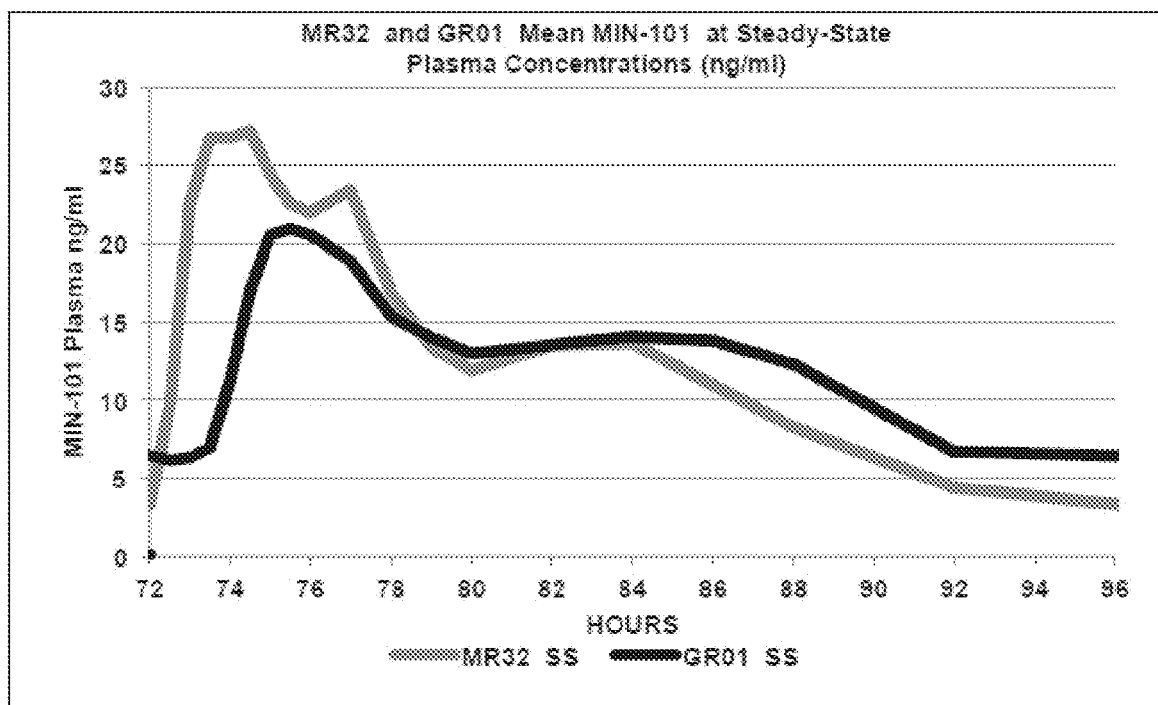

FIG. 14 is a pair of graphs of predicted Compound (I) steady state plasma concentrations time profile for subjects administered 4 daily doses of a MR 32 mg tablet or a GR-01 tablet (32 mg) based on actual data observed following Day 1 dosing. The time profile is through 96 hours.

Figure 15:
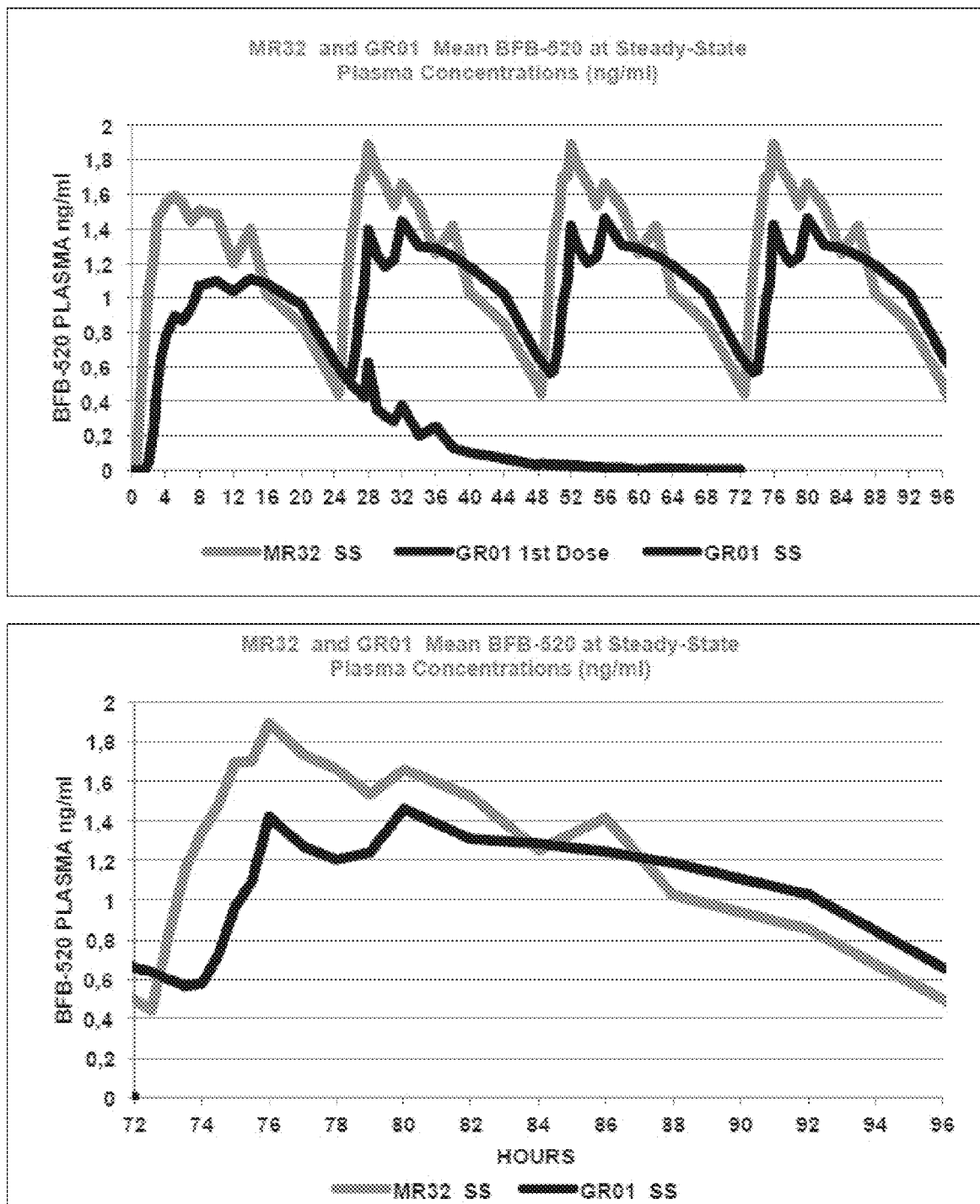

FIG. 15 is a pair of graphs of predicted BFB-520 steady state plasma concentrations time profile for subjects administered 4 daily doses of a MR 32 mg tablet or a GR-01 tablet (32 mg) based on actual data observed following Day 1 dosing. The time profile is through 96 hours.

Figure 16:
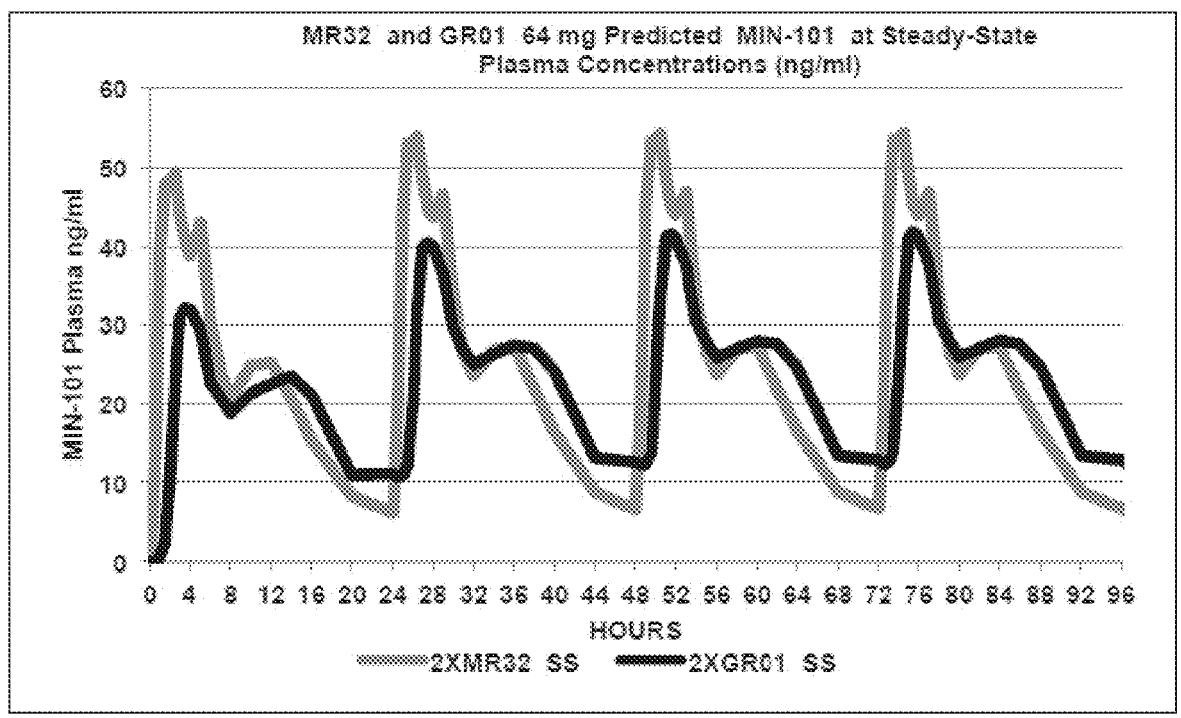
Figure 16:
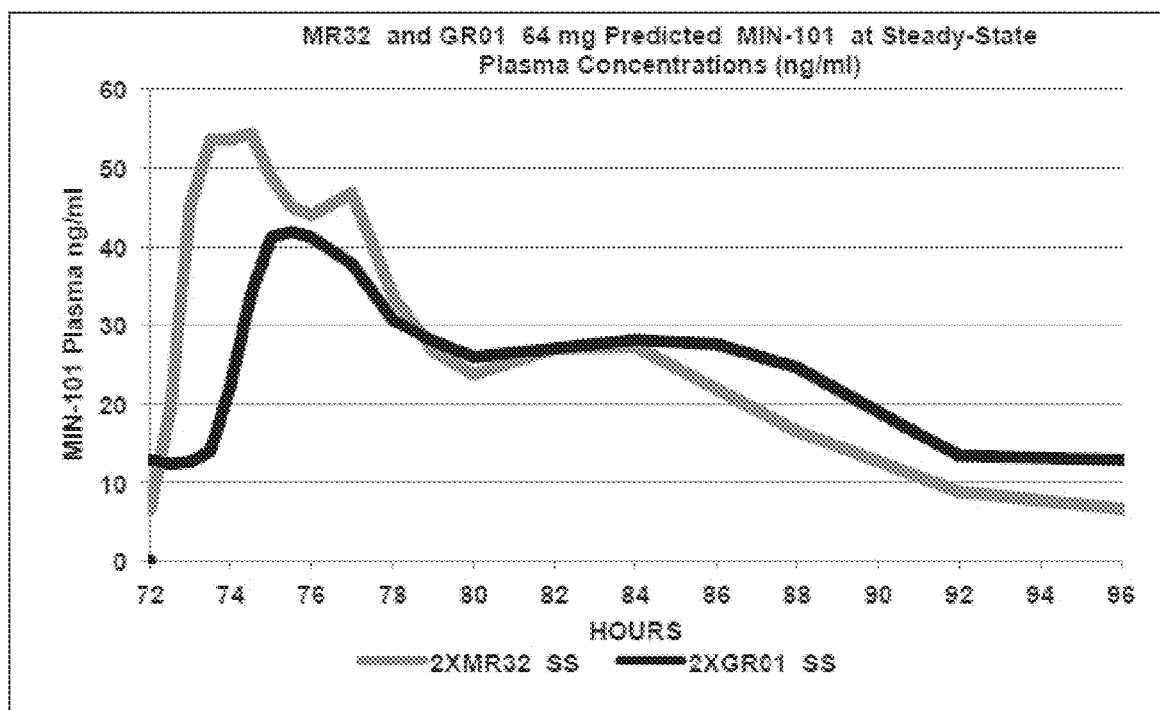

FIG. 16 is a pair of graphs of predicted Compound (I) steady state plasma concentrations time profile for subjects administered 4 daily 64 mg (2×32 mg) doses of a MR 32 mg tablet or a GR-01 tablet. The time profile is through 96 hours.

Figure 17:
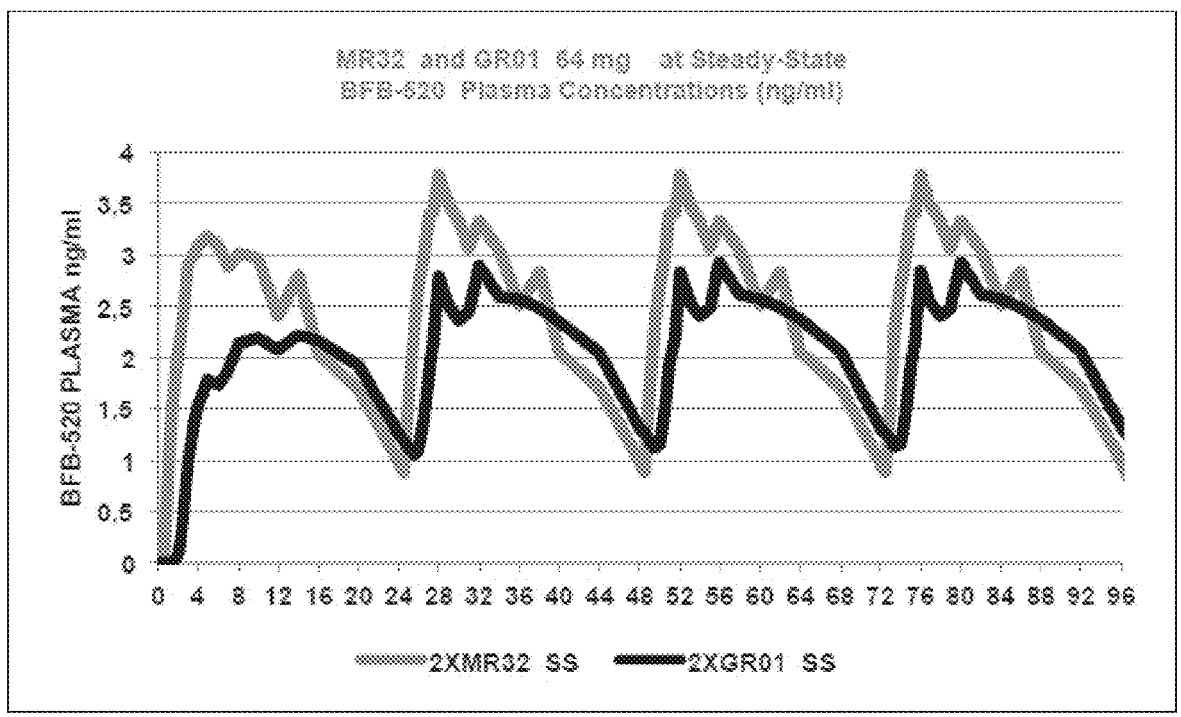
Figure 17:
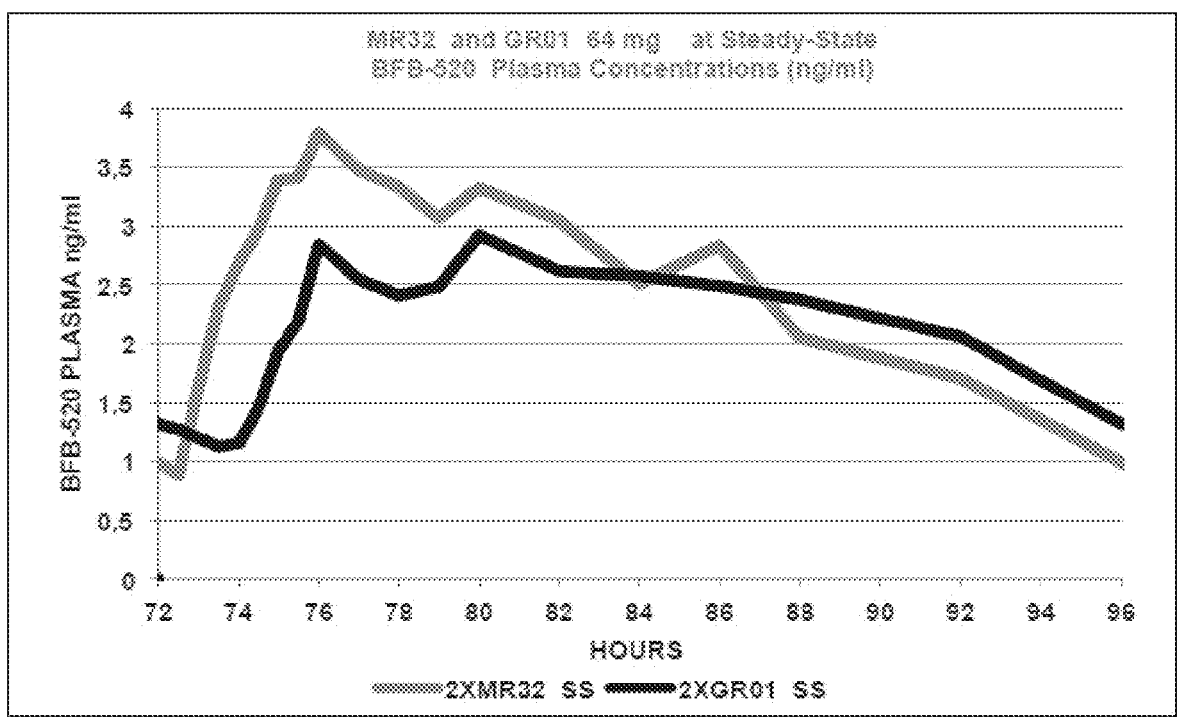

FIG. 17 is a pair of graphs of predicted BFB-520 steady state plasma concentrations time profile for subjects administered 4 daily 64 mg (2×32 mg) doses of a MR 32 mg tablet or a GR-01 tablet. The time profile is through 96 hours.

Figure 18:
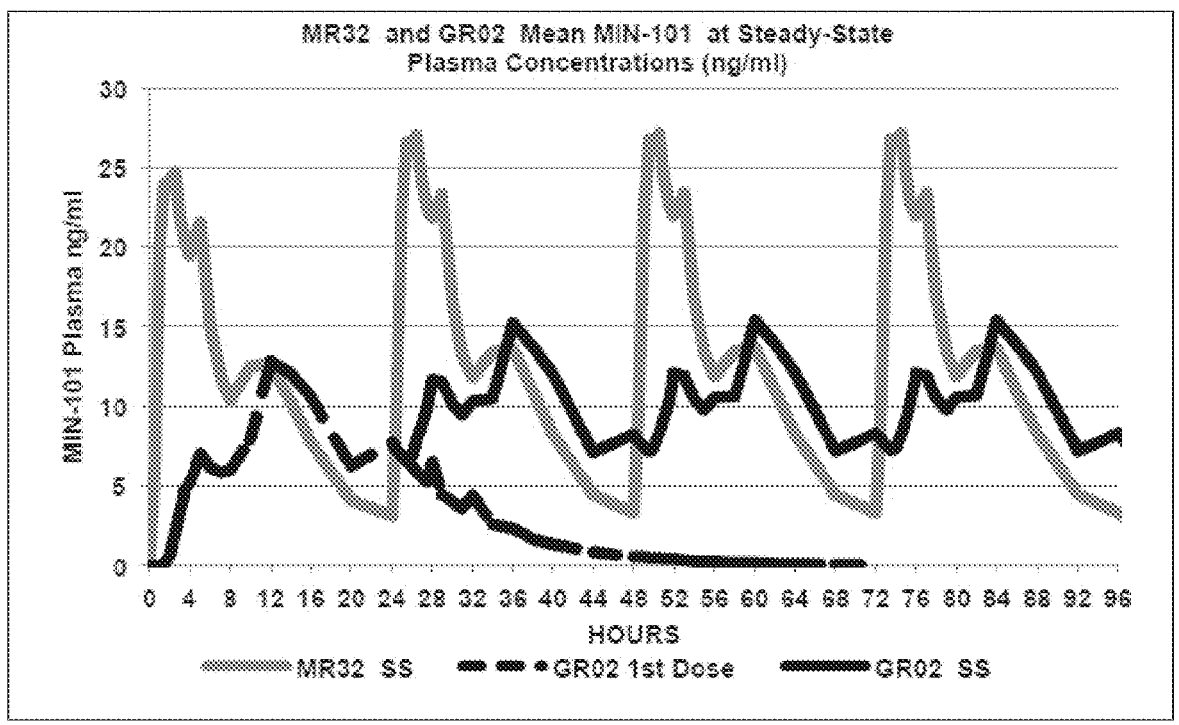
Figure 18:
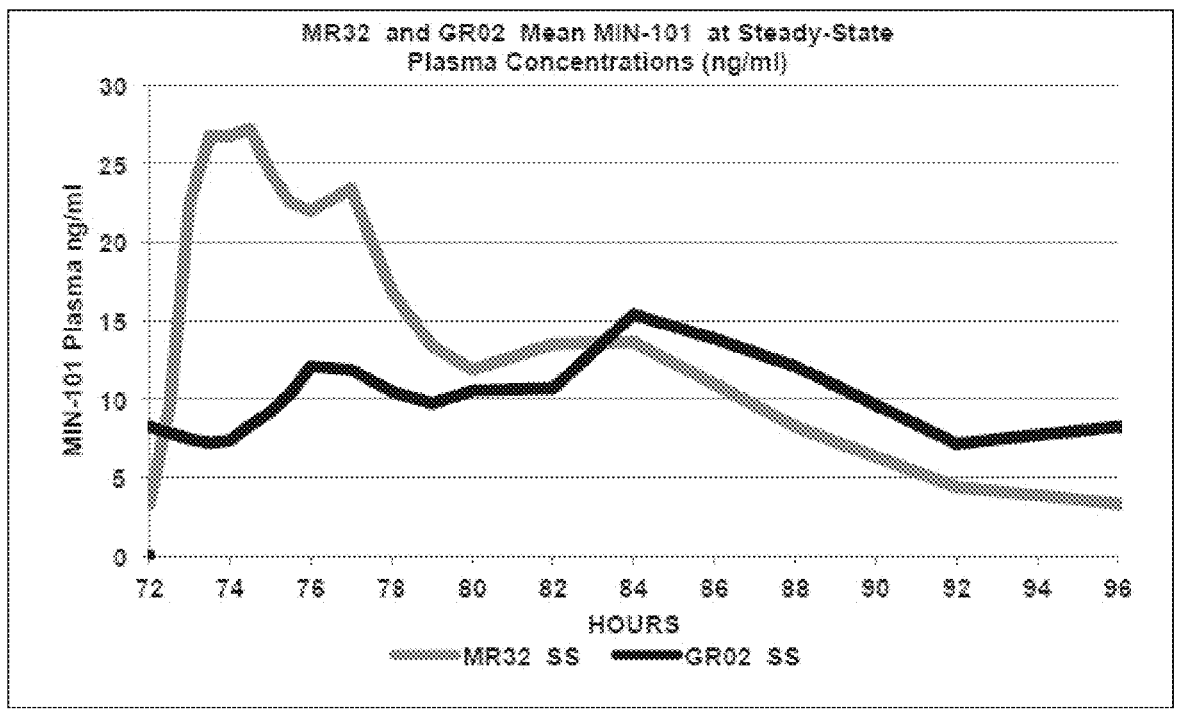

FIG. 18 is a pair of graphs of predicted Compound (I) steady state plasma concentrations time profile for subjects administered 4 daily doses of a MR 32 mg tablet or a GR-02 tablet (32 mg) based on actual data observed following Day 1 dosing. The time profile is through 96 hours.

Figure 19:
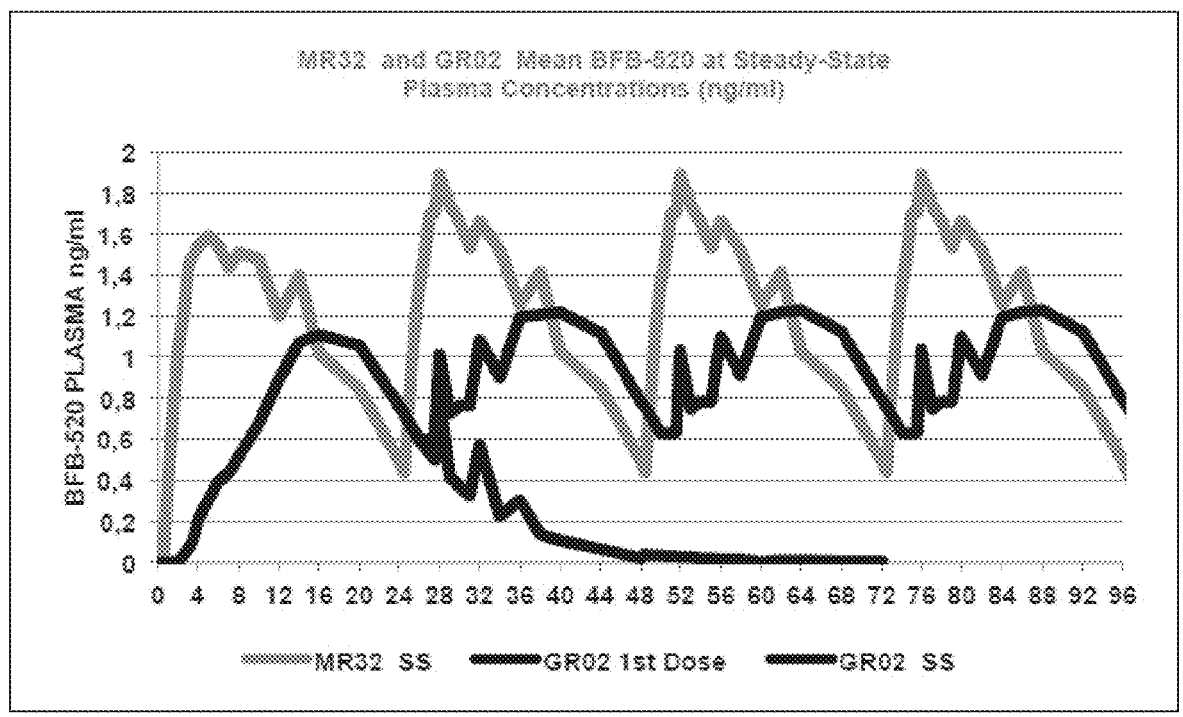
Figure 19:
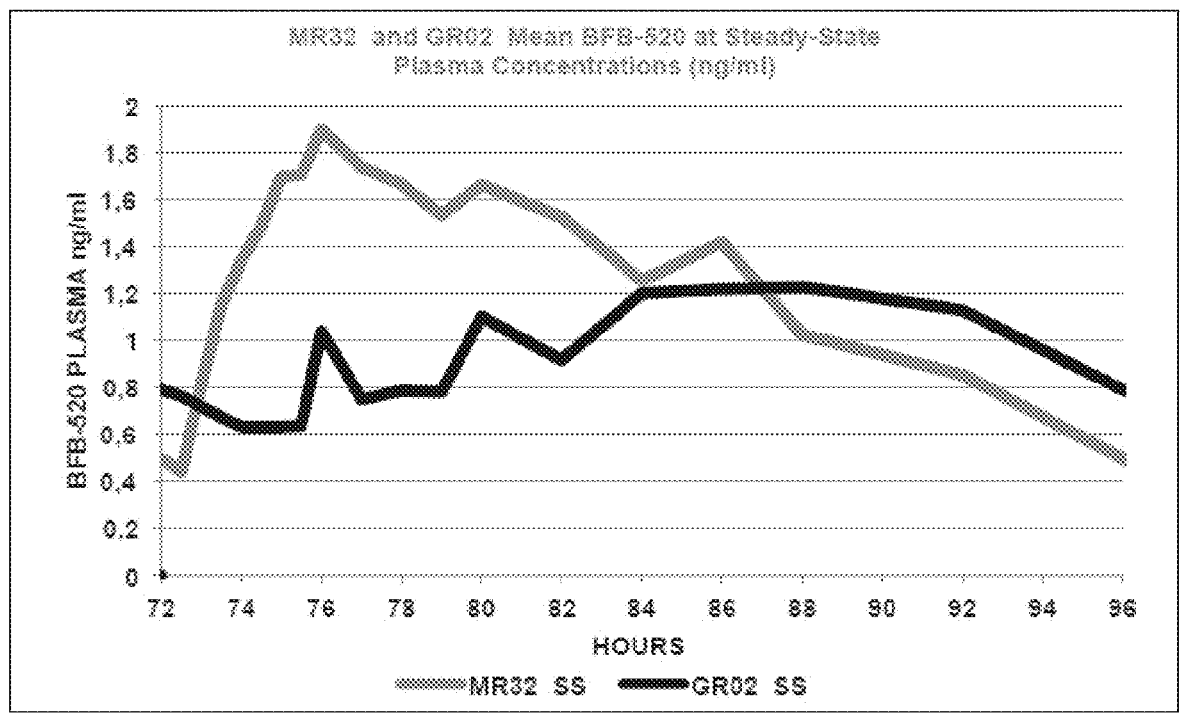

FIG. 19 is a pair of graphs of predicted BFB-520 steady state plasma concentrations time profile for subjects administered 4 daily doses of a MR 32 mg tablet or a GR-02 tablet (32 mg) based on actual data observed following Day 1 dosing. The time profile is through 96 hours.

Figure 20:
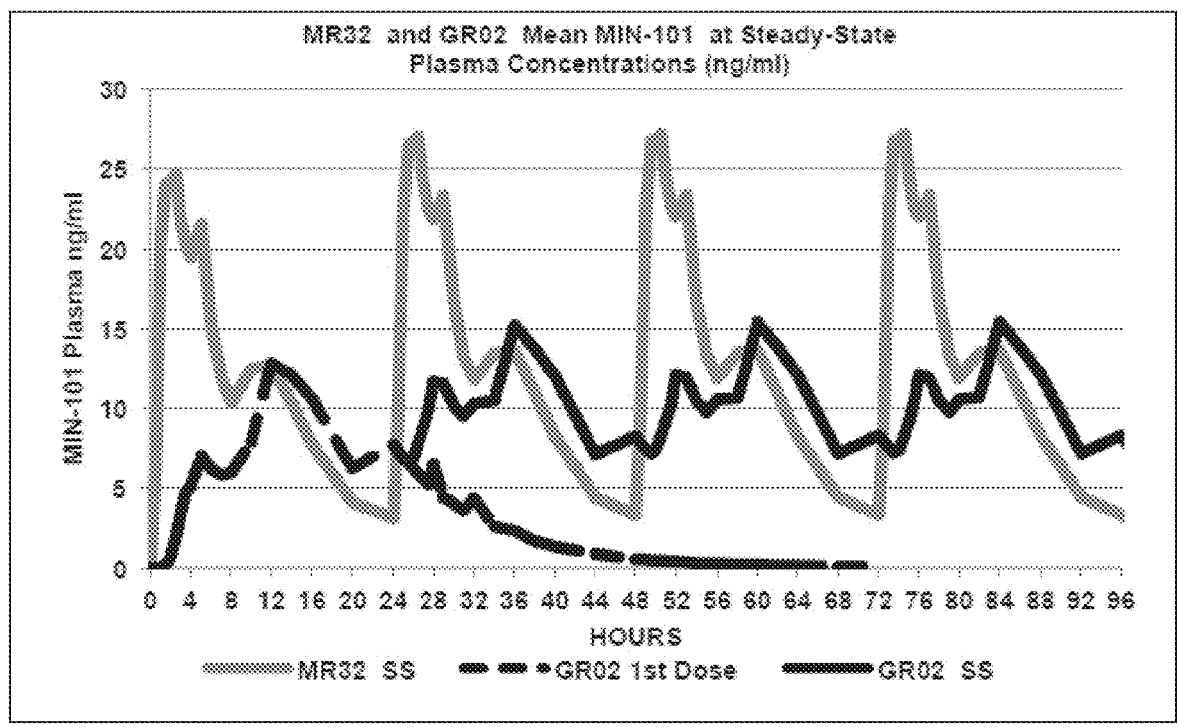
Figure 20:
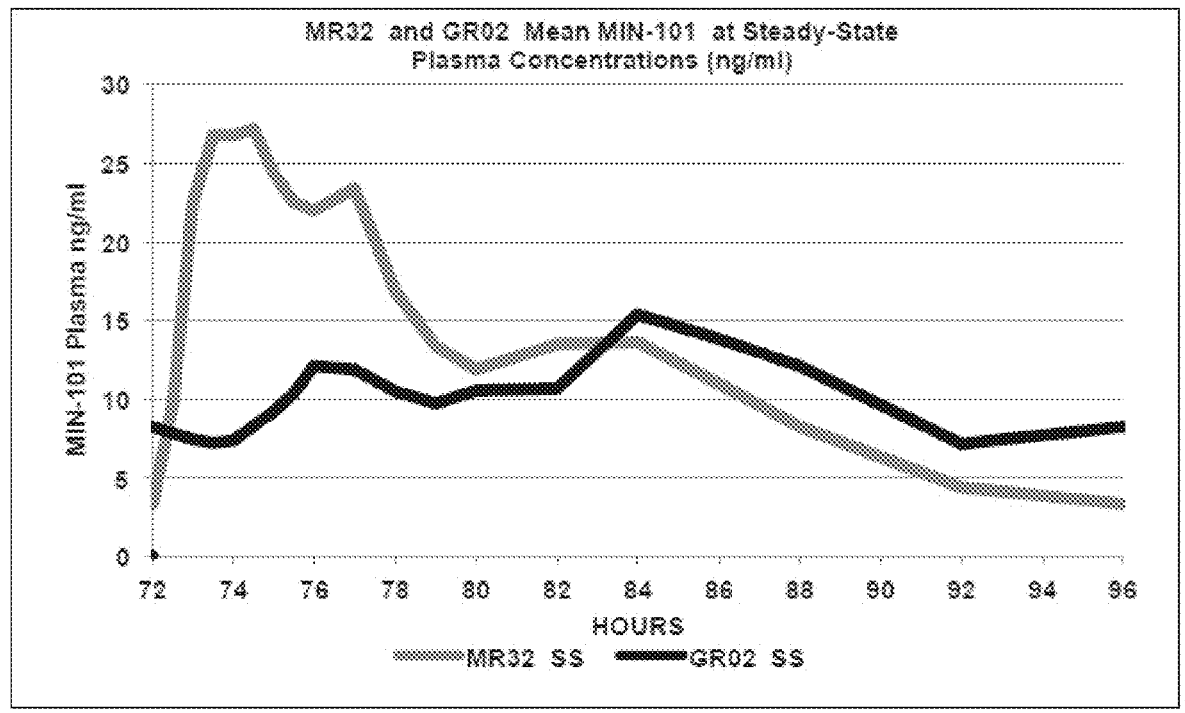

FIG. 20 is a pair of graphs of predicted Compound (I) steady state plasma concentrations time profile for subjects administered 4 daily doses of a MR 32 mg tablet or a GR-02 tablet based on actual data observed following Day 1 dosing. The time profile is through 96 hours.

Figure 21:
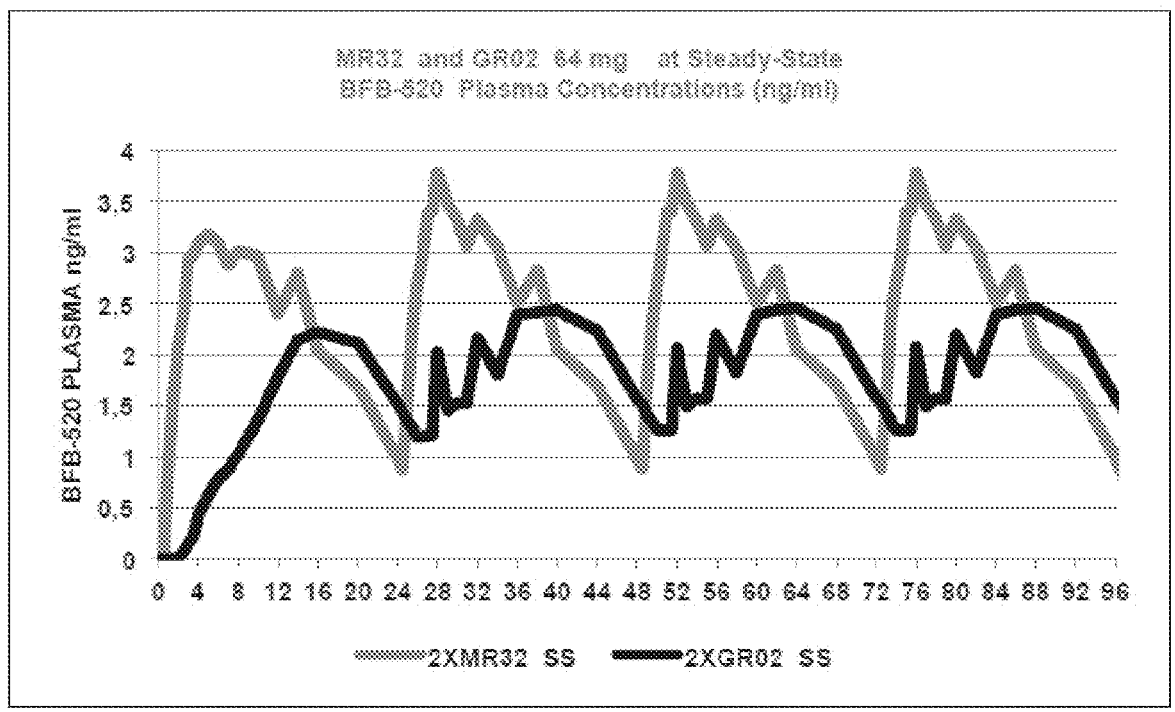
Figure 21:
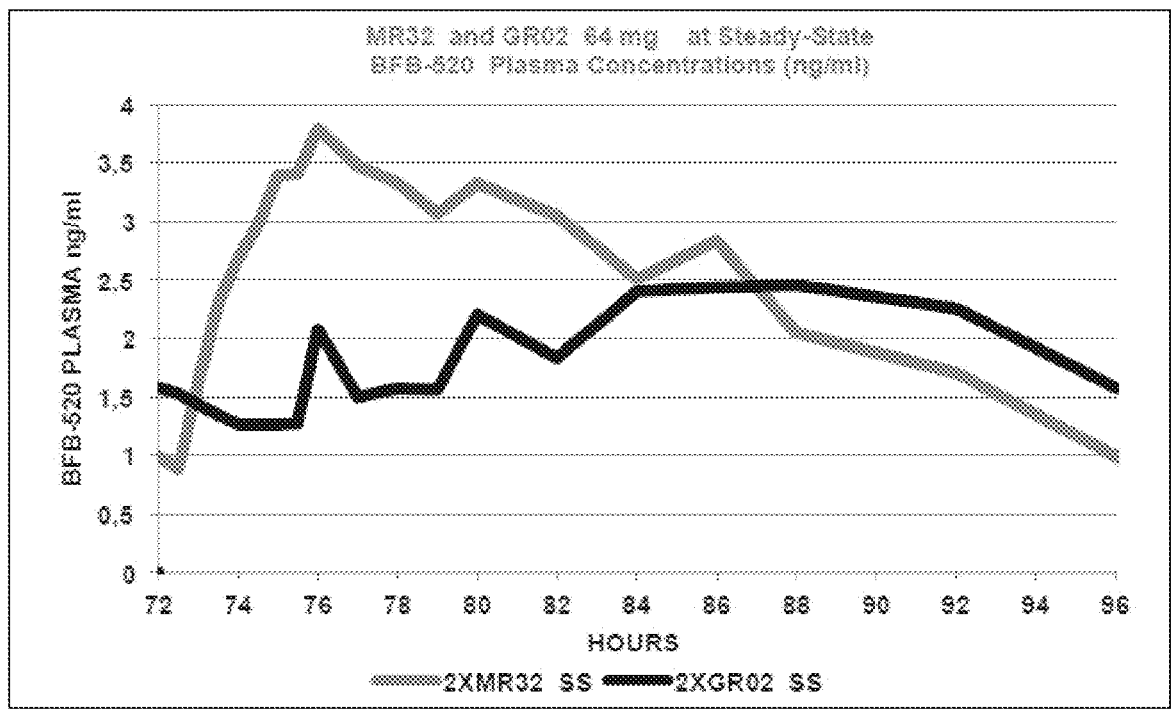

FIG. 21 is a pair of graphs of predicted BFB-520 steady state plasma concentrations time profile for subjects administered 4 daily 64 mg (2×32 mg) doses of a MR 32 mg tablet or a GR-02 tablet. The time profile is through 96 hours.

Figure 22:
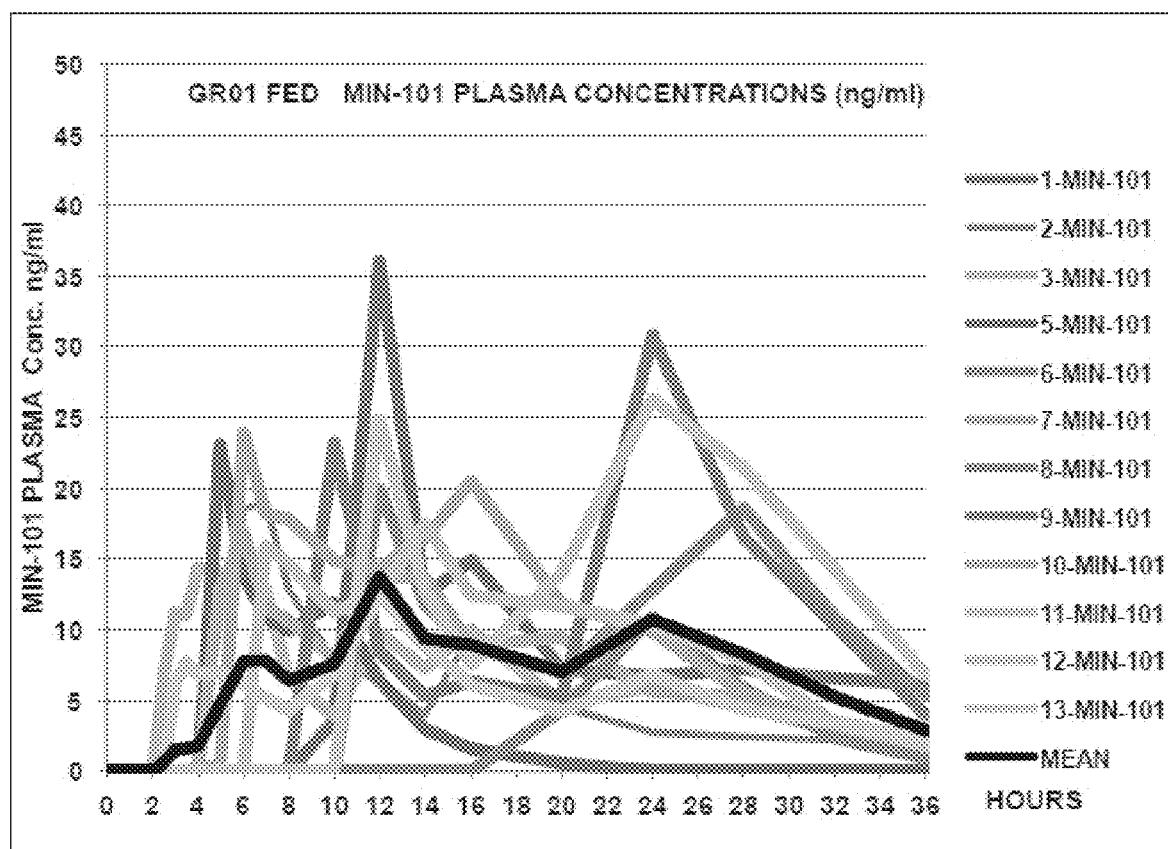

FIG. 22 is a graph of Compound (I) plasma concentrations time profile for subjects administered GR-01 tablets in fed state. The time profile is through 36 hours.

Figure 23:
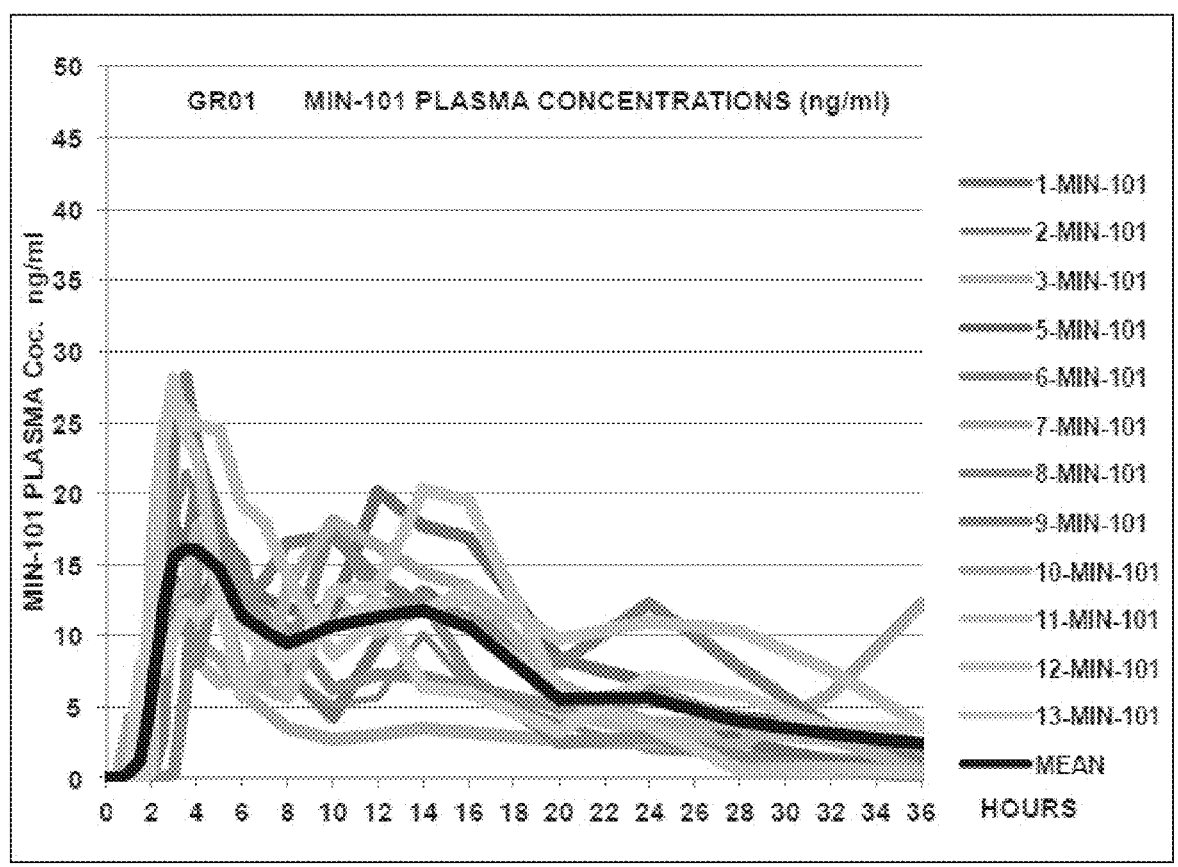

FIG. 23 is a graph of Compound (I) plasma concentrations time profile for subjects administered GR-01 tablets in fasted state. The time profile is through 36 hours.

Figure 24:
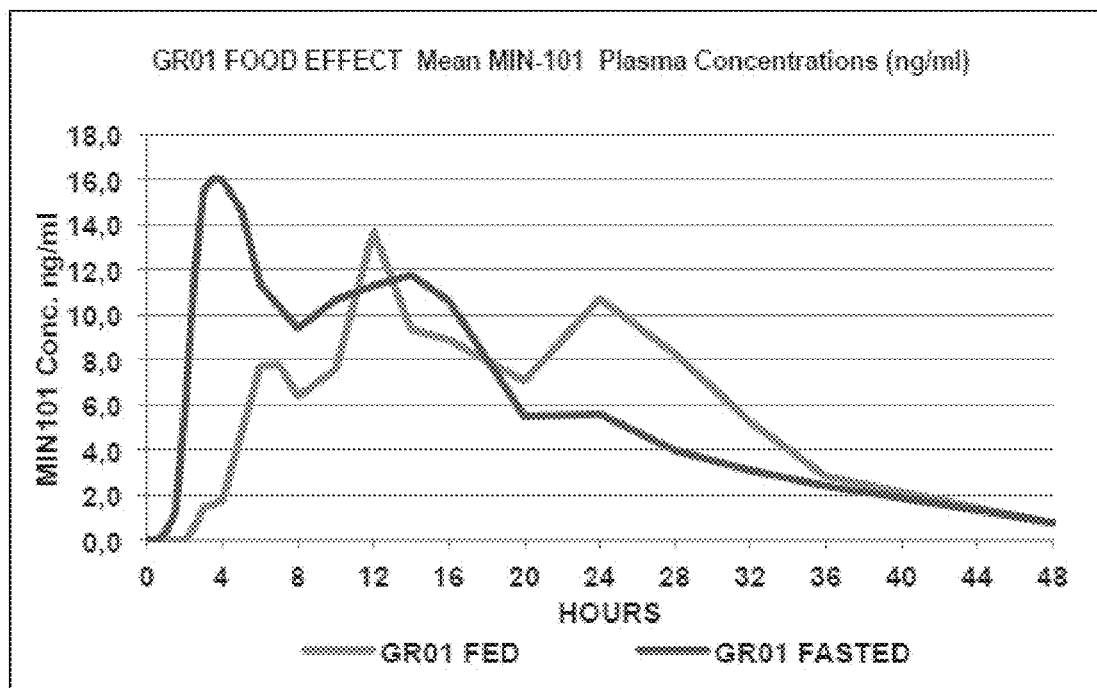

FIG. 24 is graph comparing mean Compound (I) plasma concentrations time profile for subjects administered GR-01 tablets in fed or fasted state. The time profile is through 48 hours.

Figure 25:
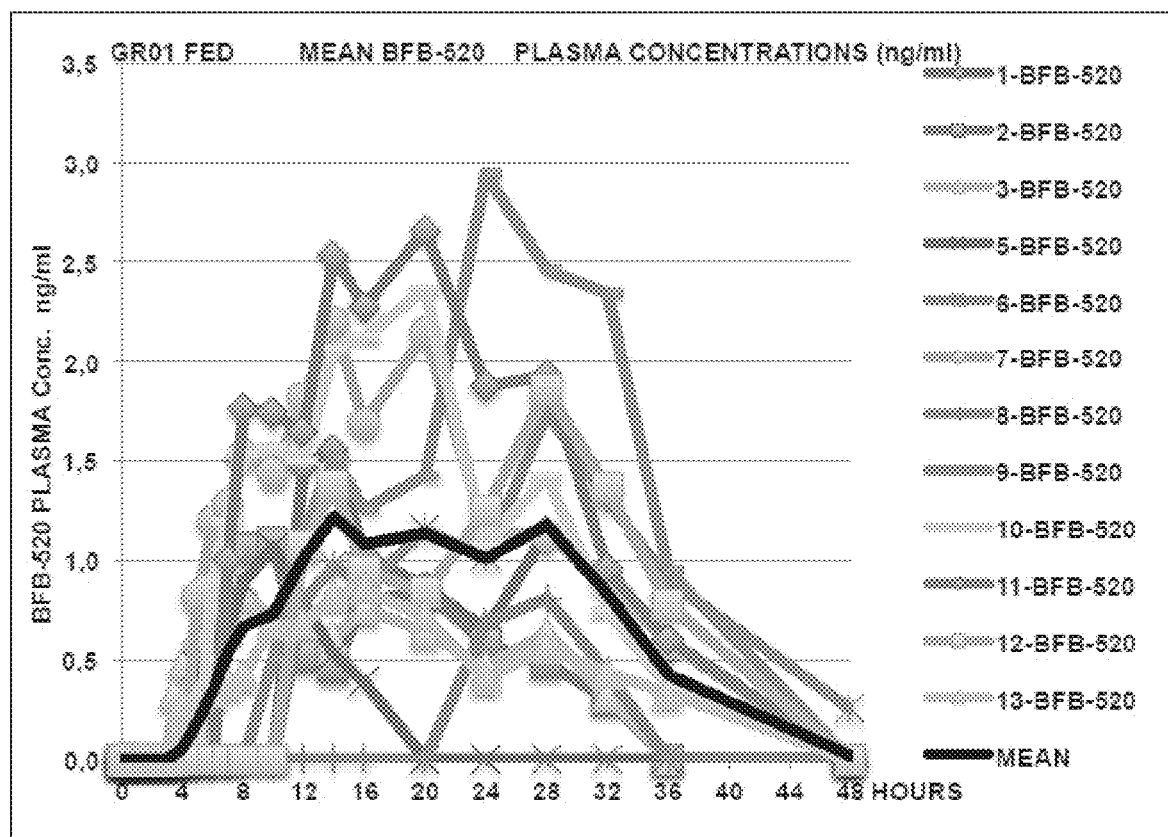

FIG. 25 is a graph of BFB-520 plasma concentrations time profile for subjects administered GR-01 tablets in fed state. The time profile is through 48 hours.

Figure 26:
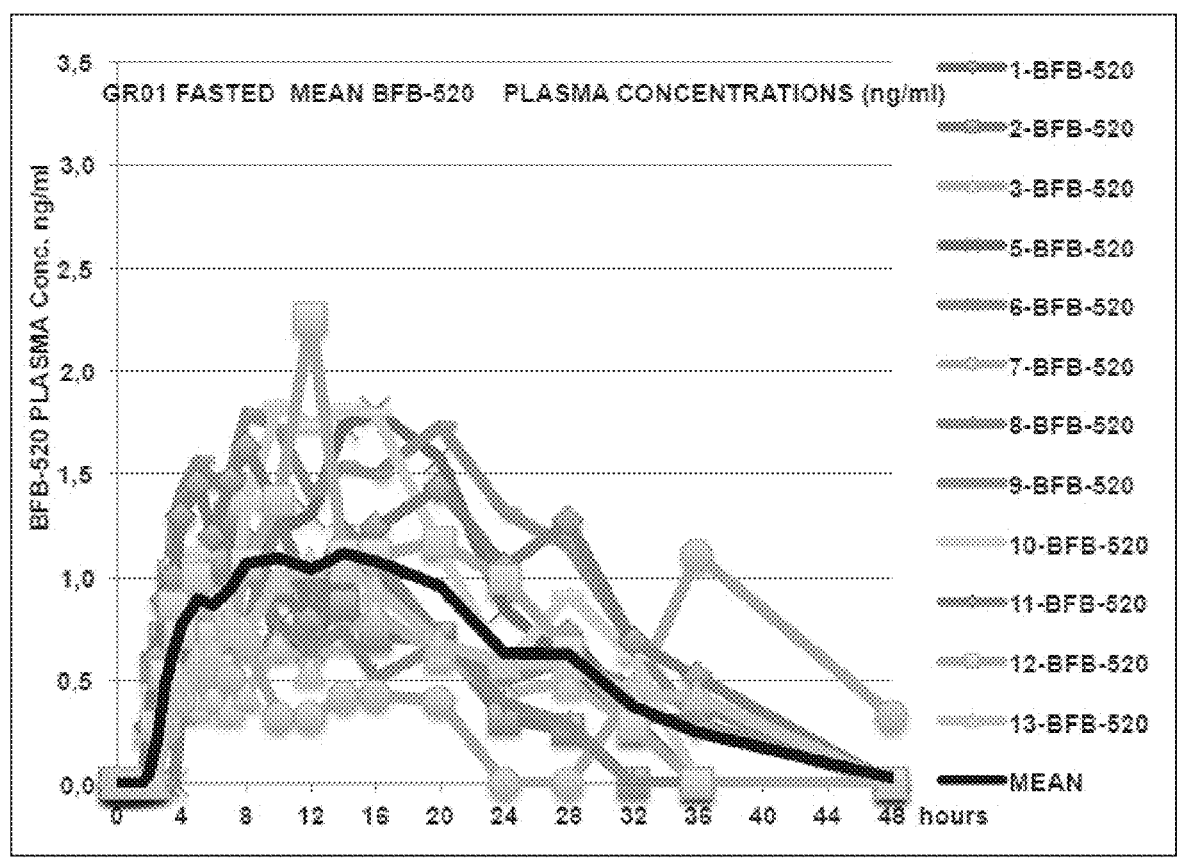

FIG. 26 is a graph of BFB-520 plasma concentrations time profile for subjects administered GR-01 tablets in fasted state. The time profile is through 48 hours.

Figure 27:
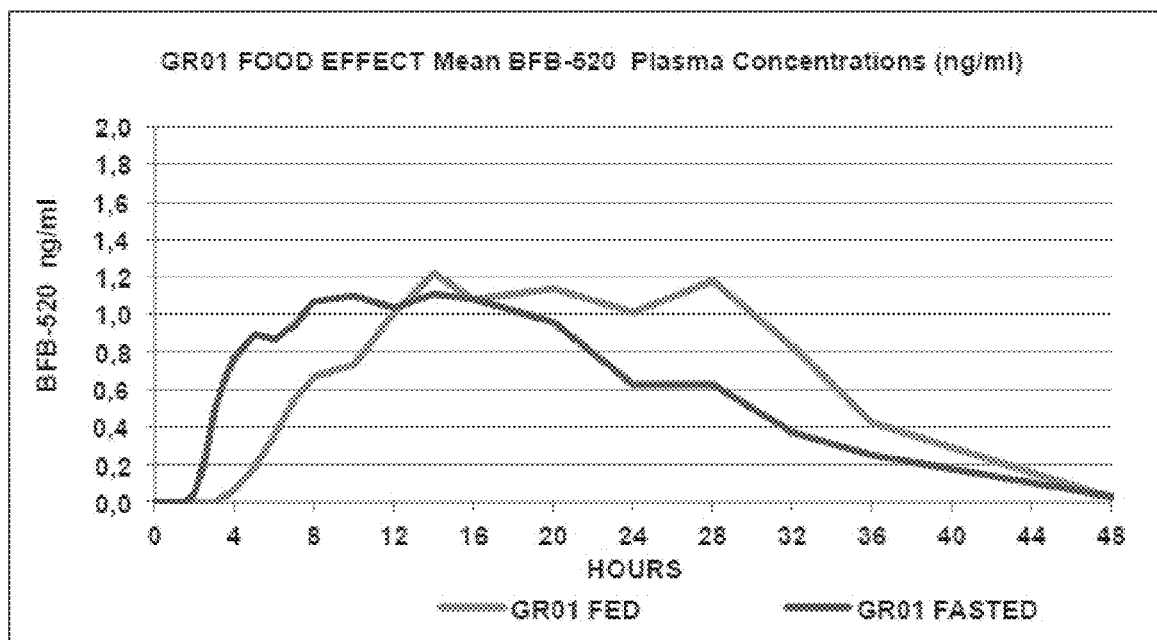

FIG. 27 is graph comparing mean BFB-520 plasma concentrations time profile for subjects administered GR-01 tablets in fed or fasted state. The time profile is through 48 hours.

Figure 28:
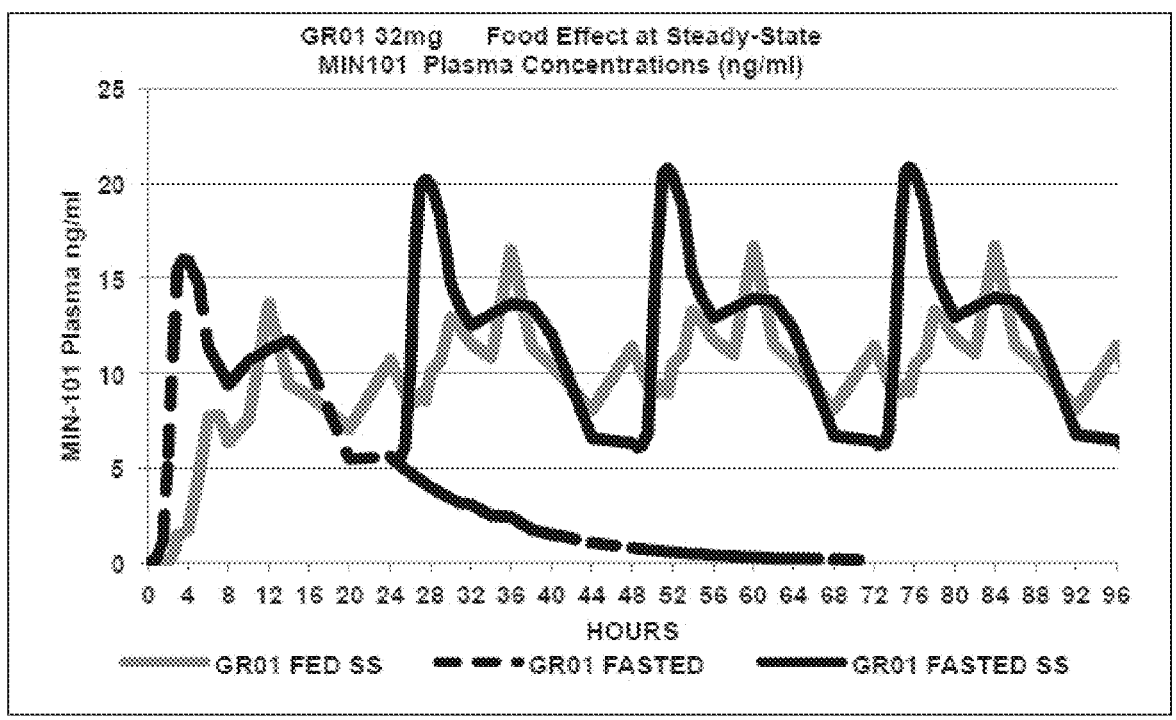
Figure 28:
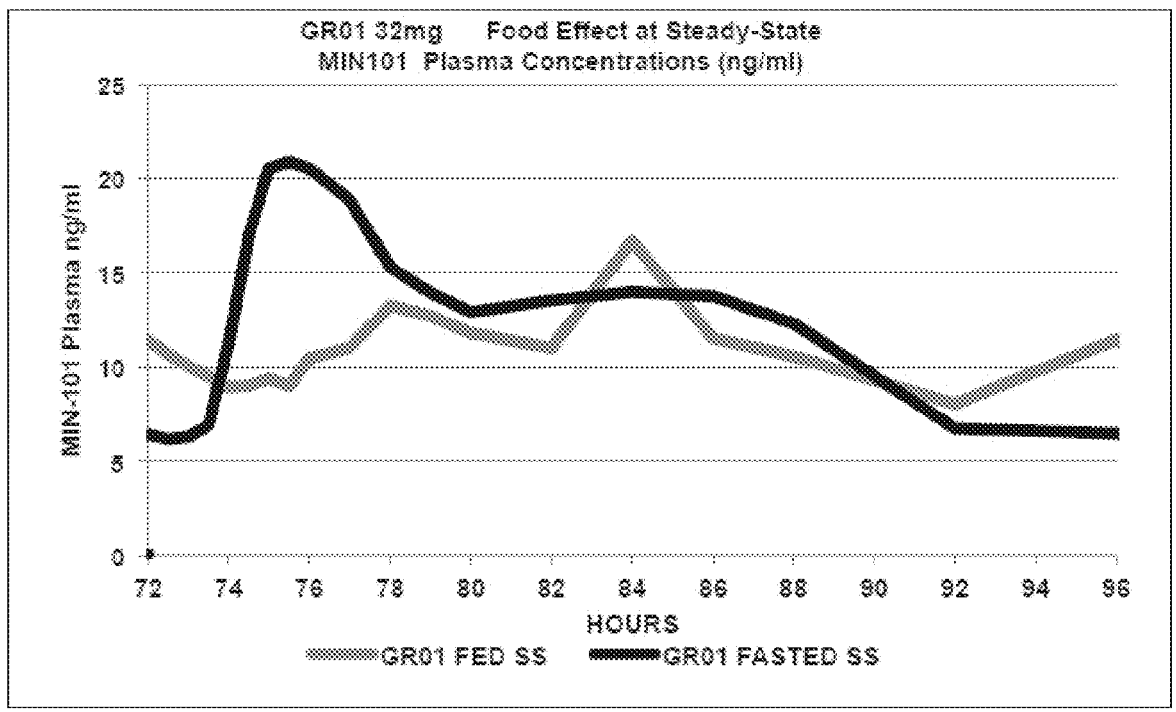

FIG. 28 is a pair of graphs of predicted Compound (I) steady state plasma concentrations time profile for subjects administered 4 daily doses of a GR-01 tablet (32 mg) based on actual data observed following Day 1 dosing in fed or fasted state. The time profile is through 96 hours.

Figure 29:
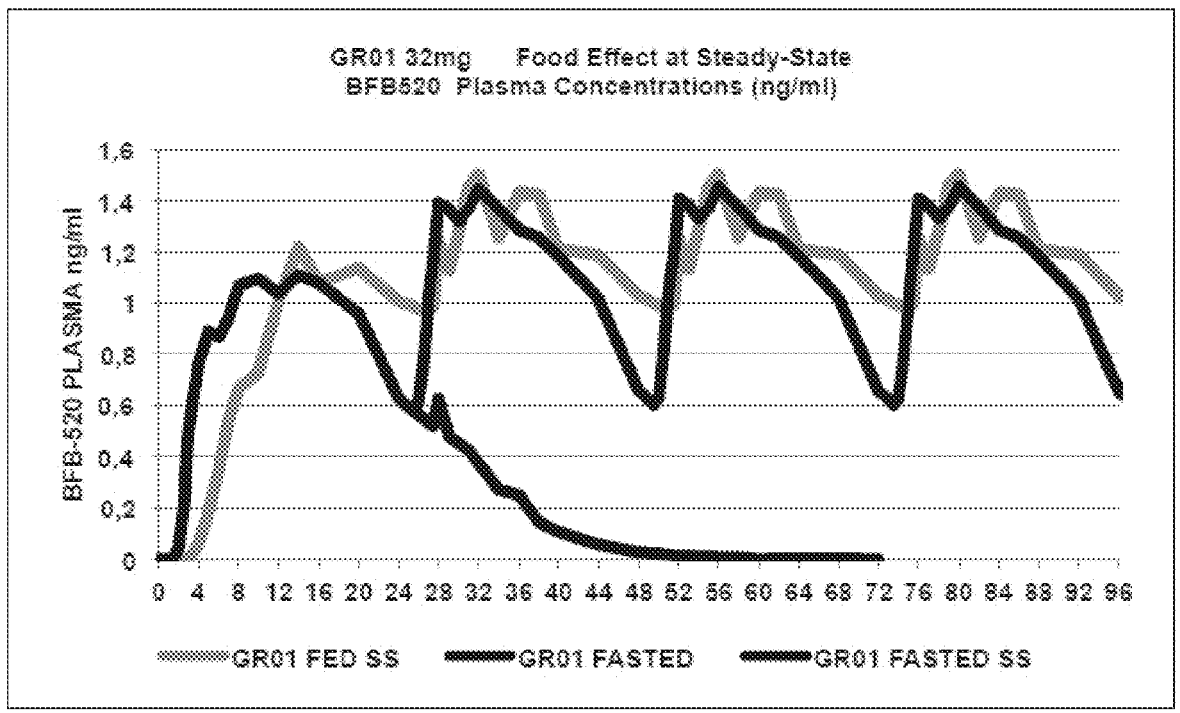
Figure 29:
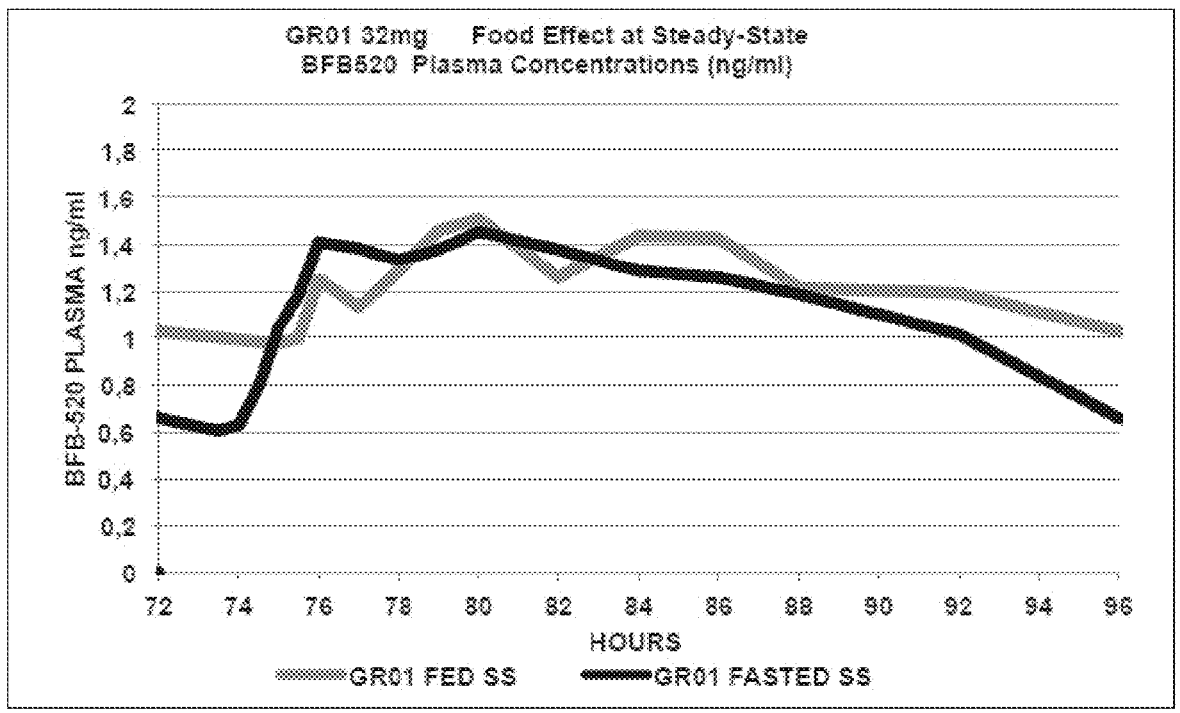

FIG. 29 is a pair of graphs of predicted BFB-520 steady state plasma concentrations time profile for subjects administered 4 daily doses of a GR-01 tablet (32 mg) based on actual data observed following Day 1 dosing in fed or fasted state. The time profile is through 96 hours.

Figure 30:
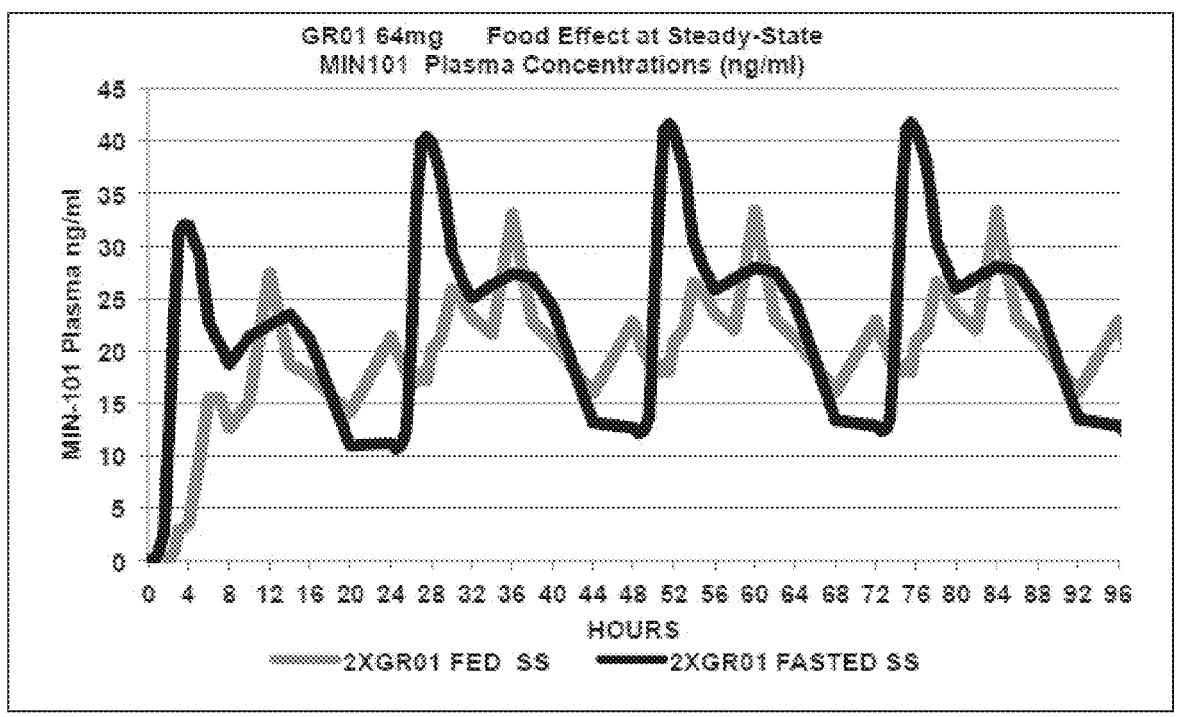
Figure 30:
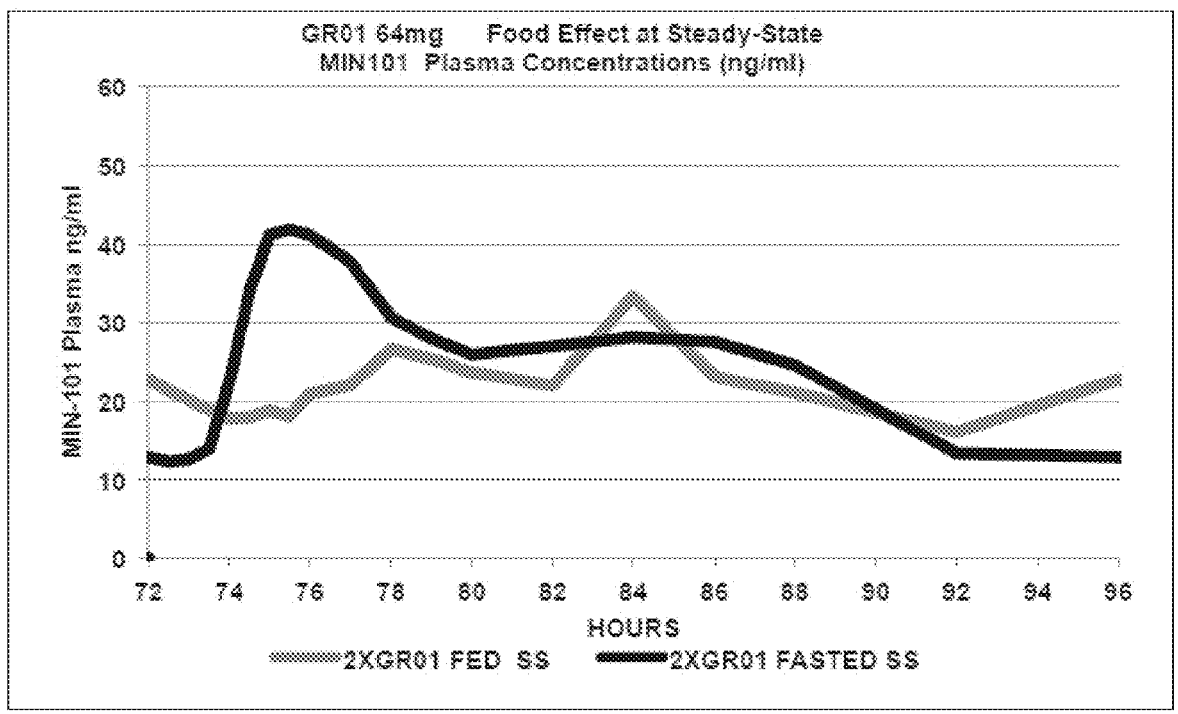

FIG. 30 is a pair of graphs of predicted Compound (I) steady state plasma concentrations time profile for subjects administered 4 daily 64 mg (2×32 mg) doses of a GR-01 tablet in fed or fasted state. The time profile is through 96 hours.

Figure 31:
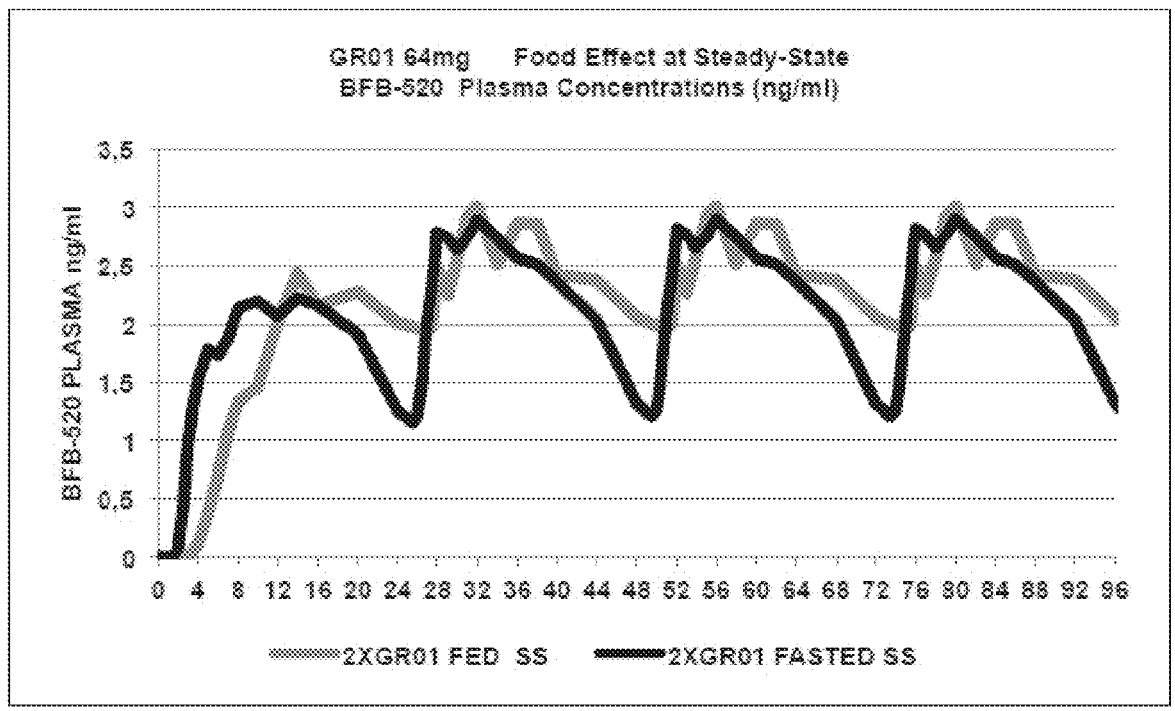
Figure 31:
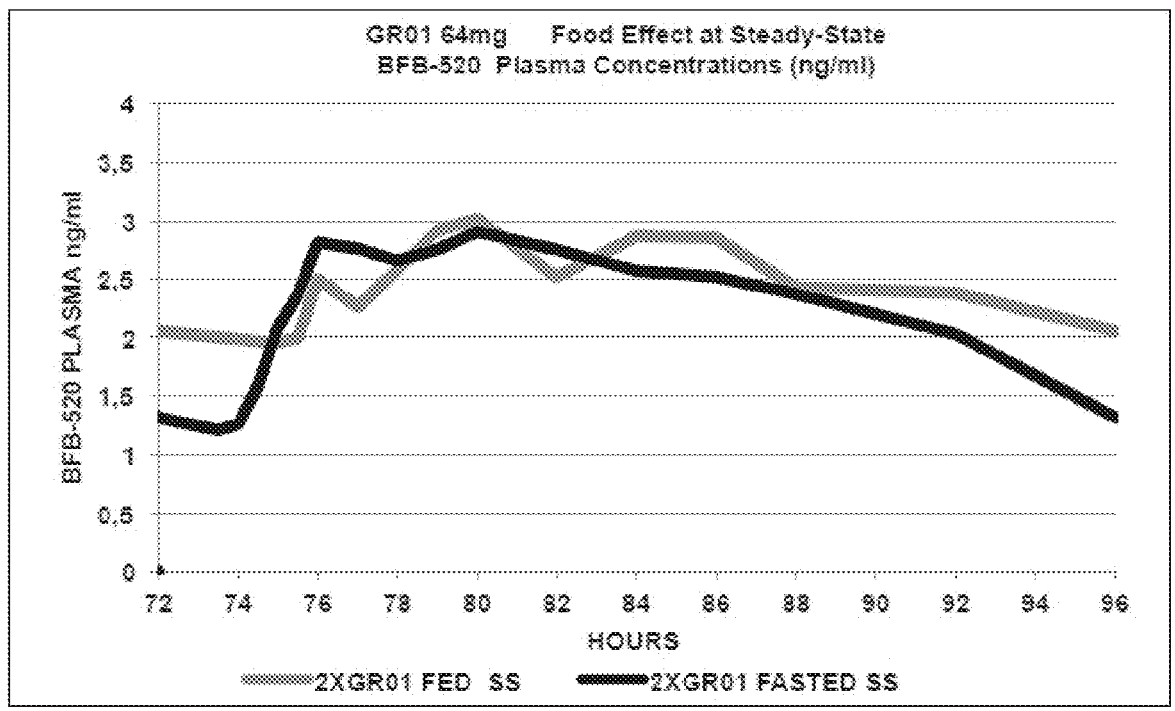

FIG. 31 is a pair of graphs of predicted BFB-520 steady state plasma concentrations time profile for subjects administered 4 daily 64 mg (2×32 mg) doses of a GR-01 tablet (64 mg) in fed or fasted state. The time profile is through 96 hours.

DETAILED DESCRIPTION

The present disclosure relates to novel gastro-resistant CR oral dosage forms comprising Compound (I) or a pharmaceutically acceptable salt and/or solvate thereof, bulk compositions and processes for manufacturing the dosage forms, and use of the dosage forms for therapeutic treatment of patients suffering from various disorders and conditions.

In one embodiment, the present disclosure relates to novel gastro-resistant CR oral dosage forms comprising Compound (I), or a pharmaceutically acceptable salt and/or solvate thereof, wherein upon oral administration to a subject, the $C_{max}$ of Compound (I) and its metabolite, BFB-520, are reduced while the $AUC_{(0-tau)}$ is maintained compared to previously disclosed formulations and/or dosage forms, e.g., those as disclosed in U.S. Pat. No. 9,458,130.

In one embodiment, the present disclosure relates to novel gastro-resistant CR oral dosage forms comprising Compound (I), or a pharmaceutically acceptable salt and/or solvate thereof, wherein upon oral administration to a subject, similar AUC-based exposure of Compound (I) is maintained compared to a previous study with previously disclosed formulations and/or dosage forms, e.g., those as disclosed in U.S. Pat. No. 9,458,130, which achieved its primary endpoint of improving negative symptoms in patients with schizophrenia with both doses tested, 64 mg and 32 mg.

In one embodiment, the present disclosure relates to novel gastro-resistant CR oral dosage forms comprising Compound (I) or a pharmaceutically acceptable salt and/or solvate thereof, wherein upon oral administration to a subject, the $t_{1/2}$ of Compound (I) is prolonged compared to previously disclosed formulations and/or dosage forms, e.g., those as disclosed in U.S. Pat. No. 9,458,130.

In one embodiment, the present disclosure relates to novel gastro-resistant CR oral dosage forms comprising Compound (I) or a pharmaceutically acceptable salt and/or solvate thereof, wherein upon oral administration to a subject, the $C_{max}$ of BFB-520 in the subject's plasma is reduced to promote drug safety.

In one embodiment, the present disclosure relates to novel gastro-resistant CR oral dosage forms comprising Compound (I) or a pharmaceutically acceptable salt and/or solvate thereof, wherein upon oral administration to a subject, the $C_{max}$ of BFB-520 is reduced by about 30% or more (e.g., 30%, 35%, or 40%) compared to previously disclosed formulations and/or dosage forms, e.g., those as disclosed in U.S. Pat. No. 9,458,130.

In one embodiment, the reduction of the $C_{max}$ of BFB-520 in the subject leads to a reduction in the potential for transient QTc increases observed in a previous study at the higher dose but not at the lower dose. In one example, administration of novel gastro-resistant CR oral dosage forms described herein comprising Compound (I), or a pharmaceutically acceptable salt and/or solvate thereof, does not result in an observable QTc prolongations.

In one embodiment, the present disclosure relates to novel gastro-resistant CR oral dosage forms comprising Compound (I) or a pharmaceutically acceptable salt and/or solvate thereof, wherein the administration of the dosage form does not result in an observable food effect, i.e., the administration of the dosage form may occur with or without food without changing its pharmacokinetic properties.

In one embodiment, the present disclosure relates to novel gastro-resistant CR oral dosage forms comprising Compound (I) or a pharmaceutically acceptable salt and/or solvate thereof, wherein the dosage forms comprising Compound (I) retain previously established overall safety and tolerability profiles.

The novel gastro-resistant CR oral dosage forms disclosed herein allow for the delivery of Compound (I) to a lower part of the gastrointestinal tract, which unexpectedly reduced the highest concentration of BFB-520. This unexpected pharmacokinetic effect resulted in no observable QTc prolongations in the subjects who were administered these novel gastro-resistant CR oral dosage forms.

Definitions and Abbreviations

The terms used herein have their ordinary meaning and the meaning of such terms is independent at each occurrence thereof. Notwithstanding the foregoing, and except where stated otherwise, the following definitions apply throughout the specification and claims.

Chemical names, common names, and chemical structures may be used interchangeably to describe the same structure. If a chemical compound is referred to using both a chemical structure and a chemical name and an ambiguity exists between the structure and the name, the structure is understood to predominate.

All references to Compound (I) herein include all pharmaceutically acceptable salts (such as MIN-101) and/or all solvates (e.g., including hydrates) and alternative physical forms thereof unless otherwise indicated. All doses recited herein are based on the molecular weight of the free base Compound (I), which is 366.43 g/mole, rather than the molecular weight of the pharmaceutically acceptable salt or solvate (e.g., hydrate) thereof or any excipients in the composition, unless otherwise indicated.

All amounts of a component of an oral dosage form described herein that are indicated based on % w/w refer to the total weight of the oral dosage form, unless otherwise indicated.

The term "about" as part of a quantitative expression such as "about X", includes any value that is 10% higher or lower than X, and also includes any numerical value that falls between X−10% and X+10%. Thus, for example, a weight of about 40 g includes a weight of between 36 to 44 g.

"Administration" refers to introducing an agent, such as a compound or dosage form described herein, into a subject. The related terms "administering" and "administration of" (and grammatical equivalents) refer both to direct administration, which may be administration to a subject by a medical professional or by self-administration by the subject, and/or to indirect administration, which may be the act of prescribing a drug such as a dosage form described herein. For example, a physician who instructs a patient to self-administer a drug and/or provides a patient with a prescription for a drug is administering the drug to the patient.

"BFB-520" is a metabolite of Compound (I) and has the structure shown in Formula II below:

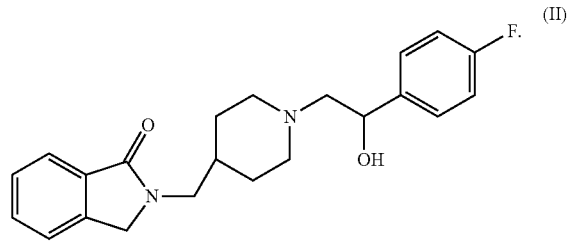 [SMILES: O=C1c2ccccc2CN1CC1CCN(CC(O)c2ccc(F)cc2)CC1]

(II)

"BFB-999" is a metabolite of Compound (I) and the structure of a maleate salt of BFB-999 shown in Formula III below:

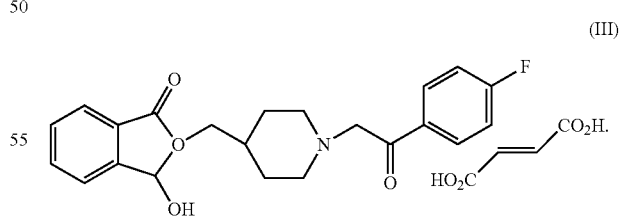

(III)

"Similar PK profile" as used herein with respect to a plasma concentration time profile produced by oral administration to a subject of a dosage form of the disclosure is a plasma concentration time profile that is substantially similar to the target profile shown in FIG. 1 such that a first dosage form comprising Compound (I) that produces the target plasma concentration time profile in FIG. 1 and a second dosage form comprising Compound (I) that produces the similar plasma concentration time profile would result in a PK property, such as AUC, considered to be bioequivalent by a regulatory agency. In an embodiment, the regulatory agency is the U.S. Food and Drug Administration.

"BNSS" is the Brief Negative Symptom Scale.

"Comprising" or "comprises" as applied to a particular dosage form, composition, method or process described or claimed herein means that the dosage form, composition or method includes all of the recited elements in a specific description or claim, but does not exclude other elements. "Consists essentially of" and "consisting essentially of" means that the described or claimed composition, dosage form, method or process does not exclude other materials or steps that do not materially affect the recited physical, pharmacological, pharmacokinetic properties or therapeutic effects of the composition, dosage form, method or process. "Consists of" and "consisting of" means the exclusion of more than trace elements of other ingredients and substantial method or process steps.

"Controlled release" or "CR" as used herein with respect to an oral dosage form of the disclosure means that Compound (I) is released from the dosage form according to a pre-determined profile that may include when and where release occurs after oral administration and/or a specified rate of release over a specified time period.

"Controlled release agent" as used herein with respect to an oral dosage form of the disclosure refers to one or more substances or materials that modulate release of Compound (I) from the dosage form. Controlled release agents may be materials which are organic or inorganic, naturally occurring or synthetic, such as polymeric materials, triglycerides, derivatives of triglycerides, fatty acids and salts of fatty acids, talc, boric acid and colloidal silica.

"CYP2D6 allele" refers to one of over 100 named versions of the CYP2D6 gene that are present in the general population, and typically classified into one of three categories: active (functional); decreased activity (partially active or decreased function) and inactive (non-functional).

Active CYP2D6 alleles include: *1, *2, *2A, *33, *35, *39, *48, and *53.

Decreased activity CYP2D6 alleles include: *9, *10, *17, *29, *41, *49, *50, *54, *55, *59, *69, and *72.

Inactive CYP2D6 alleles include: *3, *4, *5 (deletion), *6, *7, *8, *11, *12, *13, *14A, *14B, *15, *18, *19, *20, *21, *38, *40, *42, *44, *56, *56A, *56B, and *68.

"CYP2D6 Extensive Metabolizer (EM) genotype" as applied to a subject means the subject has a CYP2D6 which results in CYP2D6 metabolic activity considered as normal. CYP2D6 EM genotypes include combinations of: (a) two active CYP2D6 alleles, (b) one active and one decreased activity CYP2D6 allele, and (c) one active and one inactive CYP2D6 allele.

"CYP2D6 Intermediate Metabolizer (IM) genotype" as applied to a subject means the subject has a CYP2D6 genotype, which results in reduced CYP2D6 metabolic activity. CYP2D6 IM genotypes include combinations of: (a) one inactive and one decreased activity CYP2D6 allele; and (c) two decreased activity CYP2D6 alleles.

"CYP2D6 PM genotype" as applied to a subject means the subject has a positive test result for a CYP2D6 poor metabolizer genotype and thus likely to have no CYP2D6 activity. A CYP2D6 PM genotype is 2 inactive alleles.

"CYP2D6 UM genotype" as applied to a subject means the subject has a positive test result for a CYP2D6 ultrarapid metabolizer genotype and thus likely to have higher than average CYP2D6 activity. A CYP2D6 UM genotype is 3 or more active alleles.

"Enteric coating" as used herein with respect to a dosage form of the disclosure refers to a pH-dependent material that surrounds a core comprising Compound (I) and which remains substantially intact in the acid environment of the stomach, but which dissolves in the pH environment of the intestines.

In one embodiment, in the dosage forms of the disclosure the filler is selected from the group consisting of microcrystalline cellulose, lactose monohydrate, sucrose, glucose, and sorbitol.

"Glidant" as used herein refers to a substance used to promote powder flow by reducing interparticle cohesion. In one embodiment, in the dosage forms of the disclosure the glidant is selected from the group consisting of silica colloidal anhydrous, starch, and talc.

"Lubricant" as used herein refers to a substance that prevents ingredients from sticking and/or clumping together in the machines used in preparation of the dosage forms of the disclosure. In one embodiment, in the dosage forms of the disclosure the lubricant is selected from the group consisting of magnesium strearate, steric acid, and vegetable stearin.

"Fasted condition" or "fasted state" as used to describe a subject means the subject has not eaten for at least 4 hours before a time point of interest, such as the time of administering a dosage form described herein. In an embodiment, a subject in the fasted state has not eaten for at least any of 6, 8, 10 or 12 hours prior to administration of a dosage form described herein.

"Fed condition" or "fed state" as used to describe a subject herein means the subject has eaten less than 4 hours before a time point of interest, such as the time of administering a dosage form described herein. In an embodiment, a subject in the fed state has not eaten for at least any of 3, 2, 1 or 0.5 hours prior to administration of a dosage form described herein.

"Gastro-resistant" or "GR" as applied to a CR oral dosage form described herein means that release of Compound (I) in the stomach of a subject shall not exceed 5%, 2.5%, 1% or 0.5% of the total amount of Compound (I) in the dosage form.

"MIN-101" is a code name for 1H-Isoindol-1-one, 2-[[1-[2-(4-Fluorophenyl)-2-oxoethyl]-4-piperidinyl]methyl]-2,3-dihydro-, hydrochloride, hydrate (1:1:2), with an alternative name of 2-{1-[2-(4-Fluorophenyl)-2-oxoethyl]piperidin-4-ylmethyl}-2,3-dihydroisoindol-1-one hydrochloride dihydrate.

"Oral dosage form" as used herein refers to a pharmaceutical drug product that contains a specified amount (dose) of Compound (I) as the active ingredient, or a pharmaceutically acceptable salt and/or solvate thereof, and inactive components (excipients), formulated into a particular configuration that is suitable for oral administration, such as a tablet or capsule.

"Pharmaceutically acceptable salt" as used herein with respect to Compound (I), means a salt form of Compound (I) as well as hydrates of the salt form with one or more water molecules present. Such salt and hydrated forms retain the biological activity of Compound (I) and are not biologically or otherwise undesirable, i.e., exhibit minimal, if any, toxicological effects. In an embodiment, the pharmaceutically acceptable salt of Compound (I) has a single HCl molecule and two water molecules, i.e., 1H-Isoindol-1-one, 2-[[1-[2-(4-Fluorophenyl)-2-oxoethyl]-4-piperidinyl]methyl]-2,3-dihydro-, hydrochloride, hydrate (1:1:2).

"PANSS" is Positive and Negative Syndrome Scale.

"Pharmacokinetic parameter" means a measurement or characteristic that describes the pharmacokinetic properties of a compound of interest. PK parameters used herein are defined below.

"AUC" is total area under the plasma concentration-time curve, which is a measure of exposure to a compound of interest, and is the integral of the concentration-time curve after a single dose or at steady state. AUC is expressed in units of ng·H/mL (ng×H/mL).

"$AUC_{(0-4\ H)}$" means the AUC from 0 hours to 4 hours after administration of a single dose.

"$AUC_{(0-24\ H)}$" means the AUC from 0 hours to 24 hours after administration of a single dose.

"$AUC_{last}$" means the AUC from time 0 to the last quantifiable concentration ($C_{last}$).

"$AUC_{(0-tau)}$" means the AUC from 0 hours to the end of a dosing interval.

"$C_{max}$" means the observed maximum (peak) plasma concentration of a specified compound, such as Compound (I), after administration of a dose of a composition comprising the compound. In an embodiment, the $C_{max}$ is measured after 2 or more doses of the composition. In an embodiment, the $C_{max}$ is measured when the specified compound reaches steady-state.

"$C_{min}$" means the observed minimum plasma concentration of a specified compound, such as Compound (I), after administration of a dose of a composition comprising the compound. In an embodiment, the $C_{max}$ is measured after 2 or more doses of the composition. In an embodiment, the $C_{max}$ is measured when the specified compound reaches steady-state.

"$C_{ss}$" means the concentration at the steady state.

"$C_{ave}$" means the average concentration which is the AUC over time ratio.

"$C_p$" means the plasma concentration of a specified compound, such as Compound (I), at any time T after administration of a dose of a composition comprising the compound.

"$C_{p(last)}$" means the last measured $C_p$, with reference to the time of collection of the last of a series of blood samples for assay for the specified compound.

"$C_{p(T)}$" means the $C_p$ at the specified time; thus $C_{p(4\ H)}$ and $C_{p(12\ H)}$ are the $C_p$ at 4 hours and 24 hours, respectively.

"H" means hours.

"PK" is pharmacokinetic(s).

"Steady-state" means the rate of absorption of a specified compound of interest such as Compound (I) is equal to the rate of elimination of the compound.

"Tau" means a dosing interval (H). For example, for once daily dosing, tau is 24 H, $T_{max}$ means the time to maximum (or peak) plasma or serum concentration of a specified therapeutic compound after administration of a single dose of a composition comprising the compound and before administration of a second dose.

$V_{max}$ means the maximum absorption rate (mg/H).

"Subject" and "patient" may be used interchangeably herein, and refer to a human of any age.

"Therapeutically effective amount", as used herein with respect to therapeutic uses of a dosage form comprising Compound (I) or pharmaceutically salt and/or solvate thereof, means an amount of the free base (Compound (I)) that is sufficient to treat, ameliorate, or prevent a specified disease, disease symptom, disorder or condition, or to exhibit a detectable therapeutic or inhibitory effect. The effect can be detected by any assay method known in the art.

The effective amount for a particular subject may depend upon the subject's body weight, size, and health; the nature and extent of the condition; and whether additional therapeutics are to be administered to the subject. Therapeutically effective amounts for a given situation can be determined by routine experimentation that is within the skill and judgment of the clinician.

"Treat", "treating", "treatment" and similar terms, as used herein with respect to one or more specified disease symptoms shall include the management and care of a patient for the purpose of improving one or more of the specified symptoms, and include administration of a gastro-resistant, controlled release oral dosage form described herein at a dosing frequency and for a treatment period that are sufficient to prevent the onset of one or more of the symptoms, reduce the frequency, intensity or severity of one or more of the symptoms, delay or avoid the development of additional symptoms, or any combination of these treatment objectives. In an embodiment, the effect of treatment with a dosage form of the present disclosure is assessed by comparing the severity of the subject's symptoms at baseline (e.g., prior to treatment) and after at least one treatment period. In an embodiment, the treatment period is at least one week, at least two weeks, at least four weeks, at least six weeks, at least eight weeks, at least 10 weeks or at least twelve weeks or more. In an embodiment, the symptoms to be treated is at least one negative symptom in a schizophrenic or non-schizophrenic patient, the dosage form comprises 32 mg of Compound (I), the dosing frequency is once daily, and the treatment period is at least eight weeks.

Summary of Gastro-Resistant Controlled Release (CR) Oral Dosage Forms

In one embodiment, the present disclosure relates to a gastro-resistant, CR oral dosage form comprising between about 4 mg to about 100 mg of Compound (I) or an equivalent amount of a pharmaceutically acceptable salt and/or solvate of Compound (I), wherein the gastro-resistant, CR oral dosage form is selected from the group consisting of a 32 mg CR GR-01 tablet, 32 mg CR GR-02 tablet, a 32 mg CR GR-01/B tablet, a 64 mg CR GR-01/B tablet, a 32 mg CR GR-01/C tablet, and a 64 mg CR GR-01/C tablet.

In one embodiment, the 32 mg CR GR-01 tablet has the following composition:

| Composition | CR GR-01 tablet | | Function |
|---|---|---|---|
| | % w/w | mg/tablet | |
| MIN-101[1] | 12.09 | 38.40 | Active ingredient |
| Hypromellose (Metolose ® 90SH 100 SR) | 9.45 | 30.00 | Controlled release excipient |
| Hypromellose (Methocel ™ K100M CR) | 22.67 | 72.00 | Controlled release excipient |
| Microcrystalline Cellulose | 29.95 | 95.10 | Filler |
| Lactose Monohydrate | 18.89 | 60.00 | Filler |
| Silica Colloidal Anhydrous | 0.47 | 1.50 | Glidant |
| Magnesium stearate | 0.94 | 3.00 | Lubricant |
| Total (Core Tablet) | 94.47 | 300.00 | |
| Eudragit L30D55 | 4.72 | 15.00 | Controlled release excipient |
| Plasacryl HTP20 | 0.80 | 2.55 | Anti-tacking agent |
| Total | 100.00 | 317.55 | |

[1] Salt correction factor of 1.2 applied
NA: Not Applicable

In one embodiment, the 32 mg CR GR-02 tablet has the following composition:

| Composition | % w/w | mg/tablet | Function |
|---|---|---|---|
| MIN-101[1] | 11.98 | 38.40 | Active ingredient |
| Hypromellose (Methocel™ K15M CR) | 9.36 | 30.00 | Controlled release excipient |
| Hypromellose (Methocel™ K100M CR) | 22.46 | 72.00 | Controlled release excipient |
| Microcrystalline Cellulose | 29.67 | 95.10 | Filler |
| Lactose Monohydrate | 18.72 | 60.00 | Filler |
| Silica Colloidal Anhydrous | 0.47 | 1.50 | Glidant |
| Magnesium stearate | 0.94 | 3.00 | Lubricant |
| Total (Core Tablet) | 93.59 | 300.00 | |
| Eudragit L30D55 | 4.68 | 15.00 | Controlled release excipient |
| Plasacryl HTP20 | 0.80 | 2.55 | Anti-tacking agent |
| Surelease E-7-19040 | 0.94 | 3.00 | Controlled release excipient |
| Total | 100.00 | 320.55 | |

[1]Salt correction factor of 1.2 applied
NA: Not Applicable

In one embodiment, the 32 mg CR GR-01/B tablet has the following composition:

| Component/Ingredient | GR-01/B-32 mg mg/tablet | % (w/w) |
|---|---|---|
| MIN-101[1] | 38.40 | 12.11 |
| Hypromellose (METHOCEL™ K100LV CR) | 30.00 | 9.45 |
| Hypromellose (Methocel™ K100M CR) | 72.00 | 22.67 |
| Microcrystalline Cellulose | 96.60 | 30.42 |
| Lactose | 60.00 | 18.89 |
| Silica Colloidal Anhydrous | 1.50 | 0.47 |
| Magnesium stearate | 1.50 | 0.47 |
| Eudragit L30D55 | 15.0 | 4.72 |
| Plasacryl HTP20 | 2.55 | 0.80 |
| Total | 317.55 | 100.00 |

[1]Salt correction factor of 1.2 applied

In one embodiment, the 32 mg CR GR-01/C tablet has the following composition:

| Component/Ingredient | GR-01/C-32 mg mg/tablet | % (w/w) |
|---|---|---|
| MIN-101[1] | 38.40 | 12.11 |
| Hypromellose (METHOCEL™ K100LV CR) | 30.00 | 9.45 |
| Hypromellose (Methocel™ K100M CR) | 72.00 | 22.67 |
| Microcrystalline Cellulose | 95.10 | 29.95 |
| Lactose | 60.00 | 18.89 |
| Silica Colloidal Anhydrous | 1.50 | 0.47 |
| Magnesium stearate | 3.00 | 0.94 |
| Eudragit L30D55 | 15.0 | 4.72 |
| Plasacryl HTP20 | 2.55 | 0.80 |
| Total | 317.55 | 100.00 |

In one embodiment, the 64 mg CR GR-01/B tablet has the following composition:

| Component/Ingredient | GR-01/B-64 mg mg/tablet | % (w/w) |
|---|---|---|
| MIN-101[1] | 76.8 | 24.19 |
| Hypromellose (METHOCEL™ K100LV CR) | 30.00 | 9.45 |
| Hypromellose (Methocel™ K100M CR) | 72.00 | 22.67 |
| Microcrystalline Cellulose | 77.40 | 24.37 |
| Lactose | 40.80 | 12.85 |
| Silica Colloidal Anhydrous | 1.50 | 0.47 |
| Magnesium stearate | 1.50 | 0.47 |
| Eudragit L30D55 | 15.0 | 4.72 |
| Plasacryl HTP20 | 2.55 | 0.80 |
| Total | 317.55 | 100.00 |

[1]Salt correction factor of 1.2 applied

In one embodiment, the 64 mg CR GR-01/C tablet has the following composition:

| Component/Ingredient | GR-01/C-64 mg mg/tablet | % (w/w) |
|---|---|---|
| MIN-101[1] | 76.8 | 24.19 |
| Hypromellose (METHOCEL™ K100LV CR) | 30.00 | 9.45 |
| Hypromellose (Methocel™ K100M CR) | 72.00 | 22.67 |
| Microcrystalline Cellulose | 75.90 | 23.91 |
| Lactose | 40.80 | 12.85 |
| Silica Colloidal Anhydrous | 1.50 | 0.47 |
| Magnesium stearate | 3.00 | 0.94 |
| Eudragit L30D55 | 15.0 | 4.72 |
| Plasacryl HTP20 | 2.55 | 0.80 |
| Total | 317.55 | 100.00 |

Design and Manufacture of Gastro-Resistant Controlled Release Oral Dosage Forms

An object of the present disclosure is to provide a gastro-resistant, controlled release oral dosage form comprising between about 4 mg to about 100 mg of Compound (I) or an equivalent amount of a pharmaceutically acceptable salt and/or solvate of Compound (I). The dosage form is formulated to exhibit, upon oral administration to a subject, a specific, desired release profile for Compound (I) which reduces the maximum plasma concentrations of BFB-520 while providing a therapeutically effective amount of Compound (I) during one or more dosing intervals. This desired release profile is achieved in two ways: (a) delay release of Compound (I) until after gastric emptying pushes the dosage form to the small intestine and then (b) provide sustained release of at least about 90%, 95% or 100% of the amount of Compound (I) in the dosage form at a rate that provides a plasma PK profile which comprises a $T_{max}$ for Compound (I) of between about 4 and about 22 hours.

This in vivo release profile for Compound (I) is designed to reduce the subject's plasma levels of BFB-520 below a threshold that is correlated with a greater risk for QT prolongation. In an embodiment, the threshold is a $C_{max}$ for BFB-520 that is below 5.0 ng/mL, below 4.5 ng/mL, below 4.0 ng/mL, below 3.5 ng/mL, below 3.0 ng/mL, below 2.5 ng/mL, below 2.0 ng/mL, below 1.5 ng/mL, below 1.0 ng/mL, or below 0.5 ng/mL.

In some embodiments, the plasma PK profile for Compound (I) is further characterized in terms of one or more additional PK parameters, such as $C_{max}$, $AUC_{(0-tau)}$, $C_{min}$ and other PK parameters defined above. It will be understood by the skilled person that the values for some of these additional PK parameters will depend, at least in part, on the amount of Compound (I) in the dosage form.

The values for the $T_{max}$ and other plasma PK parameters produced by a dosage form described herein may exhibit some inter-individual variation within a population of subjects. Thus, in some embodiments, certain plasma PK parameters are expressed as mean values determined for a population of at least 2, 4, 8, 16 or more subjects. In an embodiment, the population consists of healthy volunteers. In an embodiment, each subject in the population has a positive test for an EM genotype. In an embodiment, each subject in the population has a positive test for an EM genotype or an IM genotype. In an embodiment, each subject in the population has a positive test for an IM genotype or a PM genotype. In an embodiment, each subject in the population has a positive test for a PM genotype.

Compound (I) may be synthesized using standard synthetic methods and procedures for the preparation of organic molecules and functional group transformations and manipulations, including the use of protective groups, as can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. A method for preparing Compound (I) is described in U.S. Pat. No. 7,166,617, the contents of which are incorporated herein in their entirety.

In an embodiment, the drug substance form of Compound (I) used in the dosage form is a dihydrate of a hydrochloride salt of Compound (I), which has the chemical name 1H-Isoindol-1-one, 2-[[1-[2-(4-Fluorophenyl)-2-oxoethyl]-4-piperidinyl]methyl]-2,3-dihydro-, hydrochloride, hydrate (1:1:2), which has a molecular formula of $C_{22}H_{23}FN_2O_2$, HCl, $2H_2O$ and a molecular weight of 438.92. Methods for preparing this Compound (I) drug substance are described in U.S. Pat. Nos. 7,166,617 and 9,458,130. An amount of this drug substance that is equivalent to a specified amount of free base may be calculated by multiplying the specified amount of Compound (I) by 1.2; thus, 38.4 mg of this drug substance is equivalent to 32.0 mg of Compound (I).

In an embodiment, the delayed and sustained-release properties of the CR oral dosage form may be provided by encasing a sustained-release composition comprising the desired amount of Compound (I), or a pharmaceutically acceptable salt and/or solvate thereof, within an enteric coating.

Various physical and chemical approaches for designing sustained-release compositions are well known in the art. Any sustained-release composition that is capable of releasing Compound (I) to provide the in vivo plasma PK profile described herein may be used to prepare a dosage form of the disclosure. In an embodiment, the sustained-release composition comprises at least one polymeric material that modulates release of Compound (I). Suitable polymeric materials include, but are not limited to, cross-linked polyvinylpyrrolidone, hydroxypropylmethylcellulose, hydroxypropylcellulose, cross-linked sodium carboxymethylcellulose, carboxymethyl starch, starch and derivatives thereof, acrylic and methacrylic acid polymers and copolymers, polyesters, polyanhydrides, polymethylvinylether/anhydride copolymers, potassium methacrylate-divinylbenzene copolymers, polyvinylalcohols, glucan, scleroglucan, mannan, betacyclodextrins and cyclodextrin derivatives containing linear and/or branched polymeric chains. In one embodiment, the polymeric material is a hydroxyproplymethocellulose.

In an embodiment, a mixture of a low viscosity and a high viscosity hypromellose is used as the controlled release agent in the sustained-release composition. The viscosity properties of suitable hypromelloses may be determined in a 2% by weight solution in water at 20° C. as described in USP Hypromellose Monograph, Official Dec. 1, 2016, which is available at http://www.usp.org/usp-nf/official-text/stage-6/hypromellose-2015-11-20.

The enteric coating, which typically comprises a pH-sensitive polymer, begins to dissolve in an aqueous solution at pH greater than 5.5, and in one embodiment, begins to dissolve in an aqueous solution at pH greater than 6.0. In one embodiment, the pH-sensitive polymer begins to dissolve in an aqueous solution at pH greater than 6.5. In one embodiment, the pH-sensitive polymer begins to dissolve in an aqueous solution at pH 6.7. In an embodiment, the amounts of Compound (I) released in the stomach from a gastro-resistant CR dosage form administered to subjects in a fed state or a fasted state are about the same (e.g., less than 5%, less than 2% or less than 1% difference).

The composition and thickness of the enteric coating are typically chosen to substantially maintain its integrity in the stomach, while allowing substantially all of the enteric coating to dissolve after the dosage form leaves the stomach. In an embodiment, substantially all of the enteric coating dissolves within 15 minutes, 30 minutes, 1 hour or 2 hours after the dosage form leaves the stomach.

The design and preparation of gastro-resistant enteric coatings are well-known in the formulation art. Polyacids having an appropriate pKa range may be used to prepare enteric coatings. Non-limiting examples of suitable enteric coating materials are polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters. For example, the enteric coating may comprise a copolymer based on methacrylic acid and ethyl acrylate marketed as EUDRAGIT® L 30 D-55 by Evonik Industries AG. In an embodiment, the coating comprises a mixture of (i) EUDRAGIT® L 30 D-55 at 4.5% to 5.0%, w/w, or about 4.7% w/w and (ii) PlasACRYL™ HTP20 at 0.80% w/w.

In another aspect, the disclosure provides a batch composition and process for manufacturing a gastro-resistant CR oral dosage form described herein. In an embodiment, a batch composition for manufacturing a 32 mg-dosage form comprises the components listed in Table 4 in Example 4 below. In another embodiment, a batch composition for manufacturing a 32 mg-dosage form comprises the components listed in Table 5 in Example 4 below. or Table in Example 4 below. Examples of processes that are suitable for manufacturing these 32-mg dosage forms are described in flowcharts 1 and 2 of Example 4.

Analytical Methods

A. In Vitro Dissolution Testing

To assess the potential for a proposed gastro-resistant CR oral dosage form comprising Compound (I) to produce the desired in in vivo release profile and plasma PK provide for Compound (I), in vitro dissolution testing as described in the Examples below may be performed.

In an embodiment, the dosage form comprises 32 mg and produces cumulative dissolution and dissolution rate profiles that are substantially similar to the target profile, the CR-GR-01 profile or the CR-GR-02 profile shown in FIG. 1 and in Tables 6 and 7 below. In an embodiment, the cumulative dissolution amount and dissolution rate at each time point in substantially similar profiles are within +/−10% of the values for the corresponding time point in the target, CR-GR-01 or CR-GR-02 dissolution profiles shown in Tables 6 and 7.

B. Detection of Compound (I) and BFB-520 in Human Plasma

To assess whether a gastro-resistant CR oral dosage form comprising Compound (I) produces the desired PK profile for one or both of Compound (I) and BFB-520, plasma concentrations of the compound(s) of interest may be determined at various time points after administration of the dosage form to a single subject, but is typically determined in a group of two or more subjects. In an embodiment, PK profile is determined in a group of at least 8, 12, 16 or 20 subjects. In an embodiment, the group comprises healthy male and female subjects. In an embodiment, the number of subjects in the group is chosen to allow a statistically significant assessment of whether the PK profile produced by a test oral dosage form is a bioequivalent PK profile with respect to the PK profile shown in FIG. 1.

An open-label, randomized, 3-treatment sequence, 3-period study to evaluate the PK profile of Compound (I) and its metabolite BFB-520 after single oral administration of 3 formulations of MIN-101 (2 prototypes of CR gastro-resistant (GR) formulations (GR-01 and GR-02) and 1 comparator MR formulation (MR32)) is summarized in Scheme 1 (MIN-101) and Scheme 2 (BFB-520). Full details of these experiments are found in the Examples section.

Scheme 1. Summary of MIN-101 PK Study for MR32, GR-01, and GR-02 Formulations.

MR32 MIN101 DATA AND PARAMETERS
(from n = 12 subjects cross-over)

| CMAX | 29.52 ng/ml | | |
|---|---|---|---|
| AUC | 291.55 H · ng/ml | | TMax 2.4 H |

GR01 MIN101 RELATVIE BIOAVAILABILITY VERSUS MR32
(from n= 12 subjects cross-over)

| CMAX | 19.59 ng/ml | F = 69.9% | |
|---|---|---|---|
| AUC | 284.5 H · ng/ml | F = 101.3% | TMax 6.0 H |

GR02 MIN101 RELATIVE BIOAVAILABILITY VERSUS MR32
(from n = 13 subjects cross-over)

| CMAX | 15.43 ng/ml | F = 54.33% | |
|---|---|---|---|
| AUC | 253.01 H · ng/ml | F = 86.9% | TMax 15.2 H |

Scheme 1. Summary of MIN-101 PK Study for MR32, GR-01, and GR-02 Formulations.

PLASMA CONCENTRATIONS RATE OF MIN101 INCREASE (VMax)

| | MR32 | GR01 | GR02 |
|---|---|---|---|
| VMax ng/ml/H | 26.2 | 11.9 | 2.9 |
| RATIO Test/MR32 | REF | 0.45 | 0.4 |

Scheme 2. Summary of BFB-520 PK Study for MR32, GR-01, and GR-02 Formulations.

MR32 BFB-520 DATA AND PARAMETERS
(from n = 12 subjects cross-over)

| CMAX | 1.91 ng/ml | | |
|---|---|---|---|
| AUC | 30.26 H · ng/ml | | TMax 6.9 H |

GR01 BFB-520 RELATIVE BIOAVAILABILITY VERSUS MR32
(from n = 12 subjects cross-over)

| CMAX | 1.43 ng/ml | F = 80.48% | |
|---|---|---|---|
| AUC | 27.48 H · ng/ml | F = 96.1 % | TMax 12.5 H |

GR02 BFB-520 RELATIVE BIOAVAILABILTIY VERSUS MR32
(from n = 12 subjects cross-over)

| CMAX | 1.27 ng/ml | F = 69.48% | |
|---|---|---|---|
| AUC | 27.53 H · ng/ml | F = 88.46% | TMax 17.5 H |

PLASMA CONCENTRATIONS RATE OF BFB-520 INCREASE (VMax)

| | MR32 | GR01 | GR02 |
|---|---|---|---|
| VMax ng/ml/H | 0.84 | 0.54 | 0.2 |
| RATIO Test/MR32 | REF | 0.64 | 0.24 |

The PK profiles of MIN-101 and its metabolite BFB-520 were predicted for 3 formulations of MIN-101 (2 prototypes of CR gastro-resistant (GR) formulations (GR-01 and GR-02) and 1 comparator MR formulation (MR32)) at 2 doses. (32 mg and 64 mg), based on 4 daily dosings. These studies are summarized in Scheme 3 (32 mg) and Scheme 4 (64 mg). Full details are found in the Examples section.

Scheme 3. Summary of Predicted Plasma Concentrations of MIN-101 and BFB-520 for MR32, GR-01, and GR-02 Formulations (32 mg).
PREDICTED 32 mg MR32 GR01 AND GR02 PLASMA CONCENTRATIONS AT DAY 4

|  | MR32 | GR01 | GR01 | GR02 | GR02 |
|---|---|---|---|---|---|
| MIN101 CMaxSS | 27.1 | 20.9 ng/ml | F = 76.9% | 15.4 ng/ml | F = 56.7% |
| AUCSS72-96 | 292.6 | 287.6 H · ng/ml | F = 98.3% | 248.3 H · ng/ml | F = 84.9% |
| CMinSS | 3.32 | ng/ml | | 7.17 ng/ml | |
| BFB-520CMaxSS | 1.89 | 1.46 ng/ml | F = 77.2% | 1.23 ng/ml | F = 64.8% |
| AUCSS72-96 | 29.1 | 26.3 H · ng/ml | F = 90.6% | 23.6 H · ng/ml | F = 81.4% |
| CMinSS | 0.5 | 0.66 ng/ml | | 0.79 ng/ml | |

Scheme 4. Summary of Predicted Plasma Concentrations of MIN-101 and BFB-520 for MR32, GR-01, and GR-02 Formulations (64 mg).
PREDICTED 64 mg MR32 GR01 AND GR02 PLASMA CONCENTRATIONS AT DAY 4

|  | 2xMR32 | 2xGR01 | 2xGR01 | 2xGR02 | 2xGR02 |
|---|---|---|---|---|---|
| MIN101 CMaxSS | 54.28 | 41.77 ng/ml | F = 76.9% | 30.77 ng/ml | F = 56.7% |
| AUCSS72-96 | 585.2 | 577.6 H · ng/ml | F = 98.7% | 498.6 ng/ml | F = 85.2% |
| CMinSS | 6.64 | 12.93 ng/ml | | 14.35 ng/ml | |
| BFB-520 CMaxSS | 3.79 | 2.92 ng/ml | F = 77.2% | 2.45 ng/ml | F = 64.8% |
| AUCSS72-96 | 58.1 | 52.8 H · ng/ml | F = 90.8% | 47.4 H · ng/ml | F = 81.6% |
| CMinSS | 0.99 | 1.32 ng/ml | | 1.58 ng/ml | |

The PK profiles of the GR-01 formulation in healthy CYP2D6 EM male and female subjects in fed and fasted states are summarized in Scheme 5 (MIN-101) and Scheme 6 (BFB-520). Subjects who completed part 1 of the study (evaluation of the PK profile of MIN-101 and its metabolite BFB-520 in the GR-01, GR-02, and MR32 formulations) returned and received a further single oral dose of GR-01 under fed or fasted conditions to allow the assessment of food effect by comparison of the PK properties to those obtained in part 1 (Examples 9-12). There was a wash-out period of 14±2 days after part 1. Full details of these experiments are found in the Examples section.

Scheme 5. Summary of MIN-101 PK Study for GR-01 Formulation in Fed and Fasted States.

GR01 FED MIN101 (from n = 12 subjects cross-over)

| CMAX | 20.89 ng/ml | F = 108.97% versus FASTED |
|---|---|---|
| AUC | 269.19 H · ng/ml | F = 95.14% versus FASTED |
| TMax | 12.5 H | |

GR01 FASTED MIN101 (from n = 12 subjects cross-over)

| CMAX | 19.59 ng/ml |
|---|---|
| AUC | 284.52 H · ng/ml |
| TMax | 6.0 H |

Scheme 6. Summary of BFB-520 PK Study for GR-01 Formulation in Fed and Fasted States.

GR01 FED BFB-520 (from n = 12 subjects cross-over)

| CMAX | 1.69 ng/ml | F = 121.32% versus FASTED |
|---|---|---|
| AUC | 30.12 H · ng/ml | F = 111.58% versus FASTED |
| TMax | 18.25 H | |

GR01 FASTED BFB-520 (from n = 12 subjects cross-over)

| CMAX | 1.43 ng/ml |
|---|---|
| AUC | 27.48 H · ng/ml |
| TMax | 12.5 H |

The PK profiles of MIN-101 and its metabolite BFB-520 were predicted in the fed and fasted states for gastro-resistant formulation GR-01 at 2 doses (32 mg and 64 mg), based on 4 daily dosings. These studies are summarized in Scheme 7 (32 mg) and Scheme 8 (64 mg), respectively. Full details are found in the Examples section.

Scheme 7. Summary of Predicted Plasma Concentrations of MIN-101 and BFB-520 for GR-01 (32 mg) in the Fed and Fasted States.
PREDICTED 32 mg GR01 FED AND FASTED PLASMA CONCENTRATIONS AT DAY 4

|  |  | GR01 FED |  | GR01 FASTED |
|---|---|---|---|---|
| MIN101 | CMaxSS | 16.7 | F = 80.0% | 20.9 ng/ml |
|  | AUCSS72-96 | 263.8 | F = 91.7% | 287.6 H · ng/ml |
|  | CMinSS | 3.32 |  | 6.46 ng/ml |
| BFB-520 | CMaxSS | 1.51 | F = 103.7% | 1.46 ng/ml |
|  | AUCSS72-96 | 29.5 | F = 109.4% | 26.3 H · ng/ml |
|  | CMinSS | 1.03 |  | 0.66 ng/ml |

Scheme 8. Summary of Predicted Plasma Concentrations of MIN-101 and BFB-520 for GR-01 (64 mg) in the Fed and Fasted States.
PREDICTED 64 mg GR01 FED AND FASTED PLASMA CONCENTRATIONS AT DAY 4

|  |  | GR01 FED |  | GR01 FASTED |
|---|---|---|---|---|
| MIN101 | CMaxSS | 33.41 | F = 80.0% | 41.77 ng/ml |
|  | AUCSS72-96 | 527.5 | F = 91.3% | 577.6 H · ng/ml |
|  | CMinSS | 16.17 |  | 12.93 ng/ml |
| BFB-520 | CMaxSS | 3.01 | F = 103.7% | 2.91 ng/ml |
|  | AUCSS72-96 | 59.0 | F = 109.1% | 54 H · ng/ml |
|  | CMinSS | 2.06 |  | 1.32 ng/ml |

BFB-520 is believed to be metabolized in part by CYP2D6. In clinical studies of MIN-101, CYP2D6 poor metabolizers have exhibited high plasma levels of BFB-520. Thus, in an embodiment, the $C_{max}$ for BFB-520 is assessed after oral administration of a test dosage form comprising Compound (I) to only subjects who have been assigned an IM CYP2D6 genotype or an EM CYP2D6 genotype using a commercially available genotype test. In an embodiment, all of the subjects have been assigned an EM CYP2D6 genotype.

Levels of Compound (I) and the metabolite BFB-520 produced in plasma after oral administration of an oral dosage form of the disclosure may be determined by the method described below. It is expected that variations of and improvements to this method could be employed as well.

Blood samples from subjects are collected on sodium heparin tubes at various time points of interest. A suitable sampling schedule includes the following:

Day 1 (D1): at pre-dose; 1 h; 2 h; 3 h; 4 h; 6 h; 8 h; 10 h; 12 h and 16 h;

Day 2 to Day 6 (D2-D6): at pre-dose

Day 7 (D7): at pre-dose; 1 h; 2 h; 3 h; 4 h; 6 h; 8 h; 10 h; 12 h; 16; 24 h (D8) and 48 h (D9).

After blood centrifugation, a desired number of aliquots (typically 2) of each plasma sample are prepared in suitable storage containers (e.g., polypropylene tubes tightly capped to prevent leak and desiccation which could occur during storage). The containers containing the plasma samples are stored at −80° C. for up to one month before analysis.

A GLP validated method to detect and quantify Compound (I) and its metabolites BFB-520 and BFB-999 employs liquid chromatographic (LC) analysis coupled to a mass spectrometry detection (MS/MS) after a liquid/liquid extraction step of Compound (I) and metabolites BFB-520 and BFB-999 from plasma samples.

The analytical method uses two internal standards (a deuterated analog of MIN-101 (designated herein as [$^2$H$_6$]-MIN-101 or MIN-101-d6 or CYR-101-d6) and BFB-784 for both BFB-520 and BFB-999), which were submitted to the same analytical procedure as MIN-101, BFB-520 and BFB-999 in plasma samples. MIN-101-d6 and BFB-784 have the structures shown in Formulas IV and V below:

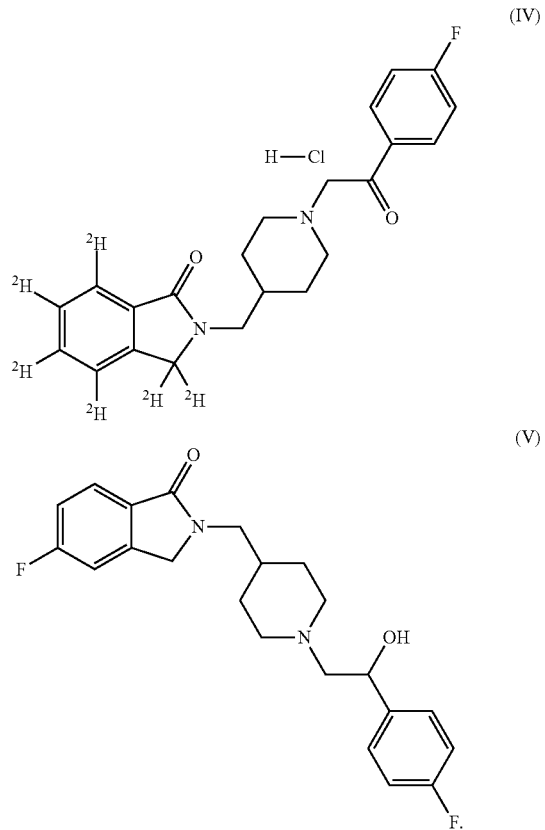

Chromatograms are processed by default in an automatic mode. Chromatographic peaks of MIN-101, BFB-520, BFB-999 and internal standards (IS) are identified according to their retention times. The recorded response is expressed as an area ratio of MIN-101 to MIN-101-d6, and of BFB-520 or BFB-999 to BFB-784.

The lower limit of quantification (LLOQ) of this analytical method in plasma is 0.25 ng/mL for MIN-101 and its metabolites BFB-520 and BFB-999.

Details of the analytical method are described in Example 7 below. It is expected that variations of and improvements to this analytical method could be employed as well.

Treatment Methods

The gastro-resistant CR oral dosage forms of the present disclosure may be useful for treating diseases or conditions that are susceptible to treatment with Compound (I). As not limiting examples, it is believed that Compound (I) can potentially be used to treat schizophrenic and non-schizophrenic patients with one or more of the following symptoms or conditions: negative symptoms, depressive symptoms, sleep disorders and cognitive impairment.

In a phase 2b study, MIN-101 at 32 mg and 64 mg doses, demonstrated rapid, statistically significant and clinically meaningful reductions in negative symptoms in patients with schizophrenia. The oral dosage forms used in this Phase 2b study were the 32 mg MR tablet described in Example 1 below and an essentially identical 64 mg MR tablet. Neither of these MR tablets had a GR coating and each produced in vitro dissolution and plasma PK profiles that are different than those produced by the gastro-resistant CR oral dosage forms of the present disclosure.

Negative symptoms generally refer to a reduction in normal functioning, and include five major sub-domains: blunted affect (affective flattening, blunted expression), alogia (poverty of speech), amotivation (loss of volition), anhedonia (reduced ability to experience or anticipate pleasure) and asociality (social withdrawal). While negative symptoms are a well-documented and intensively studied aspect of schizophrenia, this class of symptoms has been identified in patients with other psychiatric and neurological disorders, including, for example, Alzheimer's disease and other dementias, particularly frontotemporal dementia (FTD), autism spectrum disorder (ASD), bipolar disorder (BPD), major depressive disorder (MDD), Parkinson's disease, temporal lobe epilepsy, stroke, and traumatic brain injury (TBI) (see, e.g., Boone et al, J. of Internat. Neuropsycol. Soc., 2003, Vol 9, pages 698-709; Bastiaansen, J. et al., J. Autism Dev. Disord. 2011, Vol 41:1256-1266; Getz, K. et al., Am. J. Psychiatry 2002, Vol 159:644-651; Winograd-Gurvich, C. et al., Brain Res. Bulletin, 2006, Vol. 70:312-321; Galynker et al., Neuropsychiatry Neuropsychol Behav Neurol 2000, Vol 13:171-176; Galynker I, et al., J. Nerv. Ment. Dis 1997, Vol 185:616-621; Chaudhury, S., et al., Indian J. of Neurotrauma 2005, Vol 2:13-21; Ameen, S et al., German J. of Psychiatry 2007). Indeed, as early as 2001, it was proposed that negative symptoms are common to mental illnesses generally (Herbener and Harrow, Schizophrenia Bulletin 2001, Vol. 27:527-537). Furthermore, reports of several population studies have concluded that between 20-22% of the general population have one or more negative symptoms, and that the majority of subjects with negative symptoms do not exhibit a clinical diagnosed psychiatric disorder (Werbeloff, N. et al., PLoS ONE 2015, Vol 10:e0119852; Barrantes-Vidal, N., et al., Schizophr. Res. 2010, Vol 122:219-225).

Thus, it is an object of the present disclosure to treat at least one negative symptom in a subject by a method of administering to the subject a gastro-resistant CR dosage form described herein one time per day (QD). In an embodiment, the subject is diagnosed with schizophrenia. In another embodiment, the subject does not have a clinical diagnosis of schizophrenia, i.e., is a non-schizophrenic patient.

For purposes of the disclosure encompassed herein, the term "negative symptoms" is to be understood as including primary negative symptoms typically associated with schizophrenia, the negative symptoms measured in the PANSS negative symptoms subscale score, the negative factor score based on the pentagonal structure model method, and the negative symptoms measured in the BNSS.

In an embodiment, the negative symptom is one of the five major sub-domains of negative symptoms: blunted affect, alogia, amotivation, anhedonia and asociality. The core characteristics of each sub-domain are described below.

Blunted affect (affective flattening, blunted expression) is characterized by reduced intensity and range of emotional expression as manifested via vocal and non-verbal modes of communication including intonation (prosody), facial expression, hand-gestures and body movements.

Alogia (poverty of speech) is characterized by decreased quantity of speech, reduced spontaneous speech and loss of conversational fluency.

Amotivation (loss of volition) is characterized by deficits in the initiation and maintenance of goal-directed behaviors like work, study, sport, personal hygiene and daily tasks, especially when requiring and effort (cognitive or physical) and significant organization, as well as deficits in desire to undertake such activities. This sub-domain is related to apathy and lack of energy.

Anhedonia (reduced ability to experience or anticipate pleasure) is characterized by the looking forward to a reward, recreational or other pleasurable experience ("wanting") being more markedly and consistently impaired (anticipatory anhedonia) than the appreciation ("liking") of the experience itself (consummatory anhedonia).

Asociality (social withdrawal) is characterized by diminished interest in, motivation for, and appreciation of social interactions with others, like family and friends, loss of interest in intimate (sexual) relationships independent of any somatic problems, and for a child, may include loss of interest in playing with other children.

In some embodiments, the dosage form is administered to the subject once a day for a first treatment period of sufficient length to achieve improvement in at least one negative symptom. In an embodiment, the first treatment period is at least 2 weeks, at least 4 weeks, at least 6 weeks, at least 8 weeks, at least 10 weeks or at least 12 weeks. In an embodiment, positive symptoms in a subject treated with the dosage form are stable during the treatment period, i.e., remain at substantially the same level as at baseline. In an embodiment, the level of improvement in negative symptoms is a reduction of at least 3 points on the PANSS five factor (pentagonal structure model) negative symptom factor scores after 12 weeks of treatment. In an embodiment, the subject's negative symptom score continues to improve from 12 weeks to at least about 24, 36 or 48 weeks of treatment. The PANSS pentagonal structure model is described in WHITE L, HARVEY PD, OPLER L, LINDENMAYER J. EMPIRICAL ASSESSMENT OF THE FACTORIAL STRUCTURE OF CLINICAL SYMPTOMS IN SCHIZOPHRENIA. *PSYCHOPATHOLOGY.* 1997; 30(5): 263-74.

In some embodiments, if a subject experiences improvement in at least one negative symptom during the first treatment period, then administration of the therapeutically effective dose of Compound (I) is continued for a second treatment period of at least 12 weeks, at least 24 weeks, at least 48 weeks, or until the subject is determined to exhibit functional improvement subsequent to improvement in the negative symptoms. In an embodiment, positive symptoms in a subject treated with the dosage form are stable during at least part of the second treatment period, i.e., remain at substantially the same level as at baseline.

In some embodiments, the subject has a diagnosis of schizophrenia. In an embodiment, a subject selected for treatment with an oral dosage form of the disclosure has a base-line PANSS negative sub-score greater than or equal to 20. In an embodiment, the selected subject also has baseline scores of less than 4 on the following PANSS items: excitement, hyperactivity, hostility, suspiciousness, uncooperativeness and poor impulse control. In an embodiment, the selected schizophrenic subject has exhibited stable positive symptoms of schizophrenia for at least the previous one, two or three months and has exhibited negative symptoms for at least the previous one, two or three months.

In some embodiments, the schizophrenic subject treated with a gastro-resistant, CR oral dosage form of the present disclosure has prominent negative symptoms. In an embodiment, a schizophrenic subject is defined as having prominent negative symptoms when the subject has having a score ≥4 (moderate) on at least three subscale items in the PANSS negative symptoms subscale items but not on PANSS positive subscale items. In an embodiment, the subject has both prominent positive and prominent negative symptoms when the subject has scores ≥4 on items for both positive and negative symptom items.

Up to 75% of schizophrenic patients suffer from cognitive impairment, and the phase 2b study of MIN-101 discussed above showed improvement in cognitive function. Thus, in an aspect, administration of a gastro-resistant CR oral dosage form of the present disclosure to a patient with a diagnosis of schizophrenia is intended to improve cognitive function in the patient.

In some embodiments, the subject has not been previously treated with an anti-psychotic drug. In other embodiments, the subject has discontinued prior treatment with an antipsychotic drug due to experiencing one or more of the following: satisfactory reduction in positive symptoms, an inadequate response for negative symptoms, or intolerable side effects.

A secondary outcome of the phase 2b study of MIN-101 discussed above was patients' performance on the Calgary Depression Scale for Schizophrenia (CDSS) ADDINGTON D, ADDINGTON J, MATICKA-TYNDALE E. ASSESSING DEPRESSION IN SCHIZOPHRENIA: THE CALGARY DEPRESSION SCALE. BRITISH JOURNAL OF PSYCHIATRY SUPPLEMENT 1993; (22):39-44. The CDSS has little overlap with positive and negative symptoms and has become the recommended scale to assess the severity of depression in patients with schizophrenia. In the phase 2b study, the severity of symptoms as measured by the CDSS was reduced following treatment with 32 or 64 mg of MIN-101 compared to placebo. A correlation analysis between baseline treatment effects on negative symptoms and on depression symptoms in this patient cohort demonstrated there was only a small correlation between MIN-101's effects on these two symptom categories. Thus, since the effects of MIN-101 on negative symptoms and depression symptoms in schizophrenia patients were largely independent of each other, MIN-101 has the potential to alleviate one or more depression symptoms in patients who are not schizophrenic.

Thus, another object of the present disclosure is to treat at least one symptom of depression in a subject in need thereof by a method of administering a gastro-resistant CR dosage form described herein. In an embodiment, the subject has a diagnosis of schizophrenia. In an embodiment, the improvement in depression symptoms in a schizophrenic patient is measured using the CDSS.

It is another object of the present disclosure to reduce the risk for QT prolongation in a subject treated with Compound (I) by administering to the subject Compound (I) as formulated in a gastro-resistant CR dosage form described herein. In an embodiment, the subject has been identified as having one or more risk factors for drug-induced QT prolongation. In an embodiment, the subject discontinued previous treatment with a compound other than Compound (I) due to experiencing QT prolongation. In an embodiment, the subject discontinued previous treatment with a different dosage form comprising Compound (I) due to experiencing QT prolongation. In an embodiment, the subject has a diagnosis selected from the group consisting of: prominent negative symptoms of schizophrenia, prominent positive and prominent negative symptoms of schizophrenia, major depressive disorder (MDD), a sleep disorder and cognitive impairment.

In some embodiments of any of the above treatment methods, the gastro-resistant oral dosage form is administered in the morning or evening. In an embodiment, the dosage form is administered at least two hours before eating.

In some embodiments of any of the above treatment methods, the subject is 12 or more years of age. In some embodiments, the subject is at least 14, 16, 18, or 20 years old. In some embodiments, the subject is less than 50, 45, 40, 35 or 30 years old. In an embodiment, the subject is at least 16 years old and less than any of 40, 35 or 30 years old.

In some embodiments of any of the above treatment methods, the dosage form may be administered to the subject in combination with another therapeutic agent. In an embodiment, the other therapeutic agent does not inhibit CYP2D6 activity. In an embodiment, the subject is diagnosed with schizophrenia and the other therapeutic agent is an anti-psychotic drug.

In some embodiments of any of the above treatment methods, the subject may have been assigned an IM genotype or and EM genotype. In an embodiment, the subject has been assigned an EM genotype.

In some embodiments of any of the above treatment methods, the oral dosage form may comprise 32 mg of Compound (I). In an embodiment, the oral dosage form consists essentially of the components listed in Table 2 or Table 3 below.

Examples

Example 1: Description of a 32 mg MR Tablet Used in the Phase 2b Trial of MIN-101

The MR 32 mg tablets are supplied as round (diameter 10 mm and R=10) white-coated tablets free from visual defects. Each tablet contains 32 mg of Compound (I). The complete statement of the components and quantitative composition of MR 32 mg tablet is given in Table 1 below.

TABLE 1

Composition of MR 32 mg tablet

| Composition | MR 32mg tablet % w/w | mg/tablet | Function |
|---|---|---|---|
| MIN-101[1] | 12.19 | 38.40 | Active ingredient |
| Hypromellose (Methocel ™ K100LV CR) | 9.52 | 30.00 | Controlled release excipient |
| Hypromellose (Methocel ™ K4M CR) | 22.86 | 72.00 | Controlled release excipient |
| Microcrystalline Cellulose (Avicel PH102) | 30.19 | 95.10 | Filler |
| Lactose Monohydrate (Fast Flo 316) | 19.05 | 60.00 | Filler |
| Silica Colloidal Anhydrous (Aerosil 200 Pharma) | 0.48 | 1.50 | Glidant |
| Magnesium stearate (vegetable grade source Hyqual NF) | 0.95 | 3.00 | Lubricant |
| Total (core tablets) | 95.23 | 300.00 | |
| Sepifilm (LP 770 Blanc) | 4.76 | 15 | Coating Agent |
| Total | 100.00 | 315.00 | |

[1]Salt correction factor of 1.2 applied
NA: Not Applicable

Example 2: Description of an Exemplary 32 mg Gastro-Resistant CR Tablet

The CR GR-01 tablets are supplied as round (diameter 10 mm and R=10) tablets, free from visual defects. Each tablet contains 32 mg of Compound (I). The complete statement of the components and quantitative composition of CR GR-01 tablet is given in Table 2.

TABLE 2

Composition of CR GR-01 tablet

| Composition | CR GR-01 tablet % w/w | mg/tablet | Function |
|---|---|---|---|
| MIN-101[1] | 12.09 | 38.40 | Active ingredient |
| Hypromellose (Metolose ® 90SH 100 SR) | 9.45 | 30.00 | Controlled release excipient |
| Hypromellose (Methocel ™ K100M CR) | 22.67 | 72.00 | Controlled release excipient |
| Microcrystalline Cellulose (Avicel PH102) | 29.95 | 95.10 | Filler |
| Lactose Monohydrate (Fast Flo 316) | 18.89 | 60.00 | Filler |
| Silica Colloidal Anhydrous (Aerosil 200 Pharma) | 0.47 | 1.50 | Glidant |
| Magnesium stearate (vegetable grade source Hyqual NF) | 0.94 | 3.00 | Lubricant |
| Total (Core Tablet) | 94.47 | 300.00 | |
| Eudragit L30D55 | 4.72 | 15.00 | Controlled release excipient |
| Plasacryl HTP20 | 0.80 | 2.55 | Anti-tacking agent |
| Total | 100.00 | 317.55 | |

[1]Salt correction factor of 1.2 applied
NA: Not Applicable

Example 3: Description of Another Exemplary 32 mg Gastro-Resistant CR Tablet The CR GR-02 tablets are supplied as round (diameter 10 mm and R=10) tablets, free from visual defects. Each tablet contains 32 mg of Compound (I). The complete statement of the components and quantitative composition of CR GR-02 tablet is given in Table 3 below.

TABLE 3

Composition of CR GR-02 tablet

| Composition | CR GR-02 tablet % w/w | CR GR-02 tablet mg/tablet | Function |
|---|---|---|---|
| MIN-101[1] | 11.98 | 38.40 | Active ingredient |
| Hypromellose (Methocel ™ K15M CR) | 9.36 | 30.00 | Controlled release excipient |
| Hypromellose (Methocel ™ K100M CR) | 22.46 | 72.00 | Controlled release excipient |
| Microcrystalline Cellulose (Avicel PH102) | 29.67 | 95.10 | Filler |
| Lactose Monohydrate (Fast Flo 316) | 18.72 | 60.00 | Filler |
| Silica Colloidal Anhydrous (Aerosil 200 Pharma) | 0.47 | 1.50 | Glidant |
| Magnesium stearate (vegetable grade source Hyqual NF) | 0.94 | 3.00 | Lubricant |
| Total (Core Tablet) | 93.59 | 300.00 | |
| Eudragit L30D55 | 4.68 | 15.00 | Controlled release excipient |
| Plasacryl HTP20 | 0.80 | 2.55 | Anti-tacking agent |
| Surelease E-7-19040 | 0.94 | 3.00 | Controlled release excipient |
| Total | 100.00 | 320.55 | |

[1]Salt correction factor of 1.2 applied
NA: Not Applicable

Example 4: Batch Formula for CR GR-01 and CR GR-02 Tablets

A representative batch size for the CR GR-01 and CR GR-02 tablets are 5,400 tablets. The batch formulas are described in Tables 4 and 5 below.

TABLE 4

Batch Formula for CR GR-01 tablet

| Composition | kg/batch |
|---|---|
| MIN-101 | 0.206 |
| Hypromellose Metolose ® 90SH 100SR | 0.162 |
| Hypromellose Methocel ™ K100M CR | 0.389 |
| Microcrystalline Cellulose | 0.514 |
| Lactose | 0.324 |
| Silica Colloidal Anhydrous | 0.008 |
| Magnesium stearate | 0.016 |
| Eudragit L30D55 | 0.081 |
| Plasacryl HTP 20 | 0.014 |
| Total | 1.714 |

NA: Not Applicable

TABLE 5

Batch Formula for CR GR-02 tablet

| Composition | kg/batch |
|---|---|
| MIN-101 | 0.207 |
| Hypromellose Methocel ™ K15M CR | 0.162 |
| Hypromellose Methocel ™ K100M CR | 0.389 |
| Microcrystalline Cellulose | 0.514 |
| Lactose | 0.324 |
| Silica Colloidal Anhydrous | 0.008 |
| Magnesium stearate | 0.016 |
| Eudragit L30D55 | 0.081 |
| Plasacryl HTP 20 | 0.014 |
| Surelease E-7-19040 | 0.016 |
| Total | 1.731 |

TABLE 5A

Batch Formula for GR-01/B Tablets (representative batch formula size is 150 000 tablets

| Composition | kg/batch |
|---|---|
| MIN-101 | 5.75 |
| Hypromellose Methocel ™ K100 LV CR | 4.5 |
| Hypromellose Methocel ™ K100M CR | 10.80 |
| Microcrystalline Cellulose | 14.5 |
| Lactose | 9 |
| Silica Colloidal Anhydrous | 0.22 |
| Magnesium stearate | 0.22 |
| Eudragit L30D55 | 2.25 |
| Plasacryl HTP 20 | 0.380 |
| Total | 47.63 |

Example 5: Development of an Optimized In Vitro Dissolution Method

Based on Compound (I) PK profiles obtained with MIN-101 MR 32 mg tablets used in clinical studies, an in vitro/in vivo correlation (IVIVC) approach was proposed. The IVIVC approach is defined by the FDA as a predictive mathematical model describing the relationship between an in-vitro property of the dosage form and an in-vivo response. In this context, the model refers to the relationship between the in vitro dissolution of the MR 32 mg tablet and its in vivo response such as Compound (I) plasma concentration. The main objectives of the IVIVC model were to validate the use of a predictive in-vitro dissolution method and to select target optimized formulations. If the validity of the IVIVC model is confirmed by clinical results, the in-vitro dissolution method could be used as a surrogate method for clinical studies.

First, after analysis of all PK data for Compound (I) from clinical studies, an in-vitro dissolution profile of the MR 32 mg tablet described in Example 1 was defined. This target in-vitro dissolution profile was then used to develop an optimized in-vitro dissolution method. This method is described in the next Example.

Secondly, and when the in-vitro dissolution method was considered as closed enough to the expectations, the target in-vitro dissolution profile of a gastro-resistant CR oral dosage form was defined and used to design the gastro-resistant dosage forms described in Examples 2 and 3. The dissolution profiles for these two GR dosage forms (GR-01 and GR-02) and the MR 32 mg tablet of Example 1, which were generated using the optimized dissolution method, are shown in tables 6 and 7 below.

TABLE 6

Cumulative In Vitro Dissolution Profiles

Cumulative Dissolution of Compound (I) (mg)

| Time (hours) | Target profile | MR 32 mg tablet | GR-01 tablet | GR-02 tablet |
|---|---|---|---|---|
| 0 | 0 | 0 | 0 | 0 |
| 0.5 | 0 | 3.2 | 0 | 0 |
| 1 | 0 | 5.0 | 0 | 0 |
| 2 | 0 | 8.4 | 0 | 0 |
| 2.5 | 0.2 | — | 0 | 0 |
| 3 | 0.9 | 10.4 | 2.3 | 0.1 |
| 4 | 3.2 | 14.5 | 5.6 | 0.9 |
| 5 | 5.2 | — | — | 2.6 |
| 6 | 7.1 | 19.4 | 9.9 | 4.5 |
| 8 | 11.0 | 23.1 | 12.9 | 8.1 |
| 10 | 14.8 | — | — | — |
| 11 | — | 27 | 18.2 | 12.6 |
| 13 | 19.5 | 28.6 | 22.0 | 15.4 |
| 14 | 20.8 | — | — | — |
| 15 | 21.9 | — | — | — |
| 16 | — | 30.1 | 25.9 | 18.6 |
| 18 | 25.0 | — | — | — |
| 19 | — | 30.6 | 28.2 | 21.1 |
| 21 | 27.6 | — | — | 22.8 |
| 26 | 31.6 | — | 30.1 | 24.6 |

TABLE 7

In Vitro Dissolution Rate Profiles

Compound (I) Dissolution Rate (mg/hour)

| Time (hours) | Target Profile | MR 32 mg tablet | GR-01 tablet | GR-02 tablet |
|---|---|---|---|---|
| 0 | 0 | 0 | 0 | 0 |
| 0.5 | 0 | 6.4 | 0 | 0 |
| 1 | 0 | 3.7 | 0 | 0 |
| 2 | 0 | 2.7 | 0 | 0 |
| 2.5 | 0.4 | — | 0 | 0 |
| 3 | 1.5 | 2.0 | 2.3 | 0.1 |
| 4 | 2.3 | 4.1[1] | 3.3 | 0.8 |
| 5 | 2.0 | 2.4[1] | — | 1.7 |
| 6 | 1.9 | — | 2.2 | 2 |
| 8 | 1.9 | 1.9 | 1.5 | 1.8 |
| 10 | 1.9 | — | — | 1.5 |
| 11 | — | 1.3 | 1.8 | — |
| 13 | 1.6 | 0.8 | 1.9 | 1.4 |
| 14 | 1.3 | — | — | — |
| 15 | 1.2 | — | — | — |
| 16 | — | 0.5 | 1.3 | 1.1 |
| 18 | 1.0 | — | — | 0.9 |
| 19 | — | 0.2 | 0.7 | 0.9 |
| 21 | 0.9 | — | — | 0.9 |
| 24 | 0.8 | — | 0.4 | — |

[1]not considered

The CR GR-01 and CR GR-02 tablets and the MR 32 mg tablet, used as a comparator, were tested in a clinical study (MIN-101-C06) to evaluate the plasma PK profile of each dosage form.

Example 6: Analytical Method for the Assay of MIN-101, BFB-520 and BFB-999 in Human Plasma Preparation of Solvents and Reagents
All solvents and reagents listed below are recognized as analytical grade or better (relevant for the entire document).
Volumes are indicated as examples, different volumes may be prepared if proportions are kept.
Dilution Solvent: 50/50 (v/v) Acetonitrile/Water Solution
Mix 500 mL of acetonitrile with 500 mL of water.
Storage:
1 month at room temperature.
Buffer: pH 9 Buffer Solution
Transfer the content of an ampoule of pH 9 buffer concentrate (Merck, P/N 109889) in a 500 mL volumetric flask.
Fill up q.s. 500.0 mL with water.
Storage:
1 month at ca. +5° C.
Buffer: 1 M Ammonium Acetate Buffer
Dissolve 7.7 g of ammonium acetate with 100 mL of water.
Storage:
3 months at ca. +5° C.
Mobile Phase: 10 mM Ammonium Acetate Buffer Solution
Add 10 mL of 1 M ammonium acetate buffer to 990 mL of water.
Or dissolve 0.77 g of ammonium acetate with 1 L of water.
Degas if necessary (by sonication or by magnetic agitation under vacuum).
Storage:
5 days at room temperature.
Reconstitution Solvent: 80/20 (v/v) 10 mM Ammonium Acetate Buffer/Acetonitrile Solution
Mix 400 mL of 10 mM ammonium acetate buffer solution with 100 mL of acetonitrile.
Or add 4 mL of 1 M ammonium acetate buffer to 396 mL of water and 100 mL of acetonitrile.
Storage:
5 days at room temperature.
Needle Rinsing Solvent: 80/20 (v/v) Acetonitrile/Water Solution
Mix 800 mL of acetonitrile with 200 mL of water.
Degas if necessary (by sonication or by magnetic agitation under vacuum).
Storage:
1 month at room temperature.
Needle Rinsing Solvent: 65/35 (v/v) Acetonitrile/Water Solution
Mix 650 mL of acetonitrile with 350 mL of water.
Degas if necessary (by sonication or by magnetic agitation under vacuum).
Storage:
1 month at room temperature.
Column Rinsing Solvent: 90/10 (v/v) Acetonitrile/Water Solution
Mix 900 mL of acetonitrile with 100 mL of water.
Degas if necessary (by sonication or by magnetic agitation under vacuum).
Storage:
1 month at room temperature.
Sample Preparation and Extraction Procedure
Control plasma and plasma samples are thawed at room temperature and centrifuged at 1920 g for 5 minutes at +4° C.
Preparation of Samples
Blank Reagent Sample
In a 10 mL polypropylene tube:
1. Transfer 250 μL of water.
Blank and Zero Samples
In a 10 mL polypropylene tube:
1. Transfer 250 μL of control plasma.
Calibration Standards In a 1.5 mL conic polypropylene tube:
1. Transfer 900 µL of control plasma,
2. Add 100 µL of appropriate WS,
3. Mix on a vortex for 30 seconds,
4. Transfer 250 µL of the preparation into a 10 mL polypropylene tube.

QC Samples

In a 1.5 mL conic polypropylene tube:
1. Transfer 900 µL of control plasma,
2. Add 100 µL of appropriate QC-WS,
3. Mix on a vortex for 30 seconds,
4. Transfer 250 µL of the preparation into a 10 mL polypropylene tube.

Specimens

In a 10 mL polypropylene tube:
1. Transfer 250 µL of plasma sample.

20-Fold Diluted Samples [2]

In a 1.5 mL conic polypropylene tube:
1. Transfer 380 µL of control plasma,
2. Add 20 µL of plasma sample to be diluted,
3. Mix on vortex for 30 seconds,
4. Transfer 250 µL of the preparation into a 10 mL polypropylene tube.

Extraction Procedure

1. Add 25 µL of dilution solvent (blank reagent sample, blank sample) or 25 µL of IS-WS (other samples),
2. Add 1 mL of pH 9 buffer solution,
3. Mix on a vortex for 10 seconds,
4. Add 4 mL of diethylether,
5. Mix on a reciprocating shaker at slow speed for 20 minutes,
6. Centrifuge at 1920 g for 10 minutes at +4° C.,
7. Transfer the tubes at ca. −80° C. for 15 minutes,
8. Transfer the organic phase (upper phase) into a 5 mL glass tube,
9. Evaporate to dryness under a stream of nitrogen at +30° C.,
10. Reconstitute with 200 µL of reconstitution solvent,
11. Mix on a vortex for 30 seconds
12. Centrifuge at 1920 g for 5 minutes at +4° C.,
13. Transfer the final extract into a polypropylene vial,
14. Seal the vial with a cap with Teflon/silicone/Teflon septum,
15. Centrifuge at 2500 g for 7 minutes at +4° C.,
16. Place the vials in the autosampler until analysis.

Or [4]

13. Transfer the final extract into a 2 mL polypropylene 96-wells collection plate,
14. Seal the plate with a silicone pre-pierced cap mat,
15. Centrifuge at 2500 g for 7 minutes at +4° C.,
16. Place the plate in the autosampler until analysis.

Analysis Conditions

Chromatographic Conditions

Column and Oven

| Column | Gemini C18 100 × 4.6 mm, 3.0 µm (Phenomenex) |
| --- | --- |
| Filler or guard column | C18 4 × 2 mm (Phenomenex) |
| Column temperature | +40° C. ± 5° C. |
| Column rinsing solvent | 90/10 (v/v) Acetonitrile/water solution |
| Column rinsing conditions | 60 minutes at 0.6 mL/min |

Autosampler

| Injection volume | 5 µL (to be adapted according to MS sensitivity) |
| --- | --- |
| Autosampler temperature | +5° C. |

Pump

| Mobile phase A | 10 mM Ammonium acetate buffer solution |
| --- | --- |
| Mobile phase B | Acetonitrile |

Isocratic Mode

| Flow rate (mL/min) | Mobile phase A(%) | Mobile phase B (%) |
| --- | --- | --- |
| 0.6 | 35 | 65 |

Detection

| Detection type | MRM |
| --- | --- |
| Ionisation type and mode | ESI in positive ionisation mode |
| Precursor ion | $[M + H]^+$ |

MRM Transitions

| Analyte | MRM transition |
| --- | --- |
| MIN-101 (CYR-101) | 367 > 146 |
| BFB-520 | 369 > 146 |
| BFB-999 | 383 > 232 |
| CYR-101-d6 | 373 > 152 |
| BFB-784 | 387 > 164 |

LC Equipment No. 1

Description

| Equipment | Type |
| --- | --- |
| Autosampler | G1367B autosampler and G1330B thermostat (Agilent) |
| LC pump | G1311A quaternary pump and G1322A degasser (Agilent) |
| Column oven | G1316A thermostatted column compartment (Agilent) |
| Detector | EP10[+] HSID[++] (Ionics) |

System Care

| Needle rinsing solvent | 80/20 (v/v) Acetonitrile/water solution |
| --- | --- |

Needle Rinsing Programming

| Step | Description |
| --- | --- |
| 1 | Wash needle in flush port for 15 seconds |
| 2 | Drow def amount from sample, 200 µL min, 1 mm offset |
| 3 | Wash needle in flush port for 15 seconds |
| 4 | Inject |
| 5 | Remote start pulse, duration 10 × 12.5 msec |

Analysis Conditions

| Injection volume | 5 µL |
|---|---|
| Run time | 6.0 min |

Retention Times ($R_t$)

| Analyte | Rt (min) |
|---|---|
| MIN-101 (CYR-101) | ca. 2.9 |
| BFB-520 | ca. 2.3 |
| BFB-999 | ca. 2.4 |
| CYR-101-d6 | ca. 2.9 |
| BFB-784 | ca. 2.4 |

LC Equipment No. 3 [5]

Description

| Equipment | Type |
|---|---|
| Autosampler | Acquity UPLC Sample Manager FTN (Waters) |
| LC pump | Acquity UPLC I-Class (Waters) |
| Column oven | Acquity UPLC Column Heater (Waters) |
| Detector | XevoTQ-S (Waters) |

System Care

Needle Rinsing Solvent

| Exterior (Wash) | 80/20 (v/v) Acetonitrile/water solution |
|---|---|
| Interior (Purge) | 65/35 (v/v) Acetonitrile/water solution |
| Needle rinsing programming | Pre-injection wash: 0 second |

Post-injection wash: 6 seconds

Analysis Conditions

| Injection volume | 0.5 µL |
|---|---|
| Run time | 6.0 min |

Retention Times (Rt)

| Analyte | Rt (min) |
|---|---|
| MIN-101 (CYR-101) | ca. 3.0 |
| BFB-520 | ca. 2.4 |
| BFB-999 | ca. 2.4 |
| CYR-101-d6 | ca. 2.9 |
| BFB-784 | ca. 2.5 |

LC Equipment No. 2 [3]

Description

| Equipment | Type |
|---|---|
| Autosampler | Acquity UPLC (Waters) |
| LC pump | |
| Column oven | Acquity UPLC high temperature column heater (Waters) |
| Detector | API 4000 (AB Sciex) |

System Care

Needle Rinsing Solvent

| Strong solvent | 80/20 (v/v) Acetonitrile/water solution 2000 µL |
|---|---|
| Weak solvent | 65/35 (v/v) Acetonitrile/water solution 4000 µL |

Analysis Conditions

| Injection volume | 1 µL |
|---|---|
| Injection mode | Partial loop |
| Run time | 6.0 min |

Retention Times ($R_t$)

| Analyte | Rt (min) |
|---|---|
| MIN-101 (CYR.-101) | ca. 2.9 |
| BFB-520 | ca. 2.3 |
| BFB-999 | ca. 2.4 |
| CYR-101-d6 | ca. 2.9 |
| BFB-784 | ca. 2.4 |

Data Processing and Acceptance Criteria

Data Processing [2]

| | | MIN-101 (CYR-101) | BFB-520 | BFB-999 |
|---|---|---|---|---|
| Calibration range | LLOQ (ng/mL) | 0.2500 | 0.2500 | 0.2500 |
| | ULOQ (ng/mL) | 200.0 | 50.00 | 50.00 |
| Response | | MIN-101 peak area/CYR-101-d6 peak area | BFB-520 peak area/ BFB-784 peak area | BFB-999 peak area/ BFB-784 peak area |
| Regression model | | $1/X^2$ weighted simple linear regression | $1/X^2$ weighted simple linear regression | $1/X^2$ weighted simple linear regression |

Example 7: Synopsis of Protocol MIN-101C06

Name of Sponsor/Company:
Minerva Neurosciences, Inc.
Name of Investigational Product:
MIN-101
Study Title:
A Phase 1, Open-Label, Randomized, 3-Treatment Sequence, 3-Period, Single-Dose, Crossover Study in CYP2D6 Extensive Metaboliser Healthy Subjects to Compare the Pharmacokinetic Properties of 2 Gastro-Resistant and 1 Comparator Modified Release Formulations of MIN-101 and its Metabolites Followed by Food Effect Testing of the Selected Gastro-Resistant Controlled Release Formulation
Objectives:
Primary:
Part 1: PK Evaluation
    To evaluate the pharmacokinetic (PK) profiles of MIN-101 and its main metabolites (BFB-520 and BFB-999) following administration of 2 Gastro-Resistant and 1 Comparator Modified Release (MR) formulations of MIN-101 in healthy cytochrome P450 (CYP) 2D6 Extensive Metaboliser (EM) male and female subjects To Select 1 gastro-resistant MR formulation for use in fed state.

Part 2: Food Effect

To evaluate the effect of food (given as a high fat, high calorie meal) on the bioavailability of MIN-101 and its main metabolites when the selected gastro-resistant MR formulation is administered as a single dose of 32 mg to healthy CYP2D6 EM male and female subjects.

Secondary:

Part 1: PK Evaluation

To provide additional information on the safety and tolerability of single doses of MIN-101 in healthy CYP2D6 EM male and female subjects.

To evaluate the relationship between plasma levels of MIN-101 and its main metabolites on electrocardiogram (ECG) parameters including QT/QTcF Part 2: Food Effect To evaluate the safety and tolerability of the selected MR formulation in healthy CYP2D6 EM male and female subjects in fed as compared to fasted state.

Methodology:

This is a single-center, 2-part, phase 1 study.

Part 1: PK Evaluation

Part 1 is an open-label, randomised, 3-treatment sequence, 3-period study to evaluate the PK profile of MIN-101 and its metabolites (BFB-520 and BFB-999) after single oral administration of 3 formulations of MIN-101 (2 prototypes of CR gastro-resistant (GR) formulations and 1 comparator MR formulation). Each subject will receive a single dose of each of the formulations over the 3 periods. There will be a washout of 14±2 days between the three periods.

In total, 16 healthy CYP2D6 EM male or female subjects (with an ideal equal gender split, but a minimum of 6 of each sex) will be dosed to ensure data in 12 evaluable subjects. To be evaluable, subjects must have received all 3 formulations and have sufficient data for the primary objective of Part 1 of the study. Subjects must provide written informed consent to participate in the study before evaluations are performed or any laboratory samples are collected. Subjects will be evaluated for study eligibility during the screening period. After written informed consent is obtained, a complete medical history will be documented. A complete physical examination will be conducted, including measurement of vital signs, ECG (triplicate), body weight, and height. Hematology, clinical chemistry and urinalysis will be performed for all subjects. All subjects must be willing to use an acceptable double-barrier method of birth control with their partners from Screening through 90 days after the last dose.

Part 2: Food Effect

Subjects who completed part 1 of the study will return and receive a further single oral dose of one of the selected GR prototype under fed conditions to allow the assessment of food effect by comparison of the PK properties to those obtained in Part 1. Part 2 will commence after a review of the PK and safety data to decide which GR formulation will be used. There will be a wash-out period of 14±2 days after part 1 has been completed.

The end-of-study or early withdrawal assessments will be performed 5-9 days after the last received dose.

Number of Subjects (Planned):

In total, 16 healthy CYP2D6 EM male or female subjects (with an ideal equal gender split, but a minimum of 6 of each sex) will be dosed to ensure data in 12 evaluable subjects.

Subjects who are withdrawn for non-IMP related adverse events (AEs) will be replaced as required to ensure 12 evaluable subjects for Part 1 and for Part 2, at the end of the clinical study.

Subjects withdrawn due to an IMP-related AE will not be replaced.

Diagnosis and Main Criteria for Inclusion/Exclusion:

Inclusion Criteria

Subjects must satisfy all of the following inclusion criteria during screening to be enrolled in the study:

1. Confirmed CYP 2D6 extensive metaboliser genotype defined as a subject that has at least one functional allele (*1, or *2) but has no non-functional allele, meaning any combination of *1 and *2, and a decreased function allele (*10, *17 or *41) is allowed via documented testing
2. Subject has given voluntary written informed consent before performance of any study related procedure
3. Must be 18 to 45 years of age, inclusive
4. Subject must be a healthy male or female as indicated by the following:
   Clinical chemistries, haematology, and urinalysis tests must be within normal, allowable limits (if out of range, and with the exception of potassium, magnesium, and calcium, must be considered clinically significant to be exclusionary) and performed within 21 days of receiving first dose of study drug
   Body mass index of between 18 and 30 kg/m$^2$, inclusive
   Normal vital signs after 5 minutes resting in supine position:
   95 mm Hg<systolic blood pressure<140 mm Hg
   50 mm Hg<diastolic blood pressure<90 mm Hg
   50 bpm<heart rate<90 bpm
   Normal 12-lead ECG defined as: P≤120 ms, 120 ms<PR<210 ms, QRS
   <120 ms, QTc (Fridericia)≤430 msec for males and ≤440 msec for females (incomplete right bundle branch block can be accepted)
5. Agree to abstain from all medication (except for allowed birth control defined in inclusion criteria 6), including non-prescription and prescription medication (including vitamins and natural or herbal remedies, e.g. St. John's Wort) for 21 days before the first dose with IMP on period 1 until discharged from the study (end of post study medical following period 4)
6. Subject agrees to use the following methods of birth control:
   Female subjects of child bearing potential must be willing to use two methods of contraception throughout and up to 30 days after completion of the study. One of which must be a highly effective method defined as one which results in a low failure rate (i.e. less than 1% per year) when used consistently and correctly.
   The following highly effective contraception methods acceptable for this study are:
   Surgical sterilization (i.e., bilateral tubal ligation/salpingectomy, hysterectomy for female subjects or partners; vasectomy for male subjects or partners)
   Placement of an intrauterine device or intrauterine system
   Hormonal contraception (implantable, patch, injectable)
   PLEASE NOTE: Oral hormonal contraceptives are not permitted in this study.

True sexual abstinence when this is in line with the preferred and usual lifestyle of the subject, periodic abstinence (e.g. calendar ovulation, symptothermal, post-ovulation methods), declaration of abstinence for the duration of the trial and withdrawal are NOT acceptable methods of contraception)

The following acceptable methods can be used as a second form of contraception during the study:

Barrier methods for female subjects include either their partner's use of a condom or the subject's use of an occlusive cap [diaphragm or cervical/vault caps] with spermicidal foam, gel, film, cream, or suppository Female subjects who are post-menopausal (defined as spontaneous amenorrhea for at least 1 year or spontaneous amenorrhea for at least 6 months confirmed by Follicle stimulating hormone [FSH] result of ≥40 IU/mL) are eligible for this study.

Male Subjects

Male subjects who have been sterilised or have partners of non-childbearing potential (including homosexual men) are required to use one barrier method of contraception. This is to prevent unintended exposure of the partner to the study drug via seminal fluid (for male subjects, this must be a condom or their partner's use of an occlusive cap [diaphragm or cervical/vault caps].

Male subjects who have partners of childbearing potential must be willing to use one barrier method of contraception with their partners throughout the study (a condom or their partner's use of an occlusive cap [diaphragm or cervical/vault caps]). Their partners must also be using a highly effective method of birth control defined as one in which results in a low failure rate (i.e. less than 1% per year) when used consistently and correctly such as sterilisation, implants, injectables, combined oral contraceptives, and intrauterine devices for up to 90 days after completion of the study. Subjects must agree to inform the Investigator if their partner becomes pregnant during this time.

7. Must be willing and able to communicate and participate in the whole study.

8. Willing to eat all the food supplied throughout the study

Exclusion Criteria

Subjects meeting any of the following exclusion criteria are not to be enrolled in the study:

1. A history of clinically significant gastrointestinal disease (especially peptic ulcerations, gastrointestinal bleeding, ulcerative colitis, Crohn's disease or Irritable Bowel Syndrome); renal, hepatic, neurologic, hematologic, endocrine, oncologic, pulmonary, immunologic or psychiatric disease (especially those with a past history of clinically significant depression, suicidal ideation or suicide attempts), or cardiovascular disease, or any other condition which, in the opinion of the principle investigator, would jeopardize the safety of the subject or impact the validity of the study results 2. Acute diarrhea or constipation in the 7 days before the predicted first study day. If screening occurs >7 days before first study day, this criterion will be determined on first study day. Diarrhea is defined as the passage of liquid feces and/or a stool frequency of
>3 times per day. Constipation will be defined as a failure to move the bowels more frequently than every other day 3. Subject has donated blood within 90 days or plasma within 30 days of study dosing 4. Regular alcohol consumption in males >21 units per week and females >14 units per week (1 Unit=½ pint beer, 25 mL of 40% spirit or a 125 mL glass of wine)

5. Subject has a borderline or long QTc Fridericia interval as defined by screening readings of >430 msec for males and >440 for females or a personal or familial history of long QT syndrome 6. Subject has participated in a clinical trial within 90 days prior to study initiation 7. Females who are pregnant or breast feeding 8. Subject has used any prescription medication or over-the-counter (OTC) medication, including vitamin supplements, within 21 days prior to day −1

9. Subject has been treated with any known P450 2D6 or 3A4 enzymes altering drugs (e.g., beta blockers, antidepressants, antipsychotics, certain antibiotics such as erythromycin, ketoconazole, rifampicin, trimethoprim or clarithromycin, benzodiazepine such as alprazolam or midazolam, antihistamines such as chlorpheniramine, calcium channel blockers such as amlodipine or diltiazem, or PDE5 inhibitors) within 30 days prior to the study 10. Subject has smoked or used nicotine products within 2 months prior to or during the study 11. Subject has sought advice from or been referred to a GP or counsellor for abuse or misuse of alcohol, non-medical drugs, medicinal drugs or other substance abuse, e.g. solvents 12. Subject has a positive blood screen for HIV, Hepatitis B surface antigen (HBsAg), and Hepatitis C Antibody 13. Any current or previous use of drugs such as opiates, cocaine, ecstasy, or intravenous amphetamines and/or a positive urine screen for alcohol or drugs of abuse. Subjects who admit to occasional past use of *cannabis* will not be excluded as long as they have a negative drugs-of-abuse test and have been abstinent from *cannabis* use for at least 3 months 14. Subject has a current uncontrolled inter-current illness (i.e., active infection) or has had a clinically significant illness within the last 30 days prior to Day −1

15. Subject has had major surgery within 28 days of study entry, or 12 months prior to study for gastrointestinal surgery.

16. Failure to satisfy the investigator of fitness to participate for any other reason.

Test Product, Dosage, and Route of Administration:

Part 1:

After fasting for 10 hours overnight, on the morning of dosing days, study drug will be administered with 240 mL of noncarbonated water. Subjects will have their first meal at lunch time. Subjects will receive a single oral administration of each of the following regimens in a randomized manner, separated by a 14±2 days washout period:

Regimen A: 32 mg MIN-101 of the current modified-release formulation (comparator) identified as MR-32 formulation administered in the fasted state Regimen B: 32 mg MIN-101 of Gastro-resistant CR Formulation identified as GR-01: administered in the fasted state Regimen C: 32 mg MIN-101 of Gastro-resistant CR Formulation identified as GR-02: administered in the fasted state Part 2:

In Part 2, subjects will receive 1 oral dose of the selected gastro-resistant CR formulation (GR-01 or GR-02) in the fed state After fasting for 10 hours overnight, on the morning of Day 1, subjects will be given a high-fat, high-calorie breakfast before study drug administration. Subjects will consume the meal over a 25-minute period or less. After completing the meal, and 30 minutes after the start of the meal, study drug will be administered.

All study drugs will be administered orally with 240 mL of noncarbonated water. Water will be allowed as desired except for 1 hour before and 1 hour after drug administration.

Reference Therapy, Dosage and Mode of Administration:
Not Applicable. 32 mg MIN-101 of the current modified release formulation to be used as a comparator.

Duration of Subject Participation/Duration of Study/Duration of Treatment:
Selection:
Up to 21 days prior to first dose period 1
Institutionalization:
From morning of Day −1 up to Day 4 for 4 separate periods
Washout Period:
14±2 days from previous period dosing
End-of-Study Visit:
7 (+2 days) days after the last dose
Total Study Length (Including a Screening Period of 21 Days):
Up to 78 Days.
Evaluation Criteria
Pharmacokinetics:
Plasma will be stored at −80° C. until analysis. Plasma samples will be analyzed for MIN-101 and its metabolites BFB-520 and BFB-999 using a validated LC-MS/MS method.
Blood samples for MIN-101 will be collected at time 0 (pre-dose), 0.25, 0.5, 1, 1.5, 2, 2.5, 3, 3.5, 4, 5, 6, 7, 8, 10, 12, 14, 16, 20, 24, 28, 32, 36, 48, 60, and 72 hours post-dose on Day 1 of all periods. The following key plasma PK parameters will be calculated using non-compartmental methods: $C_{max}$, $T_{max}$, $T_{lag}$, partial AUC (e.g., $AUC_{12}$, $AUC_{24}$), $AUC_{last}$, $AUC_\infty$, and $t_{1/2}$. Additional PK parameters may be included if deemed appropriate.

ECG to be Detailed as there Will be PK/PD Assessment
The effects on cardiovascular variables will be evaluated by means of descriptive statistics and frequency tabulations. These tables will include observed values and changes from Baseline values (the pre-dose ECG will be used as Baseline) to allow detection of clinically relevant changes in individuals.

The ECG variables that will be analyzed are heart rate, PR interval, QRS interval, QT interval, and QTc interval corrected for heart rate using QTcF. QTcF values will be tabulated for their absolute values and also tabulated relative to Baseline measurements in order to detect individual QTcF changes.

Descriptive statistics of QTcF intervals and changes from Baseline will be summarised at each scheduled time point. The percent of subjects with QTc interval ≥450 milliseconds, >480 milliseconds, or ≥500 milliseconds will be summarised as will the percent of subjects with QTcF interval increases from Baseline of 30 to 59 milliseconds or ≥60 milliseconds.

Important abnormalities in ECG waveform that are changes from the Baseline readings will be reported (e.g., changes in T-wave morphology or the occurrence of U-waves).

Safety and Tolerability:
The incidence of adverse events and clinically significant abnormal laboratory, vital signs and ECGs values will be recorded based upon Investigator observation and subject reporting.

Statistical Considerations
Sample Size:

The sample size for this study is based upon both quantitative and qualitative consideration. In previous single dose experience with EM subjects, the inter-subject coefficient of variance (CV) for plasma AUC and $C_{max}$ for MIN-101 reference formulation is estimated to be about 30% and 50%, respectively. Therefore, the selected sample size of 12 to 16 completers should be sufficient to address the objectives of this study and to detect the occurrence of rare adverse events should such event are likely due to treatment with MIN-101. Every effort will be made to have an equal number of males and females enrolled.

Pharmacokinetics:

Pharmacokinetic parameters will be summarized by mean, standard deviation, standard error of the mean, coefficient of variation, minimum, median, and maximum, as appropriate, for each formulation and between the selected MR formulation for each food condition. The 90% confidence intervals for the ratio of mean log-transformed plasma partial AUC, $AUC_{last}$, and $AUC_\infty$ and $C_{max}$ will be constructed using the estimated least squares means and intra-subject variance from a mixed effects model.

Additional analysis will be performed if deemed necessary including the relationship between plasma levels of MIN-101 and its main metabolites and changes in QTcF intervals.

Safety:

Safety and tolerability of MIN-117 will be based upon the review of individual values and summary statistics. Incidence of treatment-emergent adverse events will be tabulated by counts and percentages. Abnormalities in clinical laboratory, vital signs, and ECG will be based on pre-defined normal ranges and will be tabulated by dose group showing subject counts and percentages.

Examples 8-11 detail an open-label, randomized, 3-treatment sequence, 3-period study to evaluate the PK profile of MIN-101 and its metabolite BFB-520 after single oral administration of 3 formulations of MIN-101 (2 prototypes of CR gastro-resistant (GR) formulations (GR-01 and GR-02) and 1 comparator MR formulation (MR32)). Each subject received a single dose of each of the formulations over the 3 periods. There was a washout of 14±2 days between the three periods.

In the Examples, various tables are shown which include the plasma concentrations time profile of various compounds, including, for example, 1H-Isoindol-1-one, 2-[[1-[2-(4-Fluorophenyl)-2-oxoethyl]-4-piperidinyl]methyl]-2,3-dihydro-, i.e., Compound (I). In these Tables, the use of the "MIN-101" or "MIN101" is intended to refer to the free base, i.e., Compound (I).

Example 8: In Vivo Pharmacokinetic Analysis of MIN-101 in CR GR-01 Tablets, CR GR-02 Tablets, and MR 32 mg Capsules (MR32) (Tau=72 h)

MR32—

12 subjects (cross-over)

Geo Mean $C_{max}$: 28.34 ng/mL

Median $T_{max}$: 2.00 H $AUC_{(0-tau)}$: 291.55 ng·H/mL

TABLE 8

MR32 Mean MIN-101 Plasma Concentrations and Parameters

| MR32 Hours | MR32 MIN-101 PLASMA CONCENTRATIONS and AUCo-t | | | |
|---|---|---|---|---|
| | MEAN | Sd | Sm | CV % |
| 0 | 0.00 | 0.00 | 0.00 | 0.00 |
| 0.25 | 0.00 | 0.00 | 0.00 | 0.00 |
| 0.5 | 6.56 | 7.42 | 6.46 | 113.08 |
| 1 | 19.68 | 7.24 | 5.44 | 36.77 |
| 1.5 | 23.96 | 7.68 | 6.33 | 32.04 |
| 2 | 24.16 | 7.89 | 5.97 | 32.64 |
| 2.5 | 24.68 | 6.47 | 5.19 | 26.24 |
| 3 | 22.06 | 5.41 | 4.71 | 24.54 |
| 3.5 | 20.34 | 5.38 | 4.21 | 26.46 |
| 4 | 19.45 | 5.61 | 4.92 | 28.83 |
| 5 | 21.54 | 10.08 | 7.17 | 46.80 |
| 6 | 15.19 | 6.89 | 4.91 | 45.33 |
| 7 | 11.89 | 5.89 | 3.82 | 49.52 |
| 8 | 10.36 | 4.69 | 3.39 | 45.27 |
| 10 | 12.46 | 5.94 | 4.95 | 47.65 |
| 12 | 12.66 | 5.64 | 4.41 | 44.58 |
| 14 | 10.33 | 4.86 | 3.96 | 47.05 |
| 16 | 7.74 | 3.14 | 2.64 | 40.56 |
| 20 | 4.12 | 2.26 | 1.85 | 54.83 |
| 24 | 3.11 | 1.62 | 1.48 | 52.21 |
| 28 | 2.39 | 2.24 | 1.38 | 93.57 |
| 32 | 1.45 | 1.42 | 0.96 | 97.56 |
| 36 | 0.96 | 1.15 | 0.65 | 119.73 |
| 48 | 0.20 | 0.35 | 0.27 | 176.68 |
| 60 | 0.03 | 0.12 | 0.06 | 346.41 |
| 72 | 0.04 | 0.13 | 0.07 | 346.41 |
| CMax ng/ml | 29.52 | 9.00 | 6.70 | 30.48 |
| Tmax H | 2.42 | 1.33 | 0.99 | 54.98 |
| AUC0-t H · ng/ml | 291.55 | 66.12 | 53.61 | 22.68 |

See FIG. 4.
GR-01-12 subjects (cross-over)
Geo Mean $C_{max}$: 18.82 ng/mL
Median $T_{max}$: 4.50 H
$AUC_{(0-tau)}$: 284.52 ng·H/mL
Relative Bioavailability versus MR32: F % $C_{max}$: 69.90%, F % $AUC_{(0-tau)}$: 101.3%

TABLE 9

GR-01 Individual MIN-101 Plasma Concentrations and Parameters

GR01 MEAN MIN-101 PLASMA CONCENTRATIONS (ng/ml) and AUCo-t (H · ng/ml)

| GR01 Hours | 1-MIN-101 | 2-MIN-101 | 3-MIN-101 | 5-MIN-101 | 6-MIN-101 | 7-MIN-101 | 8-MIN-101 | 9-MIN-101 | 10-MIN-101 | 11-MIN-101 | 12-MIN-101 | 13-MIN-101 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 4.22 | 0.00 | 0.00 | 0.00 |
| 1.5 | 0.00 | 0.00 | 6.26 | 0.00 | 0.00 | 0.00 | 0.38 | 0.00 | 0.42 | 0.00 | 0.00 | 7.98 |
| 2 | 3.83 | 5.42 | 10.68 | 2.50 | 0.00 | 0.00 | 13.23 | 0.00 | 8.71 | 16.03 | 0.48 | 8.14 |
| 2.5 | 15.95 | 13.82 | 11.87 | 12.14 | 0.00 | 3.45 | 12.42 | 3.00 | 12.78 | 24.17 | 23.30 | 7.62 |
| 3 | 17.85 | 17.61 | 11.10 | 13.88 | 0.39 | 12.78 | 11.08 | 24.02 | 12.98 | 26.68 | 28.00 | 10.13 |
| 3.5 | 15.56 | 21.53 | 10.97 | 12.31 | 6.52 | 10.89 | 10.94 | 28.19 | 13.60 | 25.78 | 24.01 | 12.18 |
| 4 | 20.60 | 19.03 | 8.23 | 11.96 | 15.23 | 9.53 | 8.04 | 22.91 | 17.64 | 24.78 | 22.59 | 11.30 |
| 5 | 17.05 | 17.24 | 6.66 | 14.68 | 15.63 | 8.44 | 14.90 | 17.95 | 12.92 | 24.46 | 12.86 | 12.69 |
| 6 | 15.26 | 14.41 | 6.89 | 13.19 | 13.39 | 6.06 | 12.36 | 11.72 | 7.62 | 19.24 | 5.64 | 10.42 |
| 7 | 9.61 | 11.29 | 6.28 | 12.62 | 10.60 | 4.71 | 11.51 | 13.95 | 6.70 | 17.83 | 9.72 | 9.08 |
| 8 | 7.46 | 7.20 | 5.58 | 11.86 | 10.51 | 3.51 | 8.19 | 16.53 | 13.39 | 14.16 | 5.82 | 8.52 |
| 10 | 4.30 | 5.10 | 12.66 | 11.69 | 6.19 | 2.71 | 18.08 | 17.00 | 18.05 | 8.68 | 13.19 | 10.59 |
| 12 | 9.45 | 5.59 | 10.24 | 20.15 | 7.24 | 3.05 | 12.22 | 13.92 | 16.31 | 11.15 | 13.39 | 12.47 |
| 14 | 13.11 | 10.14 | 12.01 | 17.73 | 7.12 | 3.52 | 12.65 | 12.02 | 14.42 | 11.67 | 20.32 | 6.36 |
| 16 | 10.98 | 6.35 | 12.59 | 16.88 | 6.40 | 3.18 | 7.19 | 11.25 | 13.43 | 13.29 | 19.44 | 6.02 |
| 20 | 5.54 | 3.88 | 4.69 | 8.36 | 4.95 | 2.65 | 2.44 | 7.99 | 6.52 | 9.76 | 5.92 | 3.23 |
| 24 | 5.57 | 1.94 | 3.21 | 6.73 | 6.31 | 2.38 | 2.90 | 12.21 | 3.90 | 10.97 | 3.63 | 7.08 |
| 28 | 4.31 | 1.64 | 3.18 | 2.55 | 3.91 | 2.35 | 1.47 | 7.67 | 3.79 | 10.31 | 0.54 | 5.80 |
| 32 | 3.50 | 1.56 | 2.73 | 1.16 | 3.55 | 5.90 | 0.66 | 3.59 | 2.79 | 7.59 | 0.67 | 3.46 |
| 36 | 2.37 | 1.06 | 1.34 | 0.54 | 2.14 | 12.25 | 0.00 | 1.06 | 0.56 | 3.73 | 0.37 | 3.60 |
| 48 | 1.33 | 0.73 | 0.28 | 0.00 | 2.04 | 2.55 | 0.00 | 0.00 | 0.00 | 0.56 | 0.00 | 1.76 |
| 60 | 0.00 | 0.48 | 0.00 | 0.00 | 1.33 | 1.33 | 0.00 | 0.00 | 0.00 | 0.00 | 0.00 | 0.45 |
| 72 | 0.00 | 0.69 | 0.00 | 0.00 | 0.41 | 0.44 | 0.00 | 0.00 | 0.00 | 0.00 | 0.00 | 0.27 |
| CMax ng/ml | 20.6 | 21.5 | 12.7 | 20.2 | 15.6 | 12.8 | 18.1 | 28.2 | 18.1 | 26.7 | 28.0 | 12.7 |
| Tmax H | 4.0 | 3.5 | 10.0 | 12.0 | 5.0 | 3.0 | 10.0 | 3.5 | 10.0 | 3.0 | 3.0 | 5.0 |
| AUC0-t H · ng/ml | 281.6 | 219.3 | 230.1 | 309.7 | 262.8 | 257.0 | 213.8 | 357.2 | 289.7 | 430.4 | 279.0 | 283.6 |
| F AUC | 84.0 | 93.6 | 98.8 | 172.8 | 92.0 | 112.6 | 80.0 | 92.5 | 76.9 | 143.9 | 76.0 | 92.5 |
| F Cmax | 65.3 | 72.9 | 48.6 | 110.5 | 54.2 | 69.1 | 74.4 | 66.4 | 37.7 | 116.9 | 76.9 | 45.7 |

TABLE 10

GR-01 Mean MIN-101 Plasma Concentrations and Parameters

| GR01 Hours | GR01 MIN-101 PLASMA CONCENTRATIONS and AUCo-t | | | |
|---|---|---|---|---|
| | MEAN | Sd | Sm | CV % |
| 0 | 0.00 | 0.00 | 0.00 | 0.00 |
| 0.25 | 0.00 | 0.00 | 0.00 | 0.00 |
| 0.5 | 0.00 | 0.00 | 0.00 | 0.00 |
| 1 | 0.35 | 1.22 | 0.65 | 346.41 |
| 1.5 | 1.25 | 2.77 | 1.95 | 220.78 |
| 2 | 5.75 | 5.57 | 4.67 | 96.91 |
| 2.5 | 11.71 | 7.46 | 5.46 | 63.69 |
| 3 | 15.54 | 7.84 | 6.08 | 50.45 |
| 3.5 | 16.04 | 7.01 | 5.89 | 43.68 |
| 4 | 15.99 | 6.08 | 5.27 | 38.00 |
| 5 | 14.62 | 4.60 | 3.26 | 31.47 |
| 6 | 11.35 | 4.17 | 3.35 | 36.70 |
| 7 | 10.33 | 3.58 | 2.64 | 34.63 |
| 8 | 9.39 | 3.93 | 3.25 | 41.81 |
| 10 | 10.69 | 5.39 | 4.42 | 50.45 |
| 12 | 11.26 | 4.66 | 3.48 | 41.34 |
| 14 | 11.76 | 4.67 | 3.33 | 39.73 |
| 16 | 10.58 | 4.87 | 3.96 | 46.01 |
| 20 | 5.49 | 2.33 | 1.85 | 42.48 |
| 24 | 5.57 | 3.30 | 2.58 | 59.31 |
| 28 | 3.96 | 2.80 | 2.04 | 70.67 |
| 32 | 3.10 | 2.06 | 1.50 | 66.68 |
| 36 | 2.42 | 3.33 | 2.05 | 137.50 |
| 48 | 0.77 | 0.92 | 0.77 | 119.51 |
| 60 | 0.30 | 0.51 | 0.40 | 171.48 |
| 72 | 0.15 | 0.24 | 0.20 | 159.83 |
| CMax ng/ml | 19.59 | 5.74 | 4.61 | 29.30 |
| Tmax H | 6.00 | 3.43 | 3.00 | 57.19 |
| AUC0-t H · ng/ml | 284.52 | 60.83 | 41.49 | 21.38 |
| F AUC | 101.30 | 29.16 | 20.90 | 28.79 |
| F Cmax | 69.90 | 23.92 | 17.04 | 34.22 |

See FIG. 5.
GR-02-12 subjects (cross-over)
Geo Mean $C_{max}$: 15.43 ng/mL
Median $T_{max}$: 14.00 H
$AUC_{(0-tau)}$: 253.01 ng·H/mL
Relative Bioavailability versus MR32: F % $C_{max}$: 54.33%, F % $AUC_{(0-tau)}$: 86.9%

TABLE 11

GR-02 Individual MIN-101 Plasma Concentrations and Parameters

GR02 MEAN MIN-101 PLASMA CONCENTRATIONS (ng/ml) and AUCo-t (H · ng/ml)

| GR02 Hours | 1-MIN-101 | 2-MIN-101 | 3-MIN-101 | 4-MIN-101 | 5-MIN-101 | 7-MIN-101 | 8-MIN-101 | 9-MIN-101 | 10-MIN-101 | 11-MIN-101 | 12-MIN-101 | 13-MIN-101 | 14-MIN-101 |
|---|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 | 2.03 |
| 2 | 0.00 | 0.00 | 0.41 | 0.00 | 0.70 | 0.00 | 0.00 | 0.00 | 0.00 | 0.00 | 0.00 | 0.88 | 6.86 |
| 2.5 | 2.13 | 0.00 | 1.87 | 0.00 | 1.17 | 1.09 | 0.00 | 1.24 | 2.48 | 1.02 | 0.00 | 2.79 | 11.97 |
| 3 | 4.71 | 0.41 | 2.66 | 0.00 | 2.98 | 1.52 | 0.66 | 2.55 | 2.87 | 5.06 | 4.14 | 2.81 | 11.48 |
| 3.5 | 6.35 | 1.16 | 3.08 | 0.35 | 2.16 | 2.14 | 1.06 | 3.14 | 5.27 | 11.72 | 7.24 | 3.02 | 14.23 |
| 4 | 8.70 | 2.20 | 3.06 | 1.17 | 2.19 | 2.25 | 1.21 | 3.45 | 6.24 | 12.69 | 8.58 | 3.45 | 12.39 |
| 5 | 8.93 | 6.06 | 3.40 | 3.00 | 10.46 | 2.87 | 2.49 | 4.07 | 7.52 | 14.53 | 7.76 | 8.84 | 11.67 |
| 6 | 7.60 | 6.39 | 2.61 | 2.92 | 10.83 | 3.37 | 1.94 | 4.24 | 6.94 | 11.33 | 5.09 | 8.09 | 81.75 |
| 7 | 5.96 | 5.09 | 3.56 | 5.85 | 7.32 | 3.15 | 2.06 | 4.52 | 4.85 | 10.76 | 5.23 | 9.19 | 8.67 |
| 8 | 5.11 | 4.28 | 2.89 | 5.14 | 6.40 | 3.30 | 2.58 | 5.76 | 5.02 | 6.39 | 11.43 | 8.98 | 10.06 |
| 10 | 4.90 | 3.27 | 3.92 | 5.82 | 12.63 | 4.26 | 3.26 | 9.25 | 5.39 | 10.25 | 12.96 | 11.15 | 15.14 |
| 12 | 15.08 | 2.81 | 6.31 | 9.24 | 20.26 | 3.27 | 6.31 | 8.07 | 21.50 | 17.68 | 13.88 | 16.18 | 25.98 |
| 14 | 11.62 | 7.94 | 7.57 | 10.68 | 18.73 | 3.42 | 3.77 | 10.16 | 11.15 | 16.50 | 15.37 | 9.96 | 29.85 |
| 16 | 9.87 | 5.79 | 11.46 | 7.68 | 15.69 | 8.22 | 2.61 | 10.94 | 9.53 | 9.32 | 19.54 | 7.85 | 19.75 |
| 20 | 10.00 | 6.27 | 6.62 | 3.77 | 6.34 | 5.19 | 0.94 | 7.50 | 4.26 | 8.94 | 9.83 | 4.94 | 6.44 |
| 24 | 9.29 | 4.59 | 5.07 | 5.95 | 6.69 | 12.66 | 0.64 | 10.97 | 6.98 | 7.46 | 12.76 | 13.32 | 3.97 |
| 28 | 8.23 | 3.21 | 4.04 | 4.43 | 1.64 | 13.20 | 0.48 | 10.56 | 10.72 | 6.28 | 10.99 | 7.05 | 3.54 |
| 32 | 8.21 | 4.06 | 2.61 | 3.35 | 0.44 | 6.48 | 0.00 | 7.92 | 9.55 | 3.03 | 4.75 | 4.90 | 1.38 |
| 36 | 4.24 | 2.75 | 1.59 | 2.12 | 0.00 | 2.87 | 0.00 | 4.57 | 4.94 | 1.66 | 2.00 | 3.42 | 0.40 |
| 48 | 1.72 | 0.93 | 0.58 | 0.58 | 0.00 | 0.43 | 0.00 | 0.91 | 0.00 | 0.55 | 0.29 | 0.54 | 0.00 |
| 60 | 0.00 | 1.34 | 0.41 | 0.00 | 0.00 | 0.00 | 0.00 | 0.65 | 0.00 | 0.00 | 0.00 | 0.31 | 0.00 |
| 72 | 0.00 | 0.28 | 0.00 | 0.00 | 0.00 | 0.00 | 0.00 | 0.00 | 0.00 | 0.00 | 0.00 | 0.00 | 0.00 |
| CMax ng/ml | 15.1 | 7.9 | 11.5 | 10.7 | 20.3 | 13.2 | 6.3 | 11.0 | 21.5 | 17.7 | 19.5 | 16.2 | 29.9 |
| Tmax H | 12.0 | 14.0 | 16.0 | 14.0 | 12.0 | 28.0 | 12.0 | 24.0 | 12.0 | 12.0 | 16.0 | 12.0 | 14.0 |
| AUC0-t H · ng/ml | 319.8 | 190.9 | 183.2 | 182.0 | 247.4 | 233.2 | 53.0 | 308.3 | 275.7 | 300.5 | 357.4 | 298.6 | 338.9 |
| F AUC | 95.4 | 81.5 | 78.6 | 101.6 | 86.6 | 102.2 | 19.8 | 79.9 | 73.2 | 100.5 | 97.3 | 97.5 | 116.3 |
| F Cmax | 47.8 | 26.9 | 44.0 | 58.6 | 70.3 | 71.4 | 26.0 | 25.8 | 45.0 | 77.5 | 53.7 | 58.3 | 101.1 |

TABLE 12

GR-02 Mean MIN-101 Plasma Concentrations and Parameters

GR02 MIN-101 PLASMA CONCENTRATIONS and AUCo-t

| GR02 Hours | MEAN | Sd | Sm | CV % |
|---|---|---|---|---|
| 0 | 0.00 | 0.00 | 0.00 | 0.00 |
| 0.25 | 0.00 | 0.00 | 0.00 | 0.00 |
| 0.5 | 0.00 | 0.00 | 0.00 | 0.00 |
| 1 | 0.00 | 0.00 | 0.00 | 0.00 |
| 1.5 | 0.16 | 0.59 | 0.31 | 375.28 |
| 2 | 0.68 | 1.95 | 1.04 | 286.76 |
| 2.5 | 1.98 | 3.29 | 1.89 | 166.30 |
| 3 | 3.22 | 3.03 | 1.90 | 94.21 |
| 3.5 | 4.69 | 4.39 | 3.38 | 93.69 |
| 4 | 5.20 | 4.14 | 3.38 | 79.73 |
| 5 | 7.05 | 3.94 | 3.24 | 55.85 |
| 6 | 6.16 | 3.20 | 2.68 | 51.99 |
| 7 | 5.86 | 2.63 | 2.09 | 44.82 |
| 8 | 5.95 | 2.84 | 2.19 | 47.70 |
| 10 | 7.86 | 4.27 | 3.79 | 54.29 |
| 12 | 12.81 | 7.69 | 6.62 | 60.04 |
| 14 | 12.06 | 7.28 | 5.35 | 60.38 |
| 16 | 10.63 | 5.24 | 3.98 | 49.25 |
| 20 | 6.23 | 2.37 | 1.75 | 37.95 |
| 24 | 7.72 | 4.01 | 3.23 | 52.01 |
| 28 | 6.49 | 4.15 | 3.47 | 63.88 |
| 32 | 4.36 | 2.90 | 2.24 | 66.52 |
| 36 | 2.35 | 1.62 | 1.26 | 69.09 |
| 48 | 0.50 | 0.34 | 0.29 | 68.40 |
| 60 | 0.21 | 0.41 | 0.30 | 197.87 |
| 72 | 0.02 | 0.08 | 0.04 | 375.28 |
| CMax ng/ml | 15.43 | 6.70 | 5.37 | 43.38 |
| Tmax H | 15.23 | 5.20 | 3.67 | 34.12 |
| AUC0-t H · ng/ml | 253.01 | 85.28 | 65.81 | 33.71 |
| F AUC | 86.94 | 24.39 | 16.36 | 28.05 |
| F Cmax | 54.33 | 23.09 | 17.99 | 42.50 |

See FIG. 6.

TABLE 13

Comparison of MR32, GR-01, and GR-02 MIN-101 Plasma Concentrations.
MR32 GR01 and GR02 Mean MIN-101 Plasma Concentrations (ng/ml)

| Hours | MR32-Mean | GR01-Mean | GR02-Mean |
|---|---|---|---|
| 0 | 0.00 | 0.00 | 0.00 |
| 0.25 | 0.00 | 0.00 | 0.00 |
| 0.5 | 6.56 | 0.00 | 0.00 |
| 1 | 19.68 | 0.35 | 0.00 |
| 1.5 | 23.96 | 1.25 | 0.16 |
| 2 | 24.16 | 5.75 | 0.68 |
| 2.5 | 24.68 | 11.71 | 1.98 |
| 3 | 22.06 | 15.54 | 3.22 |
| 3.5 | 20.34 | 16.04 | 4.69 |
| 4 | 19.45 | 15.99 | 5.20 |
| 5 | 21.54 | 14.62 | 7.05 |
| 6 | 15.19 | 11.35 | 6.16 |
| 7 | 11.89 | 10.33 | 5.86 |
| 8 | 10.36 | 9.39 | 5.95 |
| 10 | 12.46 | 10.69 | 7.86 |
| 12 | 12.66 | 11.26 | 12.81 |
| 14 | 10.33 | 11.76 | 12.06 |
| 16 | 7.74 | 10.58 | 10.63 |
| 20 | 4.12 | 5.49 | 6.23 |
| 24 | 3.11 | 5.57 | 7.72 |
| 28 | 2.39 | 3.96 | 6.49 |
| 32 | 1.45 | 3.10 | 4.36 |
| 36 | 0.96 | 2.42 | 2.35 |
| 48 | 0.20 | 0.77 | 0.50 |
| 60 | 0.03 | 0.30 | 0.21 |
| 72 | 0.04 | 0.15 | 0.02 |
| Max ng/ml | 29.5 | 19.6 | 15.4 |
| Tmax H | 2.4 | 6.0 | 15.2 |
| AUC0-t H · ng/ml | 291.6 | 284.5 | 253.01 |
| F AUC | REF | 101.3 | 86.94 |
| F Cmax | REF | 69.9 | 54.33 |

See FIG. 7.

TABLE 14

Comparison of MR32, GR-01, and GR-02 MIN-101 Plasma Concentrations - Rates of Increase and Decrease.
MR32 and GR01 Mean MIN101 Plasma Conc. Rates of Increase and Decrease (ng/ml)/H

| Hours | MR32-RATE | GR01-RATE | GR02-RATE |
|---|---|---|---|
| 0 | 0.00 | 0.00 | 0.00 |
| 0.25 | 0.00 | 0.00 | 0.00 |
| 0.5 | 26.25 | 0.00 | 0.00 |
| 1 | 26.24 | 0.70 | 0.00 |
| 1.5 | 8.56 | 1.80 | 0.31 |
| 2 | 0.39 | 9.00 | 1.05 |
| 2.5 | 1.03 | 11.92 | 2.60 |
| 3 | 0.00 | 7.66 | 2.48 |
| 3.5 | 0.00 | 1.00 | 2.94 |
| 4 | 0.00 | 0.00 | 1.02 |
| 5 | 2.09 | 0.00 | 1.85 |
| 6 | 0.00 | 0.00 | 0.00 |
| 7 | 0.00 | 0.00 | 0.00 |
| 8 | 0.00 | 0.00 | 0.09 |
| 10 | 1.05 | 0.65 | 0.96 |
| 12 | 0.10 | 0.29 | 2.48 |
| 14 | 0.00 | 0.25 | 0.00 |
| 16 | 0.00 | 0.00 | 0.00 |
| 20 | 0.00 | 0.00 | 0.00 |
| 24 | 0.00 | 0.02 | 0.37 |
| 28 | 0.00 | 0.00 | 0.00 |
| 32 | 0.00 | 0.00 | 0.00 |
| 36 | 0.00 | 0.00 | 0.00 |
| VMax (ng/ml)/H | 26.2 | 11.9 | 2.9 |
| Time of VMax | 0.50 | 2.50 | 3.50 |
| TEST/MR32 | REF | 0.45 | 0.11 |

During each time interval (dt) the plasma concentration ($C_p$) of MIN-101 increases or decreases. From t=0 to $T_{max}$, the rate of increase $V_{max}=d(C_p)/dt$. After the $V_{max}$, the rates are decreasing. See FIG. 8.

Example 9: In Vivo Pharmacokinetic Analysis of BFB-520 in CR GR-01 Tablets, CR GR-02 Tablets, and MR 32 mg Capsules (MR32) (Tau=72 h)

MR32—

12 subjects (cross-over)

Geo Mean $C_{max}$: 1.77 ng/mL

Median $T_{max}$: 6.00 H $AUC_{(0-tau)}$: 30.26 ng·H/mL

TABLE 15

MR32 Individual BFB-520 Plasma Concentrations and Parameters

MR32 BFB-520 PLASMA CONCENTRATIONS (ng/ml) and AUCo-t (H · ng/ml)

| MR32 Hours | 1-BFB-520 | 2-BFB-520 | 3-BFB-520 | 5-BFB-520 | 6-BFB-520 | 7-BFB-520 | 8-BFB-520 | 9-BFB-520 | 10-BFB-520 | 11-BFB-520 | 12-BFB-520 | 13-BFB-520 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.56 | 0.54 | 0.00 | 0.30 | 0.53 | 0.32 | 0.28 | 1.01 | 0.00 | 0.70 | 0.56 | 0.26 |
| 1.5 | 1.20 | 0.85 | 0.58 | 0.36 | 0.72 | 0.61 | 0.76 | 1.29 | 0.43 | 1.28 | 1.10 | 0.50 |
| 2 | 1.24 | 0.65 | 0.89 | 0.62 | 0.92 | 0.89 | 0.59 | 2.42 | 0.80 | 1.41 | 1.23 | 0.80 |
| 2.5 | 1.41 | 0.75 | 0.97 | 0.89 | 1.18 | 0.88 | 0.84 | 2.16 | 1.19 | 1.69 | 1.76 | 0.79 |
| 3 | 1.37 | 0.94 | 0.99 | 1.18 | 1.56 | 1.12 | 1.10 | 3.33 | 1.58 | 1.93 | 1.63 | 0.74 |
| 3.5 | 1.72 | 1.03 | 0.81 | 1.25 | 1.44 | 1.20 | 1.28 | 2.91 | 1.57 | 1.91 | 1.94 | 0.84 |
| 4 | 2.03 | 0.99 | 0.98 | 1.38 | 1.65 | 1.21 | 1.38 | 2.30 | 1.65 | 1.77 | 2.27 | 0.95 |
| 5 | 1.91 | 1.10 | 1.09 | 0.90 | 1.64 | 1.10 | 1.07 | 2.55 | 2.97 | 2.09 | 1.61 | 1.03 |
| 6 | 1.81 | 1.09 | 0.83 | 0.88 | 1.76 | 0.96 | 1.09 | 2.23 | 3.13 | 1.94 | 1.73 | 1.10 |
| 7 | 1.91 | 0.95 | 0.90 | 0.90 | 1.40 | 0.94 | 0.89 | 2.25 | 2.10 | 2.16 | 1.16 | 1.01 |
| 8 | 1.69 | 0.92 | 0.71 | 0.79 | 1.60 | 1.01 | 1.19 | 2.63 | 3.13 | 1.93 | 1.42 | 1.08 |
| 10 | 1.27 | 1.00 | 1.09 | 0.63 | 1.69 | 0.73 | 1.73 | 1.97 | 2.76 | 2.46 | 1.44 | 1.01 |
| 12 | 0.73 | 1.20 | 0.56 | 0.84 | 1.39 | 0.56 | 1.42 | 1.07 | 2.12 | 2.63 | 1.26 | 0.71 |
| 14 | 0.88 | 1.06 | 0.62 | 1.07 | 1.30 | 0.75 | 1.46 | 2.63 | 2.35 | 2.74 | 1.37 | 0.55 |
| 16 | 0.99 | 0.86 | 0.54 | 0.65 | 0.85 | 0.58 | 1.23 | 1.76 | 1.53 | 1.65 | 1.03 | 0.51 |
| 20 | 1.43 | 0.68 | 0.48 | 0.58 | 0.61 | 0.86 | 0.70 | 1.20 | 0.87 | 1.40 | 0.95 | 0.41 |
| 24 | 0.69 | 0.39 | 0.35 | 0.00 | 0.35 | 0.77 | 0.47 | 0.67 | 0.70 | 0.58 | 0.63 | 0.36 |
| 28 | 0.89 | 0.00 | 0.31 | 0.00 | 0.30 | 0.44 | 0.00 | 0.45 | 0.46 | 0.37 | 0.33 | 0.61 |
| 32 | 0.40 | 0.00 | 0.00 | 0.00 | 0.00 | 0.35 | 0.00 | 0.00 | 0.28 | 0.00 | 0.00 | 0.81 |
| 36 | 0.00 | 0.00 | 0.00 | 0.00 | 0.00 | 0.00 | 0.00 | 0.00 | 0.00 | 0.00 | 0.00 | 0.61 |
| 48 | 0.00 | 0.00 | 0.00 | 0.00 | 0.00 | 0.00 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 | 0.00 | 0.00 | 0.00 |
| 72 | 0.00 | 0.00 | 0.00 | 0.00 | 0.00 | 0.00 | 0.00 | 0.00 | 0.00 | 000 | 000 | 000 |
| Max ng/ml | 2.0 | 1.2 | 1.1 | 1.4 | 1.8 | 1.2 | 1.7 | 3.3 | 3.1 | 2.7 | 2.3 | 1.1 |
| Tmax H | 4.0 | 12.0 | 10.0 | 4.0 | 6.0 | 4.0 | 10.0 | 3.0 | 6.0 | 14.0 | 4.0 | 6.0 |
| AUC0-t H · ng/ml | 34.7 | 20.1 | 16.7 | 15.3 | 27.2 | 22.6 | 24.8 | 44.9 | 47.2 | 46.7 | 34.5 | 28.5 |

TABLE 16

MR32 Mean BFB-520 Plasma Concentrations and Parameters

| MR32 Hours | MR32 BFB-520 PLASMA CONCENTRATIONS and AUCo-t | | | |
|---|---|---|---|---|
| | MEAN | Sd | Sm | CV % |
| 0 | 0.00 | | | |
| 0.25 | 0.00 | | | |
| 0.5 | 0.00 | | | |
| 1 | 0.42 | 0.29 | 0.23 | 68.42 |
| 1.5 | 0.81 | 0.33 | 0.28 | 41.40 |
| 2 | 1.04 | 0.51 | 0.36 | 48.77 |
| 2.5 | 1.21 | 0.45 | 0.36 | 37.60 |
| 3 | 1.46 | 0.68 | 0.46 | 46.84 |
| 3.5 | 1.49 | 0.58 | 0.43 | 38.99 |
| 4 | 1.55 | 0.48 | 0.40 | 31.20 |
| 5 | 1.59 | 0.67 | 0.54 | 42.36 |
| 6 | 1.55 | 0.69 | 0.55 | 44.45 |
| 7 | 1.44 | 0.68 | 0.57 | 47.23 |
| 8 | 1.51 | 0.75 | 0.57 | 49.53 |
| 10 | 1.48 | 0.66 | 0.53 | 44.91 |
| 12 | 1.21 | 0.63 | 0.46 | 52.49 |
| 14 | 1.40 | 0.77 | 0.60 | 54.91 |
| 16 | 1.01 | 0.44 | 0.36 | 43.42 |
| 20 | 0.85 | 0.34 | 0.27 | 40.36 |
| 24 | 0.50 | 0.22 | 0.18 | 44.39 |
| 28 | 0.35 | 0.26 | 0.19 | 75.95 |
| 32 | 0.15 | 0.26 | 0.21 | 168.74 |
| 36 | 0.05 | 0.18 | 0.09 | 346.41 |
| 48 | 0.00 | | | |
| 60 | 0.00 | | | |
| 72 | 0.00 | | | |
| Max ng/ml | 1.91 | 0.80 | 0.65 | 41.65 |
| Tmax H | 6.92 | 3.65 | 3.06 | 52.84 |
| AUC0-t H · ng/ml | 30.26 | 11.35 | 9.43 | 37.51 |

See FIG. 9.

GR-01-12 subjects (cross-over)

Geo Mean $C_{max}$: 1.77 ng/mL

Median $T_{max}$: 6.00 H $AUC_{(0-tau)}$: 27.48 ng·H/mL

Relative Bioavailability versus MR32: F % $C_{max}$: 80.48%, F % $AUC_{(0-tau)}$: 96.1%

TABLE 17

GR-01 Individual BFB-520 Plasma Concentrations and Parameters

GR01 BFB-520 PLASMA CONCENTRATIONS (ng/ml) and AUCo-t (H · ng/ml)

| GR01 Hours | 1-BFB-520 | 2-BFB-520 | 3-BFB-520 | 5-BFB-520 | 6-BFB-520 | 7-BFB-520 | 8-BFB-520 | 9-BFB-520 | 10-BFB-520 | 11-BFB-520 | 12-BFB-520 | 13-BFB-520 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 |
| 2 | 0.00 | 0.00 | 0.26 | 0.00 | 0.00 | 0.00 | 0.00 | 0.00 | 0.00 | 0.28 | 0.00 | 0.00 |
| 2.5 | 0.00 | 0.56 | 0.43 | 0.00 | 0.00 | 0.00 | 0.30 | 0.00 | 0.46 | 0.60 | 0.28 | 0.00 |
| 3 | 0.42 | 0.71 | 0.45 | 0.44 | 0.00 | 0.26 | 0.60 | 0.60 | 0.63 | 0.88 | 0.53 | 0.38 |
| 3.5 | 0.54 | 1.00 | 0.50 | 0.47 | 0.00 | 0.38 | 0.57 | 1.28 | 0.74 | 1.00 | 0.86 | 0.43 |
| 4 | 0.84 | 1.04 | 0.49 | 0.63 | 0.35 | 0.39 | 0.45 | 1.41 | 1.08 | 1.29 | 0.72 | 0.51 |
| 5 | 1.01 | 0.98 | 0.39 | 0.72 | 0.62 | 0.51 | 0.75 | 1.56 | 1.13 | 1.45 | 0.99 | 0.61 |
| 6 | 1.07 | 1.07 | 0.43 | 0.78 | 0.83 | 0.54 | 0.85 | 1.47 | 0.85 | 1.19 | 0.72 | 0.64 |
| 7 | 1.20 | 1.28 | 0.37 | 0.92 | 0.93 | 0.51 | 0.88 | 1.47 | 0.71 | 1.47 | 0.74 | 0.80 |
| 8 | 1.17 | 1.07 | 0.44 | 1.10 | 1.03 | 0.68 | 0.76 | 1.80 | 1.37 | 1.63 | 1.06 | 0.74 |
| 10 | 0.68 | 0.96 | 0.68 | 1.23 | 0.77 | 0.33 | 1.28 | 1.72 | 1.84 | 1.32 | 1.37 | 0.99 |
| 12 | 0.65 | 0.77 | 0.55 | 1.30 | 0.66 | 0.32 | 0.91 | 1.40 | 1.74 | 0.78 | 2.26 | 1.08 |
| 14 | 1.00 | 0.87 | 0.72 | 1.73 | 0.74 | 0.43 | 1.24 | 1.54 | 1.82 | 1.11 | 1.11 | 1.05 |
| 16 | 1.00 | 0.71 | 0.83 | 1.80 | 0.51 | 0.43 | 1.09 | 1.49 | 1.80 | 1.24 | 1.11 | 0.95 |
| 20 | 0.69 | 0.70 | 0.63 | 1.58 | 0.67 | 0.40 | 0.71 | 1.73 | 1.13 | 1.44 | 1.17 | 0.68 |
| 24 | 0.57 | 0.31 | 0.43 | 0.85 | 0.50 | 0.00 | 0.39 | 1.31 | 0.57 | 1.05 | 0.99 | 0.58 |
| 28 | 0.72 | 0.26 | 0.50 | 0.58 | 0.59 | 0.00 | 0.28 | 1.15 | 0.92 | 1.27 | 0.65 | 0.58 |
| 32 | 0.33 | 0.00 | 0.28 | 0.30 | 0.46 | 0.44 | 0.00 | 0.67 | 0.62 | 0.68 | 0.28 | 0.43 |
| 36 | 0.29 | 0.00 | 0.00 | 0.00 | 0.38 | 1.10 | 0.00 | 0.28 | 0.00 | 0.51 | 0.00 | 0.42 |
| 48 | 0.00 | 0.00 | 0.00 | 0.00 | 0.00 | 0.33 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 | 0.00 | 0.00 | 0.00 |
| 72 | 0.00 | 0.00 | 0.00 | 000 | 000 | 000 | 000 | 000 | 000 | 000 | 000 | 000 |
| Max ng/ml | 1.2 | 1.3 | 0.8 | 1.8 | 1.0 | 1.1 | 1.3 | 1.8 | 1.8 | 1.6 | 2.3 | 1.1 |
| Tmax H | 7.0 | 7.0 | 16.0 | 16.0 | 8.0 | 36.0 | 10.0 | 8.0 | 10.0 | 8.0 | 12.0 | 12.0 |
| AUC0-t H · ng/ml | 23.5 | 18.6 | 16.1 | 31.3 | 19.7 | 19.0 | 19.6 | 43.8 | 36.1 | 40.6 | 33.7 | 27.9 |
| F AUC | 67.7 | 92.5 | 96.3 | 204.6 | 72.3 | 83.9 | 79.2 | 97.6 | 76.5 | 86.9 | 97.7 | 98.0 |
| F Cmax | 59.0 | 107.4 | 75.8 | 131.0 | 58.6 | 90.8 | 73.6 | 54.0 | 58.8 | 59.7 | 99.6 | 97.5 |

TABLE 18

GR-01 Mean BFB-520 Plasma Concentrations and Parameters

GR01 BFB-520 PLASMA CONCENTRATIONS and AUCo-t

| GR01 Hours | MEAN | Sd | Sm | CV % |
|---|---|---|---|---|
| 0 | 0.00 | | | |
| 0.25 | 0.00 | | | |
| 0.5 | 0.00 | | | |
| 1 | 0.00 | | | |
| 1.5 | 0.00 | | | |
| 2 | 0.04 | 0.10 | 0.07 | 233.68 |
| 2.5 | 0.22 | 0.25 | 0.22 | 112.01 |
| 3 | 0.49 | 0.23 | 0.17 | 45.99 |
| 3.5 | 0.65 | 0.35 | 0.27 | 53.37 |
| 4 | 0.77 | 0.36 | 0.31 | 47.35 |
| 5 | 0.89 | 0.36 | 0.29 | 40.77 |
| 6 | 0.87 | 0.29 | 0.22 | 33.50 |
| 7 | 0.94 | 0.35 | 0.28 | 37.58 |
| 8 | 1.07 | 0.39 | 0.29 | 36.81 |
| 10 | 1.10 | 0.45 | 0.36 | 40.79 |
| 12 | 1.04 | 0.55 | 0.43 | 53.43 |
| 14 | 1.11 | 0.42 | 0.31 | 37.58 |
| 16 | 1.08 | 0.45 | 0.34 | 41.52 |
| 20 | 0.96 | 0.43 | 0.38 | 45.29 |
| 24 | 0.63 | 0.36 | 0.28 | 57.32 |
| 28 | 0.63 | 0.36 | 0.26 | 57.90 |
| 32 | 0.37 | 0.23 | 0.18 | 60.48 |
| 36 | 0.25 | 0.33 | 0.25 | 133.52 |
| 48 | 0.03 | 0.09 | 0.05 | 346.41 |
| 60 | 0.00 | | | |
| 72 | 0.00 | | | |
| Max ng/ml | 1.43 | 0.43 | 0.37 | 30.06 |
| Tmax H | 12.50 | 8.04 | 5.08 | 64.32 |
| AUC0-t H · ng/ml | 27.48 | 9.46 | 8.07 | 34.41 |
| F AUC | 96.10 | 35.77 | 18.95 | 37.22 |
| F Cmax | 80.48 | 24.60 | 20.65 | 30.56 |

See FIG. 10.

GR-02-12 subjects (cross-over)

Geo Mean $C_{max}$: 1.13 ng/mL

Median $T_{max}$: 16.00 H $AUC_{(0-tau)}$: 27.53 ng·H/mL

Relative Bioavailability versus MR32: F % $C_{max}$: 69.48%, F % $AUC_{(0-tau)}$: 88.46%

TABLE 19

GR-02 Individual BFB-520 Plasma Concentrations and Parameters

GR02 BFB-520 PLASMA CONCENTRATIONS (ng/ml) and AUCo-t (H · ng/ml)

| GR02 Hours | 1-BFB-520 | 2-BFB-520 | 3-BFB-520 | 4-BFB-520 | 5-BFB-520 | 7-BFB-520 | 8-BFB-520 | 9-BFB-520 | 10-BFB-520 | 11-BFB-520 | 12-BFB-520 | 13-BFB-520 | 14-BFB-520 |
|---|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 | 0.00 | 0.00 |
| 2.5 | 0.00 | 0.00 | 0.00 | 0.00 | 0.00 | 0.00 | 0.00 | 0.00 | 0.00 | 0.00 | 0.00 | 0.00 | 0.44 |
| 3 | 0.00 | 0.00 | 0.00 | 0.00 | 0.00 | 0.00 | 0.00 | 0.00 | 0.00 | 0.26 | 0.00 | 0.00 | 0.66 |
| 3.5 | 0.00 | 0.00 | 0.00 | 0.00 | 0.00 | 0.00 | 0.00 | 0.00 | 0.00 | 0.62 | 0.00 | 0.00 | 0.76 |
| 4 | 0.38 | 0.00 | 0.00 | 0.00 | 0.00 | 0.00 | 0.00 | 0.00 | 0.00 | 0.97 | 0.27 | 0.00 | 1.08 |
| 5 | 0.35 | 0.00 | 0.00 | 0.32 | 0.00 | 0.00 | 0.27 | 0.27 | 1.37 | 0.35 | 0.35 | 0.75 | |
| 6 | 0.53 | 0.38 | 0.00 | 0.00 | 0.49 | 0.00 | 0.00 | 0.28 | 0.42 | 1.47 | 0.36 | 0.45 | 0.75 |
| 7 | 0.54 | 0.29 | 0.00 | 0.00 | 0.41 | 0.29 | 0.00 | 0.27 | 0.39 | 1.64 | 0.49 | 0.58 | 0.79 |
| 8 | 0.47 | 0.32 | 0.00 | 0.25 | 0.57 | 0.25 | 0.00 | 0.51 | 0.42 | 1.85 | 0.57 | 0.69 | 0.79 |
| 10 | 0.47 | 0.35 | 0.25 | 0.36 | 0.62 | 0.34 | 0.00 | 0.74 | 0.51 | 1.82 | 1.12 | 1.07 | 1.14 |
| 12 | 0.88 | 0.00 | 0.41 | 0.52 | 0.94 | 0.36 | 0.35 | 0.74 | 1.28 | 2.26 | 0.80 | 1.09 | 1.99 |
| 14 | 1.00 | 0.33 | 0.51 | 0.68 | 1.26 | 0.36 | 0.41 | 0.98 | 1.28 | 2.45 | 1.26 | 1.16 | 2.25 |
| 16 | 1.01 | 0.39 | 0.59 | 0.62 | 1.40 | 0.52 | 0.37 | 1.26 | 1.22 | 2.38 | 1.37 | 1.03 | 2.31 |
| 20 | 1.08 | 0.64 | 0.79 | 0.59 | 1.25 | 0.76 | 0.26 | 1.43 | 0.71 | 2.42 | 1.64 | 0.80 | 1.38 |
| 24 | 0.81 | 0.44 | 0.55 | 0.49 | 0.76 | 0.95 | 0.00 | 0.68 | 0.61 | 1.75 | 1.39 | 0.69 | 0.84 |
| 28 | 0.97 | 0.47 | 0.56 | 0.56 | 0.48 | 1.22 | 0.00 | 1.00 | 0.93 | 1.74 | 1.04 | 0.87 | 0.59 |
| 32 | 0.82 | 0.34 | 0.31 | 0.33 | 0.00 | 1.14 | 0.00 | 1.03 | 1.21 | 0.70 | 0.59 | 0.61 | 0.33 |
| 36 | 0.47 | 0.32 | 0.00 | 0.00 | 0.00 | 0.66 | 0.00 | 0.65 | 0.64 | 0.41 | 0.32 | 0.46 | 0.00 |
| 48 | 0.27 | 0.00 | 0.00 | 0.00 | 0.00 | 0.00 | 0.00 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 | 0.00 | 0.00 | 0.00 | 0.00 |
| 72 | 0.00 | 0.00 | 0.00 | 0.00 | 0.00 | 0.00 | 0.00 | 0.00 | 0.00 | 0.00 | 0.00 | 0.00 | 0.00 |
| Max ng/ml | 1.1 | 0.6 | 0.8 | 0.7 | 1.4 | 1.2 | 0.4 | 1.4 | 1.3 | 2.4 | 1.6 | 1.2 | 2.3 |
| Tmax H | 20.0 | 20.0 | 20.0 | 14.0 | 16.0 | 28.0 | 14.0 | 20.0 | 12.0 | 14.0 | 20.0 | 14.0 | 16.0 |
| AUC0-t H · ng/ml | 30.0 | 11.5 | 12.3 | 12.5 | 21.8 | 23.8 | 6.1 | 31.9 | 31.4 | 61.4 | 38.8 | 32.9 | 43.5 |
| F AUC | 86.6 | 57.0 | 73.3 | 81.9 | 80.3 | 105.2 | 24.8 | 71.1 | 66.6 | 131.5 | 112.6 | 115.5 | 143.7 |
| F Cmax | 53.1 | 53.3 | 72.2 | 49.2 | 79.9 | 100.6 | 23.9 | 42.9 | 41.0 | 89.3 | 72.3 | 104.8 | 120.8 |

TABLE 20

GR-02 Mean BFB-520 Plasma Concentrations and Parameters

GR02 BFB-520 PLASMA CONCENTRATIONS and AUCo-t

| GR02 Hours | MEAN | Sd | Sm | CV % |
|---|---|---|---|---|
| 0 | 0.00 | | | |
| 0.25 | 0.00 | | | |
| 0.5 | 0.00 | | | |
| 1 | 0.00 | | | |
| 1.5 | 0.00 | | | |
| 2 | 0.00 | | | |
| 2.5 | 0.03 | 0.13 | 0.07 | 375.28 |
| 3 | 0.07 | 0.20 | 0.13 | 280.02 |
| 3.5 | 0.11 | 0.27 | 0.19 | 254.72 |
| 4 | 0.21 | 0.40 | 0.29 | 191.24 |
| 5 | 0.31 | 0.40 | 0.27 | 130.19 |
| 6 | 0.39 | 0.42 | 0.28 | 106.04 |
| 7 | 0.44 | 0.45 | 0.30 | 102.76 |
| 8 | 0.52 | 0.49 | 0.31 | 94.19 |
| 10 | 0.68 | 0.51 | 0.41 | 75.52 |
| 12 | 0.90 | 0.68 | 0.51 | 75.73 |
| 14 | 1.07 | 0.70 | 0.53 | 65.30 |
| 16 | 1.11 | 0.69 | 0.54 | 61.68 |
| 20 | 1.06 | 0.59 | 0.47 | 55.93 |
| 24 | 0.77 | 0.45 | 0.31 | 59.06 |
| 28 | 0.80 | 0.45 | 0.34 | 55.61 |
| 32 | 0.57 | 0.41 | 0.33 | 71.69 |
| 36 | 0.30 | 0.28 | 0.24 | 92.16 |
| 48 | 0.02 | 0.00 | | |
| 60 | 0.00 | | | |
| 72 | 0.00 | | | |
| Max ng/ml | 1.27 | 0.63 | 0.47 | 49.77 |
| Tmax H | 17.54 | 4.46 | 3.56 | 25.42 |
| AUC0-t H · ng/ml | 27.53 | 15.99 | 12.65 | 58.08 |
| F AUC | 88.46 | 33.92 | 27.56 | 38.35 |
| F Cmax | 69.48 | 29.58 | 24.00 | 42.56 |

See FIG. 11.

TABLE 21

Comparison of MR32, GR-01, and GR-02 BFB-520 Plasma Concentrations.
MR32 GR01 and GR02 Mean BFB-520 Plasma Concentrations (ng/ml)

| Hours | MR32-MEAN | GR01-Mean | GR02-Mean |
|---|---|---|---|
| 0 | 0.00 | 0.00 | 0.00 |
| 0.25 | 0.00 | 0.00 | 0.00 |
| 0.5 | 0.00 | 0.00 | 0.00 |
| 1 | 0.42 | 0.00 | 0.00 |
| 1.5 | 0.81 | 0.00 | 0.00 |

TABLE 21-continued

Comparison of MR32, GR-01, and GR-02 BFB-520 Plasma Concentrations.
MR32 GR01 and GR02 Mean BFB-520
Plasma Concentrations (ng/ml)

| Hours | MR32-MEAN | GR01-Mean | GR02-Mean |
|---|---|---|---|
| 2 | 1.04 | 0.04 | 0.00 |
| 2.5 | 1.21 | 0.22 | 0.03 |
| 3 | 1.46 | 0.49 | 0.07 |
| 3.5 | 1.49 | 0.65 | 0.11 |
| 4 | 1.55 | 0.77 | 0.21 |
| 5 | 1.59 | 0.89 | 0.31 |
| 6 | 1.55 | 0.87 | 0.39 |
| 7 | 1.44 | 0.94 | 0.44 |
| 8 | 1.51 | 1.07 | 0.52 |
| 10 | 1.48 | 1.10 | 0.68 |
| 12 | 1.21 | 1.04 | 0.90 |
| 14 | 1.40 | 1.11 | 1.07 |
| 16 | 1.01 | 1.08 | 1.11 |
| 20 | 0.85 | 0.96 | 1.06 |
| 24 | 0.50 | 0.63 | 0.77 |
| 28 | 0.35 | 0.63 | 0.80 |
| 32 | 0.15 | 0.37 | 0.57 |
| 36 | 0.05 | 0.25 | 0.30 |
| 48 | 0.00 | 0.03 | 0.02 |
| 60 | 0.00 | 0.00 | 0.00 |
| 72 | 0.00 | 0.00 | 0.00 |
| CMax ng/ml | 1.9 | 1.4 | 1.27 |
| Tmax H | 6.9 | 12.5 | 17.5 |
| AUC0-8 H · ng/ml | 9.7 | 4.5 | 1.66 |
| AUC0-12 H · ng/ml | 15.4 | 8.8 | 4.4 |
| AUC0-t H · ng/ml | 30.3 | 27.5 | 27.5 |
| F AUC | REF | 96.1 | 88.5 |
| F Cmax | REF | 80.5 | 69.5 |

See FIG. 12.

TABLE 22

Comparison of MR32, GR-01, and GR-02 BFB-520 Plasma Concentrations - Rates of Increase and Decrease.
MR32 GR01 and GR02 Mean BFB-520
Plasma Conc. Rates of Increase and Decrease (ng/ml)/H

| Hours | MR32-RATE | GR01-RATE | GR02-RATE |
|---|---|---|---|
| 0 | 0.00 | 0.00 | 0.00 |
| 0.25 | 0.00 | 0.00 | 0.00 |
| 0.5 | 0.00 | 0.00 | 0.00 |
| 1 | 0.84 | 0.00 | 0.00 |
| 1.5 | 0.77 | 0.00 | 0.00 |
| 2 | 0.46 | 0.09 | 0.00 |
| 2.5 | 0.34 | 0.35 | 0.07 |
| 3 | 0.49 | 0.54 | 0.07 |
| 3.5 | 0.07 | 0.31 | 0.07 |
| 4 | 0.11 | 0.24 | 0.20 |
| 5 | 0.04 | 0.13 | 0.10 |
| 6 | 0.00 | 0.00 | 0.08 |
| 7 | 0.00 | 0.07 | 0.04 |
| 8 | 0.07 | 0.13 | 0.08 |
| 10 | 0.00 | 0.01 | 0.08 |
| 12 | 0.00 | 0.00 | 0.11 |
| 14 | 0.10 | 0.04 | 0.09 |
| 16 | 0.00 | 0.00 | 0.02 |
| 20 | 0.00 | 0.00 | 0.00 |
| 24 | 0.00 | 0.00 | 0.00 |
| 28 | 0.00 | 0.00 | 0.01 |
| 32 | 0.00 | 0.00 | 0.00 |
| 36 | 0.00 | 0.00 | 0.00 |
| VMax (ng/ml)/H | 0.84 | 0.54 | 0.20 |
| Time of VMax | 1.00 | 3.00 | 4.00 |
| TEST/MR32 | REF | 0.64 | 0.24 |

During each time interval (dt) the plasma concentration ($C_p$) of BFB-520 increases or decreases. From t=0 to $T_{max}$, the rate of increase $V_{max}=d(C_p)/dt$. After the $V_{max}$, the rates are decreasing. See FIG. 13.

Example 10: Predicted Plasma Concentrations of MIN-101 and BFB-520 at Steady State in MR32 And GR-01 Tablets (32 and 64 mg)

TABLE 23

Predicted Plasma Concentrations of MIN-101 at Steady State in MR32 and GR-01, 32 mg Tablets
MR32 and GR01 Mean MIN-101 at Steady-State
Plasma Concentrations (ng/ml)

| HOURS | MR32SS | GR01 SS |
|---|---|---|
| 72 | 3.32 | 6.45 |
| 72.5 | 9.68 | 6.20 |
| 73 | 22.62 | 6.30 |
| 73.5 | 26.74 | 6.96 |
| 74 | 26.78 | 11.23 |
| 74.5 | 27.14 | 16.97 |
| 75 | 24.39 | 20.59 |
| 75.5 | 22.54 | 20.89 |
| 76 | 21.96 | 20.58 |
| 77 | 23.38 | 18.91 |
| 78 | 16.83 | 15.30 |
| 79 | 13.34 | 13.96 |
| 80 | 11.89 | 12.95 |
| 82 | 13.49 | 13.53 |
| 84 | 13.66 | 14.02 |
| 86 | 10.97 | 13.80 |
| 88 | 8.24 | 12.32 |
| 92 | 4.44 | 6.75 |
| 96 | 3.32 | 6.46 |
| CMaxSS ng/ml | 27.1 | 20.9 |
| CMinSS | 3.32 | 6.46 |
| TmaxSS H | 2.50 | 3.5 |
| AUC72-96 H · ng/ml | 292.6 | 287.6 |
| F AUC | REF | 98.3 |
| F Cmax | REF | 76.9 |

See FIG. 14.

TABLE 24

Predicted Plasma Concentrations of BFB-520 at Steady State in MR32 and GR-01, 32 mg Tablets
MR32 and GR01 BFB-520 at Steady-State
Plasma Concentrations (ng/ml)

| HOURS | MR32 SS | GR01 SS |
|---|---|---|
| 72 | 0.50 | 0.66 |
| 72.5 | 0.44 | 0.63 |
| 73 | 0.81 | 0.60 |
| 73.5 | 1.15 | 0.57 |
| 74 | 1.35 | 0.58 |
| 74.5 | 1.48 | 0.72 |
| 75 | 1.70 | 0.97 |
| 75.5 | 1.71 | 1.10 |
| 76 | 1.89 | 1.42 |
| 77 | 1.74 | 1.27 |
| 78 | 1.66 | 1.21 |
| 79 | 1.54 | 1.24 |
| 80 | 1.66 | 1.46 |
| 82 | 1.53 | 1.31 |
| 84 | 1.26 | 1.29 |
| 86 | 1.41 | 1.25 |
| 88 | 1.03 | 1.19 |
| 92 | 0.85 | 1.03 |
| 96 | 0.50 | 0.86 |
| CMaxSS ng/ml | 1.89 | 1.46 |
| CMinSS | 0.50 | 0.66 |
| TmaxSS H | 4.00 | 3.5 |

TABLE 24-continued

Predicted Plasma Concentrations of BFB-520 at Steady
State in MR32 and GR-01, 32 mg Tablets
MR32 and GR01 BFB-520 at Steady-State
Plasma Concentrations (ng/ml)

| HOURS | MR32 SS | GR01 SS |
|---|---|---|
| AUC72-96 H · ng/ml | 29.1 | 26.3 |
| F AUC | REF | 90.6 |
| F Cmax | REF | 77.2 |

See FIG. 15.

TABLE 25

Predicted Plasma Concentrations of MIN-101 at Steady
State in MR32 and GR-01, 64 mg Tablets
MR32 and GR01 64 mg at Steady-State
MIN101 Plasma Concentrations (ng/ml)

| HOURS | MR32SS | GR01 SS |
|---|---|---|
| 72 | 6.64 | 12.90 |
| 72.5 | 19.36 | 12.40 |
| 73 | 45.24 | 12.60 |
| 73.5 | 53.47 | 13.93 |
| 74 | 53.55 | 22.46 |
| 74.5 | 54.28 | 33.94 |
| 75 | 48.77 | 41.18 |
| 75.5 | 45.07 | 41.77 |
| 76 | 43.93 | 41.17 |
| 77 | 46.76 | 37.82 |
| 78 | 33.65 | 30.60 |
| 79 | 26.69 | 27.92 |
| 80 | 23.78 | 25.90 |
| 82 | 26.97 | 27.06 |
| 84 | 27.31 | 28.05 |
| 86 | 21.94 | 27.61 |
| 88 | 16.49 | 24.64 |
| 92 | 8.89 | 13.49 |
| 96 | 6.64 | 12.93 |
| CMaxSS ng/ml | 54.28 | 41.77 |
| CMinSS | 6.64 | 12.93 |
| TmaxSS H | 2.50 | 3.50 |
| AUC72-96 H · ng/ml | 585.2 | 577.6 |
| F AUC | REF | 98.7 |
| F Cmax | REF | 76.9 |

See FIG. 16.

TABLE 26

Predicted Plasma Concentrations of BFB-520 at Steady
State in MR32 and GR-01, 64 mg Tablets
MR32 and GR01 64 mg at Steady-State
BFB-520 Plasma Concentrations (ng/ml)

| HOURS | MR32SS | GR01 SS |
|---|---|---|
| 72 | 0.99 | 1.32 |
| 72.5 | 0.88 | 1.27 |
| 73 | 1.63 | 1.20 |
| 73.5 | 2.31 | 1.13 |
| 74 | 2.69 | 1.16 |
| 74.5 | 2.96 | 1.45 |
| 75 | 3.40 | 1.93 |
| 75.5 | 3.41 | 2.19 |
| 76 | 3.79 | 2.84 |
| 77 | 3.48 | 2.54 |
| 78 | 3.33 | 2.41 |
| 79 | 3.07 | 2.48 |
| 80 | 3.32 | 2.92 |
| 82 | 3.05 | 2.62 |
| 84 | 2.51 | 2.57 |
| 86 | 2.83 | 2.49 |

TABLE 26-continued

Predicted Plasma Concentrations of BFB-520 at Steady
State in MR32 and GR-01, 64 mg Tablets
MR32 and GR01 64 mg at Steady-State
BFB-520 Plasma Concentrations (ng/ml)

| HOURS | MR32SS | GR01 SS |
|---|---|---|
| 88 | 2.05 | 2.37 |
| 92 | 1.70 | 2.05 |
| 96 | 0.99 | 1.32 |
| CMaxSS ng/ml | 3.79 | 2.92 |
| CMinSS | 0.99 | 1.32 |
| TmaxSS H | 4.00 | 8.00 |
| AUC72-96 H · ng/ml | 58.1 | 52.8 |
| F AUC | REF | 90.8 |
| F Cmax | REF | 77.2 |

See FIG. 17.

Example 11: Predicted Plasma Concentrations of
MIN-101 and BFB-520 at Steady State in MR32
and GR-02 Tablets (32 and 64 mg)

TABLE 27

Predicted Plasma Concentrations of MIN-101 at Steady
State in MR32 and GR-02, 32 mg Tablets
MR32 and GR02 Mean MIN-101 at Steady-State
Plasma Concentrations (ng/ml)

| HOURS | MR32SS | GR02 SS |
|---|---|---|
| 72 | 3.32 | 8.26 |
| 72.5 | 9.68 | 7.88 |
| 73 | 22.62 | 7.46 |
| 73.5 | 26.74 | 7.23 |
| 74 | 26.78 | 7.37 |
| 74.5 | 27.14 | 8.32 |
| 75 | 24.39 | 9.22 |
| 75.5 | 22.54 | 10.37 |
| 76 | 21.96 | 12.08 |
| 77 | 23.38 | 11.87 |
| 78 | 16.83 | 10.49 |
| 79 | 13.34 | 9.74 |
| 80 | 11.89 | 10.56 |
| 82 | 13.49 | 10.66 |
| 84 | 13.66 | 15.38 |
| 86 | 10.97 | 13.87 |
| 88 | 8.24 | 12.09 |
| 92 | 4.44 | 7.17 |
| 96 | 3.32 | 8.27 |
| CMaxSS ng/ml | 27.1 | 15.4 |
| CMinSS | 3.32 | 7.17 |
| TmaxSS H | 2.50 | 12 |
| AUC72-96 H · ng/ml | 292.6 | 248.3 |
| F AUC | REF | 84.9 |
| F Cmax | REF | 56.7 |

See FIG. 18.

TABLE 28

Predicted Plasma Concentrations of BFB-520 at Steady
State in MR32 and GR-02, 32 mg Tablets
MR32 and GR02 Mean MIN-101 at Steady-State
Plasma Concentrations (ng/ml)

| HOURS | MR32SS | GR02 SS |
|---|---|---|
| 72 | 0.50 | 0.79 |
| 72.5 | 0.44 | 0.76 |
| 73 | 0.81 | 0.72 |
| 73.5 | 1.15 | 0.67 |
| 74 | 1.35 | 0.63 |

TABLE 28-continued

Predicted Plasma Concentrations of BFB-520 at Steady State in MR32 and GR-02, 32 mg Tablets
MR32 and GR02 Mean MIN-101 at Steady-State Plasma Concentrations (ng/ml)

| HOURS | MR32SS | GR02 SS |
|---|---|---|
| 74.5 | 1.48 | 0.63 |
| 75 | 1.70 | 0.63 |
| 75.5 | 1.71 | 0.63 |
| 76 | 1.89 | 1.04 |
| 77 | 1.74 | 0.75 |
| 78 | 1.66 | 0.78 |
| 79 | 1.53 | 0.78 |
| 80 | 1.66 | 1.10 |
| 82 | 1.53 | 0.92 |
| 84 | 1.26 | 1.20 |
| 86 | 1.41 | 1.22 |
| 88 | 1.03 | 1.23 |
| 92 | 0.85 | 1.13 |
| 96 | 0.50 | 0.79 |
| CMaxSS ng/ml | 1.89 | 1.23 |
| CMinSS | 0.50 | 0.79 |
| TmaxSS H | 4.00 | 16.00 |
| AUC72-96 H · ng/ml | 29.1 | 23.6 |
| F AUC | REF | 81.4 |
| F Cmax | REF | 64.8 |

See FIG. 19.

TABLE 29

Predicted Plasma Concentrations of MIN-101 at Steady State in MR32 and GR-02, 64 mg Tablets
MR32 and GR02 64 mg at Steady-State MIN101 Plasma Concentrations (ng/ml)

| HOURS | MR32SS | GR02 SS |
|---|---|---|
| 72 | 6.64 | 16.53 |
| 72.5 | 19.36 | 15.77 |
| 73 | 45.24 | 14.93 |
| 73.5 | 53.47 | 14.45 |
| 74 | 53.55 | 14.75 |
| 74.5 | 54.28 | 16.64 |
| 75 | 48.77 | 18.44 |
| 75.5 | 45.07 | 20.74 |
| 76 | 43.93 | 24.16 |
| 77 | 46.76 | 23.75 |
| 78 | 33.65 | 20.98 |
| 79 | 26.69 | 19.49 |
| 80 | 23.78 | 21.12 |
| 82 | 26.97 | 21.32 |
| 84 | 27.31 | 30.77 |
| 86 | 21.94 | 27.73 |
| 88 | 16.49 | 24.18 |
| 92 | 8.89 | 14.35 |
| 96 | 6.64 | 16.53 |
| CMaxSS ng/ml | 54.28 | 30.77 |
| CMinSS | 6.64 | 14.35 |
| TmaxSS H | 2.50 | 12.00 |
| AUC72-96 H · ng/ml | 585.2 | 498.6 |
| F AUC | REF | 85.2 |
| F Cmax | REF | 56.7 |

See FIG. 20.

TABLE 30

Predicted Plasma Concentrations of BFB-520 at Steady State in MR32 and GR-02, 64 mg Tablets
MR32 and GR02 64 mg at Steady-State BFB-520 Plasma Concentrations (ng/ml)

| HOURS | MR32SS | GR02 SS |
|---|---|---|
| 72 | 0.99 | 1.58 |
| 72.5 | 0.88 | 1.52 |
| 73 | 1.63 | 1.43 |
| 73.5 | 2.31 | 1.35 |
| 74 | 2.69 | 1.27 |
| 74.5 | 2.96 | 1.26 |
| 75 | 3.40 | 1.26 |
| 75.5 | 3.41 | 1.27 |
| 76 | 3.79 | 2.07 |
| 77 | 3.48 | 1.50 |
| 78 | 3.33 | 1.57 |
| 79 | 3.07 | 1.57 |
| 80 | 3.32 | 2.20 |
| 82 | 3.05 | 1.83 |
| 84 | 2.51 | 2.40 |
| 86 | 2.83 | 2.44 |
| 88 | 2.05 | 2.45 |
| 92 | 1.70 | 2.25 |
| 96 | 0.99 | 1.58 |
| CMaxSS ng/ml | 3.79 | 2.45 |
| CMinSS | 0.99 | 1.58 |
| TmaxSS H | 4.00 | 16.00 |
| AUC72-96 H · ng/ml | 58.1 | 47.4 |
| F AUC | REF | 81.6 |
| F Cmax | REF | 64.8 |

See FIG. 21.

Examples 12-15 detail an evaluation of the PK profile of the GR-01 formulation in healthy CYP2D6 EM male and female subjects in fed and fasted states (or predictions thereof). Subjects who completed part 1 of the study (evaluation of the PK profile of MIN-101 and its metabolite BFB-520 in the GR-01, GR-02, and MR32 formulations) returned and received a further single oral dose of GR-01 under fed or fasted conditions to allow the assessment of food effect by comparison of the PK properties to those obtained in part 1 (Examples 9-12). There was a wash-out period of 14±2 days after part 1.

Example 12: In Vivo Pharmacokinetic Analysis of MIN-101 in CR GR-01 Tablets in Subjects in Fed Versus Fasted States. (Tau=72 h)

Fed State—12 subjects (cross-over)

Geo Mean $C_{max}$: 19.70 ng/mL $T_{max}$: 12.00 H $AUC_{(0-tau)}$: 269.19 ng·H/mL

TABLE 31

CR GR-01 Individual MIN-101 Plasma Concentrations and Parameters (Fed State)

GR01 FED MIN-101 PLASMA CONCENTRATIONS (ng/ml) and AUCo-t (H · ng/ml)

| GR01 Hours | 1-MIN-101 | 2-MIN-101 | 3-MIN-101 | 5-MIN-101 | 6-MIN-101 | 7-MIN-101 | 8-MIN-101 | 9-MIN-101 | 10-MIN-101 | 11-MIN-101 | 12-MIN-101 | 13-MIN-101 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 | 0.00 |
| 2.5 | 0.00 | 0.00 | 6.78 | 0.00 | 0.00 | 0.00 | 0.00 | 0.00 | 0.00 | 0.00 | 0.00 | 0.00 |
| 3 | 0.00 | 0.00 | 11.16 | 0.00 | 0.00 | 0.00 | 0.00 | 0.00 | 0.00 | 0.00 | 0.00 | 6.11 |
| 3.5 | 0.00 | 0.00 | 11.00 | 0.00 | 0.00 | 0.00 | 0.00 | 0.00 | 0.00 | 0.00 | 0.00 | 7.61 |
| 4 | 0.00 | 0.00 | 14.38 | 0.00 | 0.00 | 0.29 | 0.00 | 0.00 | 0.00 | 0.00 | 0.00 | 6.83 |
| 5 | 0.00 | 0.00 | 14.05 | 23.02 | 0.00 | 12.75 | 0.00 | 0.00 | 0.53 | 0.00 | 0.00 | 6.91 |
| 6 | 0.00 | 18.46 | 13.78 | 13.78 | 0.00 | 16.81 | 0.00 | 0.00 | 23.86 | 0.00 | 0.00 | 6.14 |
| 7 | 0.00 | 18.93 | 12.69 | 10.82 | 0.00 | 11.65 | 0.00 | 0.00 | 18.16 | 15.83 | 0.00 | 5.15 |
| 8 | 0.00 | 12.77 | 6.36 | 9.89 | 0.00 | 10.59 | 0.00 | 0.00 | 17.78 | 14.65 | 0.00 | 4.24 |
| 10 | 3.52 | 7.72 | 3.90 | 11.82 | 0.00 | 7.97 | 0.00 | 23.19 | 14.80 | 11.23 | 0.00 | 6.86 |
| 12 | 35.98 | 6.41 | 9.71 | 6.41 | 19.91 | 13.62 | 0.00 | 8.39 | 14.32 | 12.39 | 24.84 | 12.40 |
| 14 | 12.33 | 3.95 | 7.26 | 2.94 | 11.75 | 13.61 | 0.00 | 5.32 | 16.35 | 17.47 | 12.74 | 8.83 |
| 16 | 14.86 | 9.72 | 10.01 | 1.55 | 8.72 | 8.89 | 0.00 | 6.30 | 20.47 | 12.39 | 7.55 | 6.04 |
| 20 | 7.18 | 4.51 | 4.76 | 0.52 | 6.95 | 9.42 | 4.24 | 5.28 | 11.74 | 11.01 | 14.00 | 4.23 |
| 24 | 6.70 | 2.72 | 5.92 | 0.00 | 12.81 | 5.57 | 10.84 | 30.76 | 9.83 | 10.33 | 26.27 | 6.75 |
| 28 | 7.17 | 2.40 | 4.48 | 0.00 | 18.56 | 5.20 | 5.81 | 16.53 | 5.52 | 7.82 | 21.35 | 4.34 |
| 32 | 6.56 | 2.19 | 2.84 | 0.00 | 10.82 | 3.49 | 2.32 | 10.29 | 3.17 | 3.44 | 14.17 | 3.32 |
| 36 | 5.97 | 1.15 | 1.61 | 0.00 | 5.35 | 2.19 | 0.92 | 3.93 | 1.80 | 1.85 | 6.78 | 2.42 |
| 48 | 1.66 | 0.39 | 0.90 | 0.00 | 1.57 | 0.67 | 0.00 | 0.83 | 0.50 | 0.47 | 0.91 | 0.59 |
| 60 | 0.00 | 0.00 | 0.35 | 0.00 | 0.63 | 0.33 | 0.00 | 0.00 | 0.31 | 0.00 | 0.00 | 0.36 |
| 72 | 0.00 | 0.00 | 0.00 | 0.00 | 0.30 | 0.00 | 0.00 | 0.00 | 0.00 | 0.00 | 0.00 | 0.00 |
| CMax ng/ml | 36.0 | 18.9 | 14.4 | 23.0 | 19.9 | 16.8 | 10.8 | 30.8 | 23.9 | 17.5 | 26.3 | 12.4 |
| Tmax H | 12.0 | 7.0 | 4.0 | 5.0 | 12.0 | 6.0 | 24.0 | 24.0 | 6.0 | 14.0 | 24.0 | 12.0 |
| AUC0-t H · ng/ml | 305.0 | 177.2 | 241.3 | 108.5 | 347.8 | 272.9 | 92.2 | 367.3 | 359.7 | 303.5 | 444.8 | 210.2 |
| F AUC | 108.3 | 80.8 | 104.8 | 35.0 | 132.3 | 106.2 | 43.1 | 102.8 | 124.2 | 70.5 | 159.4 | 74.1 |
| F Cmax | 174.7 | 87.9 | 113.6 | 114.2 | 127.4 | 131.5 | 60.0 | 109.1 | 132.2 | 65.5 | 93.8 | 97.7 |

TABLE 32

CR GR-01 Mean MIN-101 Plasma Concentrations and Parameters (Fed State)

GR01 FED MIN-101 PLASMA CONCENTRATIONS and AUCo-t

| GR01 Hours | MEAN | Sd | Sm | CV % |
|---|---|---|---|---|
| 0 | 0.00 | | | |
| 0.25 | 0.00 | | | |
| 0.5 | 0.00 | | | |
| 1 | 0.00 | | | |
| 1.5 | 0.00 | | | |
| 2 | 0.00 | | | |
| 2.5 | 0.57 | 1.96 | 1.04 | 346.41 |
| 3 | 1.44 | 3.53 | 2.40 | 245.26 |
| 3.5 | 1.55 | 3.69 | 2.59 | 238.14 |
| 4 | 1.79 | 4.42 | 2.94 | 246.80 |
| 5 | 4.77 | 7.77 | 6.27 | 162.90 |
| 6 | 7.74 | 9.01 | 8.00 | 116.41 |
| 7 | 7.77 | 7.71 | 6.91 | 99.30 |
| 8 | 6.36 | 6.59 | 5.65 | 103.62 |
| 10 | 7.58 | 6.94 | 5.20 | 91.54 |
| 12 | 13.70 | 9.54 | 6.71 | 69.63 |
| 14 | 9.38 | 5.54 | 4.66 | 59.09 |
| 16 | 8.88 | 5.51 | 3.85 | 62.03 |
| 20 | 7.04 | 3.93 | 3.13 | 55.89 |
| 24 | 10.71 | 9.09 | 6.31 | 84.89 |
| 28 | 8.26 | 6.76 | 5.27 | 81.78 |
| 32 | 5.22 | 4.30 | 3.50 | 82.42 |
| 36 | 2.83 | 2.17 | 1.79 | 76.52 |
| 48 | 0.71 | 0.52 | 0.39 | 73.23 |
| 60 | 0.16 | 0.22 | 0.19 | 133.11 |
| 72 | 0.03 | 0.09 | 0.05 | 346.41 |
| CMax ng/ml | 20.89 | 7.48 | 5.91 | 35.83 |
| Tmax H | 12.50 | 7.65 | 6.00 | 61.16 |
| AUC0-t H · ng/ml | 269.19 | 107.53 | 86.11 | 39.95 |
| F AUC | 95.14 | 36.15 | 28.68 | 38.00 |
| F Cmax | 108.97 | 31.40 | 23.32 | 28.81 |

See FIG. 22

Fasted State—12 subjects (cross-over)

Geo Mean $C_{max}$: 18.82 ng/mL

Median $T_{max}$: 4.50 H $AUC_{(0-tau)}$: 284.52 ng·H/mL

TABLE 33

CR GR-01 Individual MIN-101 Plasma Concentrations and Parameters (Fasted State)

GR01 FASTED MEAN MIN-101 PLASMA CONCENTRATIONS (ng/ml) and AUCo-t (H · ng/ml)

| GR01 Hours | 1-MIN-101 | 2-MIN-101 | 3-MIN-101 | 5-MIN-101 | 6-MIN-101 | 7-MIN-101 | 8-MIN-101 | 9-MIN-101 | 10-MIN-101 | 11-MIN-101 | 12-MIN-101 | 13-MIN-101 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 4.22 | 0.00 | 0.00 | 0.00 |
| 1.5 | 0.00 | 0.00 | 6.26 | 0.00 | 0.00 | 0.00 | 0.38 | 0.00 | 0.42 | 0.00 | 0.00 | 7.98 |
| 2 | 3.83 | 5.42 | 10.68 | 2.50 | 0.00 | 0.00 | 13.23 | 0.00 | 8.71 | 16.03 | 0.48 | 8.14 |
| 2.5 | 15.95 | 13.82 | 11.87 | 12.14 | 0.00 | 3.45 | 12.42 | 3.00 | 12.78 | 24.17 | 23.30 | 7.62 |
| 3 | 17.85 | 17.61 | 11.10 | 13.88 | 0.39 | 12.78 | 11.08 | 24.02 | 12.98 | 16.68 | 28.00 | 10.13 |
| 3.5 | 15.56 | 21.53 | 10.97 | 12.31 | 6.52 | 10.89 | 10.94 | 28.19 | 13.60 | 25.78 | 24.01 | 12.18 |
| 4 | 20.60 | 19.02 | 8.23 | 11.96 | 15.23 | 9.53 | 8.04 | 22.91 | 17.64 | 24.78 | 22.59 | 11.30 |
| 5 | 17.05 | 17.24 | 6.66 | 14.68 | 15.63 | 8.44 | 14.90 | 17.95 | 12.92 | 24.46 | 12.86 | 12.69 |
| 6 | 15.26 | 14.41 | 6.89 | 13.19 | 13.39 | 6.06 | 12.36 | 11.72 | 7.62 | 19.24 | 5.64 | 10.42 |
| 7 | 9.61 | 11.29 | 6.28 | 12.62 | 10.60 | 4.71 | 11.51 | 13.95 | 6.70 | 17.83 | 9.72 | 9.08 |
| 8 | 7.46 | 7.20 | 5.58 | 11.86 | 10.51 | 3.51 | 8.19 | 16.53 | 13.39 | 14.16 | 5.82 | 8.62 |
| 10 | 4.30 | 5.10 | 12.66 | 11.69 | 6.19 | 2.71 | 18.08 | 17.00 | 18.05 | 8.68 | 13.19 | 10.59 |
| 12 | 9.45 | 5.59 | 10.24 | 20.15 | 7.24 | 3.05 | 12.22 | 13.92 | 16.31 | 11.15 | 13.39 | 12.47 |
| 14 | 13.11 | 10.14 | 12.01 | 17.73 | 7.12 | 3.52 | 12.05 | 12.02 | 14.42 | 11.67 | 20.32 | 6.36 |
| 16 | 10.98 | 6.35 | 12.59 | 16.88 | 6.40 | 3.18 | 7.19 | 11.25 | 13.43 | 13.29 | 19.44 | 6.02 |
| 20 | 5.54 | 3.88 | 4.69 | 8.36 | 4.95 | 2.65 | 2.44 | 7.99 | 6.52 | 9.76 | 5.92 | 3.23 |
| 24 | 5.57 | 1.94 | 3.21 | 6.73 | 6.31 | 2.38 | 2.90 | 12.21 | 3.90 | 10.97 | 3.63 | 7.08 |
| 28 | 4.31 | 1.64 | 3.18 | 2.55 | 3.91 | 2.35 | 1.47 | 7.67 | 3.79 | 10.31 | 0.54 | 5.80 |
| 32 | 3.50 | 1.56 | 2.73 | 1.16 | 3.55 | 5.90 | 0.66 | 3.59 | 2.79 | 7.59 | 0.67 | 3.46 |
| 36 | 2.37 | 1.06 | 1.34 | 0.54 | 2.14 | 12.25 | 0.00 | 1.06 | 0.56 | 3.73 | 0.37 | 3.60 |
| 48 | 1.33 | 0.73 | 0.28 | 0.00 | 2.04 | 2.55 | 0.00 | 0.00 | 0.00 | 0.56 | 0.00 | 1.76 |
| 60 | 0.00 | 0.48 | 0.00 | 0.00 | 1.33 | 1.33 | 0.00 | 0.00 | 0.00 | 0.00 | 0.00 | 0.46 |
| 72 | 0.00 | 0.69 | 0.00 | 0.00 | 0.41 | 0.44 | 0.00 | 0.00 | 0.00 | 0.00 | 0.00 | 0.27 |
| CMax ng/ml | 20.6 | 21.5 | 12.7 | 20.2 | 15.6 | 12.8 | 18.1 | 28.2 | 18.1 | 26.7 | 28.0 | 12.7 |
| Tmax H | 4.0 | 3.5 | 10.0 | 12.0 | 5.0 | 3.0 | 10.0 | 3.5 | 10.0 | 3.0 | 3.0 | 5.0 |
| AUC0-t H · ng/ml | 281.6 | 219.3 | 230.1 | 309.7 | 262.8 | 257.0 | 213.8 | 357.2 | 289.7 | 430.4 | 279.0 | 283.6 |

TABLE 34

CR GR-01 Mean MIN-101 Plasma Concentrations and Parameters (Fasted State)

GR01 FASTED MIN-101 PLASMA CONCENTRATIONS and AUCo-t

| GR01 Hours | MEAN | Sd | Sm | CV % |
|---|---|---|---|---|
| 0 | 0.00 | 0.00 | 0.00 | 0.00 |
| 0.25 | 0.00 | 0.00 | 0.00 | 0.00 |
| 0.5 | 0.00 | 0.00 | 0.00 | 0.00 |
| 1 | 0.35 | 1.22 | 0.65 | 346.41 |
| 1.5 | 1.25 | 2.77 | 1.95 | 220.78 |
| 2 | 5.75 | 5.57 | 4.67 | 96.91 |
| 2.5 | 11.71 | 7.46 | 5.46 | 63.69 |
| 3 | 15.54 | 7.84 | 6.08 | 50.45 |
| 3.5 | 16.04 | 7.01 | 5.89 | 43.68 |
| 4 | 15.99 | 6.08 | 5.27 | 38.00 |
| 5 | 14.62 | 4.60 | 3.26 | 31.47 |
| 6 | 11.35 | 4.17 | 3.35 | 36.70 |
| 7 | 10.33 | 3.58 | 2.64 | 34.63 |
| 8 | 9.39 | 3.93 | 3.25 | 41.81 |
| 10 | 10.69 | 5.39 | 4.42 | 50.45 |
| 12 | 11.26 | 4.66 | 3.48 | 41.34 |
| 14 | 11.76 | 4.67 | 3.33 | 39.73 |
| 16 | 10.58 | 4.87 | 3.96 | 46.01 |
| 20 | 5.49 | 2.33 | 1.85 | 42.48 |
| 24 | 5.57 | 3.30 | 2.58 | 59.31 |
| 28 | 3.96 | 2.80 | 2.04 | 70.67 |
| 32 | 3.10 | 2.06 | 1.50 | 66.68 |
| 36 | 2.42 | 3.33 | 2.05 | 137.50 |
| 48 | 0.77 | 0.92 | 0.77 | 119.51 |
| 60 | 0.30 | 0.51 | 0.40 | 171.48 |
| 72 | 0.15 | 0.24 | 0.20 | 159.83 |
| CMax ng/ml | 19.59 | 5.74 | 4.61 | 29.30 |
| Tmax H | 6.00 | 3.43 | 3.00 | 57.19 |
| AUC0-t H · ng/ml | 284.52 | 60.83 | 41.49 | 21.38 |

See FIG. 23

TABLE 35

CR GR-01 Mean MIN-101 Plasma Concentrations and Parameters (Fed versus Fasted State)
GR01 FOOD EFFECT Mean MIN-101 MIN101 Plasma Concentrations (ng/ml)

| Hours | GR01 FED | GR01 FASTED |
|---|---|---|
| 0 | 0.00 | 0.00 |
| 0.25 | 0.00 | 0.00 |
| 0.5 | 0.00 | 0.00 |
| 1 | 0.00 | 0.35 |
| 1.5 | 0.00 | 1.25 |
| 2 | 0.00 | 5.75 |
| 2.5 | 0.57 | 11.71 |
| 3 | 1.44 | 15.54 |
| 3.5 | 1.55 | 16.04 |
| 4 | 1.79 | 15.99 |

TABLE 35-continued

CR GR-01 Mean MIN-101 Plasma Concentrations
and Parameters (Fed versus Fasted State)
GR01 FOOD EFFECT Mean MIN-101 MIN101
Plasma Concentrations (ng/ml)

| Hours | GR01 FED | GR01 FASTED |
|---|---|---|
| 5 | 4.77 | 14.62 |
| 6 | 7.74 | 11.35 |
| 7 | 7.77 | 10.33 |
| 8 | 6.36 | 9.39 |
| 10 | 7.58 | 10.69 |
| 12 | 13.70 | 11.26 |
| 14 | 9.38 | 11.76 |
| 16 | 8.88 | 10.58 |
| 20 | 7.04 | 5.49 |
| 24 | 10.71 | 5.57 |
| 28 | 8.26 | 3.96 |
| 32 | 5.22 | 3.10 |
| 36 | 2.83 | 2.42 |
| 48 | 0.71 | 0.77 |
| 60 | 0.16 | 0.30 |
| 72 | 0.03 | 0.15 |
| Max ng/ml | 20.9 | 19.6 |
| Tmax H | 12.5 | 6.0 |
| AUC0-t H · ng/ml | 269.2 | 284.5 |
| F AUC | 95.14 | REF |
| F Cmax | 108.97 | REF |

Relative bioavailability of MIN-101 in GR-01 formulation in fed versus fasted states:
F % $C_{max}$: 108.97%
F % $AUC_{(0-tau)}$: 95.14%
See FIG. 24

Example 13: In Vivo Pharmacokinetic Analysis of BFB-520 in CR GR-01 Tablets in Subjects in Fed Versus Fasted States. (Tau=72 h)

Fed State—12 subjects (cross-over)
Geo Mean $C_{max}$: 1.54 ng/mL
Median $T_{max}$: 18.00 H
$AUC_{(0-tau)}$: 30.12 ng·H/mL

TABLE 36

CR GR-01 Individual BFB-520 Plasma Concentrations and Parameters (Fed State)

GR01 FED BFB-520 PLASMA CONCENTRATIONS (ng/ml) and AUCo-t (H · ng/ml)

| GR01 Hours | 1-BFB-520 | 2-BFB-520 | 3-BFB-520 | 5-BFB-520 | 6-BFB-520 | 7-BFB-520 | 8-BFB-520 | 9-BFB-520 | 10-BFB-520 | 11-BFB-520 | 12-BFB-520 | 13-BFB-520 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 | 0.00 | 0.00 | 0.00 | 0.00 |
| 2.5 | 0.00 | 0.00 | 0.00 | 0.00 | 0.00 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 | 0.00 | 0.00 | 0.00 | 0.00 | 0.00 |
| 3.5 | 0.00 | 0.00 | 0.33 | 0.00 | 0.00 | 0.00 | 0.00 | 0.00 | 0.00 | 0.00 | 0.00 | 0.00 |
| 4 | 0.00 | 0.00 | 0.48 | 0.00 | 0.00 | 0.00 | 0.00 | 0.00 | 0.00 | 0.00 | 0.00 | 0.27 |
| 5 | 0.00 | 0.00 | 0.64 | 0.46 | 0.00 | 0.82 | 0.00 | 0.00 | 0.00 | 0.00 | 0.00 | 0.32 |
| 6 | 0.00 | 0.46 | 0.76 | 0.61 | 0.00 | 1.19 | 0.00 | 0.00 | 0.90 | 0.00 | 0.00 | 0.34 |
| 7 | 0.00 | 0.90 | 1.09 | 0.64 | 0.00 | 1.28 | 0.00 | 0.00 | 1.19 | 1.00 | 0.00 | 0.38 |
| 8 | 0.00 | 1.06 | 0.83 | 0.90 | 0.00 | 1.53 | 0.00 | 0.00 | 1.54 | 1.77 | 0.00 | 0.42 |
| 10 | 0.00 | 1.08 | 0.70 | 1.07 | 0.00 | 1.44 | 0.00 | 0.51 | 1.57 | 1.74 | 0.00 | 0.67 |
| 12 | 1.48 | 0.52 | 0.69 | 0.79 | 0.79 | 1.82 | 0.00 | 1.14 | 1.50 | 1.64 | 1.08 | 0.67 |
| 14 | 1.56 | 0.46 | 0.62 | 0.52 | 0.87 | 2.20 | 0.00 | 1.51 | 2.06 | 2.53 | 1.38 | 0.83 |
| 16 | 1.03 | 0.79 | 0.76 | 0.39 | 1.15 | 1.69 | 0.00 | 1.26 | 2.13 | 2.28 | 0.95 | 0.85 |
| 20 | 0.87 | 0.85 | 0.64 | 0.00 | 1.02 | 2.15 | 0.00 | 1.43 | 2.36 | 2.66 | 0.83 | 0.72 |
| 24 | 0.65 | 0.58 | 0.46 | 0.00 | 1.75 | 1.15 | 0.00 | 2.95 | 1.08 | 1.88 | 1.25 | 0.41 |
| 28 | 1.14 | 0.48 | 0.63 | 0.00 | 1.31 | 1.13 | 0.81 | 2.46 | 1.42 | 1.93 | 1.86 | 0.56 |
| 32 | 0.89 | 0.30 | 0.32 | 0.00 | 0.90 | 0.90 | 0.43 | 2.35 | 0.74 | 0.95 | 1.36 | 0.43 |
| 36 | 0.60 | 0.00 | 0.00 | 0.00 | 0.26 | 0.58 | 0.00 | 0.95 | 0.36 | 0.60 | 0.78 | 0.34 |
| 48 | 0.00 | 0.00 | 0.00 | 0.00 | 0.00 | 0.00 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 | 0.00 | 0.00 | 0.00 |
| 72 | 0.00 | 0.00 | 0.00 | 0.00 | 0.00 | 0.00 | 0.00 | 0.00 | 0.00 | 0.00 | 0.00 | 0.00 |
| Max ng/ml | 16 | 1.1 | 1.1. | 1.1 | 1.8 | 2.2 | 0.8 | 2.9 | 2.4 | 2.7 | 1.9 | 0.9 |
| Tmax H | 14.0 | 10.0 | 7.0 | 10.0 | 28.0 | 14.0 | 28.0 | 24.0 | 20.0 | 20.0 | 28.0 | 16.0 |
| AUC0-t H · ng/ml | 24.4 | 17.5 | 18.0 | 8.2 | 34.9 | 43.7 | 6.8 | 49.2 | 45.6 | 55.8 | 34.4 | 22.9 |
| F AUC | 104.2 | 94.2 | 112.0 | 26.1 | 177.5 | 230.2 | 34.5 | 112.5 | 126.5 | 137.5 | 102.1 | 82.0 |
| F CMax | 130.3 | 84.3 | 132.0 | 59.3 | 170.1 | 199.6 | 63.4 | 163.9 | 128.4 | 162.9 | 82.5 | 79.1 |

TABLE 37

CR GR-01 Mean BFB-520 Plasma Concentrations and Parameters (Fed State)

| GR01 Hours | GR01 FED BFB-520 PLASMA CONCENTRATIONS and AUCo-t | | | |
|---|---|---|---|---|
| | MEAN | Sd | Sm | CV % |
| 0 | 0.00 | | | |
| 0.25 | 0.00 | | | |
| 0.5 | 0.00 | | | |
| 1 | 0.00 | 0.00 | 0.00 | #DIV/0! |
| 1.5 | 0.00 | 0.00 | 0.00 | #DIV/0! |
| 2 | 0.00 | 0.00 | 0.00 | #DIV/0! |
| 2.5 | 0.00 | 0.00 | 0.00 | #DIV/0! |
| 3 | 0.00 | 0.00 | 0.00 | #DIV/0! |
| 3.5 | 0.03 | 0.09 | 0.05 | 346.41 |
| 4 | 0.06 | 0.15 | 0.10 | 244.57 |
| 5 | 0.19 | 0.30 | 0.25 | 159.98 |
| 6 | 0.35 | 0.43 | 0.36 | 120.06 |
| 7 | 0.54 | 0.53 | 0.48 | 98.36 |
| 8 | 0.67 | 0.69 | 0.60 | 102.84 |
| 10 | 0.73 | 0.65 | 0.54 | 88.88 |
| 12 | 1.01 | 0.53 | 0.43 | 52.69 |
| 14 | 1.22 | 0.78 | 0.65 | 64.14 |
| 16 | 1.08 | 0.67 | 0.50 | 61.50 |
| 20 | 1.14 | 0.86 | 0.68 | 75.79 |
| 24 | 1.01 | 0.78 | 0.54 | 77.24 |
| 28 | 1.18 | 0.72 | 0.54 | 77.24 |
| 32 | 0.83 | 0.63 | 0.46 | 75.80 |
| 36 | 0.42 | 0.36 | 0.31 | 85.11 |
| 48 | 0.01 | | | |
| 60 | 0.00 | | | |
| 72 | 0.00 | | | |
| Max ng/ml | 1.69 | 0.73 | 0.61 | 43.32 |
| Tmax H | 18.25 | 7.56 | 6.42 | 41.41 |
| AUC0-t H · ng/ml | 30.12 | 16.26 | 13.82 | 53.98 |
| F AUC | 111.58 | 55.50 | 37.75 | 49.74 |
| F Cmax | 121.32 | 46.86 | 39.66 | 38.63 |

See FIG. 25

Fasted State—12 subjects (cross-over)

Geo Mean $C_{max}$: 1.32 ng/mL

Median $T_{max}$: 12.5 H $AUC_{(0-tau)}$: 27.48 ng·H/mL

TABLE 38

CR GR-01 Individual BFB-520 Plasma Concentrations and Parameters (Fasted State)

GR01 FASTED BFB-520 PLASMA CONCENTRATIONS (ng/ml) and AUCo-t (H · ng/ml)

| GR01 Hours | 1-BFB-520 | 2-BFB-520 | 3-BFB-520 | 5-BFB-520 | 6-BFB-520 | 7-BFB-520 | 8-BFB-520 | 9-BFB-520 | 10-BFB-520 | 11-BFB-520 | 12-BFB-520 | 13-BFB-520 |
|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 |
| 0.25 | 0.00 | 0.00 | 0.00 | 0.00 | 0.00 | 0.00 | 0.00 | 0.00 | 0.00 | 0.00 | 0.00 | 0.00 |
| 0.5 | 0.00 | 0.00 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 | 0.00 | 0.00 |
| 1.5 | 0.00 | 0.00 | 0.00 | 0.00 | 0.00 | 0.00 | 0.00 | 0.00 | 0.00 | 0.00 | 0.00 | 0.00 |
| 2 | 0.00 | 0.00 | 0.26 | 0.00 | 0.00 | 0.00 | 0.00 | 0.00 | 0.00 | 0.28 | 0.00 | 0.00 |
| 2.5 | 0.00 | 0.00 | 0.00 | 0.00 | 0.00 | 0.00 | 0.00 | 0.00 | 0.00 | 0.00 | 0.00 | 0.00 |
| 3 | 0.42 | 0.71 | 0.45 | 0.44 | 0.00 | 0.26 | 0.60 | 0.60 | 0.63 | 0.88 | 0.28 | 0.00 |
| 3.5 | 0.54 | 1.00 | 0.50 | 0.47 | 0.00 | 0.38 | 0.57 | 1.28 | 0.74 | 1.00 | 0.86 | 0.43 |
| 4 | 0.84 | 1.04 | 0.49 | 0.63 | 0.35 | 0.39 | 0.45 | 1.41 | 1.08 | 1.29 | 0.72 | 0.51 |
| 5 | 1.01 | 0.98 | 0.39 | 0.72 | 0.62 | 0.51 | 0.75 | 1.56 | 1.13 | 1.45 | 0.99 | 0.61 |
| 6 | 1.07 | 1.07 | 0.43 | 0.78 | 0.83 | 0.54 | 0.85 | 1.47 | 0.85 | 1.19 | 0.72 | 0.64 |
| 7 | 1.20 | 1.28 | 0.37 | 0.92 | 0.93 | 0.51 | 0.88 | 1.47 | 0.71 | 1.47 | 0.74 | 0.80 |
| 8 | 1.17 | 1.07 | 0.44 | 1.10 | 1.03 | 0.68 | 0.76 | 1.80 | 1.37 | 1.63 | 1.06 | 0.74 |
| 10 | 0.68 | 0.96 | 0.68 | 1.23 | 0.77 | 0.33 | 1.28 | 1.72 | 1.84 | 1.32 | 1.37 | 0.99 |
| 12 | 0.65 | 0.77 | 0.55 | 1.30 | 0.66 | 0.32 | 0.91 | 1.40 | 1.74 | 0.78 | 2.26 | 1.08 |
| 14 | 1.00 | 0.87 | 0.72 | 1.73 | 0.74 | 0.43 | 1.24 | 1.54 | 1.82 | 1.11 | 1.11 | 1.05 |
| 16 | 1.00 | 0.71 | 0.83 | 1.80 | 0.51 | 0.43 | 1.09 | 1.49 | 1.80 | 1.24 | 1.11 | 0.95 |
| 20 | 0.69 | 0.70 | 0.63 | 1.58 | 0.67 | 0.40 | 0.71 | 1.73 | 1.13 | 1.44 | 1.17 | 0.68 |
| 24 | 0.57 | 0.31 | 0.43 | 0.85 | 0.50 | 0.00 | 0.39 | 1.31 | 0.57 | 1.05 | 0.99 | 0.58 |
| 28 | 0.72 | 0.26 | 0.50 | 0.58 | 0.59 | 0.00 | 0.28 | 1.15 | 0.92 | 1.27 | 0.65 | 0.58 |
| 32 | 0.33 | 0.00 | 0.28 | 0.30 | 0.46 | 0.44 | 0.00 | 0.67 | 0.62 | 0.68 | 0.28 | 0.43 |
| 36 | 0.29 | 0.00 | 0.00 | 0.00 | 0.38 | 1.10 | 0.00 | 0.28 | 0.00 | 0.51 | 0.00 | 0.42 |
| 48 | 0.00 | 0.00 | 0.00 | 0.00 | 0.00 | 0.33 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 | 0.00 | 0.00 | 0.00 |
| 72 | 0.00 | 0.00 | 0.00 | 0.00 | 0.00 | 0.00 | 0.00 | 0.00 | 0.00 | 0.00 | 0.00 | 0.00 |
| Max ng/ml | 1.2 | 1.3 | 0.8 | 1.8 | 1.0 | 1.1 | 1.3 | 1.8 | 1.8 | 1.6 | 2.3 | 1.1 |
| Tmax H | 7.0 | 7.0 | 16.0 | 16.0 | 8.0 | 36.0 | 10.0 | 8.0 | 10.0 | 8.0 | 12.0 | 12.0 |
| AUC0-t H · ng/ml | 23.5 | 18.6 | 16.1 | 31.3 | 19.7 | 19.0 | 19.6 | 43.8 | 36.1 | 40.6 | 33.7 | 27.9 |

TABLE 39

CR GR-01 Mean BFB-520 Plasma Concentrations and Parameters (Fasted State)

| GR01 Hours | GR01 BFB-520 PLASMA CONCENTRATIONS and AUCo-t | | | |
|---|---|---|---|---|
| | MEAN | Sd | Sm | CV % |
| 0 | 0.00 | | | |
| 0.25 | 0.00 | | | |
| 0.5 | 0.00 | | | |
| 1 | 0.00 | | | |
| 1.5 | 0.00 | | | |
| 2 | 0.04 | 0.10 | 0.07 | 233.68 |
| 2.5 | 0.22 | 0.25 | 0.22 | 112.01 |
| 3 | 0.49 | 0.23 | 0.17 | 45.99 |
| 3.5 | 0.65 | 0.35 | 0.27 | 53.37 |
| 4 | 0.77 | 0.36 | 0.31 | 47.35 |
| 5 | 0.89 | 0.36 | 0.29 | 40.77 |
| 6 | 0.87 | 0.29 | 0.22 | 33.50 |
| 7 | 0.94 | 0.35 | 0.28 | 37.58 |
| 8 | 1.07 | 0.39 | 0.29 | 36.81 |
| 10 | 1.10 | 0.45 | 0.36 | 40.79 |
| 12 | 1.04 | 0.55 | 0.43 | 53.43 |
| 14 | 1.11 | 0.42 | 0.31 | 37.58 |
| 16 | 1.08 | 0.45 | 0.34 | 41.52 |
| 20 | 0.96 | 0.43 | 0.38 | 45.29 |
| 24 | 0.63 | 0.36 | 0.28 | 57.32 |
| 28 | 0.63 | 0.36 | 0.26 | 57.90 |
| 32 | 0.37 | 0.23 | 0.18 | 60.48 |
| 36 | 0.25 | 0.33 | 0.25 | 133.52 |
| 48 | 0.03 | 0.09 | 0.05 | 346.41 |
| 60 | 0.00 | | | |
| 72 | 0.00 | | | |
| Max ng/ml | 1.43 | 0.43 | 0.37 | 30.06 |
| Tmax H | 12.50 | 8.04 | 5.08 | 64.32 |
| AUC0-t H · ng/ml | 27.48 | 9.46 | 8.07 | 34.41 |
| F AUC | 96.10 | 35.77 | 18.95 | 37.22 |
| F Cmax | 80.48 | 24.60 | 20.65 | 30.56 |

See FIG. 26

TABLE 40

CR GR-01 Mean BFB-520 Plasma Concentrations and Parameters (Fed versus Fasted State)

| GR01 Hours | GR01 BFB-520 PLASMA CONCENTRATIONS and AUCo-t | | | |
|---|---|---|---|---|
| | MEAN | Sd | Sm | CV % |
| 0 | 0.00 | | | |
| 0.25 | 0.00 | | | |
| 0.5 | 0.00 | | | |
| 1 | 0.00 | | | |
| 1.5 | 0.00 | | | |
| 2 | 0.04 | 0.10 | 0.07 | 233.68 |
| 2.5 | 0.22 | 0.25 | 0.22 | 112.01 |
| 3 | 0.49 | 0.23 | 0.17 | 45.99 |
| 3.5 | 0.65 | 0.35 | 0.27 | 53.37 |
| 4 | 0.77 | 0.36 | 0.31 | 47.35 |
| 5 | 0.89 | 0.36 | 0.29 | 40.77 |
| 6 | 0.87 | 0.29 | 0.22 | 33.50 |
| 7 | 0.94 | 0.35 | 0.28 | 37.58 |
| 8 | 1.07 | 0.39 | 0.29 | 36.81 |
| 10 | 1.10 | 0.45 | 0.36 | 40.79 |
| 12 | 1.04 | 0.55 | 0.43 | 53.43 |
| 14 | 1.11 | 0.42 | 0.31 | 37.58 |
| 16 | 1.08 | 0.45 | 0.34 | 41.52 |
| 20 | 0.96 | 0.43 | 0.38 | 45.29 |
| 24 | 0.63 | 0.36 | 0.28 | 57.32 |
| 28 | 0.63 | 0.36 | 0.26 | 57.90 |
| 32 | 0.37 | 0.23 | 0.18 | 60.48 |
| 36 | 0.25 | 0.33 | 0.25 | 133.52 |
| 48 | 0.03 | 0.09 | 0.05 | 346.41 |
| 60 | 0.00 | | | |
| 72 | 0.00 | | | |
| Max ng/ml | 1.43 | 0.43 | 0.37 | 30.06 |
| Tmax H | 12.50 | 8.04 | 5.08 | 64.32 |
| AUC0-t H · ng/ml | 27.48 | 9.46 | 8.07 | 34.41 |
| F AUC | 96.10 | 35.77 | 18.95 | 37.22 |
| F Cmax | 80.48 | 24.60 | 20.65 | 30.56 |

Relative bioavailability of BFB-520 in GR-01 formulation in fed versus fasted states:

F % $C_{max}$: 121.32%

F % $AUC_{(0-tau)}$: 111.58%

See FIG. 27

Example 14: Predicted Food Effect on Plasma Concentrations of MIN-101 and BFB-520 at Steady State in GR-01 Tablets (32 mg)

Determination of elimination slopes from the mean plasma concentrations time curves before numerical computations.

MIN-101

Fed State: $K_e$=0.119/H

Fasted State: $K_e$=0.082/H

BFB-520:

Fed State: from 14 H to 28 H during the flip flop phase $K_e$=0.014/H; post absorption $K_e$=0.233/H Fasted State: from 14 H to 28 H during the flip flop phase $K_e$=0.005545/H; post absorption $K_e$=0.1586/H

TABLE 41

Predicted Plasma Concentrations of MIN-101 at Steady State in GR-01, 32 mg Tablets (Fed and Fasted states)
GR01 32 mg FED and FASTED MIN-101 at Steady-State
MIN101 Plasma Concentrations (ng/ml)

| HOURS | GR01 FED SS | GR01 FASTED SS |
|---|---|---|
| 72 | 11.45 | 6.45 |
| 72.5 | 10.70 | 6.20 |
| 73 | 10.09 | 6.30 |
| 73.5 | 9.50 | 6.96 |
| 74 | 8.95 | 11.23 |
| 74.5 | 9.00 | 16.97 |
| 75 | 9.39 | 20.59 |
| 75.5 | 9.04 | 20.89 |
| 76 | 10.46 | 20.58 |
| 77 | 11.04 | 18.91 |
| 78 | 13.30 | 15.30 |
| 79 | 12.71 | 13.96 |
| 80 | 11.83 | 12.95 |
| 82 | 11.04 | 13.53 |
| 84 | 16.70 | 14.02 |
| 86 | 11.53 | 13.80 |
| 88 | 10.57 | 12.32 |
| 92 | 8.09 | 6.75 |
| 96 | 11.45 | 6.46 |
| CMaxSS ng/ml | 16.7 | 20.9 |
| CMinSS | 8.09 | 6.46 |

TABLE 41-continued

Predicted Plasma Concentrations of MIN-101 at Steady
State in GR-01, 32 mg Tablets (Fed and Fasted states)
GR01 32 mg FED and FASTED MIN-101 at Steady-State
MIN101 Plasma Concentrations (ng/ml)

| HOURS | GR01 FED SS | GR01 FASTED SS |
|---|---|---|
| TmaxSS H | 12.00 | 3.5 |
| AUC72-96 H · ng/ml | 263.8 | 287.6 |
| F AUC | 91.7 | REF |
| F Cmax | 80.0 | REF |

See FIG. 28.

TABLE 42

Predicted Plasma Concentrations of BFB-520 at Steady
State in GR-01, 32 mg Tablets (Fed and Fasted states)
GR01 32 mg FED and FASTED BFB-520 at Steady-State
BFB-520 Plasma Concentrations (ng/ml)

| HOURS | GR01 FED SS | GR01 FASTED SS |
|---|---|---|
| 72 | 1.03 | 0.66 |
| 72.5 | 1.02 | 0.64 |
| 73 | 1.01 | 0.62 |
| 73.5 | 1.00 | 0.60 |
| 74 | 0.99 | 0.63 |
| 74.5 | 0.99 | 0.79 |
| 75 | 0.98 | 1.04 |
| 75.5 | 1.00 | 1.18 |
| 76 | 1.25 | 1.41 |
| 77 | 1.13 | 1.38 |
| 78 | 1.29 | 1.33 |
| 79 | 1.46 | 1.38 |
| 80 | 1.51 | 1.45 |
| 82 | 1.26 | 1.37 |
| 84 | 1.43 | 1.29 |
| 86 | 1.43 | 1.26 |
| 88 | 1.21 | 1.19 |
| 92 | 1.19 | 1.02 |
| 96 | 1.03 | 0.66 |
| CMaxSS ng/ml | 1.51 | 1.45 |
| CMinSS | 1.03 | 0.66 |
| TmaxSS H | 8.00 | 8.00 |
| AUC72-96 H · ng/ml | 29.5 | 27.0 |
| F AUC | 109.4 | REF |
| F Cmax | 103.7 | REF |

See FIG. 29.

Example 15: Predicted Food Effect on Plasma
Concentrations of MIN-101 and BFB-520 at Steady
State in GR-01 Tablets (64 mg)

Determination of elimination slopes from the mean plasma concentrations time curves before numerical computations.

MIN-101

Fed State: $K_e = 0.119/H$

Fasted State: $K_e = 0.082/H$

BFB-520:

Fed State: from 14 H to 28 H during the flip flop phase $K_e = 0.014/H$; post absorption $K_e = 0.233/H$ Fasted State: from 14 H to 28 H during the flip flop phase $K_e = 0.005545/H$; post absorption $K_e = 0.1586/H$

TABLE 43

Predicted Plasma Concentrations of MIN-101 at
Steady State in GR-01, 64 mg Tablets (Fed and Fasted states)
GR01 64 mg FED and FASTED MIN-101 at Steady-State
MIN101 Plasma Concentrations (ng/ml)

| HOURS | GR01 FED SS | GR01 FASTED SS |
|---|---|---|
| 72 | 22.91 | 12.90 |
| 72.5 | 21.41 | 12.40 |
| 73 | 20.17 | 12.60 |
| 73.5 | 19.01 | 13.93 |
| 74 | 17.91 | 22.46 |
| 74.5 | 18.00 | 33.94 |
| 75 | 18.78 | 41.18 |
| 75.5 | 18.08 | 41.77 |
| 76 | 20.92 | 41.17 |
| 77 | 22.08 | 37.82 |
| 78 | 26.60 | 30.60 |
| 79 | 25.42 | 27.92 |
| 80 | 23.65 | 25.90 |
| 82 | 22.08 | 27.06 |
| 84 | 33.41 | 28.05 |
| 86 | 23.05 | 27.61 |
| 88 | 21.14 | 24.64 |
| 92 | 16.17 | 13.49 |
| 96 | 22.91 | 12.93 |
| CMaxSS ng/ml | 33.41 | 41.77 |
| CMinSS | 16.17 | 12.93 |
| TmaxSS H | 12.00 | 3.50 |
| AUC72-96 H · ng/ml | 527.5 | 577.6 |
| F AUC | 91.3 | REF |
| F Cmax | 80.0 | REF |

See FIG. 30.

TABLE 44

Predicted Plasma Concentrations of BFB-520 at Steady
State in GR-01, 64 mg Tablets (Fed and Fasted states)
GR01 64 mg FED and FASTED BFB-520 at Steady-State
BFB-520 Plasma Concentrations (ng/ml)

| HOURS | GR01 FED SS | GR01 FASTED SS |
|---|---|---|
| 72 | 2.06 | 1.32 |
| 72.5 | 2.04 | 1.28 |
| 73 | 2.02 | 1.24 |
| 73.5 | 2.00 | 1.21 |
| 74 | 1.99 | 1.26 |
| 74.5 | 1.97 | 1.58 |
| 75 | 1.95 | 2.09 |
| 75.5 | 1.99 | 2.37 |
| 76 | 2.50 | 2.82 |
| 77 | 2.27 | 2.77 |
| 78 | 2.57 | 2.66 |
| 79 | 2.92 | 2.76 |
| 80 | 3.01 | 2.91 |
| 82 | 2.51 | 2.75 |
| 84 | 2.87 | 2.57 |
| 86 | 2.86 | 2.52 |
| 88 | 2.42 | 2.37 |
| 92 | 2.38 | 2.03 |
| 96 | 2.06 | 1.32 |
| CMaxSS ng/ml | 3.01 | 2.91 |
| CMinSS | 2.06 | 1.32 |

TABLE 44-continued

Predicted Plasma Concentrations of BFB-520 at Steady State in GR-01, 64 mg Tablets (Fed and Fasted states)
GR01 64 mg FED and FASTED BFB-520 at Steady-State BFB-520 Plasma Concentrations (ng/ml)

| HOURS | GR01 FED SS | GR01 FASTED SS |
|---|---|---|
| TmaxSS H | 8.00 | 8.00 |
| AUC72-96 H · ng/ml | 59.0 | 54.1 |
| F AUC | 109.1 | REF |
| F Cmax | 103.7 | REF |

See FIG. 31.

Example 16: Description of 32 mg Gastro-Resistant CR Tablet (GR01/B-32 mg)

The CR GR-01/B tablets are supplied as round (diameter 10 mm and R=10) tablets, free from visual defects. Each tablet contains 32 mg of Compound (I). The complete statement of the components and quantitative composition of CR GR-01/B tablet is given in Table 45.

TABLE 45

Composition of CR GR-01/B 32 mg tablet

| | GR-01/B-32 mg | |
|---|---|---|
| Component/Ingredient | mg/tablet | % (w/w) |
| MIN-101[1] | 38.40 | 12.09 |
| Hypromellose (METHOCEL ™ K100LV CR) | 30.00 | 9.45 |
| Hypromellose (Methocel ™ K100M CR) | 72.00 | 22.67 |
| Microcrystalline Cellulose | 96.67 | 30.42 |
| Lactose | 60.00 | 18.89 |
| Silica Colloidal Anhydrous | 1.50 | 0.47 |
| Magnesium stearate | 1.50 | 0.47 |
| Eudragit L30D55 | 15.0 | 4.72 |
| Plasacryl HTP20 | 2.55 | 0.80 |
| Total | 317.62 | 100.00 |

[1]Salt correction factor of 1.2 applied

Example 17: Description of 64 mg gastro-resistant CR tablet (GR-01/B-64 mg)

The CR GR-01/B tablets are supplied as round (diameter 10 mm and R=10) tablets, free from visual defects. Each tablet contains 64 mg of Compound (I). The complete statement of the components and quantitative composition of CR GR-01/B tablet is given in Table 46.

TABLE 46

Composition of CR GR-01/B 64 mg tablet

| | GR-01/B-64 mg | |
|---|---|---|
| Component/Ingredient | mg/tablet | % (w/w) |
| MIN-101[1] | 76.8 | 24.14 |
| Hypromellose (METHOCEL ™ K100LV CR) | 30.00 | 9.45 |
| Hypromellose (Methocel ™ K100M CR) | 72.00 | 22.67 |
| Microcrystalline Cellulose | 77.40 | 24.37 |
| Lactose | 40.80 | 12.85 |
| Silica Colloidal Anhydrous | 1.50 | 0.47 |
| Magnesium stearate | 1.50 | 0.47 |
| Eudragit L30D55 | 15.0 | 4.72 |
| Plasacryl HTP20 | 2.55 | 0.80 |
| Total | 317.55 | 100.00 |

[1]Salt correction factor of 1.2 applied

Example 18: Comparison of GR-01 32 mg Tablet, GR-01/B 32 mg Tablet, and GR-01/B 64 mg Tablet

TABLE 47

Tablet Composition: GR01 vs GR01/B

| | Ingredient | | | | | |
|---|---|---|---|---|---|---|
| | GR01-32 mg | | GR01/B-32 mg | | GR01/B-64 mg | |
| Component | mg/tablet | % (w/w) | mg/tablet | % (w/w) | mg/tablet | % (w/w) |
| MIN-101[1] | 38.40 | 12.09 | 38.40 | 12.09 | 76.8 | 24.14 |
| Hypromellose (Metolose ® 90SH 100 SR) | 30.00 | 9.45 | | | | |
| Hypromellose (METHOCEL ™ K100LV CR) | | | 30.00 | 9.45 | 30.00 | 9.45 |
| Hypromellose (Methocel ™ K100M CR) | 72.00 | 22.67 | 72.00 | 22.67 | 72.00 | 22.67 |
| Microcrystalline Cellulose | 95.10 | 29.95 | 96.60 | 30.42 | 77.40 | 24.37 |
| Lactose | 60.00 | 18.89 | 60.00 | 18.89 | 40.80 | 12.85 |
| Silica Colloidal Anhydrous | 1.50 | 0.47 | 1.50 | 0.47 | 1.50 | 0.47 |
| Magnesium stearate | 3.00 | 0.94 | 1.50 | 0.47 | 1.50 | 0.47 |
| Eudragit L30D55 | 15.0 | 4.72 | 15.0 | 4.72 | 15.0 | 4.72 |
| Plasacryl HTP20 | 2.55 | 0.80 | 2.55 | 0.80 | 2.55 | 0.80 |
| Total | 317.55 | 5.53 | 317.55 | 100.00 | 317.55 | 100.00 |

[1]Salt correction factor of 1.2 applied

Example 19: Stability Data Experiments:
Comparison of GR-01 and GR-01/B 32 mg Tablets "Impurity A," "2-isomer," and "PMIC" refer to impurities from the manufacturing process for MIN-101.

TABLE 48

Stability data at 25° C./60% RH

| Product Name: | MIN-101 | Product Manufacturer: Amatsi Aquitaine |
| --- | --- | --- |
| Strength: | 32 mg | API Manufacturer: PCAS |
| Storage Condition: | 25° C./60% RH | Container Closure: TEKNIFLEX ® VPOA 10200 and aluminum blister packs |

| | Stability Interval (Months) | | | | | |
| --- | --- | --- | --- | --- | --- | --- |
| Test | Initial | 1 | 3 | 6 | 9 | 12 |
| | GR01 tablets | | | | | |
| Related Sub. (%) | | | | | | |
| Impurity A | <LOQ | 0.02 | 0.03 | 0.04 | 0.03 | <LOQ |
| 2-isomer | <LOQ | <LOQ | <LOQ | 0.02 | <LOQ | <LOQ |
| PMIC | 0.08 | 0.13 | 0.18 | 0.20 | 0.24 | 0.26 |
| Unspecified imp. | <0.1% each | <0.1% each | RRT0.67: 0.11 | RRT0.67: 0.12 | RRT 0.67: 0.12 | RRT 0.67: 0.15 |
| Total impurities | 0.15 | 0.29 | 0.46 | 0.51 | 0.52 | 0.59 |
| | GR01/B tablets | | | | | |
| Related Sub. (%) | | | | | | |
| Impurity A | ND | ND | ND | ND | | |
| 2-isomer | 0.07 | 0.07 | 0.07 | 0.07 | | |
| PMIC | 0.09 | 0.11 | 0.15 | 0.16 | | |
| Unspecified imp. | <0.1% each | <0.1% each | <0.1% each | <0.1% each | | |
| Total impurities | 0.26 | 0.29 | 0.37 | 0.38 | | |

TABLE 49

Stability data at 40° C./75% RH

| Product Name: | | Product Manufacturer: Amatsi Aquitaine |
| --- | --- | --- |
| Strength: | MIN-101 | API Manufacturer: PCAS |
| Storage Condition: | 32 mg<br>40° C./75% RH | Container Closure: TEKNIFLEX ® VPOA 10200 and aluminum blister packs |

| | Stability Interval (Months) | | | |
| --- | --- | --- | --- | --- |
| Test | Initial | 1 | 3 | 6 |
| | GR01 tablets | | | |
| Related Sub. (%) | | | | |
| Impurity A | <LOQ | 0.04 | 0.06 | 0.08 |
| 2-isomer | <LOQ | <LOQ | <LOQ | <LOQ |
| PMIC | 0.08 | 0.27 | 0.44 | 0.77 |
| Unspecified imp. | <0.1% each | RRT0.67 = 0.12 | RRT0.67: 0.18 | RRT0.67: 0.24 |
| Total impurities | 0.15 | 0.57 | 0.94 | 1.46 |

TABLE 49-continued

Stability data at 40° C./75% RH

Product Name:
Strength: MIN-101
Storage: 32 mg
Condition: 40° C./75% RH

Product Manufacturer: Amatsi Aquitaine
API Manufacturer: PCAS
Container Closure: TEKNIFLEX ® VPOA 10200 and aluminum blister packs

| Test | Stability Interval (Months) | | | |
|---|---|---|---|---|
| | Initial | 1 | 3 | 6 |
| GR01/B tablets | | | | |
| Related Sub. (%) | | | | |
| Impurity A | ND | ND | ND | ND |
| 2-isomer | 0.07 | 0.07 | 0.07 | 0.06 |
| PMIC | 0.09 | 0.23 | 0.34 | 0.52 |
| Unspecified imp. | <0.1% each | <0.1% each | RRT 0.67: 0.11 | RRT 0.67: 0.15 |
| Total impurities | 0.26 | 0.51 | 0.71 | 1.00 |

Example 20: In Vitro Dissolution Specifications for GR-01/B Tablets

TABLE 50

Specifications for GR-01/B tablets

| Test | Method | Acceptance Criteria |
|---|---|---|
| Dissolution (%) | HPLC | Report results (±10%) |
| 2 hours | | 0.0% |
| 4 hours | | 24.1% |
| 8 hours | | 59.2% |
| 16 hours | | 88.6% |

Example 21: Description of 32 mg Gastro-Resistant CR Tablet (GR-01/C-32 mg)

The CR GR-01/C tablets are supplied as round (diameter 10 mm and R=10) tablets, free from visual defects. Each tablet contains 32 mg of Compound (I). The complete statement of the components and quantitative composition of CR GR-01/C tablet is given in Table 51.

TABLE 51

Composition of CR GR-01/C 32 mg tablet

| | GR-01/C-32 mg | |
|---|---|---|
| Component/Ingredient | mg/tablet | % (w/w) |
| MIN-101[1] | 38.40 | 12.11 |
| Hypromellose (METHOCEL ™ K100LV CR) | 30.00 | 9.45 |
| Hypromellose (Methocel ™ K100M CR) | 72.00 | 22.67 |
| Microcrystalline Cellulose | 95.10 | 29.95 |
| Lactose | 60.00 | 18.89 |
| Silica Colloidal Anhydrous | 1.50 | 0.47 |
| Magnesium stearate | 3.00 | 0.94 |
| Eudragit L30D55 | 15.0 | 4.72 |
| Plasacryl HTP20 | 2.55 | 0.80 |
| Total | 317.55 | 100.00 |

Example 22: Description of 64 mg Gastro-Resistant CR Tablet (GR-01/C-64 mg)

The CR GR-01/C tablets are supplied as round (diameter 10 mm and R=10) tablets, free from visual defects. Each tablet contains 64 mg of Compound (I). The complete statement of the components and quantitative composition of CR GR-01/C tablet is given in Table 53.

TABLE 53

Composition of CR GR-01/C 64 mg tablet

| | GR-01/C-64 mg | |
|---|---|---|
| Component/Ingredient | mg/tablet | % (w/w) |
| MIN-101[1] | 76.8 | 24.19 |
| Hypromellose (METHOCEL ™ K100LV CR) | 30.00 | 9.45 |
| Hypromellose (Methocel ™ K100M CR) | 72.00 | 22.67 |
| Microcrystalline Cellulose | 75.90 | 23.91 |
| Lactose | 40.80 | 12.85 |
| Silica Colloidal Anhydrous | 1.50 | 0.47 |
| Magnesium stearate | 3.00 | 0.94 |
| Eudragit L30D55 | 15.0 | 4.72 |
| Plasacryl HTP20 | 2.55 | 0.80 |
| Total | 317.55 | 100.00 |

EQUIVALENTS AND INCORPORATION BY REFERENCE

The dosage forms, compositions and methods of the disclosure have been described herein by reference to certain preferred embodiments. However, as particular variations thereon will become apparent to those skilled in the art, based on the disclosure set forth herein, the disclosure is not to be considered as limited thereto.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise.

It is to be understood that at least some of the descriptions of the disclosure have been simplified to focus on elements that are relevant for a clear understanding of the disclosure, while eliminating, for purposes of clarity, other elements that those of ordinary skill in the art will appreciate may also comprise a portion of the disclosure. However, because such elements are well known in the art, and because they do not necessarily facilitate a better understanding of the disclosure, a description of such elements is not provided herein.

Further, to the extent that a method does not rely on the particular order of steps set forth herein, the particular order of the steps recited in a claim should not be construed as a limitation on that claim.

All patents, patent applications, references and publications cited herein are fully and completely incorporated by reference as if set forth in their entirety. Such documents are not admitted to be prior art to the present disclosure.

What is claimed is:

1. A gastro-resistant, controlled release dosage form, comprising:
   about 19 to about 29% w/w 1H-isoindol-1-one, 2-[[1-[2-(4-fluorophenyl)-2-oxoethyl]-4-piperidinyl]methyl]-2,3-dihydro-, hydrochloride, hydrate (1:1:2) (roluperidone hydrochloride);
   about 4 to about 14% w/w of a low-viscosity, controlled-release grade hypromellose, that is about 19 to about 24% methoxy, about 7 to about 12% hydroxypropoxy, and wherein the hypromellose has a viscosity of about 80 to about 120 mPa·s at 2% concentration in water at 20° C.;
   about 17 to about 27% w/w of a controlled-release grade hypromellose, that is about 19 to about 24% methoxy, about 7 to about 12% hydroxypropoxy, and wherein the hypromellose has a viscosity of about 80,000 to about 120,000 mPa·s at 2% concentration in water at 20° C.;
   about 19 to about 29% w/w microcrystalline cellulose;
   about 8 to about 18% w/w lactose monohydrate;
   about 0.1 to about 4% w/w silica colloidal anhydrous;
   about 0.1 to about 4% magnesium stearate;
   about 1 to about 10% w/w methacrylic acid and ethyl acrylate copolymer dispersion; and
   about 0.5 to about 5% w/w of an anti-tacking agent.

2. The gastro-resistant, controlled release dosage form of claim 1, wherein the dosage form produces, upon oral administration to a subject, a plasma pharmacokinetic profile for the BFB-520 metabolite of roluperidone hydrochloride which comprises a $C_{max}$ that is below 4.0 ng/mL, below 3.5 ng/mL, below 3.0 ng/mL, or below 2.5 ng/mL.

3. The gastro-resistant, controlled release dosage form of claim 1, wherein the dosage form comprises about 24% w/w of roluperidone hydrochloride.

4. The gastro-resistant, controlled release dosage form of claim 1, comprising:
   about 24% w/w roluperidone hydrochloride;
   about 9% w/w of a low-viscosity, controlled-release grade hypromellose, that is about 19 to about 24% methoxy, about 7 to about 12% hydroxypropoxy, and wherein the hypromellose has a viscosity of about 80 to about 120 mPa·s at 2% concentration in water at 20° C.;
   about 23% w/w of a controlled-release grade hypromellose, that is about 19 to about 24% methoxy, about 7 to about 12% hydroxypropoxy, and wherein the hypromellose has a viscosity of about 80,000 to about 120,000 mPa·s at 2% concentration in water at 20° C.;
   about 24% w/w microcrystalline cellulose;
   about 13% w/w lactose monohydrate;
   about 0.5% w/w silica colloidal anhydrous;
   about 0.5% w/w magnesium stearate;
   about 5% w/w methacrylic acid and ethyl acrylate copolymer dispersion; and
   about 1% w/w of an anti-tacking agent.

5. The gastro-resistant, controlled release dosage form of claim 1, comprising:
   about 24% w/w roluperidone hydrochloride;
   about 9% w/w of a low-viscosity, controlled-release grade hypromellose, that is about 19 to about 24% methoxy, about 7 to about 12% hydroxypropoxy, and wherein the hypromellose has a viscosity of about 80 to about 120 mPa·s at 2% concentration in water at 20° C.;
   about 23% w/w of a controlled-release grade hypromellose, that is about 19 to about 24% methoxy, about 7 to about 12% hydroxypropoxy, and wherein the hypromellose has a viscosity of about 80,000 to about 120,000 mPa·s at 2% concentration in water at 20° C.;
   about 24% w/w microcrystalline cellulose;
   about 13% w/w lactose monohydrate;
   about 0.5% w/w silica colloidal anhydrous;
   about 1% w/w magnesium stearate;
   about 5% w/w methacrylic acid and ethyl acrylate copolymer dispersion; and
   about 1% w/w of an anti-tacking agent.

6. A method of treating negative symptoms in a subject comprising administering to the subject the gastro-resistant, controlled release dosage form of claim 1, wherein the subject has a diagnosis of schizophrenia.

7. The method of claim 6, wherein the subject having a diagnosis of schizophrenia has a CYP2D6 EM genotype.

8. The method of claim 6, wherein the method further comprises reducing the risk of QT prolongation in the subject.

9. A method of reducing a risk of QT prolongation in a subject when administering roluperidone hydrochloride to said subject comprising administering to the subject the gastro-resistant, controlled release dosage form of claim 1.

10. The method of claim 6, wherein the gastro-resistant, controlled release dosage form is administered once daily.

11. The method of claim 6, wherein the subject is in a fed state prior to oral administration of the dosage form.

12. The method of claim 6, wherein the subject is in a fasted state prior to oral administration of the dosage form.

* * * * *